United States Patent
Bamberg et al.

(10) Patent No.: US 6,759,428 B2
(45) Date of Patent: *Jul. 6, 2004

(54) INDOLE NITRILES

(75) Inventors: Joe Timothy Bamberg, East Palo Alto, CA (US); Tobias Gabriel, San Francisco, CA (US); Nancy Elisabeth Krauss, Mountain View, CA (US); Taraneh Mirzadegan, Los Altos, CA (US); Wylie Solang Palmer, Mountain View, CA (US); David Bernard Smith, San Mateo, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/453,112

(22) Filed: Jun. 2, 2003

(65) Prior Publication Data

US 2004/0077646 A1 Apr. 22, 2004

Related U.S. Application Data

(63) Continuation-in-part of application No. 10/308,963, filed on Dec. 3, 2002.
(60) Provisional application No. 60/336,750, filed on Dec. 4, 2001.

(51) Int. Cl.$^7$ ..................... A61K 31/404; C07D 209/12
(52) U.S. Cl. ..................... 514/419; 548/492; 548/491; 548/361.1; 548/311.4; 548/180; 548/150; 546/87; 546/112; 546/201; 546/278.1; 544/143; 544/373; 514/235.2; 514/253; 514/323; 514/339; 514/367; 514/397; 514/403
(58) Field of Search ............................ 514/419, 235.2, 514/253, 339; 548/492, 361.1, 180, 150; 546/87, 112, 201, 278.1; 544/143, 373

(56) References Cited

U.S. PATENT DOCUMENTS 5,691,321 A 11/1997 Schaper et al.
6,462,076 B2 * 10/2002 Gabriel et al. .............. 514/463

FOREIGN PATENT DOCUMENTS

| DE | 2624290 A1 | 4/1977 |
|---|---|---|
| WO | WO 98/03540 A2 | 1/1998 |
| WO | WO 99/24460 A2 | 5/1999 |
| WO | WO 01/49288 A1 | 7/2001 |
| WO | WO 01/96285 A1 | 12/2001 |
| WO | WO 03/041649 A2 | 5/2003 |

OTHER PUBLICATIONS

Brömme, "The new discoveries made regarding cysteine proteases may offer therapeutic targets for bone disease, cancer and neurodegeneration," *Drug News Perspect*, 1999, pp. 73–82, vol. 12(2).
Chapman et al., "Emerging roles for cysteine proteases in human biology," *Annu. Rev. Phys.*, 1997, pp. 63–88, vol. 59.
Tezuka et al., "Molecular Cloning of a Possible Cysteine Proteinase Predominantly Expressed in Osteoclasts," *J. Biol. Chem.*, 1994, pp. 1106–1109, vol. 269:2.
Lerner, et al, "Human Cystatin C, a Cysteine Proteinase Inhibitor, Inhibits Bone Resorption In Vitro Stimulated by Parathyroid Hormone and Parathyroid Hormone–Related Peptide of Malignancy," *J. Bone Min Res.*, 1992, pp. 433–440, vol. 7:4.
Everts, et al., "Degradation of Collagen in the Bone–Resorbing Compartment Underlying the Osteoclast Involves Both Cysteine–Proteinases and Matrix Metalloproteinases," *J. Cell. Physiol.*, 1992, pp. 221–231, vol. 150, Wiley–Liss.
Hummel, et al., "Cysteine Proteinase Cathepsin K mRNA Is Expressed in Synovium of Patients with Rheumatoid Arthritis and Is Detected at Sites of Synovial Bone Destruction," *J. Rheumatol.*, 1998, pp. 1887–1894, vol. 25:10.
Sukhova, et al., "Expression of the Elastolytic Cathepsins S and K in Human Atheroma and Regulation of their Production in Smooth Muscle Cells," *J. Clin. Invest.*, 1998, pp. 576–583, vol. 102:3.
Littlewood–Evans et al, "The Osteoclast–associated Protease Cathepsin K Is Expressed in Human Breast Carcinoma," *Cancer Res.*, 1997, pp. 5386–5390, vol. 57.
Otto et al., "Cysteine Proteases and Their Inhibitors," *Chem. Rev.*, 1997, pp. 133–171, vol. 97.
Thompson et al., "Design of potent and selective human cathepsin K inhibitors that span the active site," *Proc. Natl. Acad. Sci. USA*, 1997, pp. 14249–14254, vol. 94.
Maubach et al, "The inhibition of cathepsin S by its propeptide," *Eur. J. Biochem.*, 1997, pp. 745–750, vol. 250:2.
Rink, "Solid–phase synthesis of protected peptide fragments using a trialkoxy–diphenyl–methylester resin," *Tetrahedron Lett.*, 1987, pp. 3787–3790, vol. 28:33, Pergamon Journals.
Atkins & Burgess, "The Reactions of an N–Sulfonylamine Inner Salt," *J. Am. Chem. Soc.*, 1968, pp. 4744–4745, vol. 90:17.
Kobayashi et al., "Chiral Synthon Obtained with Pig Liver Esterase: Introduction of Chiral Centers into Cyclohexene Skeleton," *Chem. Pharm. Bull.*, 1990, pp. 350–354 vol. 38:2.
Davies, et al., "Asymmetric Synthesis of (−)–(1R, 2S)–Cispentacin and Related cis– and trans–2–Amino Cyclopentane– and Cyclohexane– 1–carboxylic Acids," *J. Chem. Soc. Perkin Trans.*, 1994, pp. 1411–1415, vol. 1.

* cited by examiner

Primary Examiner—Charanjit S. Aulakh
(74) Attorney, Agent, or Firm—Robert C. Hall

(57) ABSTRACT

Compounds of the formula (I)

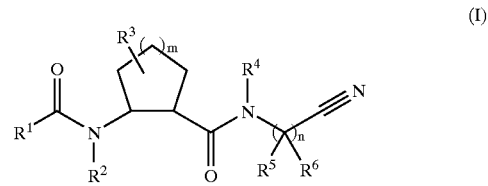

(I)

wherein m, n, $R^1$, $R^2$, $R^3$, $R^4$, $R^5$ and $R^6$ are as described herein, together with methods for making the compounds and using the compounds for treatment of diseases or conditions mediated by Cathepsin K.

57 Claims, No Drawings

INDOLE NITRILES

CROSS REFERENCE TO RELATED APPLICATIONS

This application is a Continuation-in-Part of U.S. patent application Ser. No. 10/308,963, filed on Dec. 3, 2002, and is entitled to the benefit of U.S. Provisional Patent Application No. 60/336,750, filed Dec. 4, 2001, the disclosures of which are incorporated herein by reference.

BACKGROUND OF THE INVENTION

Cysteine proteases have been viewed as lysosomal mediators of terminal protein degradation. Several newly discovered members of this enzyme class, however, are regulated proteases with limited tissue expression, which implies specific roles in cellular physiology and thus would allow a specific targeting of these activities without interfering with the general lysosomal protein degragation. Development of inhibitors of specific cysteine proteases promises to provide new drugs for modifying immunity, osteoporosis, neurodegeneration, chronic inflammation, cancer and malaria (Brömme, *Drug News Perspect* 1999, 12(2), 73–82; Chapman et al., *Annu. Rev. Phys.* 1997, 59, 63–88).

Cysteine proteases can be grouped into two superfamilies: the family of enzymes related to interleukin 1β converting enzyme (ICE), and the papain superfamily of cysteine proteases. Presently there are at least 12 human proteases of the papain family from which sequences have been obtained (cathepsin B, L, H, S, O, K, C, W, F, V(L2), Z(X) and bleomycin hydrolase). Cathepsin K was first discovered as a cDNA prominent in rabbit osteoclasts and referred to as OC-2 (Tezuka et al., *J. Biol. Chem.* 1994, 269, 1106–1109). Recent observations indicate that cathepsin K is the most potent mammalian elastase yet described. Cathepsin K, as well as cathepsins S and L, are also potent collagenases and gelatinases. Macrophages appear capable of mobilizing the active proteases within endosomal and/or lysosomal compartments to the cell surface under special circumstances. In this case, the cell surface/substrate interface becomes a compartment from which endogenous inhibitors are excluded and can be viewed as a physiological extension of the lysosome. This type of physiology is an innate trait of osteoclasts, a bone macrophage, and may also be exploited by other macrophages or cells in the context of inflammation. The abundance of cathepsin K in osteoclasts leads to the suggestion that cathepsin K plays an important role in bone resorption. Studies revealed that cathepsin K is the predominant cysteine protease in osteoclasts and is specifically expressed in human osteoclasts. A correlation between inhibition of cysteine protease activity and bone resorption has been reported (Lerner et al., *J. Bone Min. Res.* 1992, 7, 433; Everts et al., *J. Cell. Physiol.* 1992, 150, 221). Cathepsin K has been detected in synovial fibroblasts of RA patients, as well as in mouse hypertrophic chondrocytes (Hummel et al., *J. Rheumatol.* 1998, 25(10), 1887–1894.). Both results indicate a direct role of cathepsin K in cartilage erosion. P. Libby (Libby et al., *J. Clin. Invest.* 1998, 102 (3), 576–583) reported that normal arteries contain little or no cathepsin K or S whereas macrophages in atheroma contained abundant immunoreactive cathepsins K and S. Most of the elastolytic activity of tissue extracts associated with human atheroma compared to non-atherosclerotic arteries could be inhibited with E64, a non-selective cysteine protease inhibitor.

Tumor progression and metastasis are characterized by the invasion of tumors into adjacent tissues as well as by the dissociation of cancer cells from primary tumors and the infiltration of metastatic cells into organs. These processes are associated with the degradation of extracellular matrix proteins and thus require proteolytic activity. Cathepsin K has been identified in primary breast tumors, as well as in breast tumor-derived bone metastasis (Littlewood-Evans et al., *Cancer Res.* 1997, 57, 5386–5390).

Different classes of compounds, such as aldehydes, alpha-ketocarbonyl compounds, halomethyl ketones, diazomethyl ketones, (acyloxy)methyl ketones, ketomethylsulfonium salts, epoxy succinyl compounds, vinyl sulfones, aminoketones, and hydrazides have been identified as cysteine protease inhibitors (Schirmeister et al., *Chem. Rev.* 1997, 97, 133–171; Veber et al., *Proc. Natl. Acad. Sci. USA* 1997, 94, 14249–14254). The shortcomings these compounds suffer from include lack of selectivity, poor solubility, rapid plasma clearance and cytotoxicity. A need therefore exists for novel inhibitors useful in treating diseases caused by pathological levels of proteases, especially cysteine proteases, including cathepsins, especially cathepsin K.

SUMMARY OF THE INVENTION

The subject compounds are of the formula (I)

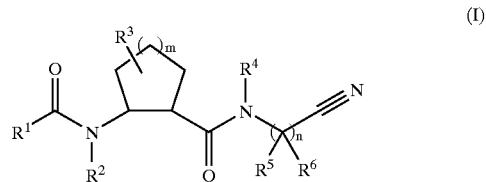

(I)

wherein:

m is from 1 to 3;

n is 1 or 2;

p is from 0 to 2;

$R^1$ is: optionally substituted indolyl; optionally substituted indazolyl; optionally substituted benzothiazole; optionally substituted indolizinyl; optionally substituted tetrahydropyridoindolyl; optionally substituted pyridinylthiophenyl; or optionally substituted benzopyrrolothiazolyl;

$R^2$, $R^3$, $R^4$ and $R^5$ each independently is hydrogen or alkyl; and $R^6$ is: hydrogen; alkyl; cycloalkyl; or —$(CR^aR^b)_q$—A: wherein $R^a$ and $R^b$ each independently is hydrogen or alkyl, q is from 0 to 3, and wherein A is:

hydroxy; alkoxy; cyano; optionally substituted phenyl; optionally substituted pyridyl; optionally substituted imidazolyl; optionally substituted thienyl; —S(O)$_r$—$R^c$ wherein r is from 0 to 2 and $R^c$ is hydrogen or alkyl; —COR$^d$ wherein $R^d$ is: hydroxy; alkoxy; morpholinyl; or cycloalkylamino; or —NR$^e$R$^f$ wherein $R^e$ and $R^f$ each independently is hydrogen or alkyl, or $R^e$ and $R^f$ together with the nitrogen to which they are attached may form a five or six membered ring that optionally includes an additional heteroatom selected from O, N and S;

and pharmaceutically acceptable salts, solvates or prodrugs thereof.

The invention further relates to a process for the manufacture or preparation of compounds of general formula (I), which process comprises:

a) reacting a compound of formula i

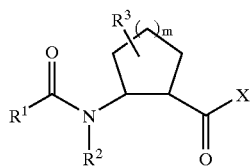

wherein X is a leaving group such as halo, alkoxy or tosyl, and $R^1$, $R^2$, $R^3$ and m are defined herein;
with a compound of formula ii

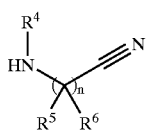

wherein $R^4$, $R^5$, $R^6$ and n are as defined herein; or
b) reacting a compound of formula iii:

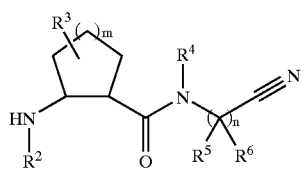

wherein $R^2$, $R^3$, $R^4$, $R^5$ and $R^6$ are as defined herein, with a compound of formula iv

wherein X is a leaving group and $R^1$ is as defined herein; to provide a compound of formula (I) above.

DETAILED DESCRIPTION OF THE INVENTION

The compounds of the invention have an inhibitory activity on cysteine proteases, more particularly on cysteine proteases of the papain superfamily, even more particularly on cysteine proteases of the cathepsin family, most particularly on cathepsin K. It was surprisingly found that this inhibiting effect on cathepsin K is selective with respect to other cathepsins. While compounds of general formula (I) very efficiently inhibit cathepsin K, the inhibition of other protease inhibitors such as cathepsin S, cathepsin L and cathepsin B is much weaker. Therefore the new compounds of general formula (I) are useful for specifically inhibiting cathepsin K. They can accordingly be used for the treatment of disorders which are associated with cysteine proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease.

Accordingly, the present invention relates to a method for the prophylactic and/or therapeutic treatment of diseases which are associated with cystein proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease, which method comprises administering a compound of formula (I) to a human being or an animal. The present invention also relates to pharmaceutical compositions comprising a compound of formula (I) and a pharmaceutically acceptable carrier and/or adjuvant. Furthermore, the present invention relates to the use of such compounds for the preparation of medicaments for the treatment of disorders which are associated with cystein proteases. The present invention also relates to processes for the preparation of the compounds of formula (I).

Definitions

Unless otherwise indicated the following definitions are set forth to illustrate and define the meaning and scope of the various terms used to describe the invention herein.

In this specification the term "lower" is used to mean a group consisting of one to seven, preferably of one to four carbon atom(s).

The term "alkyl" refers to a branched or straight chain monovalent saturated aliphatic hydrocarbon radical of one to eight carbon atoms.

The term "lower-alkyl" refers to a branched or straight chain monovalent alkyl radical of one to six carbon atoms, preferably one to four carbon atoms. This term is further exemplified by such radicals as methyl, ethyl, n-propyl, isopropyl, n-butyl, s-butyl, t-butyl and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof such as cyclohexenyl, cyclopentenyl, and the like.

"Cycloalkylalkyl" means a moiety of the formula —R'R", where R' is alkylene and R" is cycloalkyl as defined herein.

"Alkylamino" or "Monoalkylamino" means a radical —NHR where R represents an alkyl, cycloalkyl or cycloalkyl-alkyl group as defined herein. Representative examples include, but are not limited to methylamino, ethylamino, isopropylamino, cyclohexylamino, and the like.

"Dialkylamino" means a radical —NRR' where R and R' independently represent an alkyl, cycloalkyl, or cycloalkylalkyl group as defined herein. Representative examples include, but are not limited to dimethylamino, methylethylamino, di(1-methylethyl)amino, (cyclohexyl) (methyl)amino, (cyclohexyl)(ethyl)amino, (cyclohexyl) (propyl)amino, (cyclohexylmethyl)(methyl)amino, (cyclohexylmethyl)(ethyl)amino, and the like.

The term "halo" refers to fluorine, chlorine, bromine and iodine, with fluorine, chlorine and bromine being preferred.

"Haloalkyl" means alkyl substituted with one or more same or different halo atoms, e.g., —CH$_2$Cl, —CF$_3$, —CH$_2$CF$_3$, —CH$_2$CCl$_3$, and the like.

"Heteroalkyl" means an alkyl radical as defined herein wherein one, two or three hydrogen atoms have been replaced with a substituent independently selected from the group consisting of —ORa, —NRbRc, and —S(O)nRd (where n is an integer from 0 to 2), with the understanding that the point of attachment of the heteroalkyl radical is through a carbon atom, wherein Ra is hydrogen, acyl, alkyl, cycloalkyl, or cycloalkylalkyl; Rb and Rc are independently of each other hydrogen, acyl, alkyl, cycloalkyl, or cycloalkylalkyl; when n is 0, Rd is hydrogen, alkyl, cycloalkyl, or cycloalkylalkyl, and when n is 1 or 2, Rd is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently with one or more substituents, preferably one or two substituents, selected from alkyl, haloalkyl, hydroxyalkyl, heteroalkyl, acyl, alkylene-C(O)—XR (where X is a bond, O or NR' (where R' is hydrogen or lower-alkyl) and R is hydrogen, alkyl, alkenyl, hydroxy, alkoxy, amino, monoalkylamino or dialkylamino) acylamino, amino, monoalkylamino, dialkylamino, NR'C(O)OR" (where R' is hydrogen or alkyl and R" is alkyl or alkenyl), alkylthio, alkylsulfinyl, alkylsulfonyl, —SO$_2$NR'R" (where R' and R" are independently hydrogen, alkyl, cycloalkyl or cycloalkylalkyl), NRSO$_2$R' (where R is hydrogen or lower alkyl, and R' is alkyl, cycloalkyl, cycloalkyl-alkyl, amino, monoalkylamino or dialkylamino), alkoxy, haloalkoxy, alkoxycarbonyl, carbamoyl, hydroxy, halo, nitro, cyano, cyanoalkyl, mercapto, methylenedioxy, ethylenedioxy, benzyloxy, heterocyclyl-alkoxy or optionally substituted phenyl. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl, thazinanyl and the like, including partially hydrogenated derivatives thereof.

"Heteroarylalkyl" and "heteroaralkyl", which may be used interchangeably, mean a radical —R$^a$R$^b$ where R$^a$ is an alkylene group and R$^b$ is a heteroaryl group as defined herein; e.g., thienylmethyl, pyridinylmethyl, imidazolylethyl, pyrazolylpropyl, and the like are examples of heteroarylalkyl.

"Heterocyclyl" means a saturated or unsaturated non-aromatic cyclic radical of 3 to 8 ring atoms in which one or two ring atoms are heteroatoms selected from N, N(O), O, or S(O)$_n$ (where n is an integer from 0 to 2), the remaining ring atoms being C. The heterocyclyl ring may be optionally substituted independently with one, two, or three substituents selected from alkyl, haloalkyl, heteroalkyl, halo, nitro, cyanoalkyl, hydroxy, alkoxy, amino, monoalkylamino or dialkylamino. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like, including partially unsaturated derivatives thereof.

"Heterocyclylalkyl" means a group —R$^x$—R$^y$ where R$^x$ is an alkylene group and R$^y$ is a heterocyclyl group. Representative examples include, but are not limited to, 2-(morpholin-4-yl)ethyl, 2-(4-methyl-piperazin-1-yl)ethyl, 3-(piperidin-1-yl)propyl and the like.

"Heterocyclyl-alkoxy" means a group —OR$^x$—R$^y$ where R$^x$ is an alkylene group and R$^y$ is a heterocyclyl group. Representative examples include, but are not limited to 2-(morpholin-4-yl)ethoxy, 2-(4-methyl-piperazin-1-yl) ethoxy and the like.

"Hydroxyalkyl" means an alkyl radical as defined herein, substituted with one or more, preferably one, two or three hydroxy groups, provided that the same carbon atom does not carry more than one hydroxy group. Representative examples include, but are not limited to, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl, preferably 2-hydroxyethyl, 2,3-dihydroxypropyl and 1-(hydroxymethyl)-2-hydroxyethyl. Accordingly, as used herein, the term "hydroxyalkyl" is used to define a subset of heteroalkyl groups.

The term "alkoxy" refers to the group R'—O—, wherein R' is an alkyl. The term "lower-alkoxy" refers to the group R'—O—, wherein R' is a lower-alkyl.

The term "alkenyl" stands for alone or in combination with other groups, a straight-chain or branched hydrocarbon residue containing an olefinic bond and up to 20, preferably up to 16 C-atoms. The term "lower-alkenyl" refers to a straight-chain or branched hydrocarbon residue containing an olefinic bond and up to 7, preferably up to 4 C-atoms.

"Aryl" means a monocyclic or bicyclic aromatic hydrocarbon radical which is optionally substituted with one or more substituents, preferably one, two or three, substituents preferably selected from the group consisting of alkyl, haloalkyl, hydroxyalkyl, heteroalkyl, acyl, acylamino, amino, alkylamino, dialkylamino, alkylthio, alkylsulfinyl, alkylsulfonyl, —SO$_2$NR'R" (where R' and R" are independently hydrogen or alkyl), alkoxy, haloalkoxy, alkoxycarbonyl, carbamoyl, hydroxy, halo, nitro, cyano, mercapto, methylenedioxy or ethylenedioxy. More specifically the term aryl includes, but is not limited to, phenyl, chlorophenyl, fluorophenyl, methoxyphenyl, 1-naphthyl, 2-naphthyl, and the derivatives thereof.

"Arylalkyl" and "Aralkyl", which may be used interchangeably, mean a radical —R$^a$R$^b$ where R$^a$ is an alkylene group and R$^b$ is an aryl group as defined herein; e.g., benzyl, phenylethyl, 3-(3-chlorophenyl)-2-methylpentyl, and the like are examples of arylalkyl.

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

The term "pharmaceutically acceptable esters" embraces esters of the compounds of formula (1), in which hydroxy groups have been converted to the corresponding esters with inorganic or organic acids such as hydrochloric acid, hydrobromic acid, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

All references, patents and publications sited in this disclosure are expressly incorporated herein by reference in their entirety.

Nomenclature and Chemical Structures

In general, the nomenclature used in this Application is based on AutoNom®, a Beilstein Institute computerized system for the generation of IUPAC systematic nomenclature. Chemical structures shown herein were prepared using ISIS® version 2.2. Any open valency shown on a carbon, nitrogen or oxygen in the structures herein indicates the presence of a hydrogen. Nitrile or cyano groups are shown in the structures herein as —CN or —≡N, which may be used interchangeably.

Compounds

The compounds of the invention have an inhibitory activity on cysteine proteases, more particularly on cysteine proteases of the papain superfamily, even more particularly on cysteine proteases of the cathepsin family, most particularly on cathepsin K. It was surprisingly found, that this inhibiting effect on cathepsin K is selective with respect to other cathepsins. While compounds of general formula (I) very efficiently inhibit cathepsin K, the inhibition of other protease inhibitors such as cathepsin S, cathepsin L and cathepsin B is much weaker. Therefore the new compounds of general formula (I) are useful for specifically inhibiting cathepsin K. They can accordingly be used for the treatment of disorders which are associated with cysteine proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease.

The subject compounds are of the formula (I)

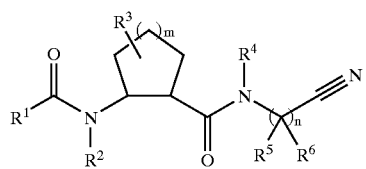

(I)

wherein:
 m is from 1 to 3;
 n is 1 or 2;
 p is from 0 to 2;
 $R^1$ is: optionally substituted indolyl; optionally substituted indazolyl; optionally substituted benzothiazole; optionally substituted indolizinyl; optionally substituted tetrahydropyridoindolyl; optionally substituted pyridinylthiophenyl; or optionally substituted benzopyrrolothiazolyl;

$R^2$, $R^3$, $R^4$ and $R^5$ each independently is hydrogen or alkyl; and $R^6$ is: hydrogen; alkyl; cycloalkyl; or —$(CR^aR^b)_q$—A:
  wherein $R^a$ and $R^b$ each independently is hydrogen or alkyl, q is from 0 to 3, and wherein A is:
   hydroxy; alkoxy; cyano; optionally substituted phenyl; optionally substituted pyridyl; optionally substituted imidazolyl; optionally substituted thienyl; —$S(O)_r$—$R^c$ wherein r is from 0 to 2 and $R^c$ is hydrogen or alkyl; —$COR^d$ wherein $R^d$ is: hydroxy; alkoxy; morpholinyl; or cycloalkylamino; or —$NR^eR^f$ wherein $R^e$ and $R^f$ each independently is hydrogen or alkyl, or $R^e$ and $R^f$ together with the nitrogen to which they are attached may form a five or six membered ring that optionally includes an additional heteroatom selected from O, N and S;

and pharmaceutically acceptable salts, solvates or prodrugs thereof.

In many embodiments, m is 2, n is 1, and $R^1$ is indolyl optionally substituted with one or more of: halo; alkyl; hydroxyalkyl; morpholinylalkyl; dialkylaminoalkyl; piperidinylalkyl; hydroxyalkoxyalkyl; alkoxyalkoxyalkyl; alkylsulfonylalkyl; hydroxyalkylaminoalkyl; 1,1-dioxothiadiaolinyl; piperidin-sulfonylalkyl; dialkylaminosulfonylalkyl; piperazinylalkyl; pyrazolylalkyl; imidazolylalkyl; 1,1-dioxothiazinanyl; pyridinyl; piperidinylsulfonylaminoalkyl; dialkylaminosulfonylaminoalkyl; or 1,1-dioxoisothiazolidinyl. $R^1$ may be, for example, indol-2-yl, indol-5-yl, or indol-6-yl.

In certain embodiments $R^1$ indol-2-yl optionally substituted at the 6-position with: fluoro; chloro; bromo; piperidin-3-yl; 2-methanesulfonyl-ethyl; pyrazol-1-yl-methyl; 3-hydroxy-3-methyl-butyl; 1,1-dioxo-1λ$^6$-isothiazolidin-2-yl; or 1,1-dioxo-1λ$^6$-[1,2]thiazinan-2-yl. The indol-2-yl may optionally be substituted at the 1-position with: alkyl; hydroxyalkyl; morpholinylalkyl; dialkylaminoalkyl; piperidinylalkyl; hydroxyalkoxyalkyl; alkoxyalkoxyalkyl; alkylsulfonylalkyl; hydroxyalkylaminoalkyl; 1,1-dioxothiadiaolinyl; piperidin-sulfonylalkyl; dialkylaminosulfonylalkyl; piperazinylalkyl; pyrazolylalkyl; imidazolylalkyl; piperidinylsulfonylaminoalkyl; or dialkylaminosulfonylaminoalkyl.

In certain embodiments $R^1$ is indol-2-yl substituted at the 1-position with: methyl; 2-hydroxy-ethyl; 3-hydroxy-propyl; 3-hydroxy-butyl; 3-hydroxy-2-hydroxymethylpropyl; 2-hydroxy-2-methyl-propyl; 3-hydroxy-3-methyl-butyl; 2-(2-hydroxy-ethoxy)-ethyl; 2-(2-methoxy-ethoxy)-ethyl; 2-dimethylaminoethyl; 3-dimethylamino-propyl; 2-methanesulfonyl-ethyl; 2-(2-hydroxy-ethyl-amino)-ethyl; 2-morpholin-4-yl-ethyl; 3-morpholin-4-yl-propyl; piperidin-4-yl-methyl; 2-piperidin-4-yl-ethyl; 3-piperidin-1-yl-propyl; 1-methylpiperidin-4-yl-methyl; 2-(1-methyl-piperidin-4-yl)-ethyl; 3-(1,1-dimethyl-piperidinium)-ethyl; 1-(2-methoxy-ethyl)-piperidin-4-yl-methyl; 2-[1-(2-methoxy-ethyl)-piperidin-4-yl]-ethyl; 3-[1-(2-methoxy-ethyl)-piperidin-4-yl]-propyl; 2-(piperidine-1-sulfonylamino)-ethyl; 2-(1,1-dioxo-1λ$^6$-[1,2,5] thiadiazolidin-2-yl)-ethyl; or 2-(dimethylamino-1-sulfonylamino)-ethyl.

In many embodiments of the subject compounds $R^6$ is hydrogen, alkyl or cycloalkyl. In certain embodiments, $R^6$ may be: hydrogen; isobutyl; cyclopropyl; 2-methanesulfanyl-ethyl; 2-methanesulfonyl-ethyl; pyridin-2-yl; 2-(methane sulfonic acid)-ethyl; phenyl; 4-nitrobenzyl; 4-aminobenzyl; 4-methoxybenzyl; 4-methanesulfonylaminobenzyl; 2-dimethylamino-ethyl; 4-(4-morpholinyl)-benzyl; pyridin-4-yl-methyl; pyridin-3-yl-methyl; 2-chloro-5-methyl-pyridin-4-yl-methyl; 2-methyl-pyridin-4-yl-methyl; 2-chloro-pyridin-4-yl-methyl; 3-hydroxy-propyl; 2-(4- methyl-piperazin-1-yl)-ethyl; 2-[4-(2-methoxy-ethyl)-piperazin-1-yl]-ethyl; 2-cyano-ethyl; 1-methyl-imidazol-4-yl-methyl; 1-morpholin-4-yl-propan-1-one-3-yl; N-cyclopropyl-propionamid-3-yl; or methyl propionate-3-yl.

In specific embodiments of the invention, R¹ may be: 1-methyl-1H-indol-2-yl; 5-fluoro-1-methyl-1H-indol-2-yl; 6-chloro-1H-indol-2-yl; 6-chloro-1-methyl-1H-indol-2-yl; 6-bromo-1H-indol-2-yl; 6-bromo-1-methyl-1H-indol-2-yl; 1-(2-hydroxy-ethyl)-1H-indol-2-yl; 1-(3-hydroxy-propyl)-1H-indol-2-yl; 1-(3-hydroxy-butyl)-1H-indol-2-yl; 1-(3-hydroxy-2-hydroxymethyl-propyl)-1H-indol-2-yl; 1-(2-hydroxy-2-methyl-propyl)-1H-indol-2-yl; 1-(3-hydroxy-3-methyl-butyl)-1H-indol-2-yl; 1-[2-(2-hydroxy-ethoxy)-ethyl]-1H-indol-2-yl; 1-[2-(2-methoxy-ethoxy)-ethyl]-1H-indol-2-yl; 1-[2-(2-methoxy-ethoxy)-ethyl]-1H-indol-2-yl; 1-(2-dimethylamino-ethyl)-1H-indol-2-yl; 1-(dimethylamino-propyl)-1H-indol-2-yl; 1-(2-morpholin-4-yl-ethyl)-1H-indol-2-yl; 1-(3-morpholin-4-yl-propyl)-1H-indol-2-yl; 1-(piperidin-4-yl-methyl)-1H-indol-2-yl; 1-(2-piperidin-4-yl-ethyl)-1H-indol-2-yl; 1-(3-piperidin-1-yl-propyl)-1H-indol-2-yl; 1-(1-methyl-piperidin-4-yl-methyl)-1H-indol-2-yl; 1-[2-(1-methyl-piperidin-4-yl)-ethyl]-1H-indol-2-yl; 1-[3-(1,1-dimethyl-piperidinium)-ethyl]-1H-indol-2-yl; 1-[1-(2-methoxy-ethyl)-piperidin-4-yl-methyl]-1H-indol-2-yl; 1-{2-[1-(2-methoxy-ethyl)-piperidin-4-yl]-ethyl}-1H-indol-2-yl; 1-{3-[1-(2-methoxy-ethyl)-piperidin-4-yl]-propyl}-1H-indol-2-yl; 1-[2-(piperidine-1-sulfonylamino)-ethyl]-1H-indol-2-yl; 1-(2-methanesulfonyl-ethyl)-1H-indol-2-yl; 1-[2-(2-hydroxy-ethyl-amino)-ethyl]-1H-indol-2-yl; 1-[2-(1,1-dioxo-1λ⁶-[1,2,5]thiadiazolidin-2-yl)-ethyl]-1H-indol-2-yl; or 1-[2-(dimethylamino-1-sulfonylamino)-ethyl]-1H-indol-2-yl.

In other embodiments R¹ may be indol-5-yl, which may be optionally substituted at the 1-position with: alkyl; hydroxyalkyl; morpholinylalkyl; dialkylaminoalkyl; piperidinylalkyl; hydroxyalkoxyalkyl; alkoxyalkoxyalkyl; alkylsulfonylalkyl; hydroxyalkylaminoalkyl; 1,1-dioxothiadiaolinyl; piperidin-sulfonylalkyl; dialkylaminosulfonylalkyl; piperazinylalkyl; pyrazolylalkyl; imidazolylalkyl; piperidinylsulfonylaminoalkyl; or dialkylaminosulfonylaminoalkyl.

More specifically, R¹ may be indol-5-yl substituted at the 1-position with: methyl; 2-hydroxy-ethyl; 3-hydroxy-propyl; 3-hydroxy-butyl; 3-hydroxy-2-hydroxymethyl-propyl; 2-hydroxy-2-methyl-propyl; 3-hydroxy-3-methyl-butyl; 2-(2-hydroxy-ethoxy)-ethyl; 2-(2-methoxy-ethoxy)-ethyl; 2-dimethylamino-ethyl; 3-dimethylamino-propyl; 2-methanesulfonyl-ethyl; 2-(2-hydroxyethyl-amino)-ethyl; 2-morpholin-4-yl-ethyl; 3-morpholin-4-yl-propyl; piperidin-1-yl-methyl; 2-piperidin-4-yl-ethyl; 3-piperidin-1-yl-propyl; 1-methyl-piperidin-4-yl-methyl; 2-(1-methyl-piperidin-4-yl)-ethyl; 3-(1,1-dimethyl-piperidinium)-ethyl; 1-(2-methoxy-ethyl)-piperidin-4-yl-methyl; 2-[1-(2-methoxy-ethyl)-piperidin-4-yl]-ethyl; 3-[1-(2-methoxy-ethyl)-piperidin-4-yl]-propyl; 2-(piperidine-1-sulfonylamino)-ethyl; 2-(1,1-dioxo-1λ⁶-[1,2,5]thiadiazolidin-2-yl)-ethyl; or 2-(dimethylamino-1-sulfonylamino)-ethyl. In specific embodiments R¹ is: 1-(3-morpholin-4-yl-propyl)-1H-indol-5-yl; 1-(2-dimethylamino-ethyl)-1H-indol-5-yl; 1-(3-dimethylamino-propyl)-1H-indol-5-yl; or 2-methyl-2,3,4,5-tetrahydro-1H-pyrido[4,3-b]indol-5-yl.

In still other embodiments R¹ may be optionally substituted indazolyl such as: 3-(3-dimethylamino-propyl)-indazol-5-yl; 2-(3-dimethylamino-propyl)-indazol-5-yl; 1-(3-dimethylamino-propyl)-indazol-5-yl; 2-(2-dimethylamino-ethyl)-indazol-5-yl; or; 1-(2-dimethylamino-ethyl)-indazol-5-yl.

In some embodiments R¹ may be optionally substituted tetrahydropyridoindolyl such as 2-methyl-2,3,4,5-tetrahydro-1H-pyrido[4,3-b]indol-8-yl. In other embodiments R¹ may be optionally substituted pyridinylthiophenyl such as 5-(6-methyl-pyridin-2-yl)-thiophene-2-yl. In still other embodiments R¹ may be optionally substituted benzopyrrolothiazolyl such as benzo[d]pyrrolo[2,1-b]thiazole-2-yl.

In certain embodiments, the compounds of the invention may be more specifically of the formula (II):

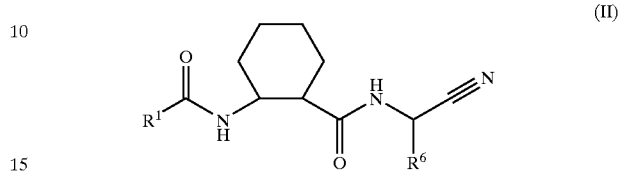

(II)

wherein R¹ and R⁶ are as defined herein.

Many embodiments of the subject compounds may be of the formula (III):

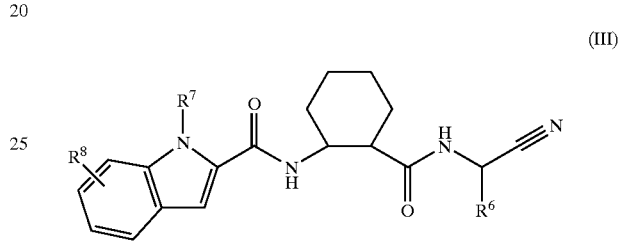

(III)

wherein R⁶ is as defined herein, and wherein:

R⁷ is: hydrogen; alkyl; hydroxyalkyl; morpholinylalkyl; dialkylaminoalkyl; piperidinylalkyl; hydroxyalkoxyalkyl; alkoxyalkoxyalkyl; alkylsulfonylalkyl; hydroxyalkylaminoalkyl; 1,1-dioxothiadiaolinyl; piperidin-sulfonylalkyl; dialkylaminosulfonylalkyl; piperazinylalkyl; pyrazolylalkyl; imidazolylalkyl; piperidinylsulfonylaminoalkyl; or dialkylaminosulfonylaminoalkyl; and R⁸ is: hydrogen; halo; piperidinyl; alkylsulfonylalkyl; pyrazolylalkyl; hydroxy-3-methyl-butyl; 1,1-dioxo-isothiazolidinyl; or 1,1-dioxo-thiazinanyl. In certain embodiments R⁸ may comprise fluoro; chloro; bromo; piperidin-3-yl; 2-methanesulfonyl-ethyl; pyrazol-1-yl-methyl; 3-hydroxy-3-methyl-butyl; 1,1-dioxo-1λ⁶-isothiazolidin-2-yl; 1,1-dioxo-1λ⁶-[1,2]thiazinan-2-yl; 4-methyl-piperazin-1-ylmethyl; pyrazol-1-ylmethyl; imidazol-1-ylmethyl; 3-hydroxy-3-methyl-butyl; phenyl; 4-chlorophenyl; 2-morpholin-4-yl-ethoxy; or 1-(acetylhydrazono)-ethyl located at the 6- or 7-position of the indole ring system.

In certain embodiments R⁷ may be: hydrogen; methyl; 2-hydroxy-ethyl; 3-hydroxy-propyl; 3-hydroxy-butyl; 3-hydroxy-2-hydroxymethyl-propyl; 2-hydroxy-2-methyl-propyl; 3-hydroxy-3-methyl-butyl; 2-(2-hydroxy-ethoxy)-ethyl; 2-(2-methoxy-ethoxy)-ethyl; 2-dimethylamino-ethyl; 3-dimethylamino-propyl; 2-methanesulfonyl-ethyl; 2-(2-hydroxy-ethyl-amino)-ethyl; 2-morpholin-4-yl-ethyl; 3-morpholin-4-yl-propyl; piperidin-4-yl-methyl; 2-piperidin-4-yl-ethyl; 3-piperidin-1-yl-propyl; 1-methyl-piperidin-4-yl-methyl; 2-(1-methylpiperidin-4-yl)-ethyl; 3-(1,1-dimethyl-piperidinium)-ethyl; 1-(2-methoxy-ethyl)-piperidinyl-methyl; 2-[1-(2-methoxy-ethyl)-piperidin-4-yl]-ethyl; 3-[1 2-methoxy-ethyl)-piperidin-4-yl]-propyl; 2-(piperidine-1-sulfonylamino)-ethyl; 2-(1,1-dioxo-1λ⁶-[1,2,5]thiadiazolidin-2-yl)-ethyl; or 2-(dimethylamino-1-sulfonylamino)-ethyl.

In certain embodiments R⁸ may be: fluoro; chloro; bromo; piperidin-3-yl; 2-methanesulfonyl-ethyl; pyrazol-1-yl-methyl; 3-hydroxy-3-methyl-butyl; 1,1-dioxo-1λ6-isothiazolidin-2-yl; or 1,1-dioxo-1λ⁶-[1,2]thiazinan-2-yl.

In certain embodiments, R⁷ may be represented by a formula selected from the substituents shown below.

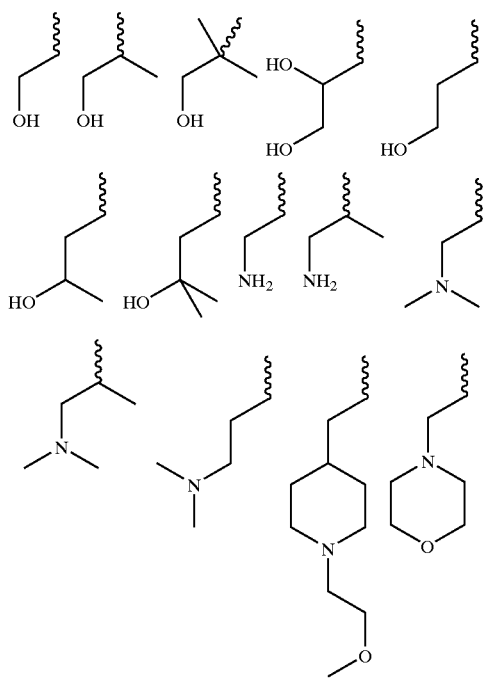

-continued

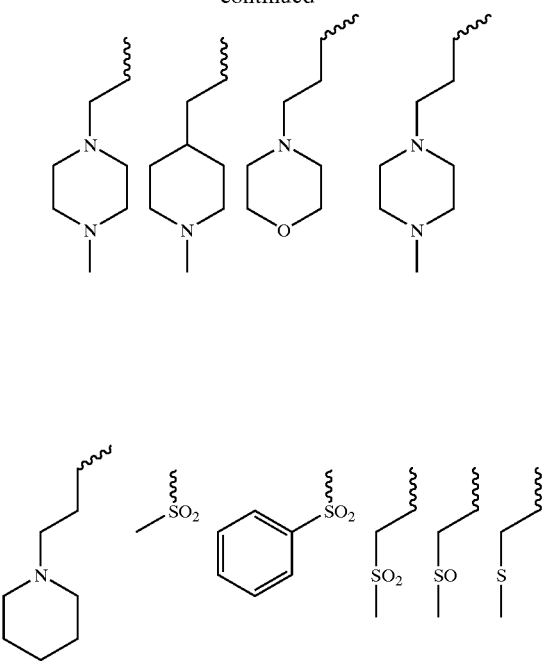

Representative compounds in accordance with the invention are shown in Tables 1 through 5. The experimental examples and methods associated with preparation of each compound are referenced in the tables.

Compound Table 1

| Cpd # | Structure | Compound Name | Method | MW | MS |
|---|---|---|---|---|---|
| 1-1 | 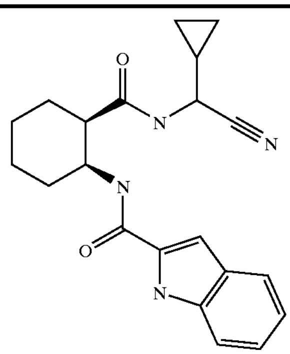 | N-[(1S,2R)-2-({[cyano(cyclopropyl)methyl]amino}carbonyl)cyclohexyl]-1H-indole-2-carboxamide | A | 364.44 | 364 |
| 1-2 | Chiral | N-((1S,2R)-2-{[(cyanomethyl)amino]carbonyl}cyclohexyl)-1H-indole-2-carboxamide | A | 324.38 | 324 |

-continued

Compound Table 1

| Cpd # | Structure | Compound Name | Method | MW | MS |
|---|---|---|---|---|---|
| 1-3 | 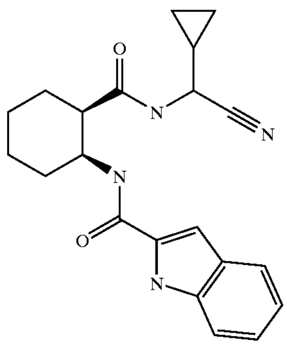 | N-[(1S,2R)-2-({[cyano(cyclopropyl)methyl]amino}carbonyl)cyclohexyl]-1H-indole-2-carboxamide | A | 364.45 | 364 |
| 1-4 | 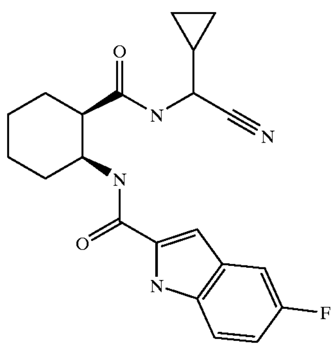 | N-[(1S,2R)-2-({[cyano(cyclopropyl)methyl]amino}carbonyl)cyclohexyl]-5-fluoro-1H-indole-2-carboxamide | A | 382.44 | 382 |
| 1-5 | 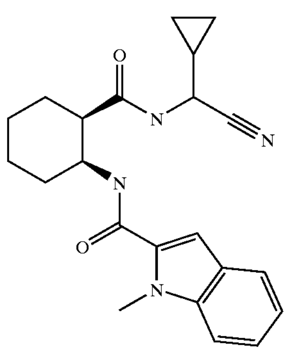 | N-[(1S,2R)-2-({[cyano(cyclopropyl)methyl]amino}carbonyl)cyclohexyl]-1-methyl-1H-indole-2-carboxamide | A | 378.48 | 378 |
| 1-6 | 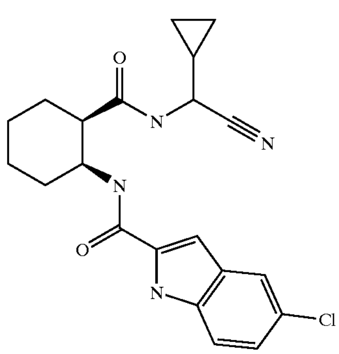 | 5-chloro-N-[(1S,2R)-2-({[cyano(cyclopropyl)methyl]amino}carbonyl)cyclohexyl]-1H-indole-2-carboxamide | A | 398.9 | 398 |

-continued

Compound Table 1

| Cpd # | Structure | Compound Name | Method | MW | MS |
|---|---|---|---|---|---|
| 1-7 | 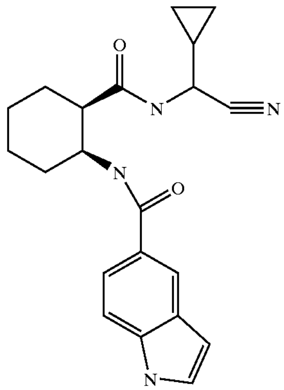 | N-[(1S,2R)-2-({[cyano(cyclopropyl)methyl]amino}carbonyl)cyclohexyl]-1H-indole-5-carboxamide | A | 364.45 | 364 |
| 1-8 | 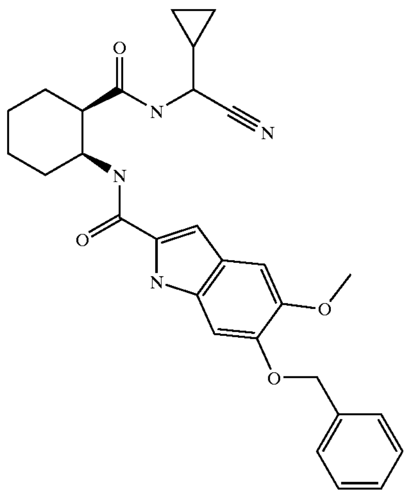 | 6-(benzyloxy)-N-[(1S,2R)-2-({[cyano(cyclopropyl)methyl]amino}carbonyl)cyclohexyl]-5-methoxy-1H-indole-2-carboxamide | A | 500.59 | 500 |
| 1-9 | 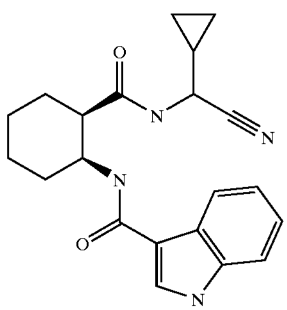 | N-[(1S,2R)-2-({[cyano(cyclopropyl)methyl]amino}carbonyl)cyclohexyl]-1H-indole-3-carboxamide | A | 364.44 | 364 |
| 1-10 | 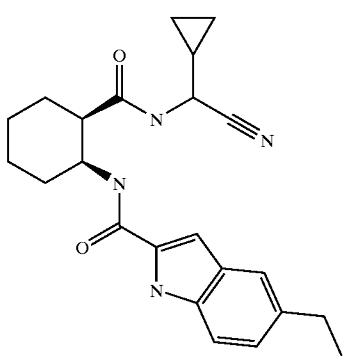 | N-[(1S,2R)-2-({[cyano(cyclopropyl)methyl]amino}carbonyl)cyclohexyl]-5-ethyl-1H-indole-2-carboxamide | A | 392.5 | 392 |

-continued

Compound Table 1

| Cpd # | Structure | Compound Name | Method | MW | MS |
|---|---|---|---|---|---|
| 1-11 | 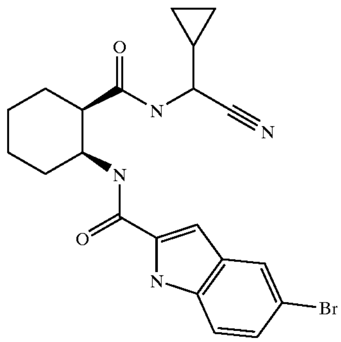 | 5-bromo-N-[(1S,2R)-2-({[cyano(cyclopropyl)methyl]amino}carbonyl)cyclohexyl]-1H-indole-2-carboxamide | A | 443.34 | 443 |
| 1-12 | 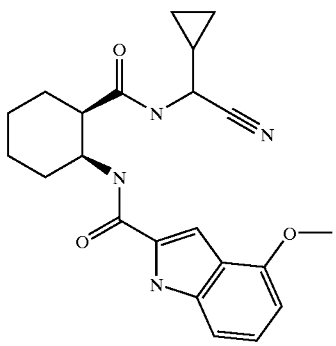 | N-[(1S,2R)-2-({[cyano(cyclopropyl)methyl]amino}carbonyl)cyclohexyl]-4-methoxy-1H-indole-2-carboxamide | A | 394.47 | 394 |
| 1-13 | 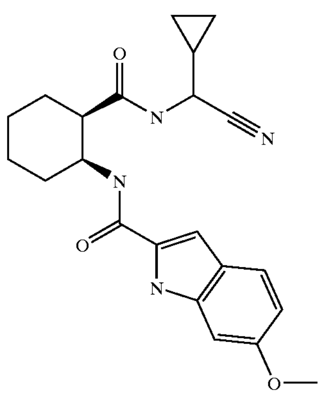 | N-[(1S,2R)-2-({[cyano(cyclopropyl)methyl]amino}carbonyl)cyclohexyl]-6-methoxy-1H-indole-2-carboxamide | A | 394.47 | 394 |
| 1-14 | 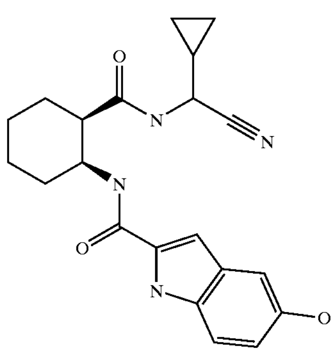 | N-[(1S,2R)-2-({[cyano(cyclopropyl)methyl]amino}carbonyl)cyclohexyl]-5-hydroxy-1H-indole-2-carboxamide | A | 380.44 | 380 |

-continued

Compound Table 1

| Cpd # | Structure | Compound Name | Method | MW | MS |
|---|---|---|---|---|---|
| 1-15 | 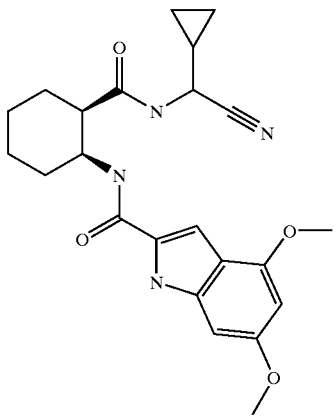 | N-[(1S,2R)-2-({[cyano(cyclopropyl)methyl]amino}carbonyl)cyclohexyl]-4,6-dimethoxy-1H-indole-2-carboxamide | A | 424.49 | 424 |
| 1-16 | 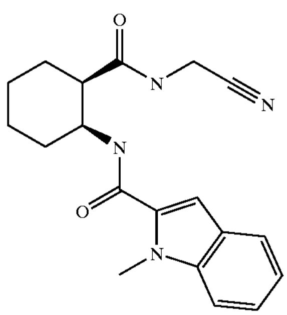 | N-((1S,2R)-2-{[(cyanomethyl)amino]carbonyl}cyclohexyl)-1-methyl-1H-indole-2-carboxamide | A | 338.40 | 338 |
| 1-17 | Chiral | N-((1S,2R)-2-{[(cyanomethyl)amino]carbonyl}cyclohexyl)-6-(methylthio)-1H-indole-2-carboxamide | A | 370.47 | 370 |
| 1-18 | 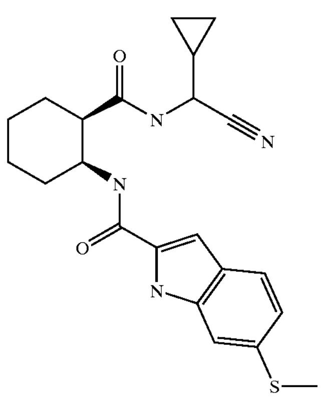 | N-[(1S,2R)-2-({[cyano(cyclopropyl)methyl]amino}carbonyl)cyclohexyl]-6-(methylthio)-1H-indole-2-carboxamide | A | 410.53 | 410 |

-continued

Compound Table 1

| Cpd # | Structure | Compound Name | Method | MW | MS |
|---|---|---|---|---|---|
| 1-19 | Chiral | 2-butyl-N-((1S,2R)-2-{[(cyanomethyl)amino]carbonyl}cyclohexyl)-1H-indole-6-carboxamide | A | 380.48 | 380 |
| 1-20 | 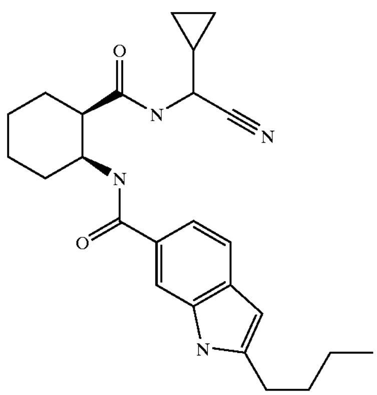 | 2-butyl-N-[(1S,2R)-2-({[cyano(cyclopropyl)methyl]amino}carbonyl)cyclohexyl]-1H-indole-6-carboxamide | A | 420.55 | 420 |
| 1-21 | 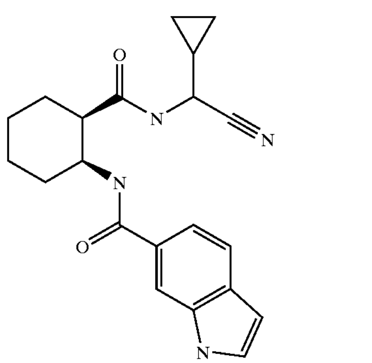 | N-[(1S,2R)-2-({[cyano(cyclopropyl)methyl]amino}carbonyl)cyclohexyl]-1H-indole-6-carboxamide | A | 364.44 | 364 |
| 1-22 | 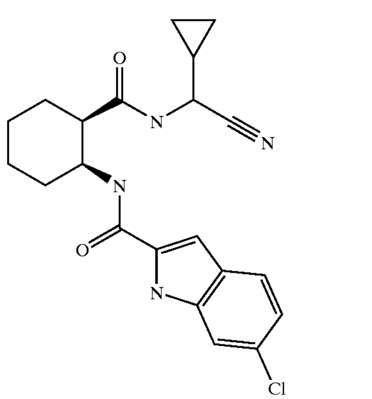 | 6-chloro-N-[(1S,2R)-2-({[cyano(cyclopropyl)methyl]amino}carbonyl)cyclohexyl]-1H-indole-2-carboxamide | A | 398.89 | 398 |

-continued

Compound Table 1

| Cpd # | Structure | Compound Name | Method | MW | MS |
|---|---|---|---|---|---|
| 1-23 | 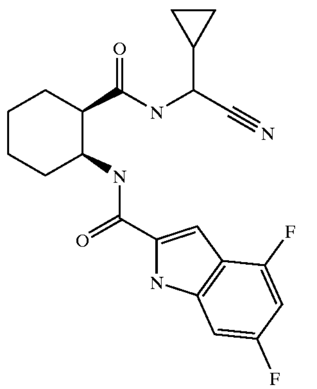 | N-[(1S,2R)-2-({[cyano(cyclopropyl)methyl]amino}carbonyl) cyclohexyl]-4,6-difluoro-1H-indole-2-carboxamide | A | 400.42 | 400 |
| 1-24 | Chiral | N-((1S,2R)-2-{[(cyanomethyl)amino]carbonyl}cyclohexyl)- 6-methoxy-1-methyl-1H-indole-2-carboxamide | A | 368.43 | 368 |
| 1-25 | Chiral | 5-(aminosulfonyl)-N-((1S,2R)-2-{[(cyanomethyl)amino] carbonyl}cyclohexyl)-1H-indole-2-carboxamide | A | 403.46 | 403 |
| 1-26 | 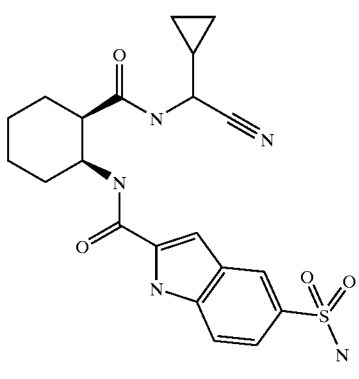 | 5-(aminosulfonyl)-N-[(1S,2R)-2-({[cyano(cyclopropyl) methyl]amino}carbonyl)cyclohexyl]-1H-indole-2-carboxamide | A | 443.5 | 443 |

-continued

Compound Table 1

| Cpd # | Structure | | Compound Name | Method | MW | MS |
|---|---|---|---|---|---|---|
| 1-27 | 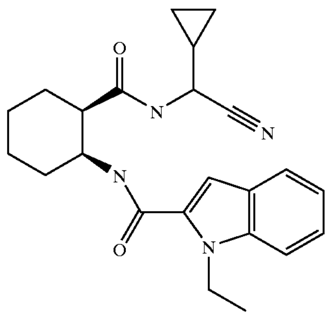 | | N-[(1S,2R)-2-({[cyano(cyclopropyl)-methyl]amino}carbonyl) cyclohexyl]-1-ethyl-1H-indole-2-carboxamide | A | 392.5 | 392 |
| 1-28 | 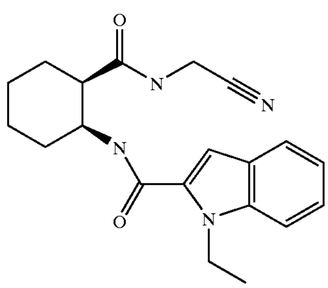 | | N-((1S,2R)-2-{[(cyanomethyl)amino]carbonyl}cyclohexyl)-1-ethyl-1H-indole-2-carboxamide | A | 352.4 | 352 |
| 1-29 | 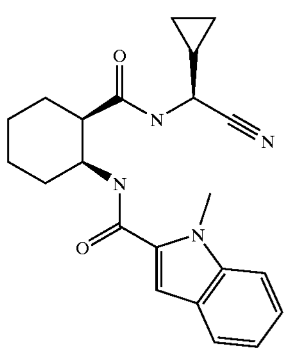 | Chiral | N-[(1S,2R)-2-({[(S)-cyano(cyclopropyl)methyl]amino} carbonyl)cyclohexyl]-1-methyl-1H-indole-2-carboxamide | B-2 | 378.4 | 378 |
| 1-30 | 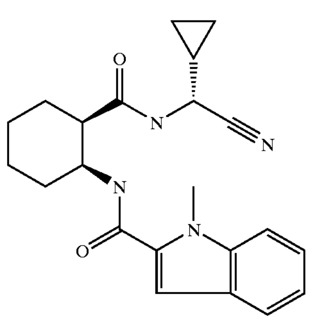 | Chiral | N-[(1S,2R)-2-({[(R)-cyano(cyclopropyl)methyl]amino} carbonyl)cyclohexyl]-1-methyl-1H-indole-2-carboxamide | B-2 | 378.4 | 378 |

-continued
Compound Table 1
| Cpd # | Structure | | Compound Name | Method | MW | MS |
|---|---|---|---|---|---|---|
| 1-31 | 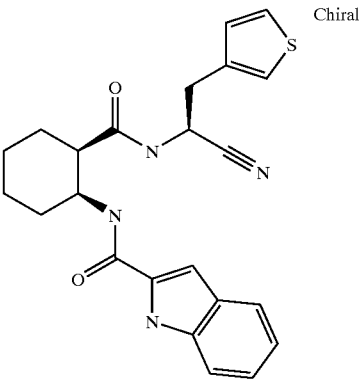 | Chiral | N-[(1S,2R)-2-({[(1S)-1-cyano-2-thien-3-ylethyl]amino}carbonyl)cyclohexyl]-1H-indole-2-carboxamide | B-1 | 420.5 | 420 |
| 1-32 | 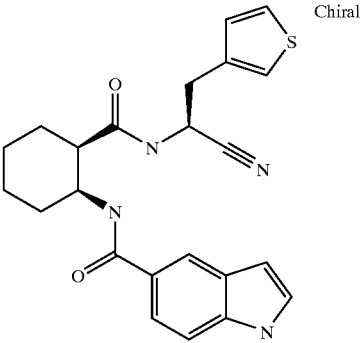 | Chiral | N-[(1S,2R)-2-({[(1S)-1-cyano-2-thien-3-ylethyl]amino}carbonyl)cyclohexyl]-1H-indole-5-carboxamide | B-1 | 420.5 | 420 |
| 1-33 | 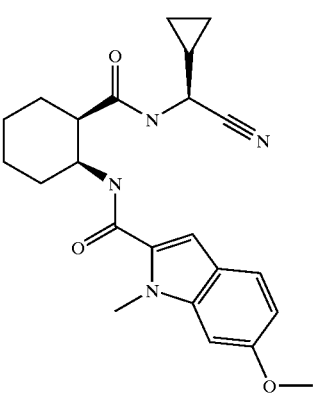 | Chiral | N-[(1S,2R)-2-({[(S)-1-cyano(cyclopropyl)methyl]amino}carbonyl)cyclohexyl]-6-methoxy-1-methyl-1H-indole-2-carboxamide | B-2 | 408.4 | 408 |

-continued

Compound Table 1

| Cpd # | Structure | | Compound Name | Method | MW | MS |
|---|---|---|---|---|---|---|
| 1-34 | 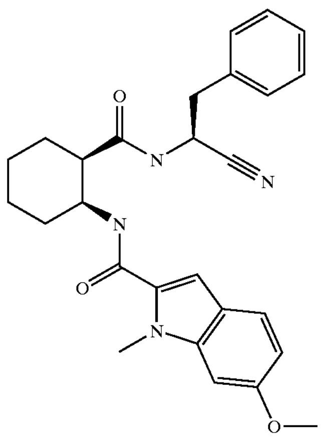 | Chiral | N-[(1S,2R)-2-({[(1S)-1-cyano-2-phenylethyl]amino}carbonyl)cyclohexyl]-6-methoxy-1-methyl-1H-indole-2-carboxamide | B-2 | 458.5 | 458 |
| 1-35 | 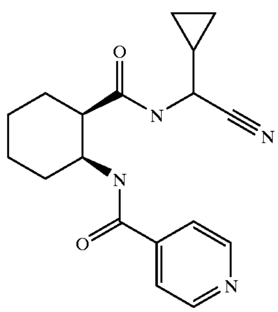 | | N-[(1S,2R)-2-({[cyano(cyclopropyl)methyl]amino}carbonyl)cyclohexyl]isonicotinamide | A | 326.3 | 326 |
| 1-36 | 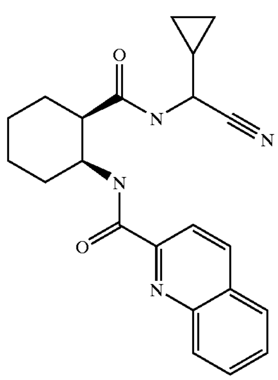 | | N-[(1S,2R)-2-({[cyano(cyclopropyl)methyl]amino}carbonyl)cyclohexyl]quinoline-2-carboxamide | A | 376.4 | 376 |
| 1-37 | 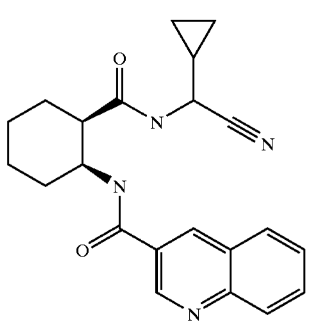 | | N-[(1S,2R)-2-({[cyano(cyclopropyl)methyl]amino}carbonyl)cyclohexyl]quinoline-3-carboxamide | A | 376.4 | 376 |

-continued

Compound Table 1

| Cpd # | Structure | Compound Name | Method | MW | MS |
|---|---|---|---|---|---|
| 1-38 | 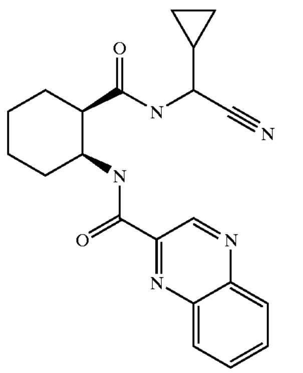 | N-[(1S,2R)-2-({[cyano(cyclopropyl)methyl]amino}carbonyl)cyclohexyl]quinoxaline-2-carboxamide | A | 377.4 | 377 |
| 1-39 | 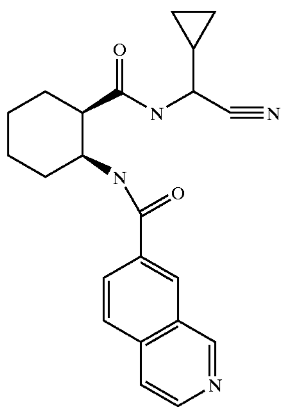 | N-[(1S,2R)-2-({[cyano(cyclopropyl)methyl]amino}carbonyl)cyclohexyl)isoquinoline-7-carboxamide | A | 376.4 | 376 |
| 1-40 | 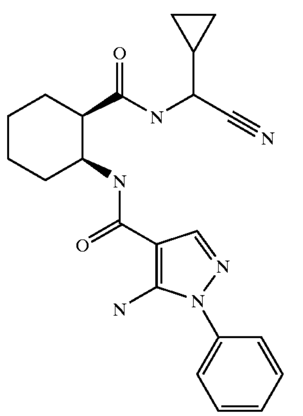 | 5-amino-N-[(1S,2R)-2-({[cyano(cyclopropyl)methyl]amino}carbonyl)cyclohexyl]-1-phenyl-1H-pyrazole-4-carboxamide | A | 406.4 | 406 |
| 1-41 | 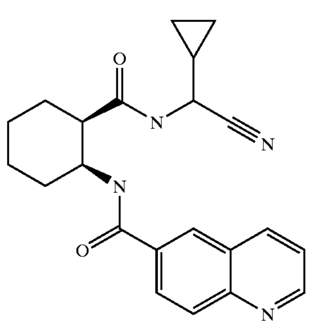 | N-[(1S,2R)-2-({[cyano(cyclopropyl)methyl]amino}carbonyl)cyclohexyl]quinoline-6-carboxamide | A | 376.4 | 376 |

-continued

Compound Table 1

| Cpd # | Structure | Compound Name | Method | MW | MS |
|---|---|---|---|---|---|
| 1-42 | Chiral | N-[(1S,2R)-2-({[(S)-cyano(cyclopropyl)methyl]amino}carbonyl)cyclohexyl]quinoline-2-carboxamide-1-oxide | A | 392.4 | 392 |
| 1-43 | 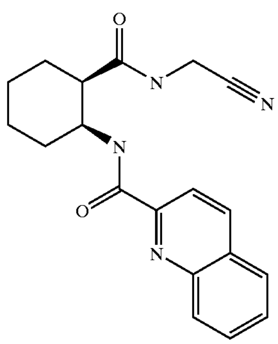 | N-((1S,2R)-2-{[[(cyanomethyl)amino]carbonyl}cyclohexyl)quinoline-2-carboxamide | A | 336.3 | 336 |
| 1-44 | Chiral | N-[(1S,2R)-2-({[(1S)-1-cyano-2-phenylethyl]amino}carbonyl)cyclohexyl]quinoline-2-carboxamide | B-1 | 426.5 | 426 |
| 1-45 | Chiral | N-[(1S,2R)-2-({[(1S)-1-cyano-2-phenylethyl]amino}carbonyl)cyclohexyl)quinoxaline-2-carboxamide | B-1 | 427.5 | 427 |

Compound Table 2

| Cpd # | Structure | | Compound Name | Method | MW | M/S |
|---|---|---|---|---|---|---|
| 2-1 | 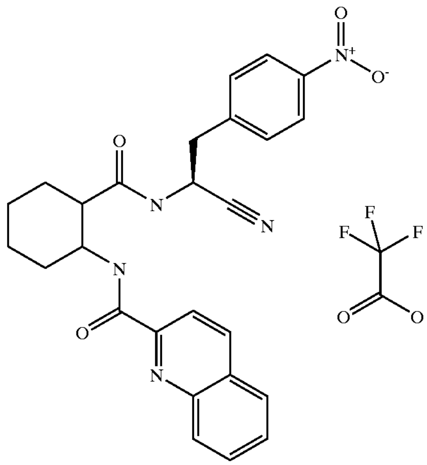 | | N-[2-({[(1S)-1-cyano-2-(4-nitrophenyl)ethyl] amino}carbonyl)cyclohexyl]quinoline-2-carboxamide trifluoroacetate | C | 471.5 | 471 |
| 2-2 | 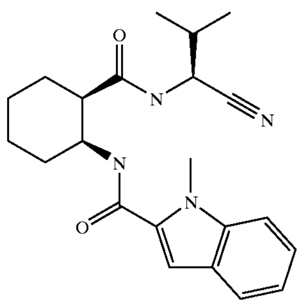 | Chiral | N-[(1S,2R)-2-({[(1S)-1-cyano-2-methylpropyl] amino}carbonyl)cyclohexyl]-1-methyl-1H-indole-2-carboxamide | B-2 | 380.489 | 380 |
| 2-3 | 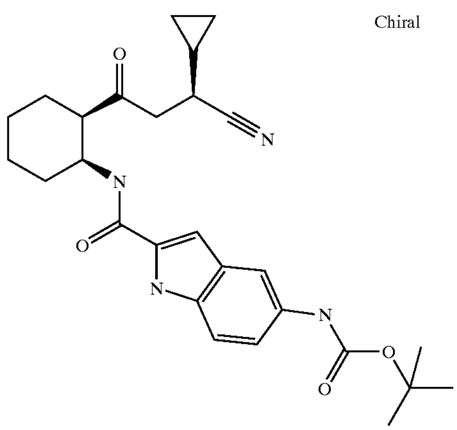 | Chiral | tert-butyl 2-({[(1S,2R)-2-({[(S)-cyano (cyclopropyl)methyl]amino}carbonyl) cyclohexyl]amino}carbonyl)-1H-indol-5-ylcarbamate | A | 479.578 | 479 |
| 2-4 | 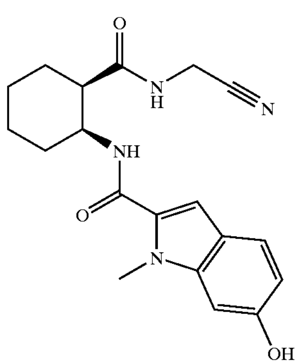 | Chiral | N-((1S,2R)-2-{[(cyanomethyl)amino]carbonyl} cyclohexyl)-6-hydroxy-1-methyl-1H-indole-2-carboxamide | A | 354.408 | 354 |

-continued

Compound Table 2

| Cpd # | Structure | | Compound Name | Method | MW | M/S |
|---|---|---|---|---|---|---|
| 2-5 | 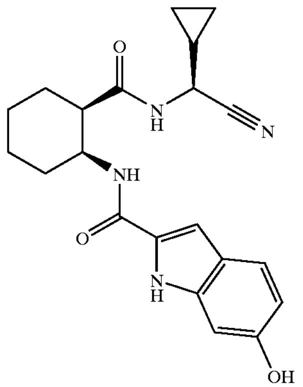 | Chiral | N-[(1S,2R)-2-({[(S)-cyano(cyclopropyl)methyl]amino}carbonyl)cyclohexyl]-6-hydroxy-1H-indole-2-carboxamide | B-2 | 380.446 | 380 |
| 2-6 | 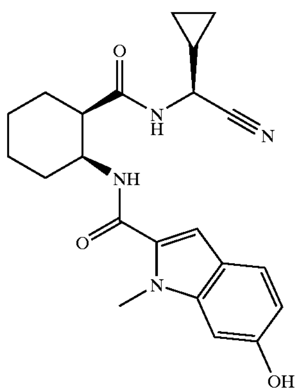 | Chiral | N-[(1S,2R)-2-({[(S)-cyano(cyclopropyl)methyl]amino}carbonyl)cyclohexyl]-6-hydroxy-1-methyl-1H-indole-2-carboxamide | B-2 | 394.472 | 394 |
| 2-7 | 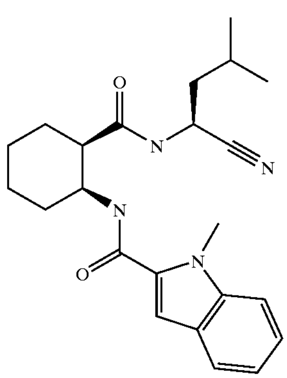 | Chiral | N-[(1S,2R)-2-({[(1S)-1-cyano-3-methylbutyl]amino}carbonyl)cyclohexyl)-1-methyl-1H-indole-2-carboxamide | B-2 | 394.516 | 394 |
| 2-8 | 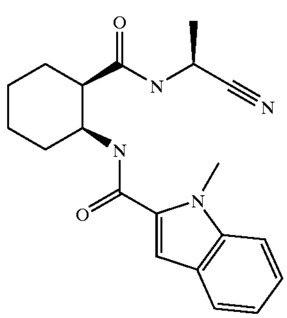 | Chiral | N-[(1S,2R)-2-({[(1S)-1-cyanoethyl]amino}carbonyl)cyclohexyl]-1-methyl-1H-indole-2-carboxamide | B-2 | 352.436 | 352 |

Compound Table 2

| Cpd # | Structure | Compound Name | Method | MW | M/S |
|---|---|---|---|---|---|
| 2-9 | 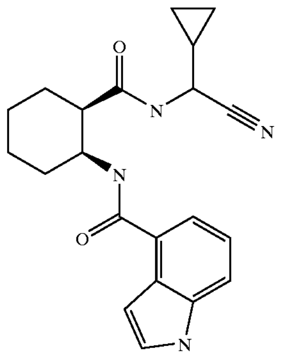 | N-[(1S,2R)-2-({[cyano(cyclopropyl)methyl)amino}carbonyl)cyclohexyl]-1H-indole-4-carboxamide | A | 364.447 | 364 |
| 2-10 | Chiral | N-((1S,2R)-2-{[(cyanomethyl)amino]carbonyl}cyclohexyl)-5-fluoro-1-methyl-1H-indole-2-carboxamide | A | 356.399 | 356 |
| 2-11 | Chiral | N-[(1S,2R)-2-({[(1R)-1-cyano-2-hydroxyethyl]amino}carbonyl)cyclohexyl]-1-methyl-1H-indole-2-carboxamide | B-3 | 368.435 | 368 |
| 2-12 | 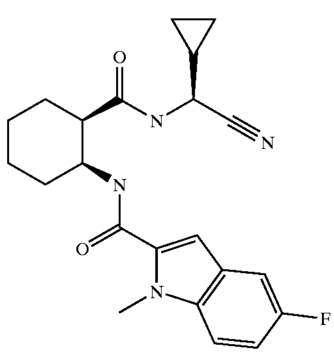 | N-[(1S,2R)-2-({[(S)-cyano(cyclopropyl)methyl]amino}carbonyl)cyclohexyl)-5-fluoro-1-methyl-1H-indole-2-carboxamide | B-2 | 396.463 | 396 |

-continued

Compound Table 2

| Cpd # | Structure | Compound Name | Method | MW | M/S |
|---|---|---|---|---|---|
| 2-13 | 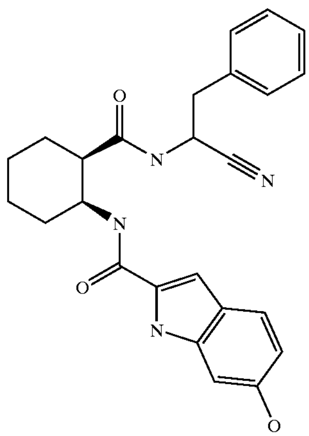 | N-((1S,2R)-2-{[(1-cyano-2-phenylethyl)amino]carbonyl}cyclohexyl)-6-hydroxy-1H-indole-2-carboxamide | B-2 | 430.505 | 430 |
| 2-14 | 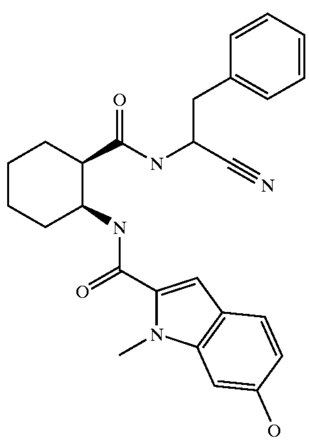 | N-((1S,2R)-2-{[(1-cyano-2-phenylethyl)amino]carbonyl}cyclohexyl)-6-hydroxy-1-methyl-1H-indole-2-carboxamide | B-2 | 444.532 | 444 |
| 2-15 | 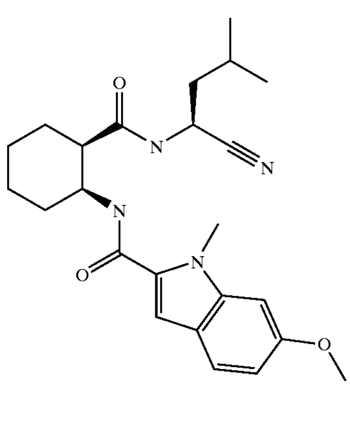 | N-[(1S,2R)-2-({[(1S)-1-cyano-3-methylbutyl]amino}carbonyl)cyclohexyl]-6-methoxy-1-methyl-1H-indole-2-carboxamide | B-2 | 424.542 | 424 |

-continued

Compound Table 2

| Cpd # | Structure | | Compound Name | Method | MW | M/S |
|---|---|---|---|---|---|---|
| 2-16 | 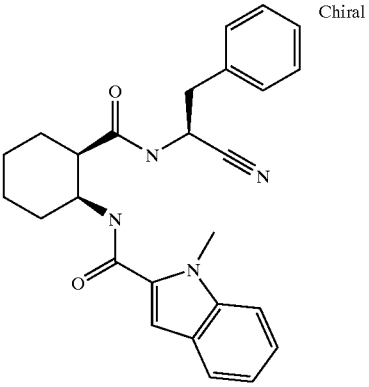 | Chiral | N-[(1S,2R)-2-({[(1S)-1-cyano-2-phenylethyl]amino}carbonyl)cyclohexyl]-1-methyl-1H-indole-2-carboxamide | B-2 | 428.533 | 428 |
| 2-17 | 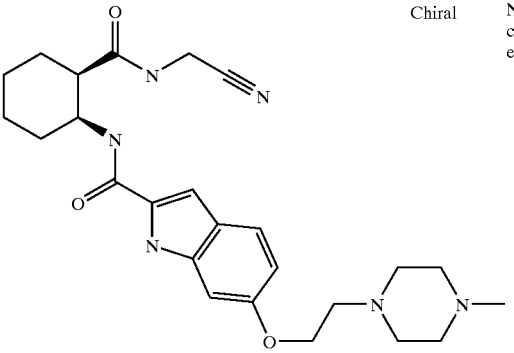 | Chiral | N-((1S,2R)-2-{[(cyanomethyl)amino]carbonyl}cyclohexyl)-6-[2-(4-methylpiperazin-1-yl)ethoxy]-1H-indole-2-carboxamide | A | 466.583 | 466 |
| 2-18 | 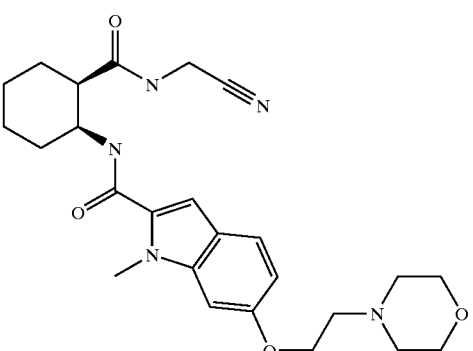 | | N-((1S,2R)-2-{[(cyanomethyl)amino]carbonyl}cyclohexyl)-1-methyl-6-(2-morpholin-4-ylethoxy)-1H-indole-2-carboxamide | A | 467.567 | 467 |
| 2-19 | 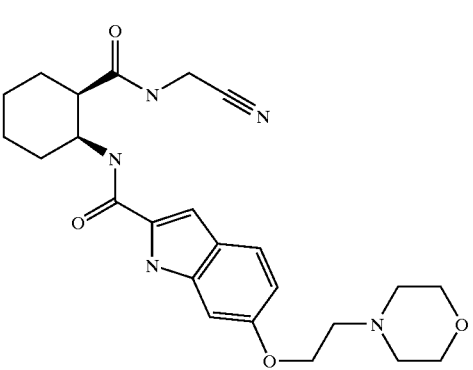 | | N-((1S,2R)-2-{[(cyanomethyl)amino]carbonyl}cyclohexyl)-6-(2-morpholin-4-ylethoxy)-1H-indole-2-carboxamide | A | 453.54 | 453 |

-continued

Compound Table 2

| Cpd # | Structure | | Compound Name | Method | MW | M/S |
|---|---|---|---|---|---|---|
| 2-20 | 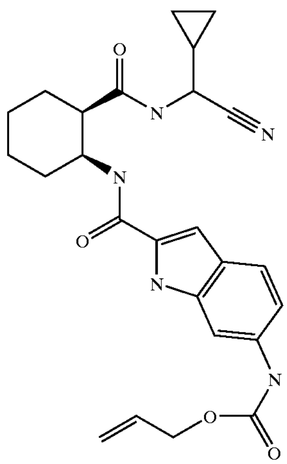 | | allyl 2-({[(1S,2R)-2-({[cyano(cyclopropyl) methyl]amino}carbonyl)cyclohexyl]amino} carbonyl)-1H-indol-6-ylcarbamate | A | 463.535 | 463 |
| 2-21 | 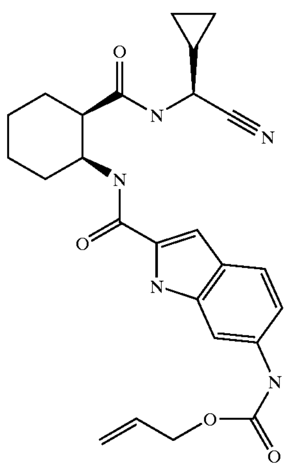 | Chiral | allyl 2-({[(1S,2R)-2-({[(S)-cyano(cyclopropyl) methyl]amino}carbonyl)cyclohexyl]amino} carbonyl)-1H-indol-6-yl-carbamate | A | 463.535 | 463 |
| 2-22 | 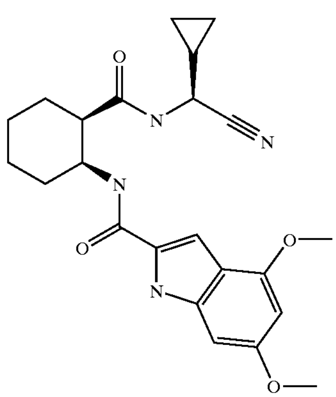 | Chiral | N-[(1S,2R)-2-({[(S)-cyano(cyclopropyl) methyl]amino}carbonyl)cyclohexyl]-4,6-dimethoxy-1H-indole-2-carboxamide | A | 424.498 | 424 |

-continued

Compound Table 2

| Cpd # | Structure | | Compound Name | Method | MW | M/S |
|---|---|---|---|---|---|---|
| 2-23 | 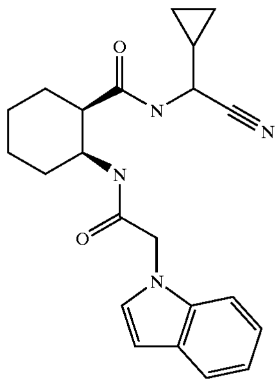 | | (1R,2S)-N-[cyano(cyclopropyl)methyl]-2-[(1H-indol-1-ylacetyl)amino]cyclohexanecarboxamide | A | 378.473 | 378 |
| 2-24 | 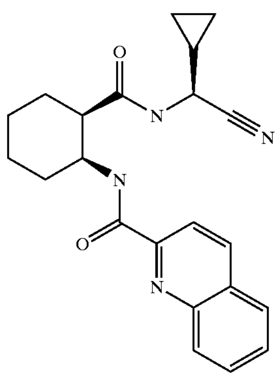 | Chiral | N-[(1S,2R)-2-({[(S)-cyano(cyclopropyl)methyl]amino}carbonyl)cyclohexyl]quinoline-2-carboxamide | A | 376.458 | 376 |
| 2-25 | 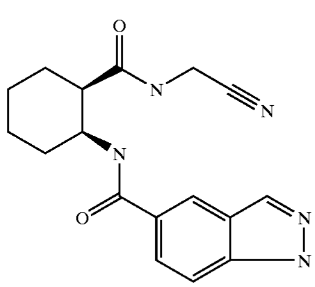 | Chiral | N-((1S,2R)-2-{[(cyanomethyl)amino]carbonyl}cyclohexyl)-1H-indazole-5-carboxamide | A | 325.37 | 325 |

Compound Table 3

| Cpd. # | Structure | Name | Method | MW | MS |
|---|---|---|---|---|---|
| 3-1 | *(structure shown)* Chiral | N-[(1S,2R)-2-({[(S)-cyano(cyclopropyl)methyl]amino}carbonyl)cyclohexyl]-6-[(methylsulfonyl)amino]-1H-indole-2-carboxamide | A | 457.552 | 457 |
| 3-2 | *(structure shown)* Chiral | N-[(1S,2R)-2-({[(1S)-1-cyano-3-(methylthio)propyl]amino}carbonyl)cyclohexyl]-1-methyl-1H-indole-2-carboxamide | B-2 | 412.555 | 412 |
| 3-3 | *(structure shown)* Chiral | N-[(1S,2R)-2-({[(1S)-1-cyano-3-methylbutyl]amino}carbonyl)cyclohexyl]-1H-indazole-5-carboxamide | B-2 | 381.477 | 381 |
| 3-4 | *(structure shown)* Chiral | N-[(1S,2R)-2-({[(1R)-1-cyano-2-(4-hydroxyphenyl)ethyl]amino}carbonyl)cyclohexyl]-1-methyl-1H-indole-2-carboxamide | B-2 | 444.532 | 444 |

| Cpd. # | Structure | | Name | Method | MW | MS |
|---|---|---|---|---|---|---|
| | | | Compound Table 3 | | | |
| 3-5 | 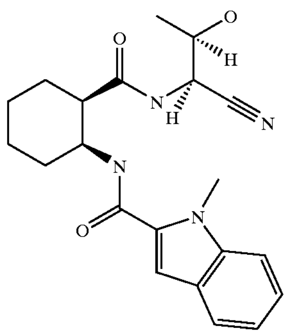 | Chiral | N-[(1S,2R)-2-({[(1R,2R)-1-cyano-2-hydroxypropyl]amino}carbonyl)cyclohexyl]-1-methyl-1H-indole-2-carboxamide | B-2 | 382.461 | 382 |
| 3-6 | 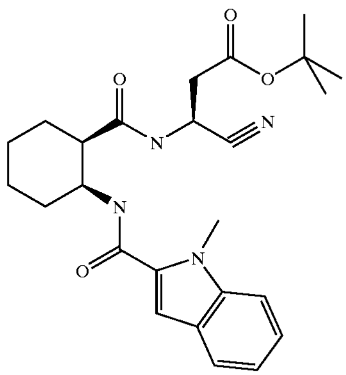 | Chiral | tert-butyl (3S)-3-cyano-3-{[((1R,2S)-2-{[(1-methyl-1H-indol-2-yl)carbonyl]amino}cyclohexyl)carbonyl]amino}propanoate | B-2 | 452.552 | 452 |
| 3-7 | 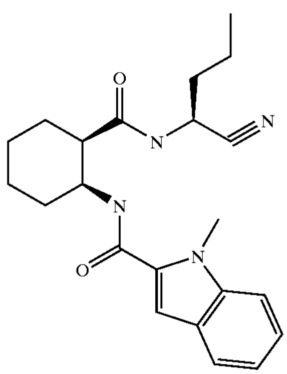 | Chiral | N-[(1S,2R)-2-({[(1S)-1-cyanobutyl]amino}carbonyl)cyclohexyl]-1-methyl-1H-indole-2-carboxamide | B-2 | 380.489 | 380 |
| 3-8 | 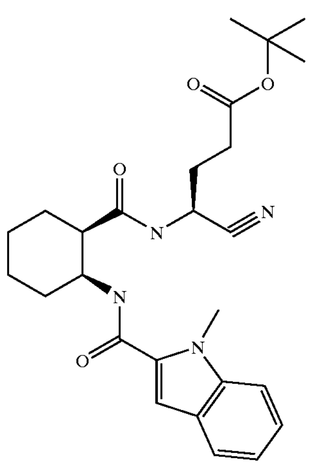 | Chiral | tert-butyl (4S)-4-cyano-4-{[((1R,2S)-2-{[(1-methyl-1H-indol-2-yl)carbonyl]amino}cyclohexyl)carbonyl]amino}-butanoate | B-2 | 466.579 | 466 |

-continued

Compound Table 3

| Cpd. # | Structure | Name | Method | MW | MS |
|---|---|---|---|---|---|
| 3-9 | Chiral | N-[(1S,2R)-2-({[(1S)-1-cyano-3-methylbutyl]amino}carbonyl)cyclohexyl]-6-fluoro-1H-indole-2-carboxamide | B-2 | 398.479 | 398 |
| 3-10 | 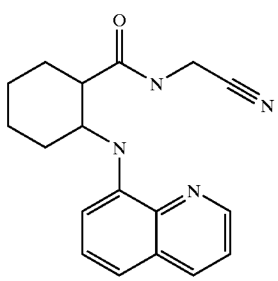 | N-(cyanomethyl)-2-(quinolin-8-ylamino)cyclohexane-carboxamide | D | 308.383 | 308 |

Compound Table 4

| Cpd. # | Structure | Name | Example | MW | MS |
|---|---|---|---|---|---|
| 4-1 | 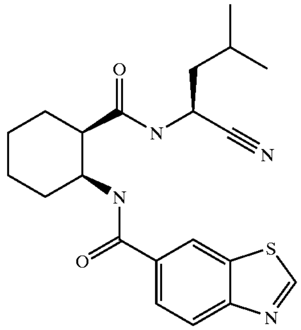 | Benzothiazole-6-carboxylic acid[(1S,2R)-2-((S)-1-cyano-3-methyl-butylcarbamoyl)-cyclohexyl]-amide | 10 | 398.528 | 398 |

-continued

Compound Table 4

| Cpd. # | Structure | Name | Example | MW | MS |
|---|---|---|---|---|---|
| 4-2 | 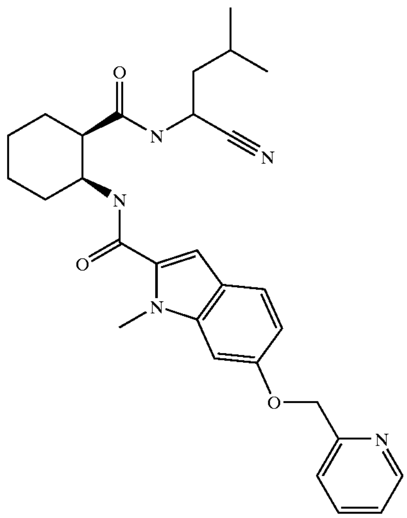 | 1-Methyl-6-(pyridin-2-ylmethoxy)-1H-indole-2-carboxylic acid[(1S,2R)-2-(1-cyano-3-methyl-butylcarbamoyl)-cyclohexyl]-amide | 12 | 501.627 | 502 |
| 4-3 | 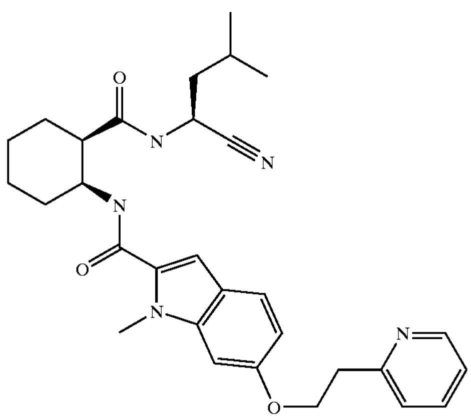 | 1-Methyl-6-(2-pyridin-2-yl-ethoxy)-1H-indole-2-carboxylic acid [(1S,2R)-2-((S)-1-cyano-3-methyl-butylcarbamoyl)-cyclohexyl]-amide | 12 | 515.654 | 515 |
| 4-4 | 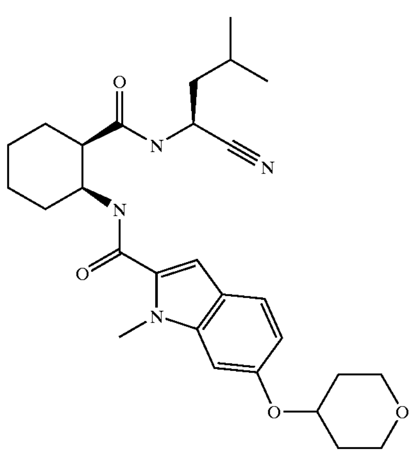 | 1-Methyl-6-(tetrahydro-pyran-4-yloxy)-1H-indole-2-carboxylic acid[(1S,2R)-2-(1-cyano-3-methyl-butylcarbamoyl)-cyclohexyl]-amide | 12 | 494.632 | 494 |

-continued

Compound Table 4

| Cpd. # | Structure | Name | Example | MW | MS |
|---|---|---|---|---|---|
| 4-5 | 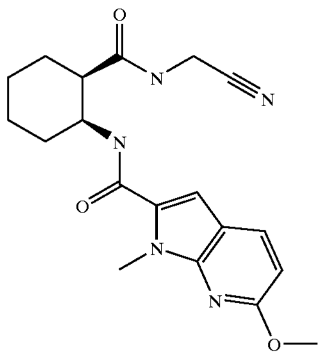 | 6-Methoxy-1-methyl-1H-pyrrolo[2,3-b]pyridine-2-carboxylic acid [(1S,2R)-2-(cyanomethyl-carbamoyl)-cyclohexyl]-amide | A | 369.423 | 369 |
| 4-6 | 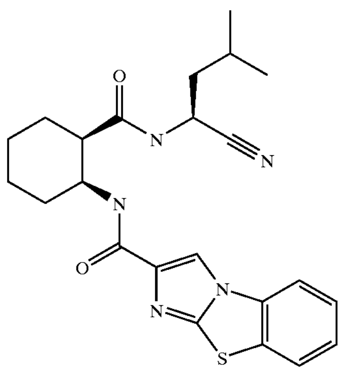 | Benzo[d]imidazo[2,1-b]thiazole-2-carboxylic acid[(1S,2R)-2-((S)-1-cyano-3-methyl-butylcarbamoyl)-cyclohexyl]-amide | 10 | 437.565 | 437 |
| 4-7 | 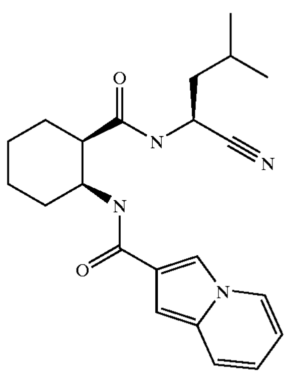 | Indolizine-2-carboxylic acid[(1S,2R)-2-((S)-1-cyano-3-methyl-butylcarbamoyl)-cyclohexyl]-amide | 10 | 380.489 | 380 |
| 4-8 | 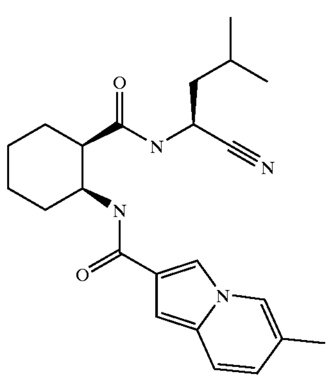 | 6-Methyl-indolizine-2-carboxylic acid[(1S,2R)-2-((S)-1-cyano-3-methyl-butylcarbamoyl)-cyclohexyl]-amide | 10 | 394.516 | 394 |

-continued

Compound Table 4

| Cpd. # | Structure | Name | Example | MW | MS |
|---|---|---|---|---|---|
| 4-9 | 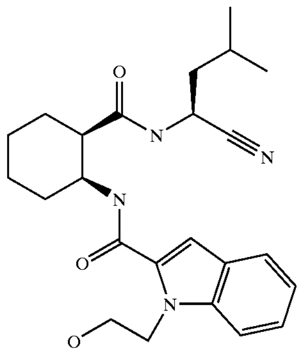 | 1-(2-Hydroxy-ethyl)-1H-indole-2-carboxylic acid [(1S,2R)-2-((S)-1-cyano-3-methyl-butylcarbamoyl)-cyclohexyl]-amide | 11 | 424.542 | 424 |

Compound Table 5

| # | Structure | Name (Autonom ®) | Example |
|---|---|---|---|
| 5-1 | 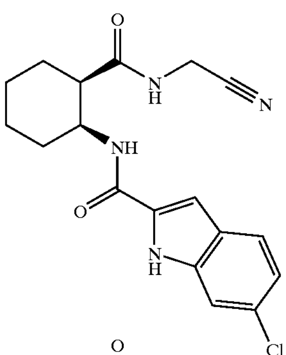 | 6-Chloro-1H-indole-2-carboxylic acid[(1S,2R)-2-(cyanomethyl-carbamoyl)cyclohexyl]-amide | 1, 18 |
| 5-2 | 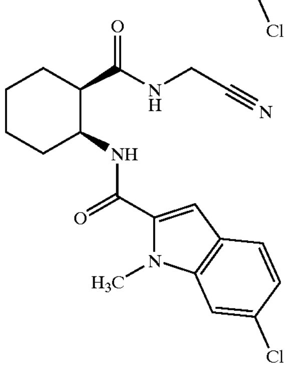 | 6-Chloro-1-methyl-1H-indole-2-carboxylic acid [(1S,2R)-2-(cyanomethyl-carbamoyl)cyclohexyl]-amide | 11, 18 |
| 5-3 | 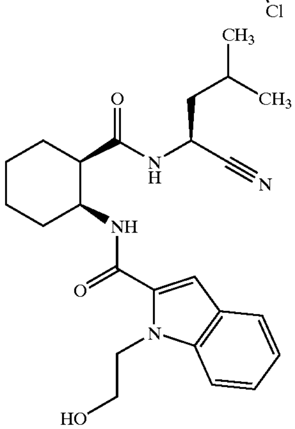 | 1-(2-Hydroxy-ethyl)-1H-indole-2-carboxylic acid [(1S,2R)-2-((S)-1-cyano-3-methyl-butylcarbamoyl)cyclohexyl]-amide | 11 |

-continued

Compound Table 5

| # | Structure | Name (Autonom ®) | Example |
|---|---|---|---|
| 5-4 | 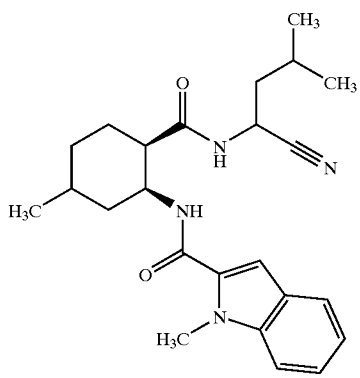 | 1-Methyl-1H-indole-2-carboxylic acid[(1S,2R)-2-(1-cyano-3-methyl-butylcarbamoyl)-5-methyl-cyclohexyl]-amide | 23 |
| 5-5 | 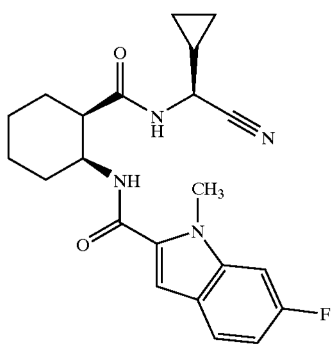 | (1R,2S)-2-Acetylamino-cyclohexanecarboxylic acid((S)-cyano-cyclopropyl-methyl)-amide; compound with 6-fluoro-1-methyl-1H-indole | 1 |
| 5-6 | 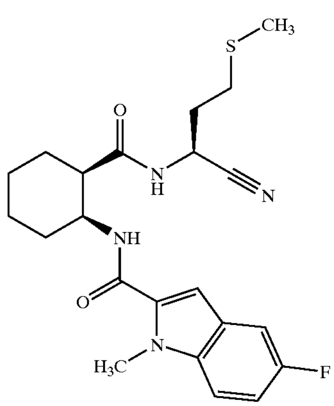 | 5-Fluoro-1-methyl-1H-indole-2-carboxylic acid[(1S,2R)-2-((S)-1-cyano-3-methylsulfanyl-propylcarbamoyl)-cyclohexyl]-amide | 3 |
| 5-7 | 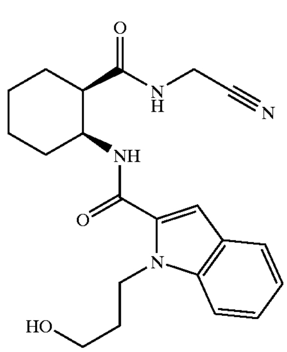 | 1-(3-Hydroxy-propyl)-1H-indole-2-carboxylic acid[(1S,2R)-2-(cyanomethyl-carbamoyl)cyclohexyl]-amide | 40 |

-continued

Compound Table 5

| # | Structure | Name (Autonom ®) | Example |
|---|---|---|---|
| 5-8 | 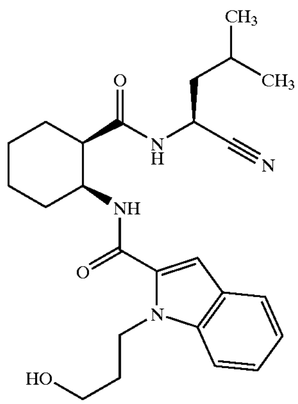 | 1-(3-Hydroxy-propyl)-1H-indole-2-carboxylic acid[(1S,2R)-2-((S)-1-cyano-3-methyl-butylcarbamoyl)-cyclohexyl]-amide | 40 |
| 5-9 | 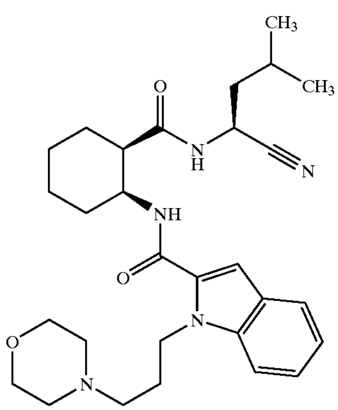 | 1-(3-Morpholin-4-yl-propyl)-1H-indole-2-carboxylic acid [(1S,2R)-2-((S)-1-cyano-3-methyl-butylcarbamoyl)-cyclohexyl]-amide | 43 |
| 5-10 | 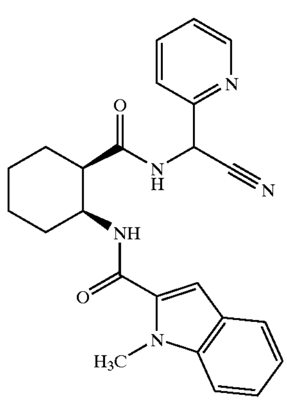 | 1-Methyl-1H-indole-2-carboxylic acid{(1S,2R)-2-[(cyano-pyridin-2-yl-methyl)-carbamoyl]-cyclohexyl}-amide | 16 |

-continued

Compound Table 5

| # | Structure | Name (Autonom ®) | Example |
|---|---|---|---|
| 5-11 | 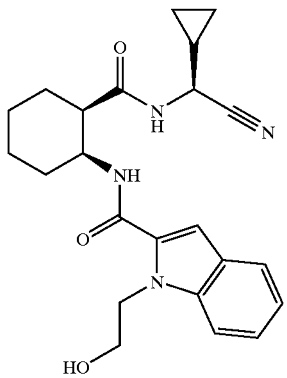 | 1-(2-Hydroxy-ethyl)-1H-indole-2-carboxylic acid{(1S,2R)-2-[((S)-cyano-cyclopropyl-methyl)-carbamoyl]-cyclohexyl}-amide | 11 |
| 5-12 | 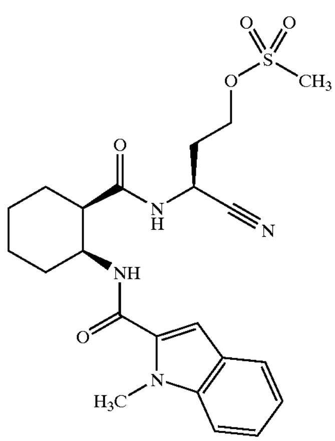 | Methanesulfonic acid(S)-3-cyano-3-({(1R,2S)-2-[(1-methyl-1H-indole-2-carbonyl)-amino]-cyclohexanecarbonyl}-amino)-propyl ester | 29 |
| 5-13 | 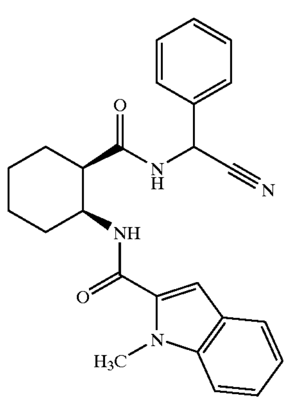 | 1-Methyl-1H-indole-2-carboxylic acid{(1S,2R)-2-[(cyano-phenyl-methyl)-carbamoyl]cyclohexyl}-amide | 16 |

-continued

Compound Table 5

| # | Structure | Name (Autonom ®) | Example |
|---|---|---|---|
| 5-14 | 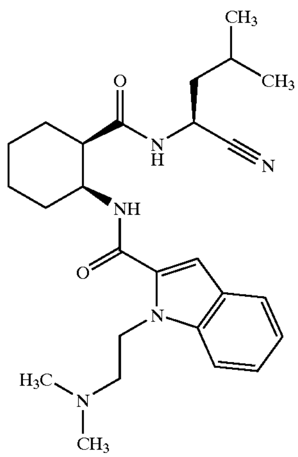 | 1-(2-Dimethylamino-ethyl)-1H-indole-2-carboxylic acid[(1S,2R)-2-((S)-1-cyano-3-methyl-butylcarbamoyl)-cyclohexyl)-amide | 44, 53 |
| 5-15 | 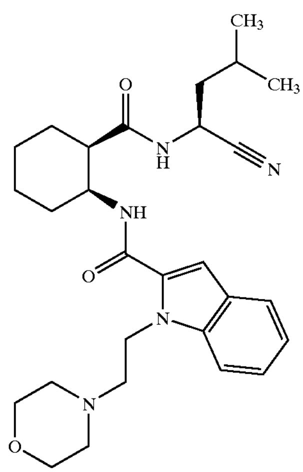 | 1-(2-Morpholin-4-yl-ethyl)-1H-indole-2-carboxylic acid[(1S,2R)-2-((S)-1-cyano-3-methyl-butylcarbamoyl)-cyclohexyl]-amid | 44, 53 |
| 5-16 | 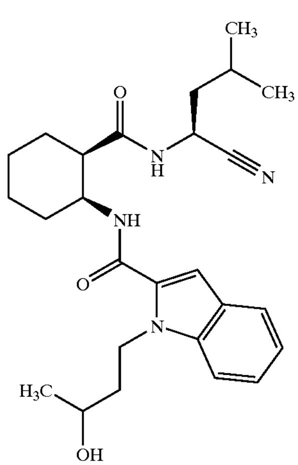 | 1-(3-Hydroxy-butyl)-1H-indole-2-carboxylic acid[(1S,2R)-2-((S)-1-cyano-3-methyl-butylcarbamoyl)-cyclohexyl]-amide | 53 |

-continued

Compound Table 5

| # | Structure | Name (Autonom ®) | Example |
|---|---|---|---|
| 5-17 | 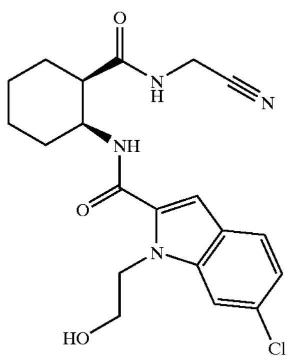 | 6-Chloro-1-(2-hydroxy-ethyl)-1H-indole-2-carboxylic acid[(1S, 2R)-2-(cyanomethyl-carbamoyl)-cyclohexyl]-amide | 44 |
| 5-18 | 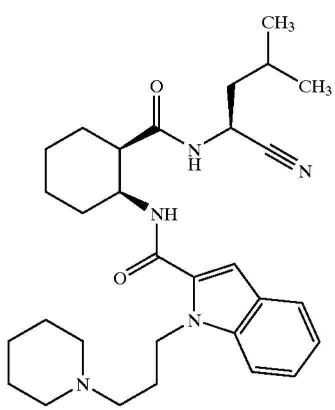 | 1-(3-Piperidin-1-yl-propyl)-1H-indole-2-carboxylic acid[(1S,2R)-2-((S)-1-cyano-3-methyl-butylcarbamoyl)-cyclohexyl]-amide | 43 |
| 5-19 | 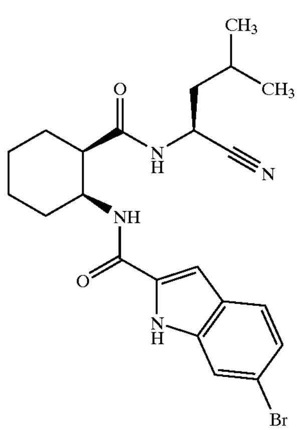 | 6-Bromo-1H-indole-2-carboxylic acid[(1S,2R)-2-((S)-1-cyano-3-methyl-butylcarbamoyl)-cyclohexyl]-amide | 1 |

-continued

Compound Table 5

| # | Structure | Name (Autonom ®) | Example |
|---|---|---|---|
| 5-20 | 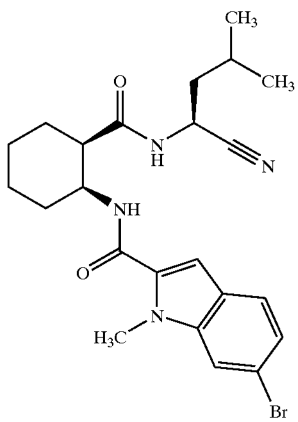 | 6-Bromo-1-methyl-1H-indole-2-carboxylic acid [(1S,2R)-2-((S)-1-cyano-3-methyl-butylcarbamoyl)-cyclohexyl]-amide | 11 |
| 5-21 | 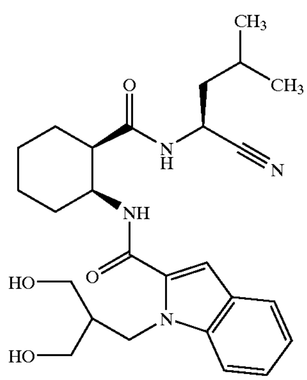 | 1-(3-Hydroxy-2-hydroxymethyl-propyl)-1H-indole-2-carboxylic acid[(1S,2R)-2-((S)-1-cyano-3-methyl-butylcarbamoyl)-cyclohexyl)-amide | 53 |
| 5-22 | 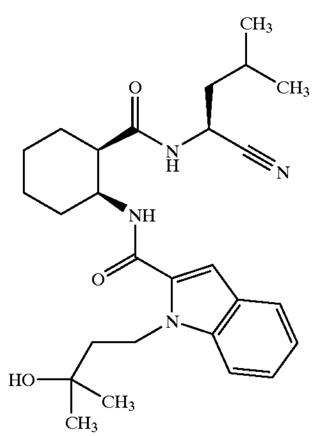 | 1-(3-Hydroxy-3-methyl-butyl)-1H-indole-2-carboxylic acid[(1S,2R)-2-((S)-1-cyano-3-methyl-butylcarbamoyl)-cyclohexyl]-amide | 53 |

-continued

Compound Table 5

| # | Structure | Name (Autonom ®) | Example |
|---|---|---|---|
| 5-23 | 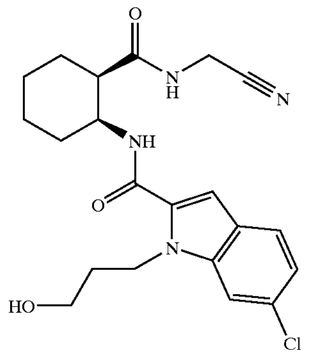 | 6-Chloro-1-(3-hydroxy-propyl)-1H-indole-2-carboxylic acid [(1S,2R)-2-(cyanomethyl-carbamoyl)-cyclohexyl]-amide | 45 |
| 5-24 | 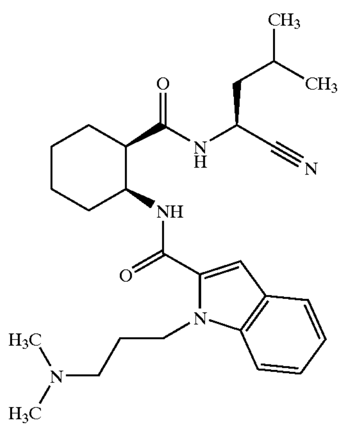 | 1-(3-Dimethylamino-propyl)-1H-indole-2-carboxylic acid[(1S, 2R)-2-((S)-1-cyano-3-methyl-butylcarbamoyl)-cyclohexyl]-amide | 43 |
| 5-25 | 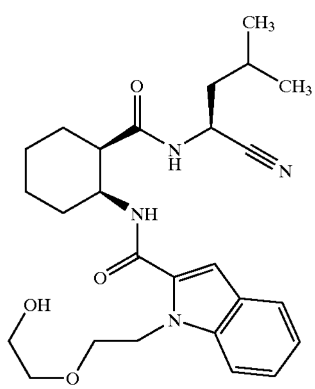 | 1-[2-(2-Hydroxy-ethoxy)-ethyl]-1H-indole-2-carboxylic acid [(1S,2R)-2-((S)-1-cyano-3-methyl-butylcarbamoyl)-cyclohexyl]-amide | 41 |
| 5-26 | 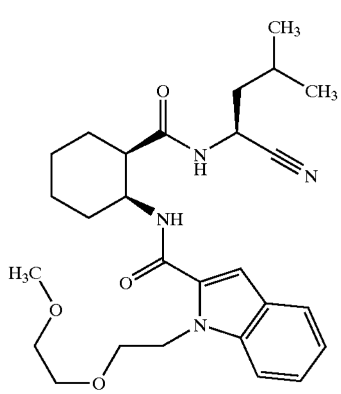 | 1-(2-(2-Methoxy-ethoxy)-ethyl)-1H-indole-2-carboxylic acid [(1S,2R)-2-((S)-1-cyano-3-methyl-butylcarbamoyl)-cyclohexyl]-amide | 42 |

-continued

Compound Table 5

| # | Structure | Name (Autonom ®) | Example |
|---|---|---|---|
| 5-27 | 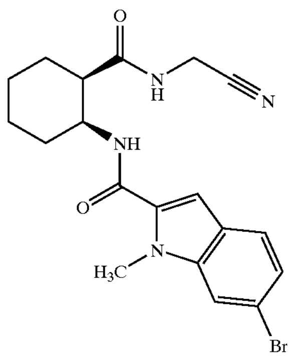 | 6-Bromo-1-methyl-1H-indole-2-carboxylic acid[(1S,2R)-2-(cyanomethyl-carbamoyl)-cyclohexyl]-amide | 24 |
| 5-28 | 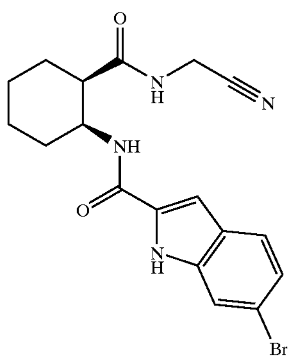 | 6-Bromo-1H-indole-2-carboxylic acid[(1S,2R)-2-(cyanomethyl-carbamoyl)-cyclohexyl]-amide | 10 |
| 5-29 | 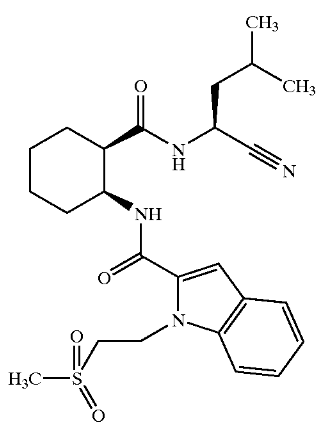 | 1-(2-Methanesulfonyl-ethyl)-1H-indole-2-carboxylic acid[(1S,2R)-2-((S)-1-cyano-3-methyl-butylcarbamoyl)-cyclohexyl]-amide | 11 |
| 5-30 | 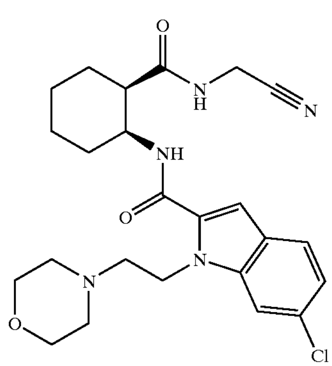 | 6-Chloro-1-(2-morpholin-4-yl-ethyl)-1H-indole-2-carboxylic acid [(1S,2R)-2-(cyanomethyl-carbamoyl)-cyclohexyl]-amide | 44 |

-continued

Compound Table 5

| # | Structure | Name (Autonom ®) | Example |
|---|-----------|------------------|---------|
| 5-31 | 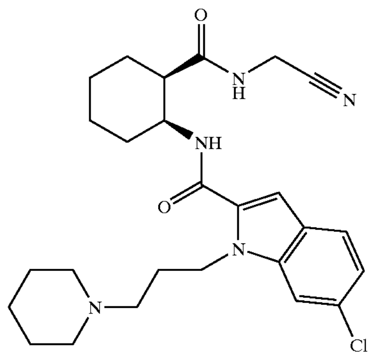 | 6-Chloro-1-(3-piperidin-1-yl-propyl)-1H-indole-2-carboxylic acid [(1S,2R)-2-(cyanomethyl-carbamoyl)-cyclohexyl]-amide | 44 |
| 5-32 | 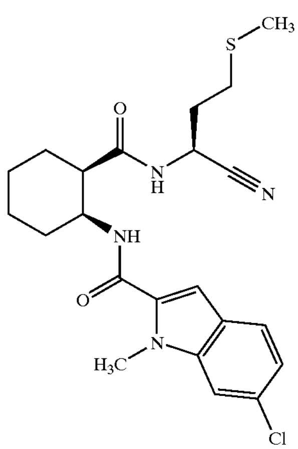 | 6-Chloro-1-methyl-1H-indole-2-carboxylic acid[(1S,2R)-2-((S)-1-cyano-3-methylsulfanyl-propylcarbamoyl)-cyclohexyl]-amide | 46 |
| 5-33 | 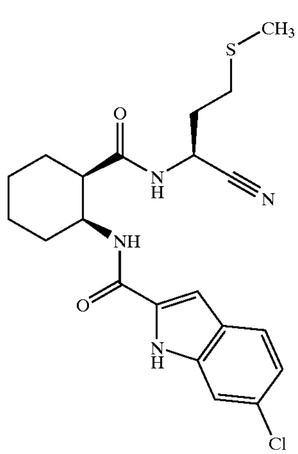 | 6-Chloro-1H-indole-2-carboxylic acid[(1S,2R)-2-((S)-1-cyano-3-methylsulfanyl-propylcarbamoyl)-cyclohexyl]-amide | 46 |

-continued

Compound Table 5

| # | Structure | Name (Autonom ®) | Example |
|---|---|---|---|
| 5-34 | 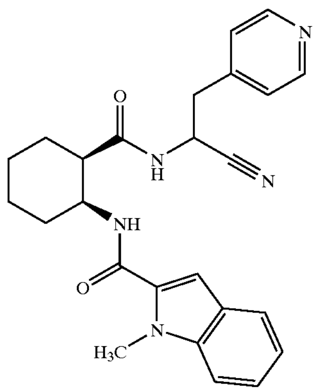 | 1-Methyl-1H-indole-2-carboxylic acid{(1S,2R)-2-[(cyano-pyridin-4-ylmethyl-methyl)-carbamoyl]-cyclohexyl}-amide | 36 |
| 5-35 | 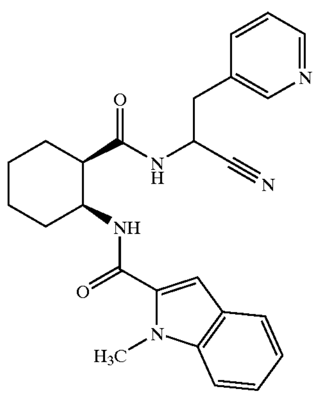 | 1-Methyl-1H-indole-2-carboxylic acid{(1S,2R)-2-[(cyano-pyridin-3-ylmethyl-methyl)-carbamoyl]-cyclohexyl}-amide | 36 |
| 5-36 | 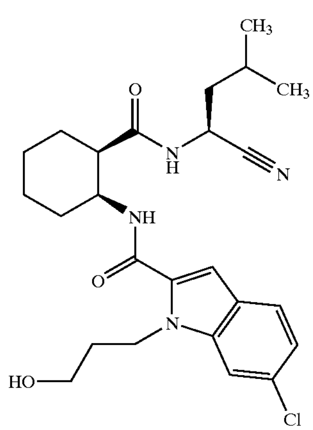 | 6-Chloro-1-(3-hydroxy-propyl)-1H-indole-2-carboxylic acid [(1S,2R)-2-((S)-1-cyano-3-methyl-butylcarbamoyl)-cyclohexyl]-amide | 40 |

-continued

Compound Table 5

| # | Structure | Name (Autonom ®) | Example |
|---|---|---|---|
| 5-37 | 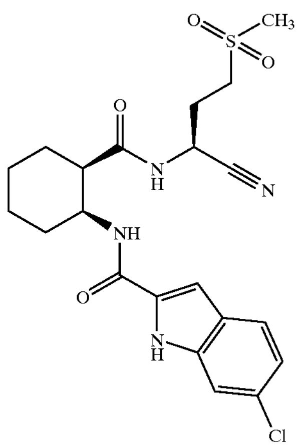 | 6-Chloro-1H-indole-2-carboxylic acid[(1S,2R)-2-((S)-1-cyano-3-methanesulfonyl-propylcarbamoyl)-cyclohexyl]-amide | 47 |
| 5-38 | 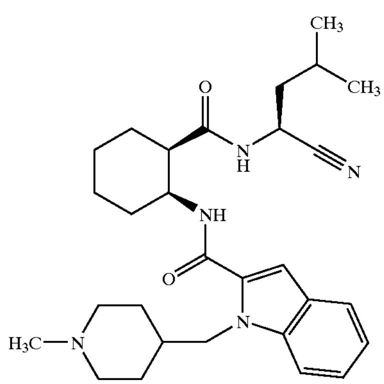 | 1-(1-Methyl-piperidin-4-ylmethyl)-1H-indole-2-carboxylic acid [(1S,2R)-2-((S)-1-cyano-3-methyl-butylcarbamoyl)-cyclohexyl]-amide | 55 |
| 5-39 | 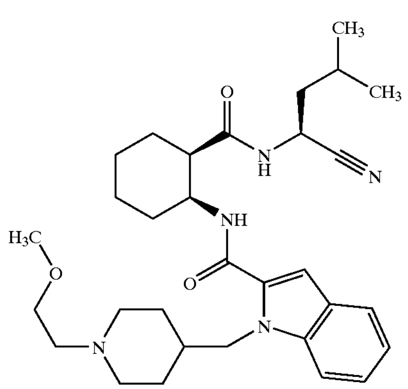 | 1-[1-(2-Methoxy-ethyl)-piperidin-4-ylmethyl)-1H-indole-2-carboxylic acid[(1S,2R)-2-((S)-1-cyano-3-methyl-butylcarbamoyl)-cyclohexyl]-amide | 55 |

-continued

Compound Table 5

| # | Structure | Name (Autonom ®) | Example |
|---|---|---|---|
| 5-40 | 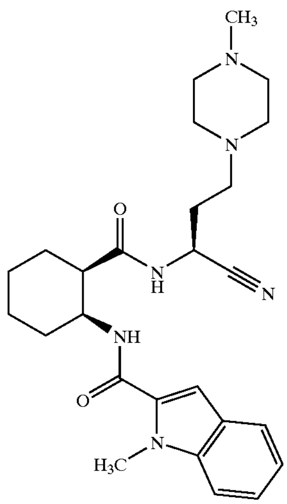 | 1-Methyl-1H-indole-2-carboxylic acid{(1S,2R)-2-[(S)-1-cyano-3-(4-methyl-piperazin-1-yl)-propylcarbamoyl]-cyclohexyl}-amide | 29 |
| 5-41 | 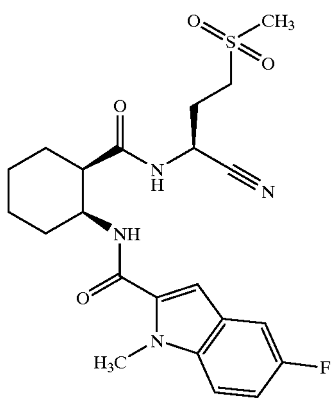 | 5-Fluoro-1-methyl-1H-indole-2-carboxylic acid[(1S,2R)-2-((S)-1-cyano-3-methanesulfonyl-propylcarbamoyl)-cyclohexyl]-amide | 35 |
| 5-42 | 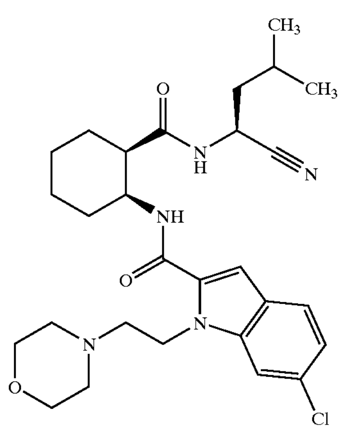 | 6-Chloro-1-(2-morpholin-4-yl-ethyl)-1H-indole-2-carboxylic acid [(1S,2R)-2-((S)-1-cyano-3-methyl-butylcarbamoyl)-cyclohexyl]-amide | 19 |

-continued

Compound Table 5

| # | Structure | Name (Autonom ®) | Example |
|---|-----------|------------------|---------|
| 5-43 | 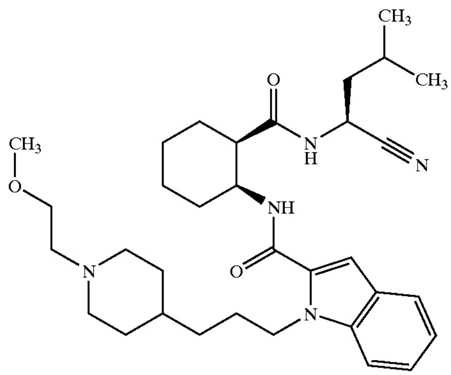 | 1-{3-[1-(2-Methoxy-ethyl)-piperidin-4-yl]-propyl}-1H-indole-2-carboxylic acid[(1S,2R)-2-((S)-1-cyano-3-methyl-butylcarbamoyl)-cyclohexyl]-amide | 55 |
| 5-44 | 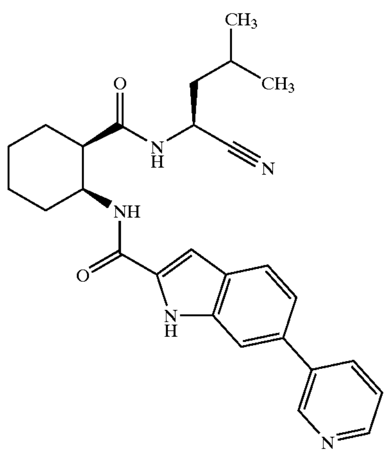 | 6-Pyridin-3-yl-1H-indole-2-carboxylic acid[(1S,2R)-2-((S)-1-cyano-3-methyl-butylcarbamoyl)-cyclohexyl]-amide | 25 |
| 5-45 | 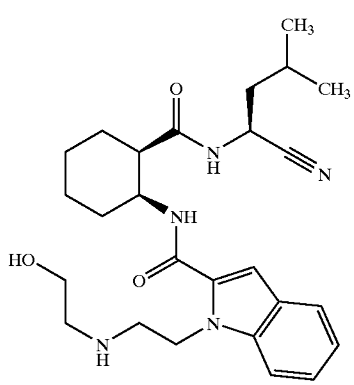 | 1-[2-(2-Hydroxy-ethylamino)-ethyl]-1H-indole-2-carboxylic acid [(1S,2R)-2-((S)-1-cyano-3-methyl-butylcarbamoyl)-cyclohexyl]-amide | 11 |

-continued

Compound Table 5

| # | Structure | Name (Autonom ®) | Example |
|---|---|---|---|
| 5-46 | 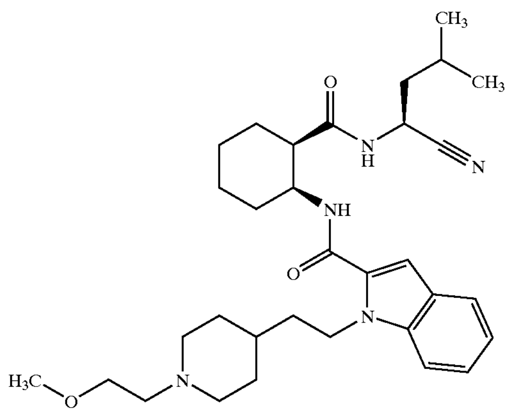 | 1-{2-[1-(2-Methoxy-ethyl)-piperidin-4-yl]-ethyl}-1H-indole-2-carboxylic acid[(1S,2R)-2-((S)-1-cyano-3-methyl-butylcarbamoyl)-cyclohexyl]-amide | 11 |
| 5-47 | 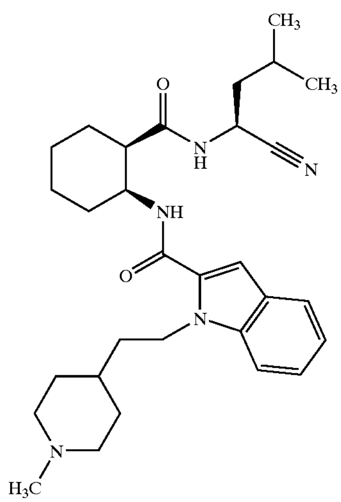 | 1-[2-(1-Methyl-piperidin-4-yl)-ethyl]-1H-indole-2-carboxylic acid [(1S,2R)-2-((S)-1-cyano-3-methyl-butylcarbamoyl)-cyclohexyl]-amide | 56 |
| 5-48 | 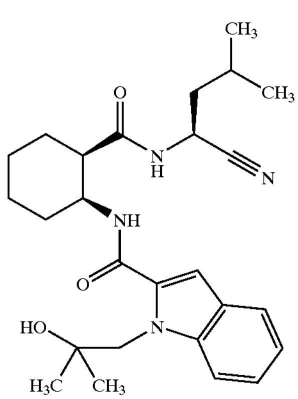 | 1-(2-Hydroxy-2-methyl-propyl)-1H-indole-2-carboxylic acid [(1S,2R)-2-((S)-1-cyano-3-methyl-butylcarbamoyl)-cyclohexyl]-amide | 52 |

-continued

Compound Table 5

| # | Structure | Name (Autonom ®) | Example |
|---|---|---|---|
| 5-49 | 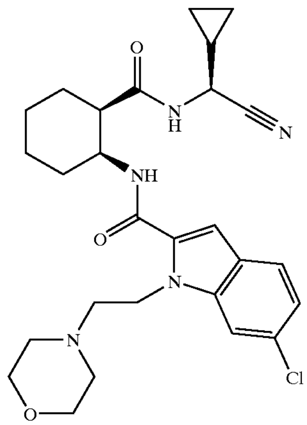 | 6-Chloro-1-(2-morpholin-4-yl-ethyl)-1H-indole-2-carboxylic acid {(1S,2R)-2-[((S)-cyano-cyclopropyl-methyl)-carbamoyl]-cyclohexyl}-amide | 11 |
| 5-50 | 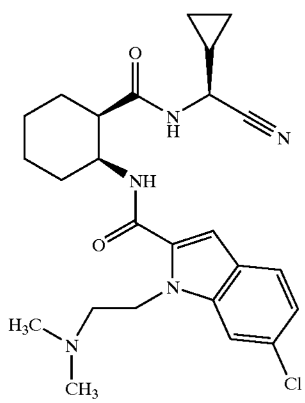 | 6-Chloro-1-(2-dimethylamino-ethyl)-1H-indole-2-carboxylic acid {(1S,2R)-2-[((S)-cyano-cyclopropyl-methyl)-carbamoyl] cyclohexyl}-amide | 11 |
| 5-51 | 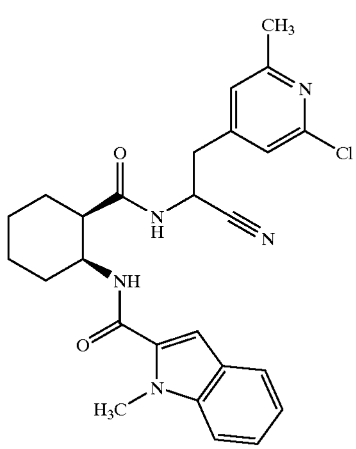 | 1-Methyl-1H-indole-2-carboxylic acid((1S,2R)-2-{[(2-chloro-6-methyl-pyridin-4-ylmethyl)-cyano-methyl]-carbamoyl}-cyclohexyl)-amide | 37 |

-continued

Compound Table 5

| # | Structure | Name (Autonom ®) | Example |
|---|---|---|---|
| 5-52 | 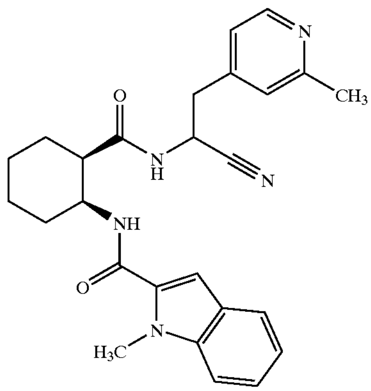 | 1-Methyl-1H-indole-2-carboxylic acid((1S,2R)-2-{[cyano-(2-methyl-pyridin-4-ylmethyl)-methyl]-carbamoyl}-cyclohexyl)-amide | 37 |
| 5-53 | 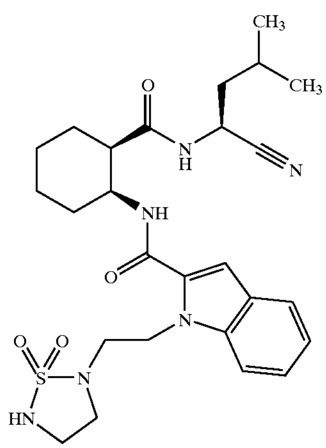 | 1-[2-(1,1-Dioxo-1$\lambda^6$-[1,2,5]thiadiazolidin-2-yl)-ethyl]-1H-indole-2-carboxylic acid[(1S,2R)-2-((S)-1-cyano-3-methyl-butylcarbamoyl)-cyclohexyl]-amide | 22 |
| 5-54 | 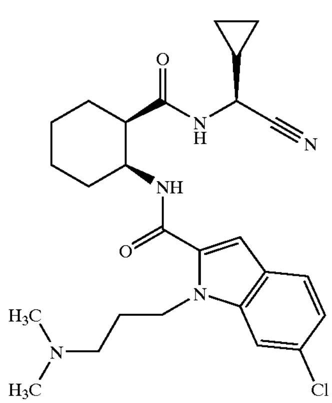 | 6-Chloro-1-(3-dimethylamino-propyl)-1H-indole-2-carboxylic acid {(1S,2R)-2-[((S)-cyano-cyclopropyl-methyl)-carbamoyl]-cyclohexyl}-amide | 11 |

-continued

Compound Table 5

| # | Structure | Name (Autonom ®) | Example |
|---|---|---|---|
| 5-55 | 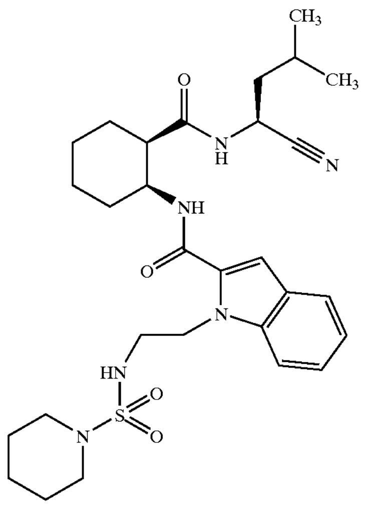 | 1-[2-(Piperidine-1-sulfonylamino)-ethyl]-1H-indole-2-carboxylic acid[(1S,2R)-2-((S)-1-cyano-3-methyl-butylcarbamoyl)-cyclohexyl]-amide | 21 |
| 5-56 | 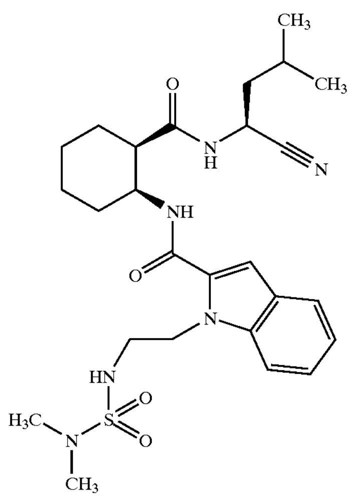 | 1-[2-(Dimethylamino-1-sulfonylamino)-ethyl]-1H-indole-2-carboxylic acid[(1S,2R)-2-((S)-1-cyano-3-methyl-butylcarbamoyl)-cyclohexyl]-amide | 21 |
| 5-57 | 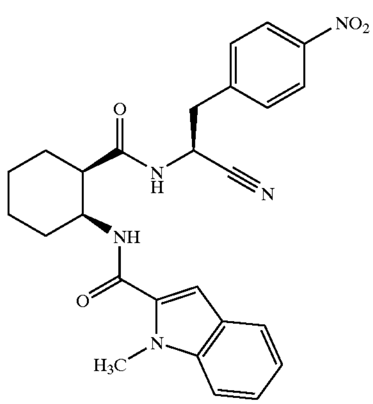 | 1-Methyl-1H-indole-2-carboxylic acid((1S,2R)-2-{[(S)-cyano-(4-nitro-benzyl)-methyl]-carbamoyl}-cyclohexyl)-amide | 48 |

-continued

Compound Table 5

| # | Structure | Name (Autonom ®) | Example |
|---|---|---|---|
| 5-58 | 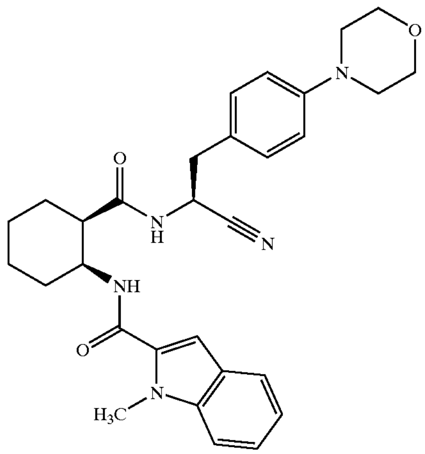 | 1-Methyl-1H-indole-2-carboxylic acid((1S,2R)-2-{[(S)-cyano-(4-morpholin-4-yl-benzyl)-methyl]-carbamoyl}-cyclohexyl)-amide | 49 |
| 5-59 | 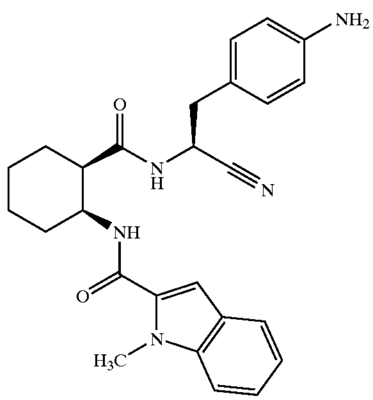 | 1-Methyl-1H-indole-2-carboxylic acid((1S,2R)-2-{[(S)-(4-amino-benzyl)-cyano-methyl]-carbamoyl}-cyclohexyl)-amide | 48 |
| 5-60 | 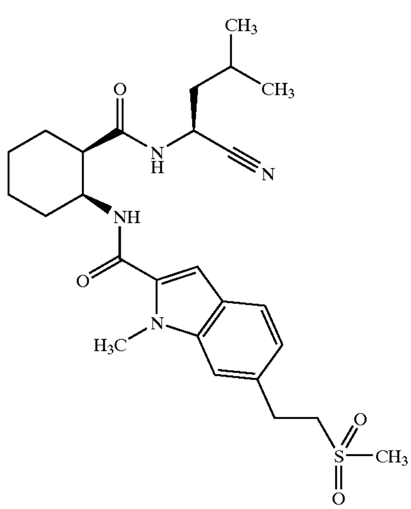 | 6-(2-Methanesulfonyl-ethyl)-1-methyl-1H-indole-2-carboxylic acid[(1S,2R)-2-((S)-1-cyano-3-methyl-butylcarbamoyl)-cyclohexyl]-amide | 26 |

-continued

Compound Table 5

| # | Structure | Name (Autonom ®) | Example |
|---|---|---|---|
| 5-61 | 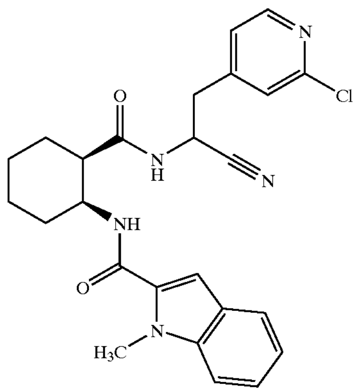 | 1-Methyl-1H-indole-2-carboxylic acid((1S,2R)-2-{[(2-chloro-pyridin-4-ylmethyl)-cyano-methyl]-carbamoyl}-cyclohexyl)-amide | 37 |
| 5-62 | 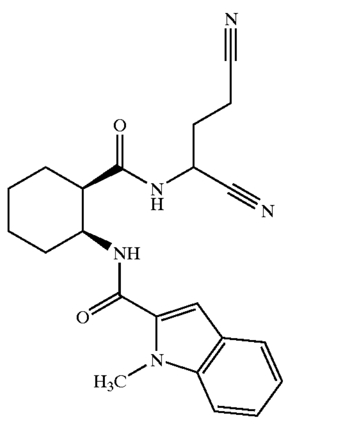 | 1-Methyl-1H-indole-2-carboxylic acid[(1S,2R)-2-(1,3-dicyano-propylcarbamoyl)-cyclohexyl]-amide | 31 |
| 5-63 | 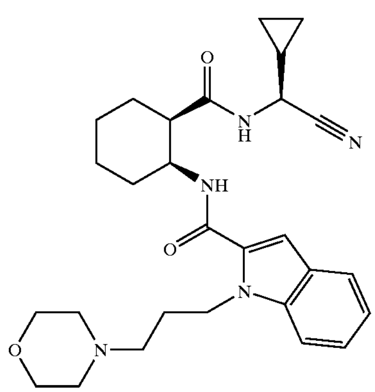 | 1-(3-Morpholin-4-yl-propyl)-1H-indole-2-carboxylic acid{(1S, 2R)-2-[((S)-cyano-cyclopropyl-methyl)-carbamoyl]-cyclohexyl}-amide | 11 |

-continued

Compound Table 5

| # | Structure | Name (Autonom ®) | Example |
|---|---|---|---|
| 5-64 | 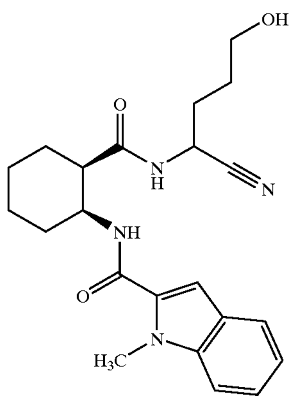 | 1-Methyl-1H-indole-2-carboxylic acid[(1S,2R)-2-(1-cyano-4-hydroxy-butylcarbamoyl)-cyclohexyl]-amide | 32 |
| 5-65 | 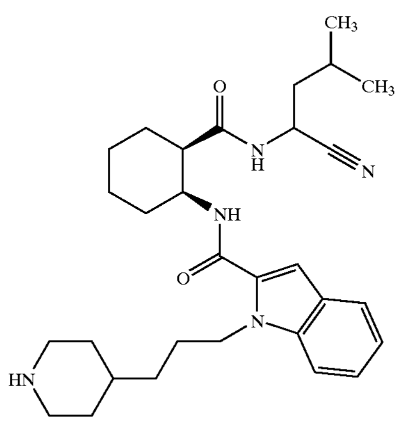 | 1-(3-Piperidin-4-yl-propyl)-1H-indole-2-carboxylic acid [(1S,2R)-2-(1-cyano-3-methyl-butylcarbamoyl)cyclohexyl]-amide | 57 |
| 5-66 | 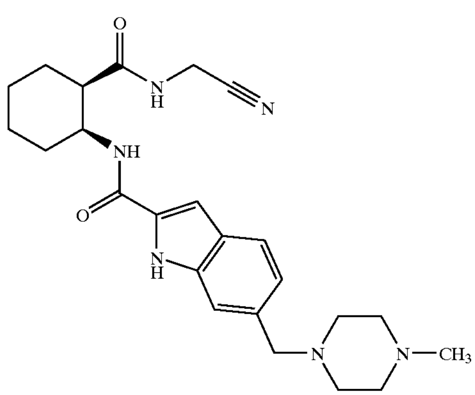 | 6-(4-Methyl-piperazin-1-ylmethyl)-1H-indole-2-carboxylic acid [(1S,2R)-2-(cyanomethyl-carbamoyl)-cyclohexyl]-amide | 14 |

-continued

Compound Table 5

| # | Structure | Name (Autonom ®) | Example |
|---|---|---|---|
| 5-67 | 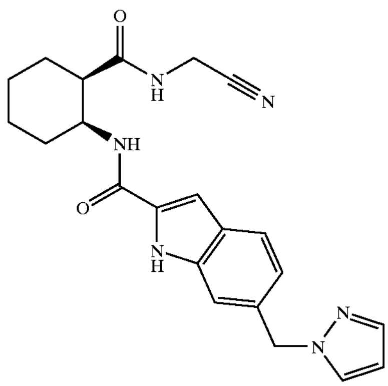 | 6-Pyrazol-1-ylmethyl-1H-indole-2-carboxylic acid[(1S,2R)-2-(cyanomethyl-carbamoyl)-cyclohexyl]-amide | 14 |
| 5-68 | 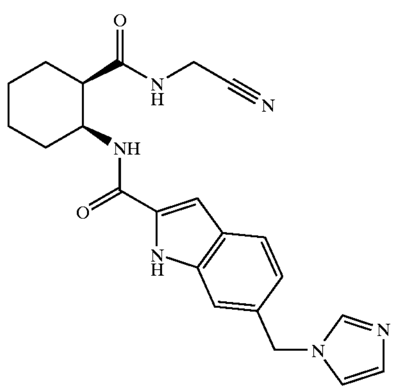 | 6-Imidazol-1-ylmethyl-1H-indole-2-carboxylic acid[(1S,2R)-2-(cyanomethyl-carbamoyl)-cyclohexyl]-amide | 14 |
| 5-69 | 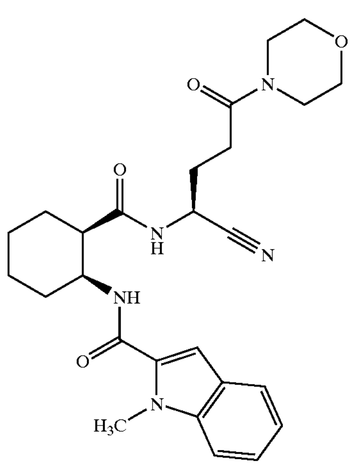 | 1-Methyl-1H-indole-2-carboxylic acid[(1S,2R)-2-((S)-1-cyano-4-morpholin-4-yl-4-oxo-butylcarbamoyl)-cyclohexyl]-amide | 30 |

-continued

Compound Table 5

| # | Structure | Name (Autonom ®) | Example |
|---|---|---|---|
| 5-70 | 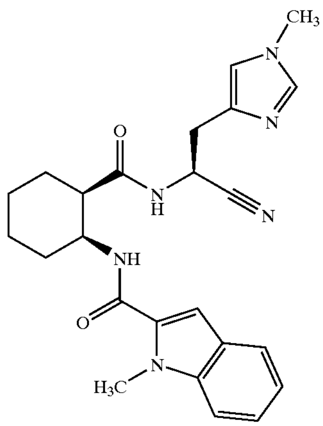 | 1-Methyl-1H-indole-2-carboxylic acid{(1S,2R)-2-[(S)-1-cyano-2-(1-methyl-1H-imidazol-4-yl)-ethylcarbamoyl]-cyclohexyl}-amide | 3 |
| 5-71 | 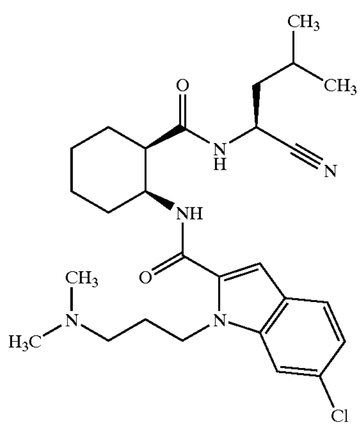 | 6-Chloro-1-(3-dimethylamino-propyl)-1H-indole-2-carboxylic acid [(1S,2R)-2-((S)-1-cyano-3-methyl-butylcarbamoyl)-cyclohexyl]-amide | 20 |
| 5-72 | 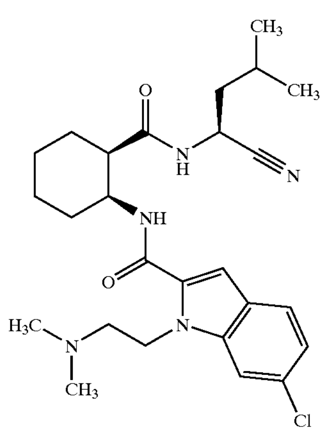 | 6-Chloro-1-(2-dimethylamino-ethyl)-1H-indole-2-carboxylic acid [(1S,2R)-2-((S)-1-cyano-3-methyl-butylcarbamoyl)-cyclohexyl]-amide | 19 |

-continued

Compound Table 5

| # | Structure | Name (Autonom ®) | Example |
|---|---|---|---|
| 5-73 | 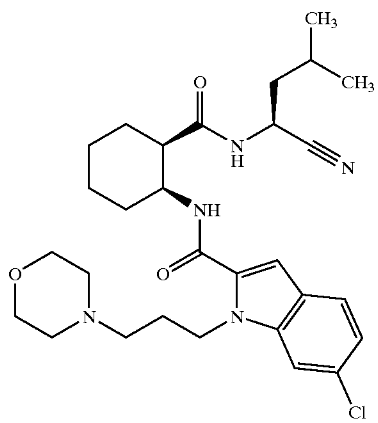 | 6-Chloro-1-(3-morpholin-4-yl-propyl)-1H-indole-2-carboxylic acid[(1S,2R)-2-((S)-1-cyano-3-methyl-butylcarbamoyl)-cyclohexyl]-amide | 20 |
| 5-74 | 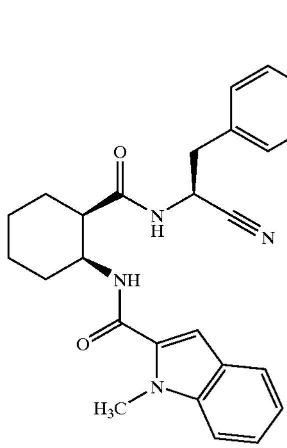 | 1-Methyl-1H-indole-2-carboxylic acid((1S,2R)-2-{[(S)-cyano-(4-methoxy-benzyl)-methyl]-carbamoyl}cyclohexyl)-amide | 33 |
| 5-75 | 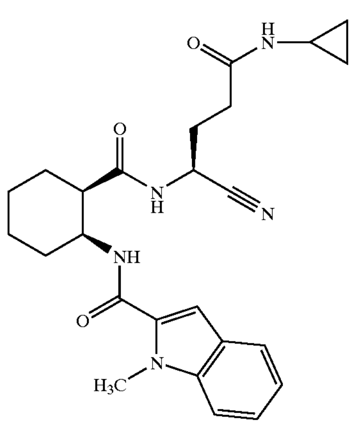 | 1-Methyl-1H-indole-2-carboxylic acid[(1S,2R)-2-((S)-1-cyano-3-cyclopropylcarbamoyl-propylcarbamoyl)-cyclohexyl]-amide | 30 |

-continued

Compound Table 5

| # | Structure | Name (Autonom ®) | Example |
|---|---|---|---|
| 5-76 | 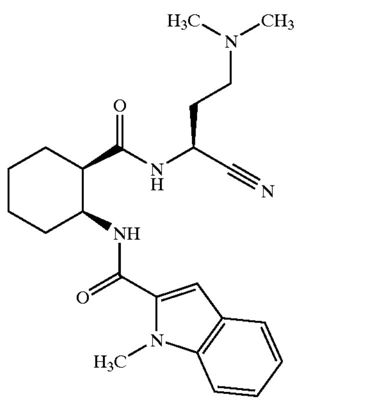 | 1-Methyl-1H-indole-2-carboxylic acid[(1S,2R)-2-((S)-1-cyano-3-dimethylamino-propylcarbamoyl)-cyclohexyl]-amide | 29 |
| 5-77 | 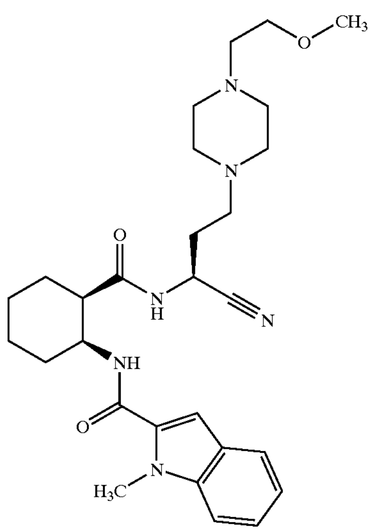 | 1-Methyl-1H-indole-2-carboxylic acid((1S,2R)-2-{(S)-1-cyano-3-[4-(2-methoxy-ethyl)-piperazin-1-yl]-propylcarbamoyl}-cyclohexyl)-amide | 29 |
| 5-78 | 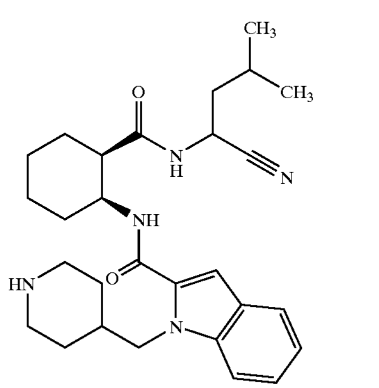 | 1-Piperidin-4-ylmethyl-1H-indole-2-carboxylic acid[(1S,2R)-2-(1-cyano-3-methyl-butylcarbamoyl)cyclohexyl]-amide | 54 |

Compound Table 5

| # | Structure | Name (Autonom ®) | Example |
|---|---|---|---|
| 5-79 | 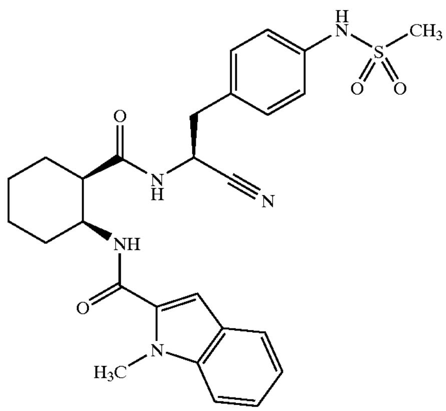 | 1-Methyl-1H-indole-2-carboxylic acid((1S,2R)-2-{[(S)-cyano-(4-methanesulfonylamino-benzyl)-methyl]-carbamoyl}-cyclohexyl)-amide | 48 |
| 5-80 | 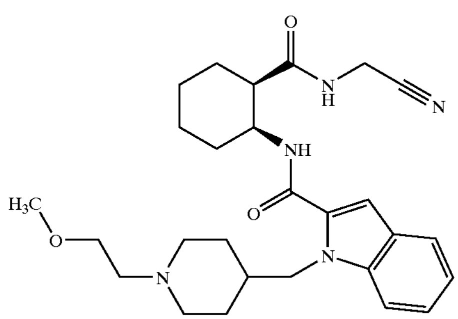 | 1-[1-(2-Methoxy-ethyl)-piperidin-4-ylmethyl]-1H-indole-2-carboxylic acid[(1S,2R)-2-(cyanomethyl-carbamoyl)-cyclohexyl]-amide | 55 |
| 5-81 | 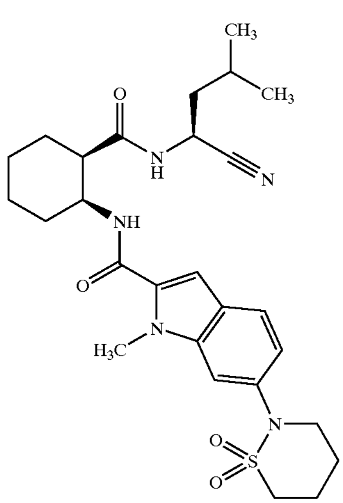 | 6-(1,1-Dioxo-1$\lambda^6$-[1,2]thiazinan-2-yl)-1-methyl-1H-indole-2-carboxylic acid[(1S,2R)-2-((S)-1-cyano-3-methyl-butylcarbamoyl)-cyclohexyl]-amide | 28 |

-continued

Compound Table 5

| # | Structure | Name (Autonom ®) | Example |
|---|---|---|---|
| 5-82 | 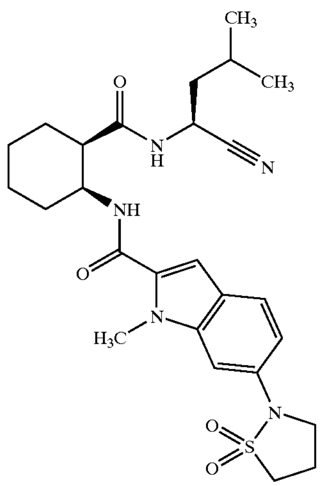 | 6-(1,1-Dioxo-1λ$^6$-isothiazolidin-2-yl)-1-methyl-1H-indole-2-carboxylic acid[(1S,2R)-2-((S)-1-cyano-3-methyl-butylcarbamoyl)-cyclohexyl]-amide | 28 |
| 5-83 | 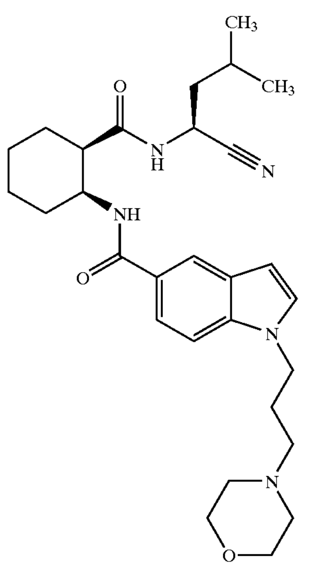 | 1-(3-Morpholin-4-yl-propyl)-1H-indole-5-carboxylic acid[(1S,2R)-2-((S)-1-cyano-3-methyl-butylcarbamoyl)-cyclohexyl]-amide | 11 |
| 5-84 | 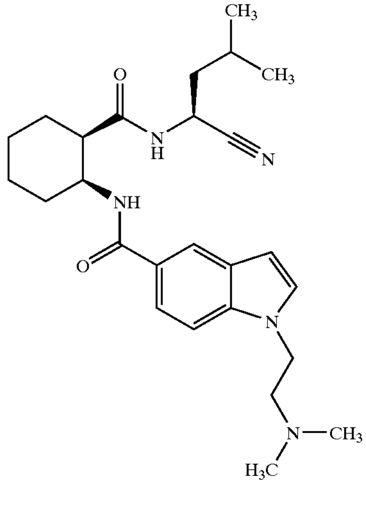 | 1-(2-Dimethylamino-ethyl)-1H-indole-5-carboxylic acid[(1S,2R)-2-((S)-1-cyano-3-methyl-butylcarbamoyl)-cyclohexyl]-amide | 11 |

-continued

Compound Table 5

| # | Structure | Name (Autonom ®) | Example |
|---|---|---|---|
| 5-85 | 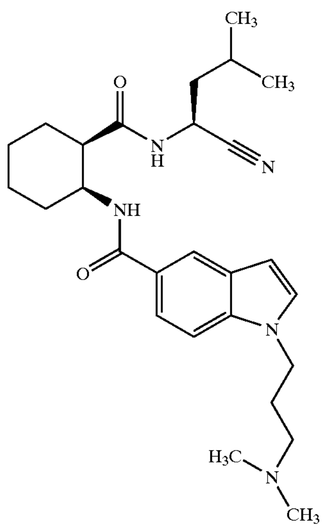 | 1-(3-Dimethylamino-propyl)-1H-indole-5-carboxylic acid [(1S,2R)-2-((S)-1-cyano-3-methyl-butylcarbamoyl)-cyclohexyl]-amide | 11 |
| 5-86 | 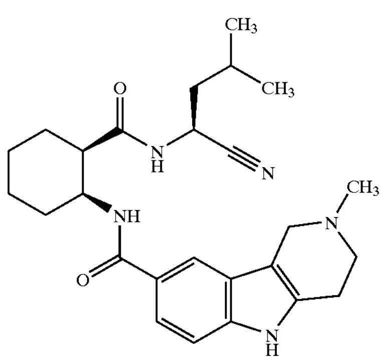 | 2-Methyl-2,3,4,5-tetrahydro-1H-pyrido[4,3-b]indole-8-carboxylic acid[(1S,2R)-2-((S)-1-cyano-3-methyl-butylcarbamoyl)-cyclohexyl]-amide | 10 |
| 5-87 | 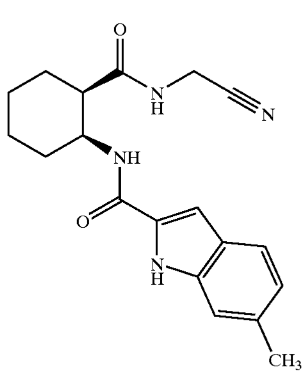 | 6-Methyl-1H-indole-2-carboxylic acid[(1S,2R)-2-(cyanomethyl-carbamoyl)-cyclohexyl]-amide | 10 |

Compound Table 5

| # | Structure | Name (Autonom ®) | Example |
|---|---|---|---|
| 5-88 | 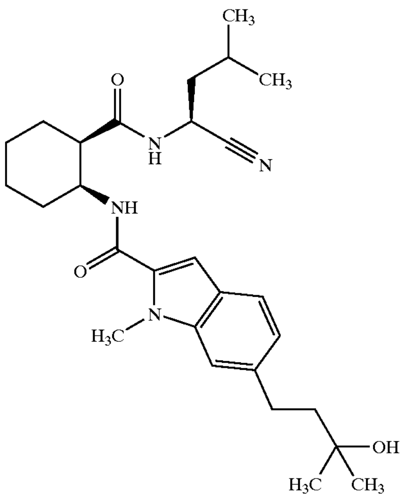 | 6-(3-Hydroxy-3-methyl-butyl)-1-methyl-1H-indole-2-carboxylic acid[(1S,2R)-2-((S)-1-cyano-3-methyl-butylcarbamoyl)-cyclohexyl]-amide | 26 |
| 5-89 | 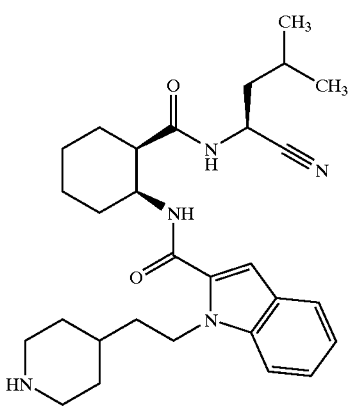 | 1-(2-Piperidin-4-yl-ethyl)-1H-indole-2-carboxylic acid[(1S,2R)-2-((S)-1-cyano-3-methyl-butylcarbamoyl)-cyclohexyl]-amide | 56 |
| 5-90 | 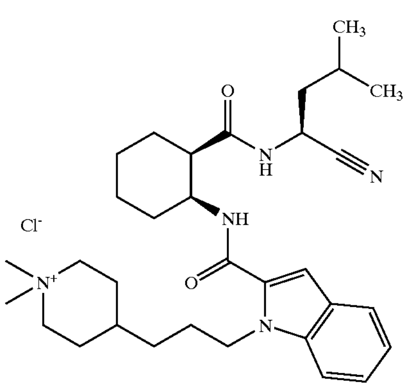 | 4-(3-{2-[(1S,2R)-2-((S)-1-Cyano-3-methyl-butylcarbamoyl)-cyclohexylcarbamoyl]-indol-1-yl}-propyl)-1,1-dimethyl-piperidinium; chloride | 55 |

-continued

Compound Table 5

| # | Structure | Name (Autonom ®) | Example |
|---|---|---|---|
| 5-91 | 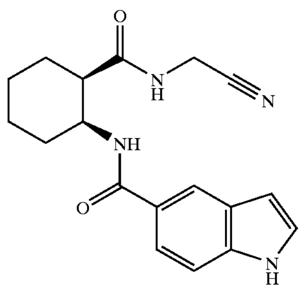 | 1H-Indole-5-carboxylic acid[(1S,2R)-2-(cyanomethyl-carbamoyl)-cyclohexyl]-amide | 10 |
| 5-92 | 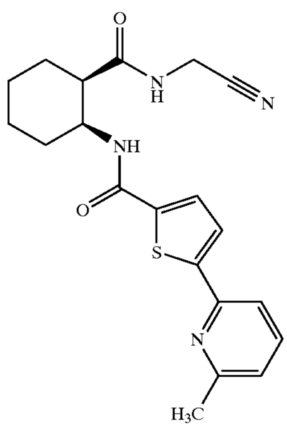 | 5-(6-Methyl-pyridin-2-yl)-thiophene-2-carboxylic acid [(1S,2R)-2-(cyanomethyl-carbamoyl)-cyclohexyl]-amide | 1 |
| 5-93 | 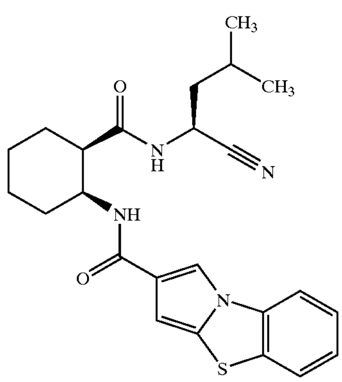 | Benzo[d]pyrrolo[2,1-b]thiazole-2-carboxylic acid[(1S,2R)-2-((S)-1-cyano-3-methyl-butylcarbamoyl)-cyclohexyl]-amide | 10 |
| 5-94 | 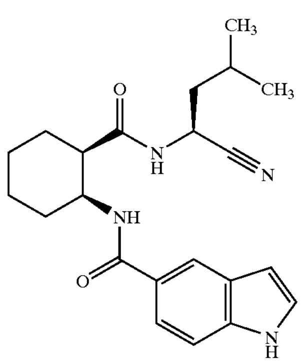 | 1H-Indole-5-carboxylic acid[(1S,2R)-2-((S)-1-cyano-3-methyl-butylcarbamoyl)-cyclohexyl]-amide | 10 |

-continued

Compound Table 5

| # | Structure | Name (Autonom ®) | Example |
|---|---|---|---|
| 5-95 | 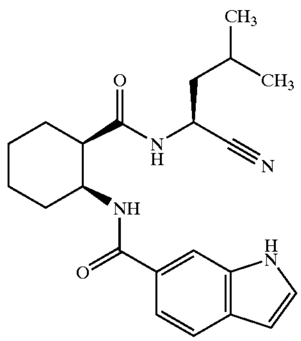 | 1H-Indole-6-carboxylic acid[(1S,2R)-2-((S)-1-cyano-3-methyl-butylcarbamoyl)-cyclohexyl]-amide | 10 |
| 5-96 | 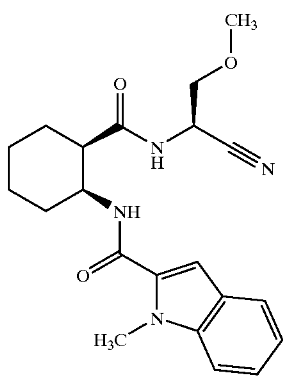 | 1-Methyl-1H-indole-2-carboxylic acid{(1S,2R)-2-[((R)-cyano-methoxymethyl-methyl)-carbamoyl]-cyclohexyl}-amide | 39 |
| 5-97 | 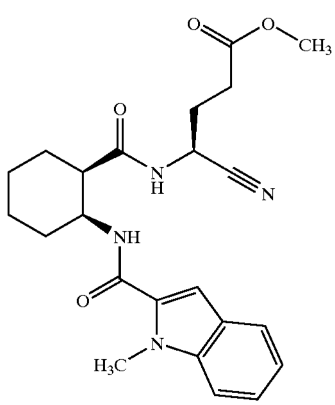 | (S)-4-Cyano-4-({(1R,2S)-2-[(1-methyl-1H-indole-2-carbonyl)-amino]-cyclohexanecarbonyl}-amino)-butyric acid methyl ester | 30 |
| 5-98 | 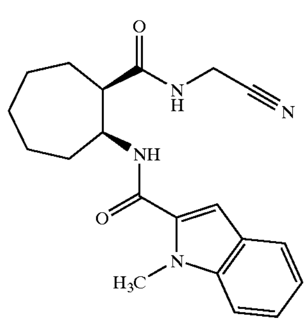 | 1-Methyl-1H-indole-2-carboxylic acid[(1S,2R)-2-(cyanomethyl-carbamoyl)-cycloheptyl]-amide | 17 |

-continued

Compound Table 5

| # | Structure | Name (Autonom ®) | Example |
|---|-----------|------------------|---------|
| 5-99 | 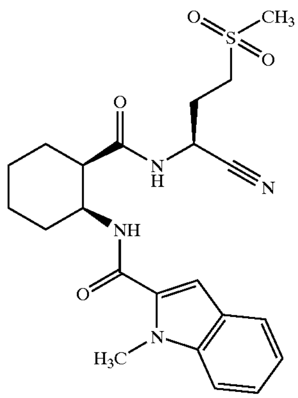 | 1-Methyl-1H-indole-2-carboxylic acid[(1S,2R)-2-((S)-1-cyano-3-methanesulfonyl-propylcarbamoyl)-cyclohexyl]-amide | 35 |
| 5-100 | 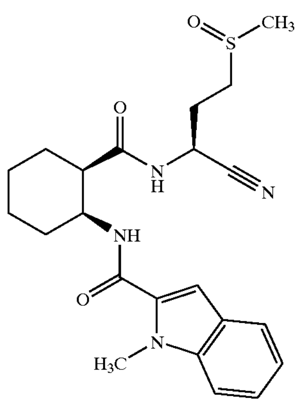 | 1-Methyl-1H-indole-2-carboxylic acid[(1S,2R)-2-((S)-1-cyano-3-methanesulfinyl-propylcarbamoyl)-cyclohexyl]-amide | 35 |
| 5-101 | 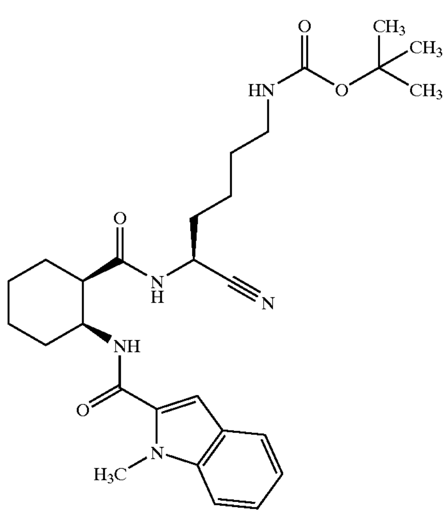 | 1-Methyl-1H-indole-2-carboxylic acid{(1S,2R)-2-[(S)-1-cyano-5-(2,2-dimethyl-propionylamino)-pentylcarbamoyl]-cyclohexyl}-amide | 3 |

-continued

Compound Table 5

| # | Structure | Name (Autonom ®) | Example |
|---|-----------|------------------|---------|
| 5-102 | 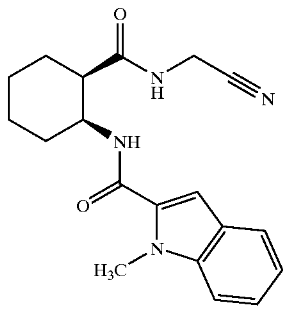 | 1-Methyl-1H-indole-2-carboxylic acid{(1S,2R)-2-(cyanomethyl-carbamoyl)-cyclohexyl]-amide | 11 |
| 5-103 | 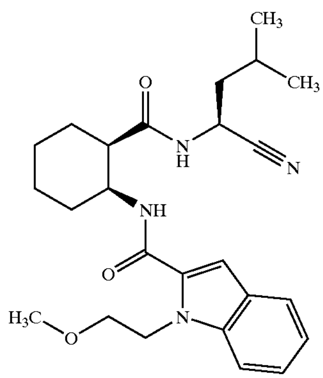 | 1-(2-Methoxy-ethyl)-1H-indole-2-carboxylic acid[(1S,2R)-2-((S)-1-cyano-3-methyl-butylcarbamoyl)-cyclohexyl]-amide | 11 |
| 5-104 | 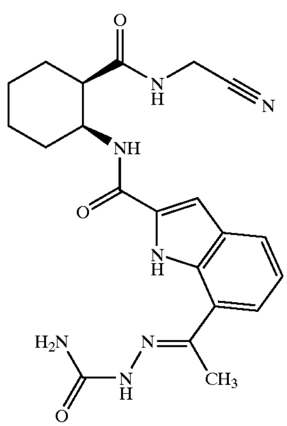 | 7-[1-(Carbamoyl-hydrazono)-ethyl]-1H-indole-2-carboxylic acid [(1S,2R)-2-(cyanomethyl-carbamoyl)cyclohexyl]-amide | 51 |
| 5-105 | 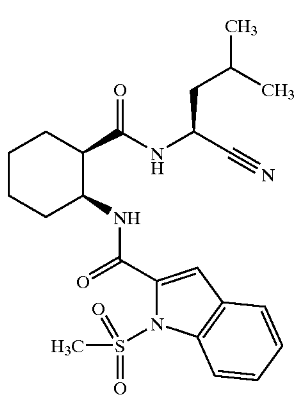 | 1-Methanesulfonyl-1H-indole-2-carboxylic acid[(1S,2R)-2-((S)-1-cyano-3-methyl-butylcarbamoyl)-cyclohexyl]-amide | 11 |

-continued

Compound Table 5

| # | Structure | Name (Autonom ®) | Example |
|---|-----------|------------------|---------|
| 5-106 | 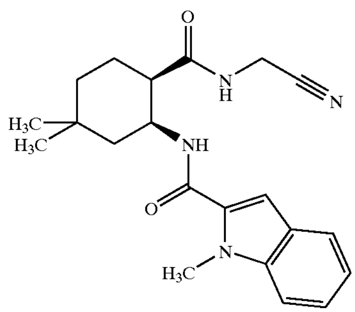 | 1-Methyl-1H-indole-2-carboxylic acid[(1S,2R)-2-(cyanomethyl-carbamoyl)-5,5-dimethyl-cyclohexyl]-amide | 23 |
| 5-107 | 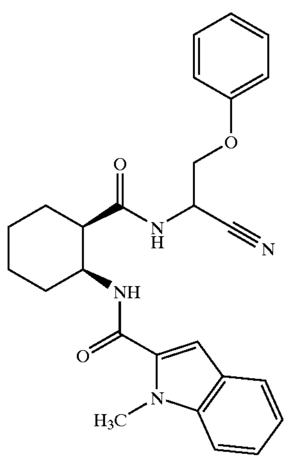 | 1-Methyl-1H-indole-2-carboxylic acid{(1S,2R)-2-[(cyano-phenoxymethyl-methyl)-carbamoyl]-cyclohexyl}-amide | 1 |
| 5-108 | 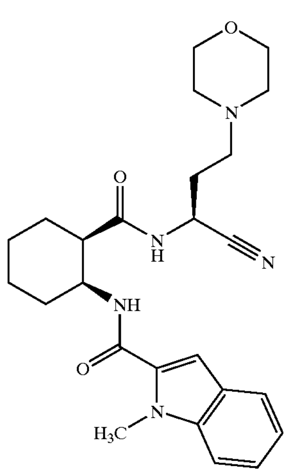 | 1-Methyl-1H-indole-2-carboxylic acid[(1S,2R)-2-((S)-1-cyano-3-morpholin-4-yl-propylcarbamoyl)-cyclohexyl]-amide | 29 |

-continued

Compound Table 5

| # | Structure | Name (Autonom ®) | Example |
|---|---|---|---|
| 5-109 | 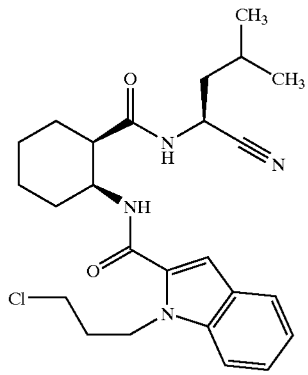 | 1-(3-Chloro-propyl)-1H-indole-2-carboxylic acid[(1S,2R)-2-((S)-1-cyano-3-methyl-butylcarbamoyl)-cyclohexyl]-amide | 19, 43 |
| 5-110 | 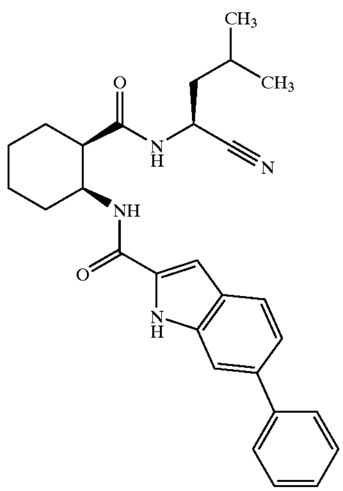 | 6-Phenyl-1H-indole-2-carboxylic acid[(1S,2R)-2-((S)-1-cyano-3-methyl-butylcarbamoyl)-cyclohexyl]-amide | 25 |
| 5-111 | 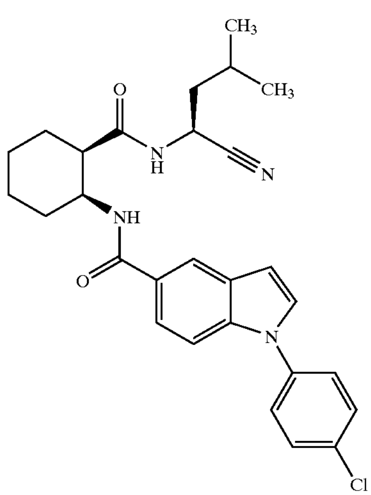 | 1-(4-Chloro-phenyl)-1H-indole-5-carboxylic acid[(1S,2R)-2-((S)-1-cyano-3-methyl-butylcarbamoyl)-cyclohexyl]-amide | 11 |

-continued
Compound Table 5
| # | Structure | Name (Autonom ®) | Example |
|---|---|---|---|
| 5-112 | 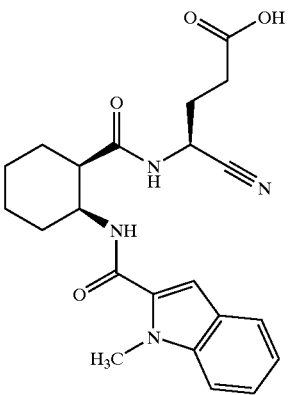 | (S)-4-Cyano-4-({{(1R,2S)-2-[(1-methyl-1H-indole-2-carbonyl)-amino]-cyclohexanecarbonyl}-amino)-butyric acid | 30 |
| 5-113 | 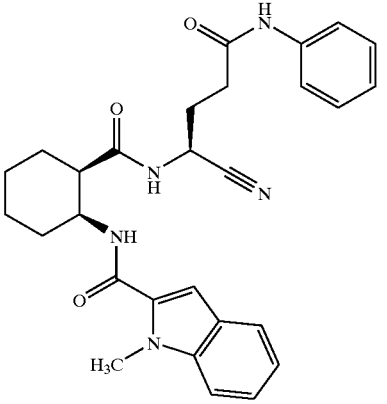 | 1-Methyl-1H-indole-2-carboxylic acid[(1S,2R)-2-((S)-1-cyano-3-phenylcarbamoyl-propylcarbamoyl)-cyclohexyl]-amide | 30 |
| 5-114 | 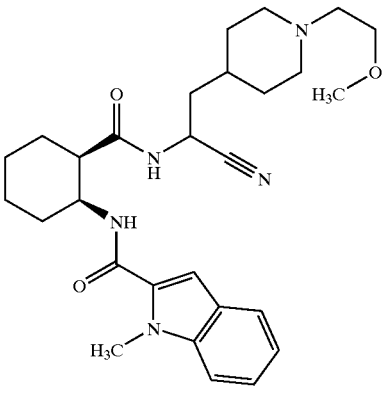 | 1-Methyl-1H-indole-2-carboxylic acid[(1S,2R)-2-({cyano-[1-(2-methoxy-ethyl)-piperidin-4-ylmethyl]-methyl}-carbamoyl)-cyclohexyl]amide | 34 |

-continued

Compound Table 5

| # | Structure | Name (Autonom ®) | Example |
|---|---|---|---|
| 5-115 | 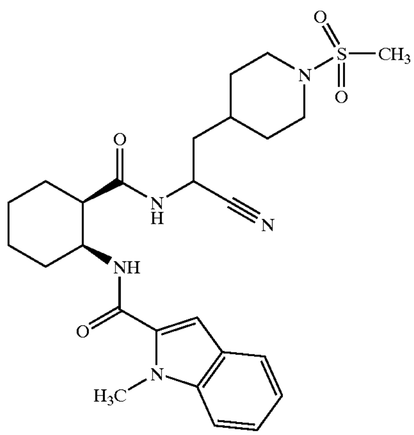 | 1-Methyl-1H-indole-2-carboxylic acid((1S,2R)-2-{(cyano-(1-methanesulfonyl-piperidin-4-ylmethyl)-methyl]-carbamoyl}-cyclohexyl)-amide | 34 |
| 5-116 | 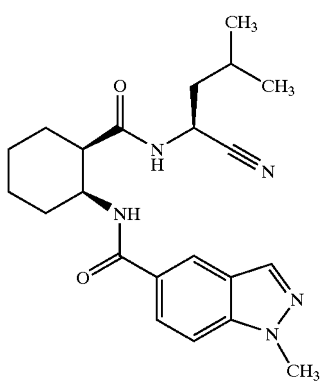 | 1-Methyl-1H-indazole-5-carboxylic acid[(1S,2R)-2-((S)-1-cyano-3-methyl-butylcarbamoyl)-cyclohexyl]-amide | 53 |
| 5-117 | 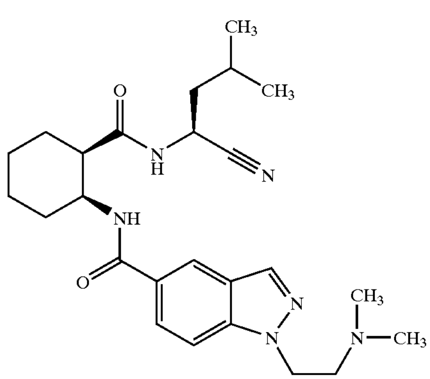 | 1-(2-Dimethylamino-ethyl)-1H-indazole-5-carboxylic acid [(1S,2R)-2-((S)-1-cyano-3-methyl-butylcarbamoyl)-cyclohexyl]-amide | 53 |

-continued

Compound Table 5

| # | Structure | Name (Autonom ®) | Example |
|---|---|---|---|
| 5-118 | 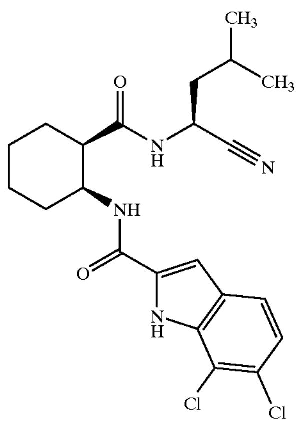 | 6,7-Dichloro-1H-indole-2-carboxylic acid[(1S,2R)-2-((S)-1-cyano-3-methyl-butylcarbamoyl)-cyclohexyl]-amide | 1 |
| 5-119 | 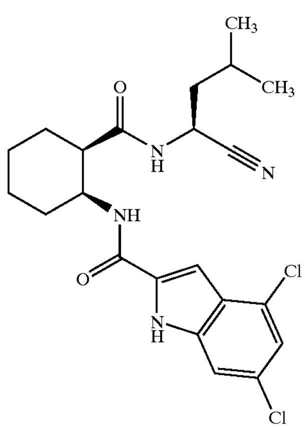 | 4,6-Dichloro-1H-indole-2-carboxylic acid[(1S,2R)-2-((S)-1-cyano-3-methyl-butylcarbamoyl)-cyclohexyl]-amide | 1 |
| 5-120 | 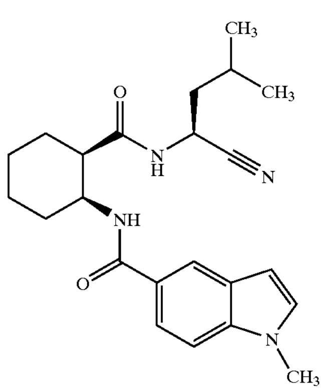 | 1-Methyl-1H-indole-5-carboxylic acid[(1S,2R)-2-((S)-1-cyano-3-methyl-butylcarbamoyl)-cyclohexyl]-amide | 10 |

-continued

Compound Table 5

| # | Structure | Name (Autonom ®) | Example |
|---|-----------|------------------|---------|
| 5-121 | 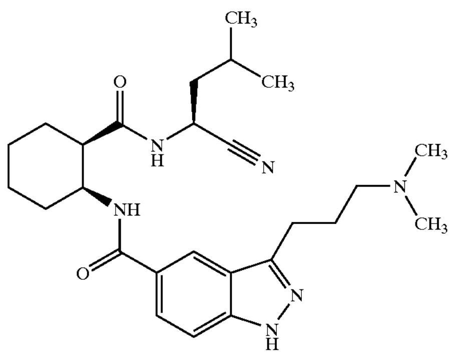 | 3-(3-Dimethylamino-propyl)-1H-indazole-5-carboxylic acid [(1S,2R)-2-((S)-1-cyano-3-methyl-butylcarbamoyl) cyclohexyl]-amide | 15 |
| 5-122 | 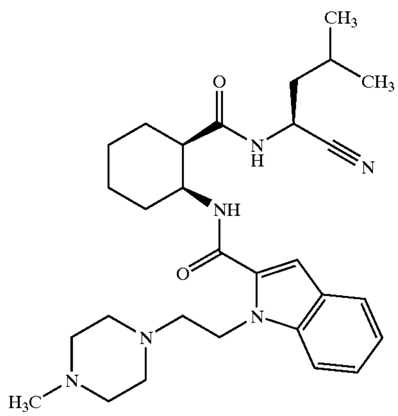 | 1-[2-(4-Methyl-piperazin-1-yl)-ethyl]-1H-indole-2-carboxylic acid [(1S,2R)-2-((S)-1-cyano-3-methyl-butylcarbamoyl)-cyclohexyl]-amide | 19 |
| 5-123 | 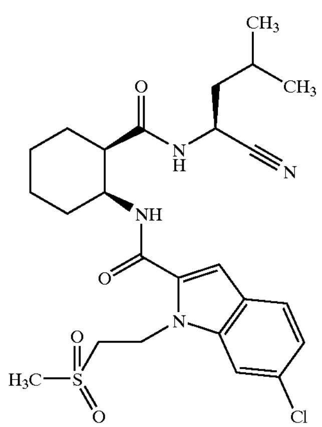 | 6-Chloro-1-(2-methanesulfonyl-ethyl)-1H-indole-2-carboxylic acid [(1S,2R)-2-((S)-1-cyano-3-methyl-butylcarbamoyl)-cyclohexyl]-amide | 19 |
| 5-124 | 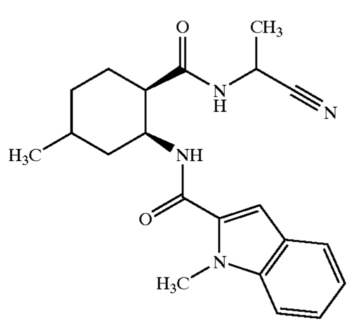 | 1-Methyl-1H-indole-2-carboxylic acid{(1S,2R)-2-[(cyano-methyl-methyl)-carbamoyl]-5-methyl-cyclohexyl}-amide | 23 |

-continued

Compound Table 5

| # | Structure | Name (Autonom ®) | Example |
|---|---|---|---|
| 5-125 | 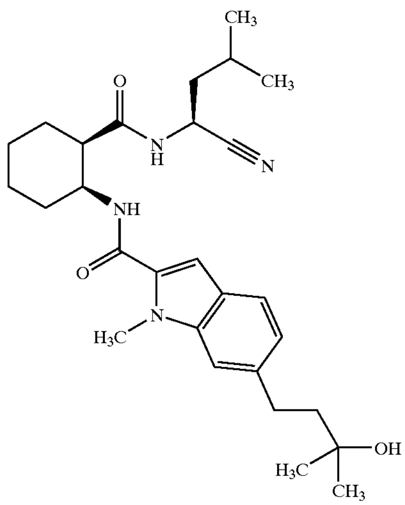 | 6-(3-Hydroxy-3-methyl-butyl)-1-methyl-1H-indole-2-carboxylic acid[(1S,2R)-2-((S)-1-cyano-3-methyl-butylcarbamoyl)-cyclohexyl)-amide | 26 |
| 5-126 | 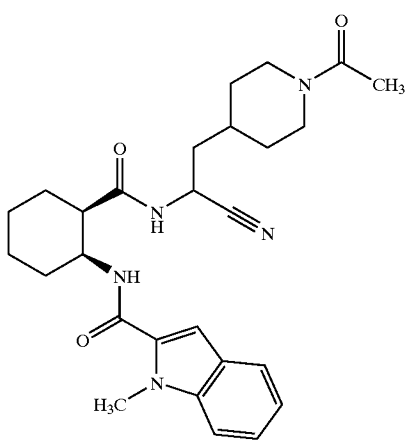 | 1-Methyl-1H-indole-2-carboxylic acid((1S,2R)-2-{[(1-acetyl-piperidin-4-ylmethyl)cyano-methyl]-carbamoyl}-cyclohexyl)-amide | 34 |
| 5-127 | 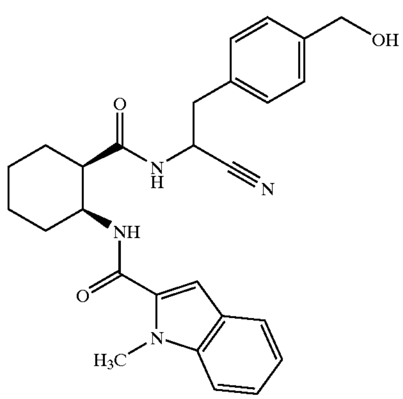 | 1-Methyl-1H-indole-2-carboxylic acid((1S,2R)-2-{[cyano-(4-hydroxymethyl-benzyl)-methyl]-carbamoyl}cyclohexyl)-amide | 38 |

-continued

Compound Table 5

| # | Structure | Name (Autonom ®) | Example |
|---|---|---|---|
| 5-128 | 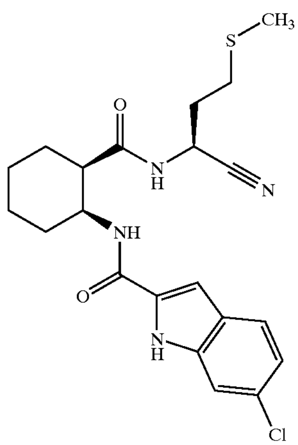 | 6-Chloro-1H-indole-2-carboxylic acid[(1S,2R)-2-((S)-1-cyano-3-methylsulfanyl-propylcarbamoyl)-cyclohexyl]-amide | 47 |
| 5-129 | 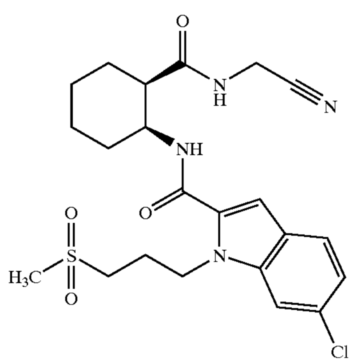 | 6-Chloro-1-(3-methanesulfonyl-propyl)-1H-indole-2-carboxylic acid[(1S,2R)-2-(cyanomethyl-carbamoyl)-cyclohexyl]-amide | 11 |
| 5-130 | 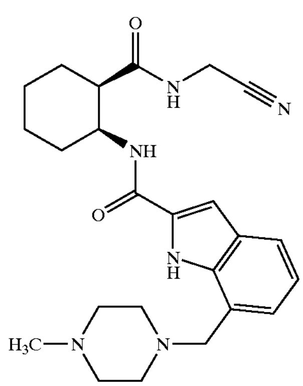 | 7-(4-Methyl-piperazin-1-ylmethyl)-1H-indole-2-carboxylic acid [(1S,2R)-2-(cyanomethyl-carbamoyl)-cyclohexyl)-amide | 14 |

-continued

Compound Table 5

| # | Structure | Name (Autonom ®) | Example |
|---|---|---|---|
| 5-131 | 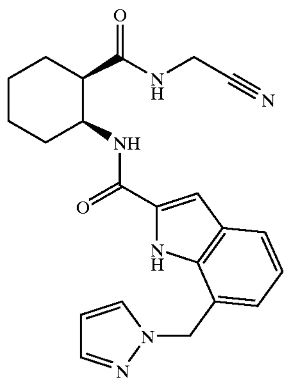 | 7-Pyrazol-1-ylmethyl-1H-indole-2-carboxylic acid[(1S,2R)-2-(cyanomethyl-carbamoyl)-cyclohexyl]-amide | 14 |
| 5-132 | 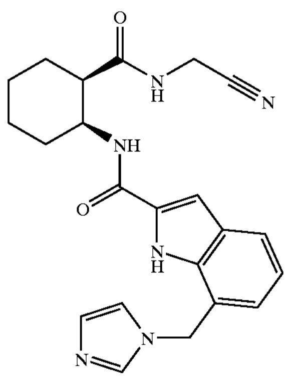 | 7-Imidazol-1-ylmethyl-1H-indole-2-carboxylic acid[(1S,2R)-2-(cyanomethyl-carbamoyl)-cyclohexyl]-amide | 14 |
| 5-133 | 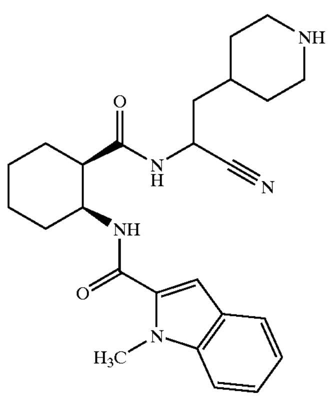 | 1-Methyl-1H-indole-2-carboxylic acid{(1S,2R)-2-[(cyano-piperidin-4-ylmethyl-methyl)-carbamoyl]-cyclohexyl}-amide | 34 |
| 5-134 | 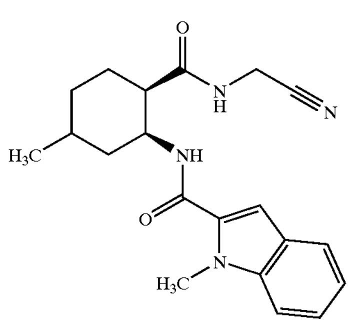 | 1-Methyl-1H-indole-2-carboxylic acid[(1S,2R)-2-(cyanomethyl-carbamoyl)-5-methyl-cyclohexyl]-amide | 23 |

Compound Table 5

| # | Structure | Name (Autonom ®) | Example |
|---|---|---|---|
| 5-135 | 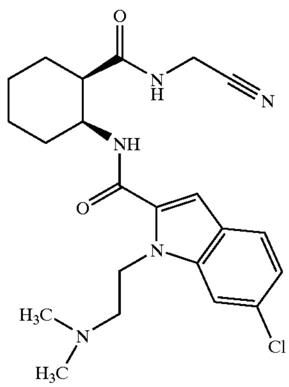 | 6-Chloro-1-(2-dimethylamino-ethyl)-1H-indole-2-carboxylic acid [(1S,2R)-2-(cyanomethyl-carbanoyl)-cyclohexyl]-amide | 11 |
| 5-136 | 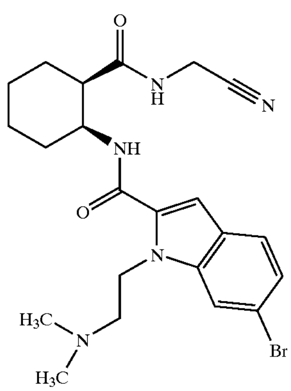 | 6-Bromo-1-(2-dimethylamino-ethyl)-1H-indole-2-carboxylic acid [(1S,2R)-2-(cyanomethyl-carbamoyl)-cyclohexyl]-amide | 10 |
| 5-137 | 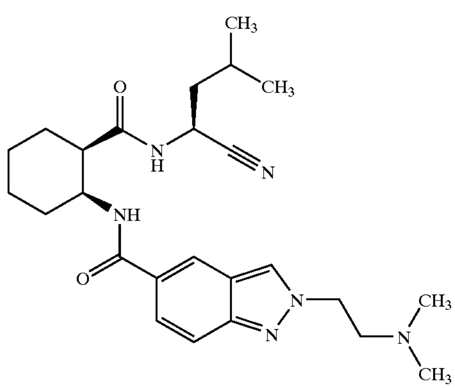 | 2-(2-Dimethylamino-ethyl)-2H-indazole-5-carboxylic acid [(1S,2R)-2-((S)-1-cyano-3-methyl-butylcarbamoyl)-cyclohexyl]-amide | 13 |

Compound Table 5

| # | Structure | Name (Autonom ®) | Example |
|---|---|---|---|
| 5-138 | 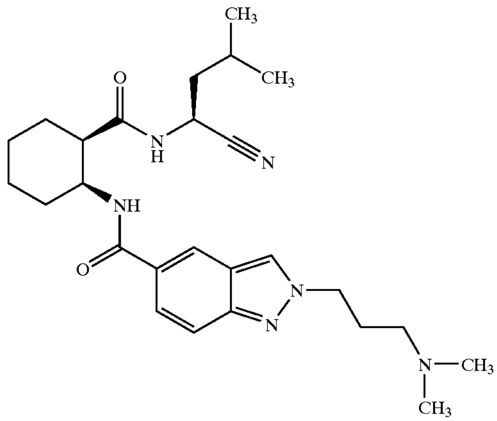 | 2-(3-Dimethylamino-propyl)-2H-indazole-5-carboxylic acid [(1S,2R)-2-((S)-1-cyano-3-methyl-butylcarbamoyl)-cyclohexyl]-amide | 53 |
| 5-139 | 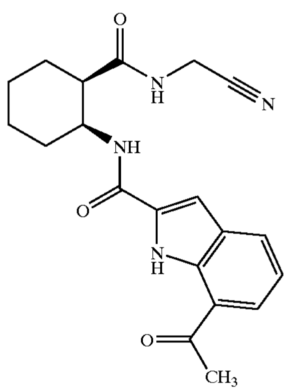 | 7-Acetyl-1H-indole-2-carboxylic acid[(1S,2R)-2-(cyanomethyl-carbamoyl)-cyclohexyl]-amide | 53 |
| 5-140 | 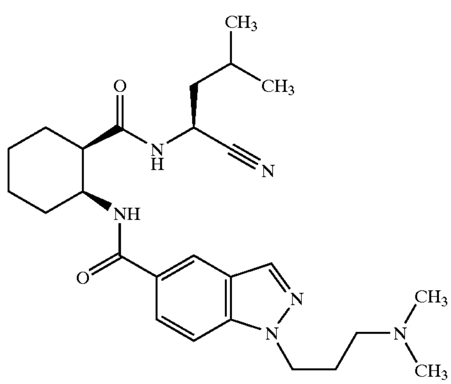 | 1-(3-Dimethylamino-propyl)-1H-indazole-5-carboxylic acid [(1S,2R)-2-((S)-1-cyano-3-methyl-butylcarbamoyl)-cyclohexyl]-amide | 53 |
| 5-141 | 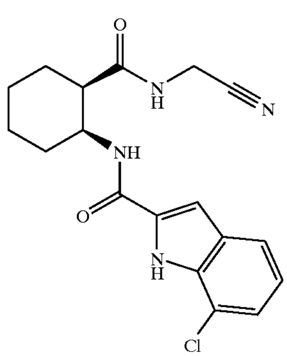 | 7-Chloro-1H-indole-2-carboxylic acid[(1S,2R)-2-(cyanomethyl-carbamoyl)-cyclohexyl]-amide | 10 |

-continued

Compound Table 5

| # | Structure | Name (Autonom ®) | Example |
|---|---|---|---|
| 5-142 | 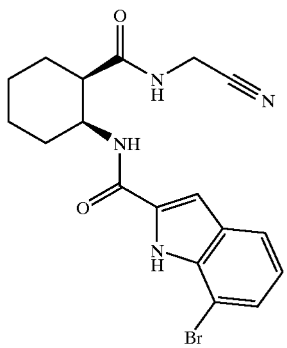 | 7-Bromo-1H-indole-2-carboxylic acid[(1S,2R)-2-(cyanomethyl-carbamoyl)-cyclohexyl]-amide | 10 |
| 5-143 | 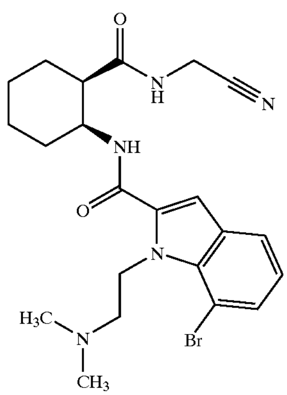 | 7-Bromo-1-(2-dimethylamino-ethyl)-1H-indole-2-carboxylic acid [(1S,2R)-2-(cyanomethyl-carbamoyl)-cyclohexyl]-amide | 53 |
| 5-144 | 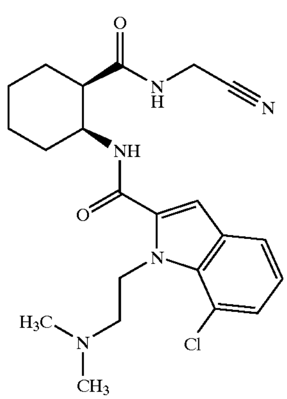 | 7-Chloro-1-(2-dimethylamino-ethyl)-1H-indole-2-carboxylic acid [(1S,2R)-2-(cyanomethyl-carbamoyl)-cyclohexyl]-amide | 53 |

Methods

The present invention also relates to a method for the prophylactic and/or therapeutic treatment of diseases which are associated with cystein proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease, which method comprises administering a compound of formula (I) to a human being or an animal.

The invention also provides for the use of the aforementioned compounds for the preparation of medicaments for the treatment or prophylaxis of diseases which are associated with cystein proteases, such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease. In one embodiment the invention relates to the use of compounds as defined above for the preparation of medicaments for the treatment or prophylaxis of osteoporosis, instable angina pectoris or plaque rupture. Such medicaments comprise a compound as defined above.

Another embodiment of the invention relates to a method for the prophylactic and/or therapeutic treatment of disorders in which cathepsin K plays a significant pathological role, such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease, which method comprises administering a compound as defined above to a human being or an animal. A preferred embodiment of the invention relates to a method for the prophylactic and/or therapeutic treatment of osteoporosis, instable angina pectoris or plaque rupture, which method comprises administering a compound as defined above to a human being or an animal.

Synthesis

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1–20; *Rodd's Chemistry of Carbon Compounds*, Elsevier Science Publishers, 1989, Volumes 1–5 and Supplementals; and *Organic Reactions*, Wiley & Sons: New York, 1991, Volumes 140. The following synthetic reaction schemes are merely illustrative of some methods by which the compounds of the present invention may be synthesized, and various modifications to these synthetic reaction schemes may be made and will be suggested to one skilled in the art having referred to the disclosure contained in this Application.

The starting materials and the intermediates of the synthetic reaction schemes may be isolated and purified if desired using conventional techniques, including but not limited to filtration, distillation, crystallization, chromatography, and the like. Such materials may be characterized using conventional means, including physical constants and spectral data.

Unless specified to the contrary, the reactions described herein preferably take place at atmospheric pressure over a temperature range from about −78° C. to about 150° C., more preferably from about 0° C. to about 125° C., and most preferably and conveniently at about room (or ambient) temperature, e.g., about 20° C.

The compounds of the invention may be prepared by several routes using techniques common to peptide chemistry, such as carbodiimide mediated amide formation. Scheme A below illustrates some synthetic routes to the subject compounds starting from a common cycloalkyl amino acid a. Amino and carboxyl protection will generally be employed with the procedures of Scheme A, but for reason of clarity the protection and deprotection steps are omitted from Scheme A. Various Boc-Fmoc- and other protecting group strategies may be used with the procedures of Scheme A and such protecting group strategies are well known to those skilled in the art. Many such protecting group strategies are described by Green et al. In "Protective Groups in Organic Synthesis", 3rd Ed., John Wiley and Sons, New York 1999. Specific protection and deprotection procedures are described in the experimental examples below.

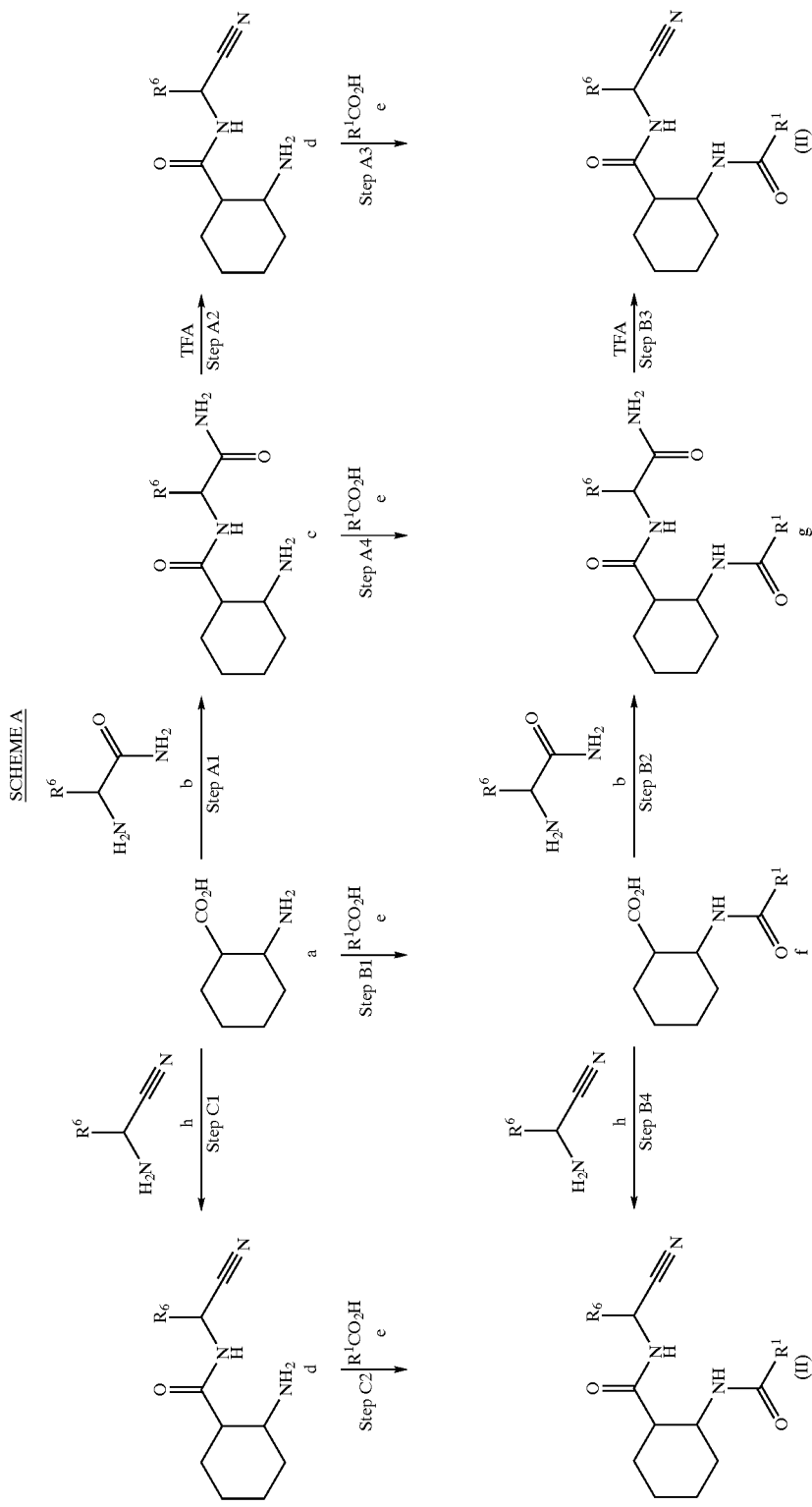

In step A1 of Scheme A, cycloalkyl amino acid a is coupled with an amino amide compound b to form amino amide c. This coupling may be performed in the presence of a carbodiimide under polar solvent conditions. In step A2, the free amide group of compound c is converted to a nitrile by treatment with trifluoroacetic anhydride in the presence of anhydrous amine base to form amide nitrile compound d. In step A3, amide nitrile compound d is coupled to carboxylic acid e using conventional coupling techniques such as those of step A1, to provide a compound of formula (II) as described above. Instead of steps A2 and A3, step A4 may be carried out by treating amino amide c with carboxylic acid e to generate amide compound g, which is used as described below.

Alternatively, cycloalkyl amino acid a may be coupled directly with carboxylic acid e to afford amide acid f. This coupling may be carried out using the conditions like those of step A1 or A3. Amide acid f in turn may be coupled to amino amide b in the manner of step A1, to provide amide compound g. Amide compound g may be treated with trifluoroacetic anhydride as described for Step A2 to provide a compound of formula (II).

In yet another procedure, an alpha aminonitrile compound h may be coupled directly to cycloalkyl amino acid a as shown in step C1 to provide amino nitrile compound d. This coupling may again be carbodiimide driven as described above. Amino nitrile compound d may then be coupled to acid e in step C2 in the same manner as in Step A3 above, to provide a compound of formula (II). Alternatively, the acid amide compound f obtained from step B1 may be coupled with amino nitrile h in step B4 to provide a compound of formula (H). Use of amino nitrile h offers the most direct routes to compounds of formula (II) in Scheme A, and the preparation and use of amino nitrites h is described further below.

The invention also relates to a process comprising the preparation of pharmaceutically acceptable salts and/or pharmaceutically acceptable esters. The formation of the esters and/or salts can be carried out at different stages of the process, e.g. with the compound of formula (I) or (II), or with the corresponding starting materials. The reaction of an amino acid compound a with an amino nitrile f can be carried out by methods known to the person skilled in the art. The reaction can conveniently be carried out by dissolving compound a, compound f, TPIU (O-1,2-Dihydro-2-oxo-1-pyridyl)-N,N,N',N'-tetramethyluronium tetrafluoroborate) and Hünigs base (N-Ethyldiisopropylamine) in acetonitrile and stirring the mixture at room temperature for 6 to 16 hours. The reaction mixture can be concentrated and the product can be obtained by methods known to the person skilled in the art, e.g. by extraction and column chromatography. Alternatively, compound a can be dissolved in $CH_2Cl_2$ and reacted for 6 to 16 hours at room temperature with a compound h in the presence of N-methylmorpholine, HOBT (1-hydroxybenzotriazole hydrate) and a carbodiimide such as EDCI (1-(3-dimethylaminopropyl)-3-ethylcarbodiimide hydrochloride). The product d can be isolated by methods known per se, e.g. by extraction and HPLC.

The reaction of an amino acid a with an amino nitrile b is conveniently carried out by preparing a solution of compound a in $CH_2Cl_2$ and adding a solution of compound h in $CH_2Cl_2$. To this mixture, triethylamine is added and after shaking 6 to 16 hours at room temperature formic acid is added. The product can be isolated and purified by methods known per se, e.g. by evaporation of the solvent and HPLC.

For compounds of formula (I), it is possible to prepare the corresponding esters and/or salts starting from the compounds of formula (I) or an earlier stage, e.g. to form the corresponding salts an/or esters of the corresponding starting materials. The methods to prepare pharmaceutically acceptable salts and/or pharmaceutically acceptable esters as defined before are known in the art.

Cycloalkyl amino acids a are prepared by methods known to the person skilled in the art. Conveniently, a cyclic beta-amino acid such as 2-aminocyclohexanecarboxylic acid of desired stereochemistry (with the acid moiety suitably protected with a removable protecting group) may be linked to the desired benzoic acid substituted with —A—$R^1$ in a manner analogous to the methods described in the examples below. The resulting compound a is isolated by methods known per se, e.g. by extraction and evaporation of the solvent.

Amino nitrile compound h can conveniently be obtained by adding a solution of the corresponding aldehyde in $CH_2Cl_2$ to a solution of $NH_4Cl$ and NaCN in $H_2O$ and MeOH at 0° C. The mixture is stirred and allowed to warm to room temperature. After addition of $NH_3$ solution and completion of the reaction, the resulting amino aldehyde h is isolated and purified by methods known to the person skilled in the art, e.g. by extraction. The corresponding hydrochloride can also be prepared by methods known per se.

Chiral amino nitrile compound h can conveniently be obtained by adding ammonium bicarbonate to a mixed anhydride (prepared from a suitable t-BOC protected amino acid and di-tert-butyl dicarbonate) at 15° C. The reaction mixture is stirred at room temperature for 1–5 h. After completion of the reaction the resulting t-BOC protected amino acid amide is isolated and purified by methods known to the person skilled in the art, e.g. by extraction. The Boc protected amino acid amide and triethylamine are dissolved in THF and trifluoroacetic acid anhydride at 0° C. The mixture is stirred for 2 h at −10° C. After isolation and purification of the resulting intermediate product, e.g. by evaporation of the solvent and flash chromatography, the t-BOC protective group can be cleaved off with HCl in acetic acid to yield the desired amino nitrile h.

Numerous amino amide compounds b, such as alaninamide, phenylalaninamide, leucinamide, tyrosinamide, methioninamide, lysinamide, serinamide, glutamic acid amide, etc., are commercially available or are easily prepared by conversion of the corresponding amino acid to an amide.

The present invention relates to all compounds of formula (I), as prepared by one of the processes described above.

Administration and Pharmaceutical Composition

The invention includes pharmaceutical compositions comprising a compound as defined above and a pharmaceutically acceptable carrier and/or adjuvant or diluent. The compositions are for use in context with diseases associated with cysteine proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and steni placement, abdominal aortic aneurysm formation, inflammation, autoimmune disease, malaria, ocular fundus tissue cytopathy and respiratory disease. In one embodiment the invention relates to pharmaceutical compositions comprising a compound as defined above and a pharmaceutically acceptable carrier and/or adjuvant for use in context with osteoporosis, instable angina pectoris or plaque rupture.

In general, the compounds of the invention will be administered in a therapeutically effective amount by any of the accepted modes of administration for agents that serve similar utilities. Suitable dosage ranges are typically 1–500 mg daily, preferably 1–100 mg daily, and most preferably 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi- dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 9th edition, Easton, Pa. Representative pharmaceutical formulations containing a compound of the present invention are described in the following examples.

EXAMPLES

The following examples and preparations are provided to enable those skilled in the art to more clearly understand and to practice the present invention. They should not be considered as limiting the scope of the invention, but merely as being illustrative and representative thereof. The starting materials used in the examples and preparations are either commercially available or can be obtained by methods known in the art (e.g. from:. DE 26 24 290; WO 98/0354; Chem. Pharm. Bull., 38(2), 350–354 (1990), Chiral Synthon Obtained with Pig Liver Esterase: Introduction of Chiral Centers into Cyclohexene Skeleton; J. Chem. Soc. Perkin Trans., 1, 1411–1415 (1994), Asymmetric Synthesis of (−)-(1R,2S)-Cispentacin and Related cis- and trans-2-Amino Cyclopentane- and Cyclohexane-1-carboxylic Acids) or can be obtained by methods analogous to the methods described before. Table 2 provides a list of acronyms for reagents and solvents used in the following examples.

| | Abbreviations/Acronyms |
|---|---|
| Burgess Reagent | (Methoxycarbonylsulfamoyl)triethylammonium hydroxide, inner salt |
| DCM, CH2Cl2 | Dichloromethane |
| DIC | 2-Dimethylaminoisopropyl chloride hydrochloride |
| DIPEA | N,N-Diisopropylethylamine |
| DMAP | 4-Dimethylaminopyridine |
| DMF | N,N-Dimethylformamide |
| EDCl | 1-(3-Dimethylaminopropyl)-3-ethylcarbodiimide hydrochloride |
| HOBT | 1-Hydroxybenzotriazole hydrate |
| MEOH | Methanol |
| NMM | N-Methylmorpholine |
| NMP | 1-Methyl-2-pyrrolidinone |
| TBS | tert-Butyldimethylsilyl protecting group |
| TFA | Trifluoroacetic acid |
| THF | Tetrahydrofuran |

Example 1

Example of Method A in Tables

N-[(1S,2R)-2-({[cyano(cyclopropyl)methyl]amino}carbonyl)cyclohexyl]-1H-indole-2-carboxamide

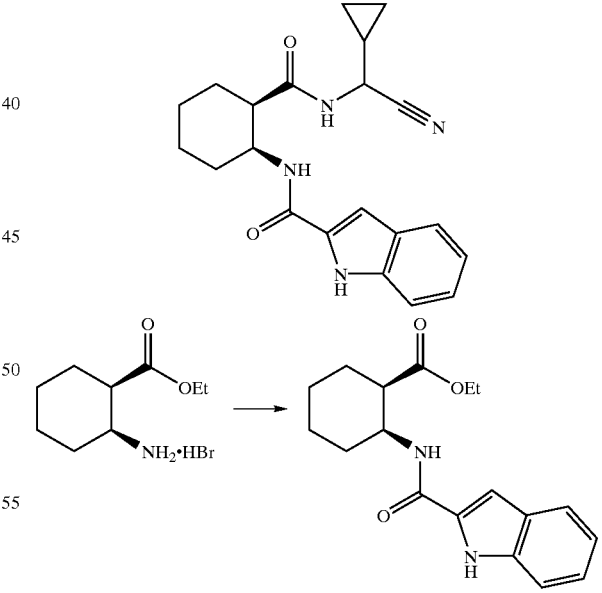

Step 1

To 300 mg (1.19 mmol) of ethyl (1R,2S)-2-aminocyclohexanecarboxylate HBr 10 salt (Xu, Daquiang et al., *Tetrahedron: Asymmetry* (1988), 9(10) 1635) dissolved in 8 mL DMF was added 192 mg (1.19 mmol) of indole-2-carboxylic acid, 228 mg (1.19 mmol) of EDCI, 161 mg (1.19 mmol) of HOBT and 0.458 mL (4.16 mmol) of N-methylmorpholine. The reaction mixture was stirred at room temperature overnight, partitioned between ethyl acetate and water, dried over magnesium sulfate and concentrated to provide ethyl (1R,2S)-2-[(1H-indol-2-ylcarbonyl)amino]cyclohexane-carboxylate.

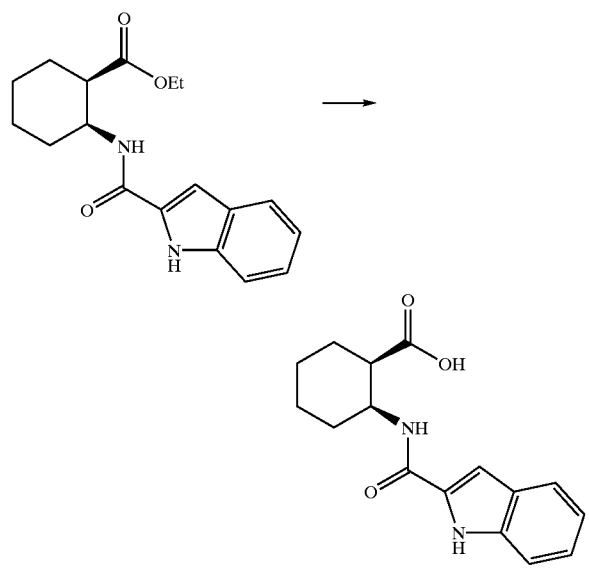

Step 2

The crude reaction mixture was dissolved in 8 mL methanol, and 110 mg (2.62 mmol) of lithium hydroxide dissolved in 2 mL water was added. The reaction mixture was stirred overnight, partitioned between dichloromethane and 1 N HCl, dried over magnesium sulfate and concentrated to provide 220 mg of (1R,2S)-2-[(1H-indol-2-ylcarbonyl)amino]cyclohexanecarboxylic acid, pure by $^1$H NMR. (66% over two steps).

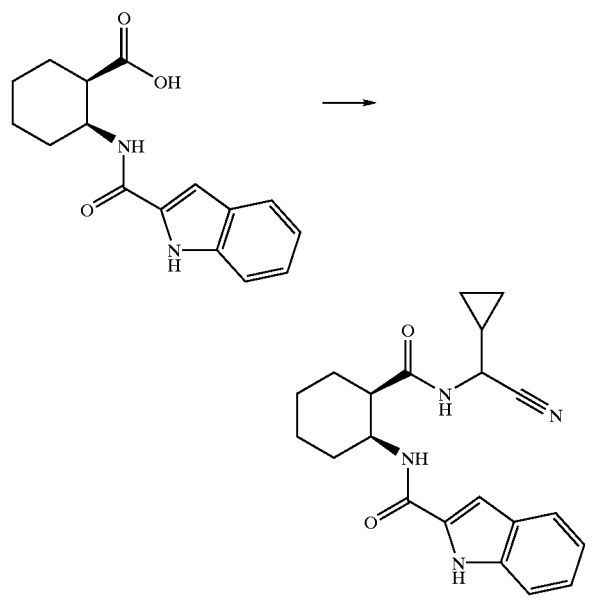

Step 3

To 110 mg (0.38 mmol) of the acid above dissolved in 2 mL DMF was added 50 mg (0.38 mmol) R,S-amino (cyclopropyl)acetonitrile, 73 mg (0.38 mmol) of EDCI, 51 mg (0.38 mmol) of HOBT and 0.146 mL (1.33 mmol) of N-methylmorpholine. The reaction mixture was stirred at room temperature overnight, partitioned between ethyl acetate and water, dried over magnesium sulfate and concentrated. Column chromatography, eluting with 10% acetone in dichloromethane, provided 67 mg of the title compound N-[(1S,2R)-2-({[cyano(cyclopropyl)methyl]amino}carbonyl)cyclohexyl]-1H-indole-2-carboxamide, 93% pure by HPLC. (48%).

Example 2

Example of Method B-1 in Tables

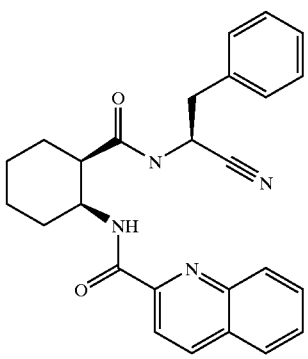

Step 1

To 190 mg (0.75 mmol) of ethyl (1R,2S)-2-aminocyclohexanecarboxylate HBr salt dissolved in 5 ml DMF was added 140 mg (0.80 mmol) of quinaldic acid, 152 mg (0.79 mmol) of EDCI, 108 mg (0.80 mmol) of HOBT and 0.26 ml (2.37 mmol) of N-methylmorpholine. The reaction mixture was stirred at room temperature overnight, partitioned between ethyl acetate and water, dried over magnesium sulfate and concentrated to provide 290 mg of ethyl (1R,2S)-2-[(1H-quino-2-ylcarbonyl)amino]cyclohexanecarboxylate (crude).

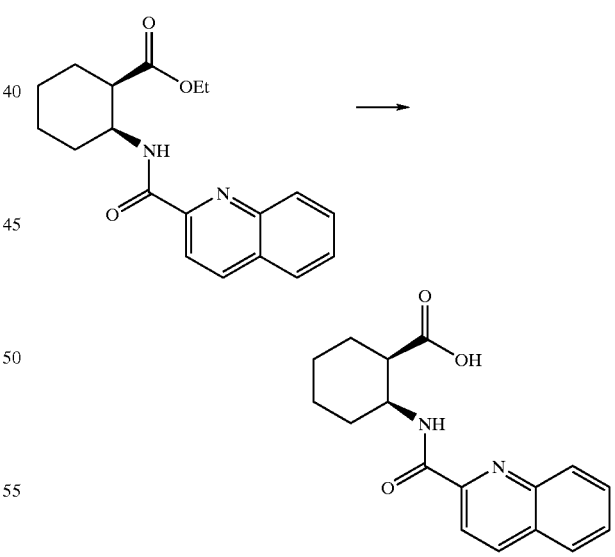

Step 2

The crude reaction material above was dissolved in 8 ml THF, and 120 mg (2.86 mmol) of lithium hydroxide dissolved in 2 ml water was added. The reaction mixture was heated to 60° C. and stirred for overnight, partitioned between dichloromethane and 1 N HCl, dried over magnesium sulfate and concentrated to provide 260 mg of (1R,2S)-2-[(1H-quino-2-ylcarbonyl)amino]cyclohexanecarboxylic acid.

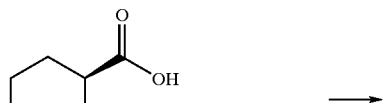

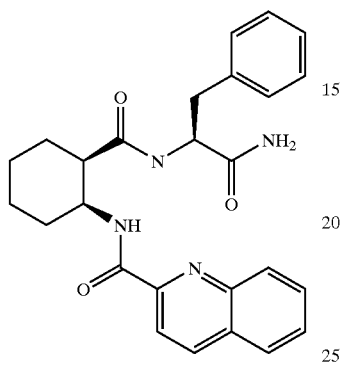

Step 3

To 260 mg (0.87 mmol) of the acid above dissolved in 5 ml DMF was added 140 mg (0.85 mmol) L-phenylalaninamide, 120 mg (0.88 mmol) of HOBT, 170 mg (0.88 mmol) of EDCI and 0.34 ml (3.06 mmol) of N-methylmorpholine. The reaction mixture was stirred at room temperature overnight, partitioned between ethyl acetate and water, dried over magnesium sulfate and concentrated to give the 388 mg of the crude product as a white solid.

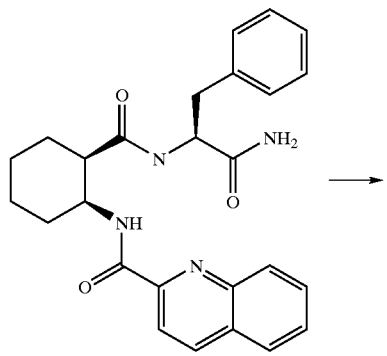

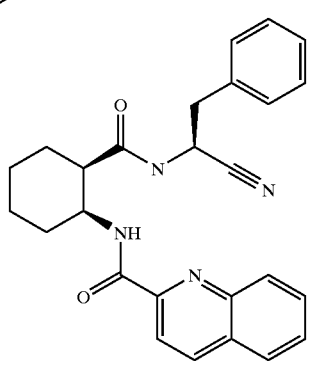

Step 4

To the solution of 388 mg (0.87 mmol) of the crude product from above in dichloromethane (10 ml) was added Burgess Reagent 210 mg (0.88 mmol). The mixture was stirred at room temperature for overnight. After the dichloromethane was removed, the residue was dissolved in 2 ml MeOH and purified with preparative thin layer chromatography (hexane:ethyl acetate 1:1) to give the product as a white foam: 88 mg (0.21 mmol). 27.5% yield.

Example 3

Example of Method B-2 in Tables

N-[(1S,2R)-2-({[(S)-cyano(cyclopropyl)methyl]amino}carbonyl)cyclohexyl-1-methyl-1H-indole-2-carboxamide

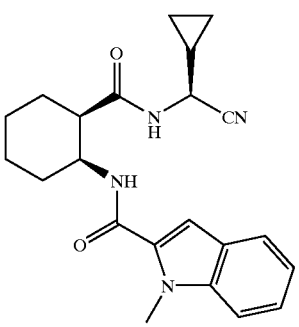

This example illustrates the preparation of N-[(1S,2R)-2-({[(S)-cyano(cyclopropyl)methyl]amino}carbonyl)cyclohexyl]-1-methyl-1H-indole-2-carboxamide starting with ethyl cis-2-amino-1-cyclohexanecarboxylate and (S)-cyclopropylglycinamide or alternatively with ethyl cis-2-amino-1-cyclohexanecarboxylate and (S)-cyclopropylglycine nitrile.

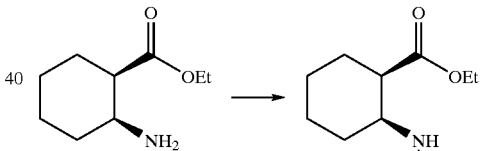

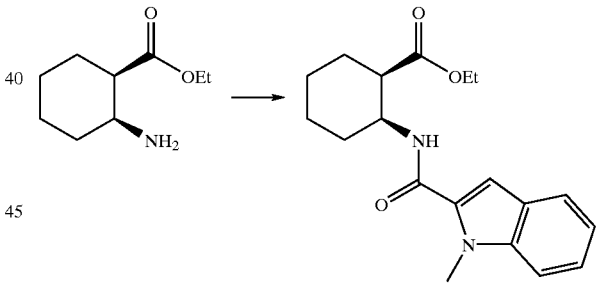

Step 1

To a 0° C. solution of ethyl cis-2-amino-1-cyclohexanecarboxylate HBr salt (9.03 g, 35.8 mmol), 1-methylindole-2-carboxylic acid (6.18 g, 35.3 mmol), HOBT (5.45 g, 40.3 mmol), and EDCI.HCl (7.45 g, 38.9 mmol) in 70 mL of anhydrous DMF was added N-methylmorpholine (7.8 mL, 71 mmol). The reaction mixture was stirred for 24 h at room temperature. The reaction mixture was cooled in an ice bath and treated with 140 mL of water. 140 mL of ethyl acetate was added to the resulting yellow suspension and stirred until the solids dissolved. An additional 140 mL of ethyl acetate was added and the organic layer was separated. The organic layer was washed with two 280 mL portions of 0.5 M HCl, 280 mL of brine, then dried over sodium sulfate, filtered and concentrated to give a crude yellow solid. Purification by column chromatography (30:70, ethyl acetate:hexanes) gave 10.9 g of the product as a pale green-tinted solid. Yield: 90%, MS: 329 (M+H$^+$), mp=98.1–99.0° C.

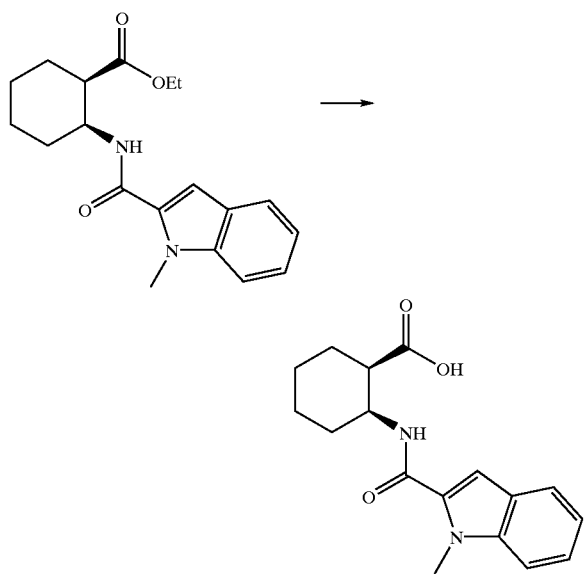

Step 2

To a 0° C. solution of the ester (10.9 g, 31.8 mmol) in 100 mL of THF was added a solution of lithium hydroxide hydrate (5.29 g, 126 mmol) in 100 mL of water. The reaction mixture stirred at room temperature for 16 hours, then slowly poured into a flask containing 150 mL of a 1M HCl solution and extracted the resulting suspension with 200 mL of ethyl acetate. The organic layer was separated and washed with 200 mL of brine, dried over sodium sulfate, filtered and concentrated to give 9.49 g of the product as a white solid. Yield: 100%, MS: 301 (M+H$^+$), mp=196.0–198.9° C.

Step 3

To a 0° C. solution of the carboxylic acid (10.23 g, 34.1 mmol), (S)-cyclopropylglycinamide (4.08 g, 35.7 mmol), HOBT (6.90 g, 51.1 mmol), and EDCI HCl (9.79 g, 51.1 mmol) in 60 mL of anhydrous DMF was added N-methylmorpholine (3.7 mL, 37 mmol). The reaction mixture was allowed to warm to room temperature and stirred for 24 hours. The reaction mixture was cooled in an ice bath and treated with 100 mL of water. The suspension was stirred for 1 hour. The precipitate was filtered and washed with copious amounts of 1M HCl followed by copious amounts of water. The precipitate was dried in vacuo to give a crude off-white solid. Purification by silica gel column chromatography (30:70, ethyl acetate:hexanes) gave 2.00 g of the amide as a white solid. Yield: 84%, MS: 397 (M+H$^+$), mp=242.5–245.6° C.

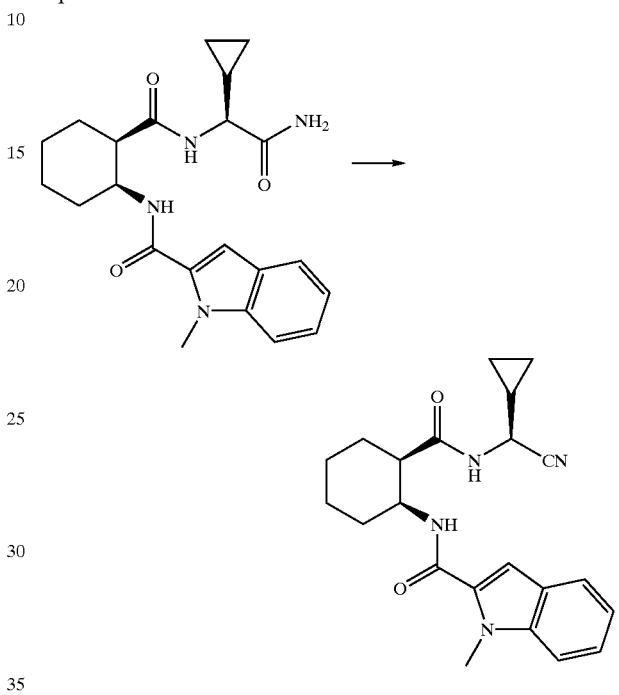

Step 4

To a 0° C. solution of the amide (10.0 g, 25.2 mmol) and anhydrous pyridine (200 mL) was added trifluoroacetic anhydride (5.34 ml, 37.8 mmol) dropwise. The reaction mixture was stirred for 15 minutes at 0° C., then 250 mL of 1M aqueous HCl was added slowly. Ethyl acetate (200 mL) was added and the aqueous layer was discarded. Another 200 mL of ethyl acetate was added and the organic layer was washed with 1M aqueous HCl until the aqueous layer remained acidic. The organic layer was then washed with three portions of water, one portion of brine, dried with sodium sulfate, and concentrated to give 9.80 g of a crude solid. Initial purification by column chromatography (30:70, ethyl acetate:hexanes) gave the product (5.68 g, 59%) as an off-white solid. Recrystallization (83:17, diethyl ether:chloroform) gave 4.63 g of the product as a white solid. Yield: 48%, MS: 379 (M+H$^+$), mp=166.0–168.5° C.

Alternative Synthesis

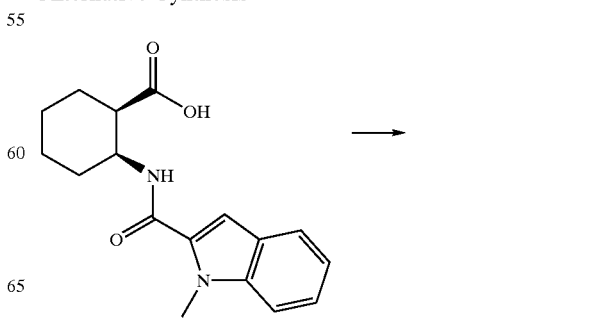

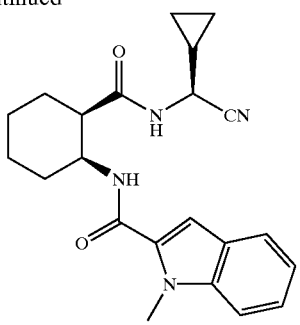

To a solution of the carboxylic acid (514 mg, 1.71 mmol), (S)-cyclopropylglycine nitrile (300 mg, 2.26 mmol), HOBT (255 mg, 1.89 mmol) and EDCI hydrochloride (366 mg, 1.91 mmol) in anhydrous DMF (8.0 mL) was added N-methylmorpholine (0.80 mL, 7.3 mmol). The reaction mixture was stirred at room temperature for 4 h, then 40 mL of water was added and extracted with 40 mL of ethyl acetate. The organic layer was washed with two 40 mL portions of 1 M HCl and 40 mL of brine, dried over sodium sulfate, filtered and concentrated to give a crude white foam. Purification by column chromatography (40–50:60–50, ethyl acetate:hexanes) gave the product (341 mg, 53%) as a white solid as an 83:17 (S:R ratio at the glycine stereocenter, as determined by $^1$H NMR spectroscopy) mixture of diastereomers.

Synthesis of (S)-cyclopropylglycine amide.

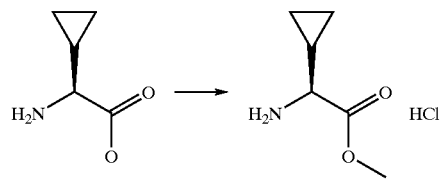

To a 0° C. solution of thionyl chloride (7.6 mL, 104 mmol) in anhydrous methanol (750 mL) was added (S)-cyclopropylglycine (10.0 g, 86.9 mmol, Eastman Chemical Company, Kingsport, Tenn.). The reaction mixture was allowed to warm to room temperature and then refluxed for 4 hrs, then cooled to room temperature and concentrated in vacuo to give a crude solid. The solids were washed with acetone to give 8.94 g of the product as a white solid. Yield: 62%, MS: 130 (M+H$^+$), mp=134.0–135.9° C.

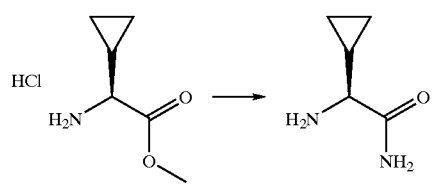

To a 0° C. solution of ammonia in methanol (100 mL, 7M) in a bomb was added (S)-cyclopropylglycine ethyl ester HCl (5.04 g, 30.4 mmol). The bomb was sealed and placed in a 70° C. oil bath for two days. The reaction mixture was cooled to room temperature and concentrated until a suspension formed. The suspension was filtered and the collected solids were washed with methanol:acetone (1:1). Another crop of solids was obtained from the mother liquor in this manner, and the combined solids were dried to give 3.52 g of the product as a white powder. Yield: 100%, MS: 115 (M+H$^+$), mp=225.0–231.0° C., $[\alpha]_D^{25}$=+63.0 (1.00, 1M HCl).

Synthesis of (S)-cyclopropylglycine nitrile

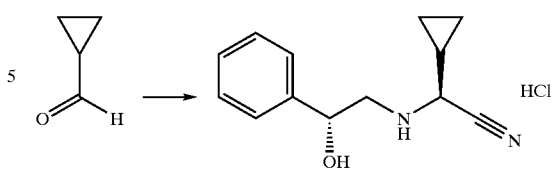

To a solution of cyclopropylcarboxaldehyde (10.27 g, 146.5 mmol) in 500 mL of anhydrous methylene chloride was added (R)-phenylglycinol (20.06 g, 146.2 mmol). The reaction mixture was stirred at room temperature for 2 h, then cooled to −26° C. with a dry ice/acetone bath. Trimethylsilyl cyanide (39.0 mL, 292 mmol) was slowly added via syringe keeping the reaction temperature below −23° C. The reaction mixture was allowed to warm to room temperature and stirred overnight. 100 mL of methanol and 150 mL of 1M HCl were added and the reaction mixture was stirred for 1 h. The reaction mixture was neutralized with 150 mL of 1M sodium hydroxide, the organic layer separated and washed with 400 mL of water, dried over sodium sulfate, filtered and concentrated to give a yellow liquid. The product was isolated as the monohydrochloride salt by treating the free amine in methylene chloride with 1M HCl in ether to give 34.24 g of a white solid as an 83:17 (S:R ratio at the glycine stereocenter, as determined by $^1$H NMR spectroscopy) mixture of diastereomers. Yield: 93%, MS: 217 (M+H$^+$), mp=106.0–108.1° C.

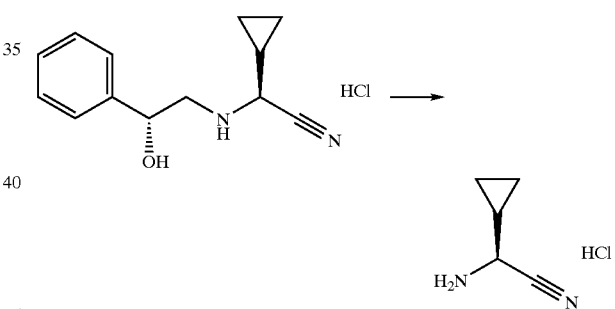

To a 0° C. solution of the glycinol adduct (5.00 g, 19.8 mmol) in 70 mL of methanol and 35 mL of methylene chloride was added lead tetracetate (9.15 g, 20.6 mmol) portionwise over a 1 minute period. The reaction mixture was stirred for 30 minutes at 0° C. and the resulting suspension was filtered through a pad of celite. The collected solids were washed with 2×100 mL of methylene chloride and the organic layer was separated, washed with 200 mL of water, dried over sodium sulfate, filtered and concentrated to the imine (3.55 g, 97%) as a clear liquid. The imine was directly hydrolyzed to give cyclopropylglycine nitrile by dissolving in ether and treating with 1M HCl in an ice bath. The hydrolysis was followed by TLC by monitoring for the disappearance of the imine (Rf=0.43, 10:90 EtOAc:hexanes). After. complete hydrolysis, the aqueous layer was separated, washed with ether, then carefully concentrated on the rotary evaporator (30–42° C. water bath) and concentrated in vacuo to give the product as a hygroscopic white solid.

Example 4

Example of Method B-3 in Tables

N-[(1S,2R)-2-({[(1R)-1-cyano-2-hydroxyethyl]amino}carbonyl)cyclohexyl]-methyl-1H-indole-2-carboxamide

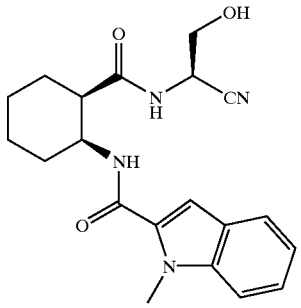

This example illustrates the preparation of N-[(1S,2R)-2-({[(1R)-1-cyano-2-hydroxyethyl]amino}carbonyl)cyclohexyl]-1-methyl-1H-indole-2-carboxamide starting with the amide, 4a, made following a procedure analogous to Example 2.

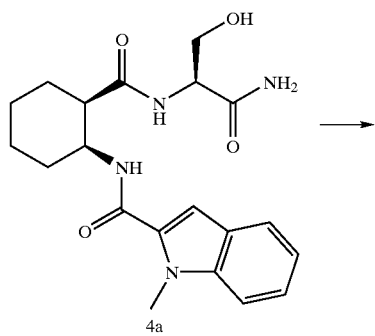

4a

To a solution of the hydroxy amide (231 mg, 0.598 mmol) in anhydrous DMF (4 mL) were added tert-butyldimethylsilyl chloride (178 mg, 1.18 mmol) and imidazole (87 mg, 1.28 mmol). The reaction mixture was stirred at room temp for 16 h. Water (20 mL) and ethyl acetate (20 mL) were added and the aqueous layer was discarded. The organic layer was washed with two portions of water, dried with sodium sulfate, and concentrated to give a crude liquid. Purification by column chromatography (5:95, methanol:dichloromethane) gave 250 mg of the product as a clear liquid. Yield: 83%.

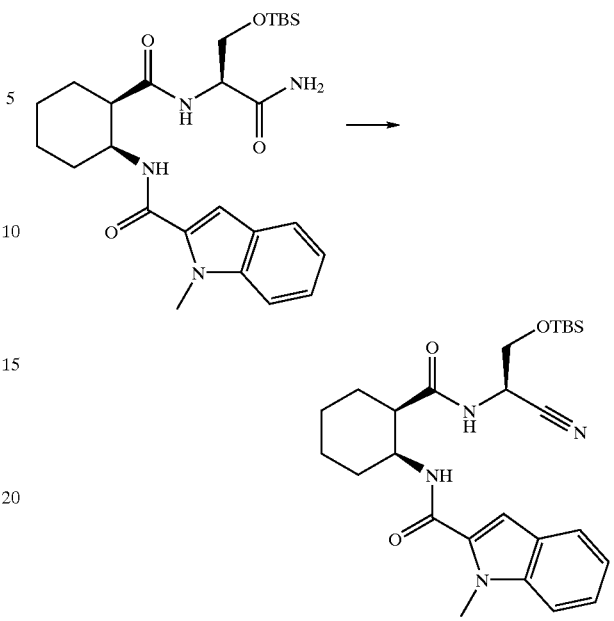

To a 0° C. solution of the amide (0.25 g, 0.50 mmol) in anhydrous pyridine (6 mL) was added trifluoroacetic anhydride (0.20 mL, 1.4 mmol) dropwise. The resulting yellow reaction mixture was stirred at 0° C. for 10 min, then 20 ml of 1M HCl solution was added. To the resulting milky suspension was added 25 mL of ethyl acetate and the aqueous layer was discarded. The organic layer was washed with two 20 mL portions of 1M HCl and 20 mL of brine, dried over sodium sulfate, filtered and concentrated to give a yellow liquid. Purification by column chromatography (20–40:80–60, ethyl acetate:hexanes) gave 127 mg of the product as a white foam solid. Yield: 53%, MS: 483.3 (M+H$^+$).

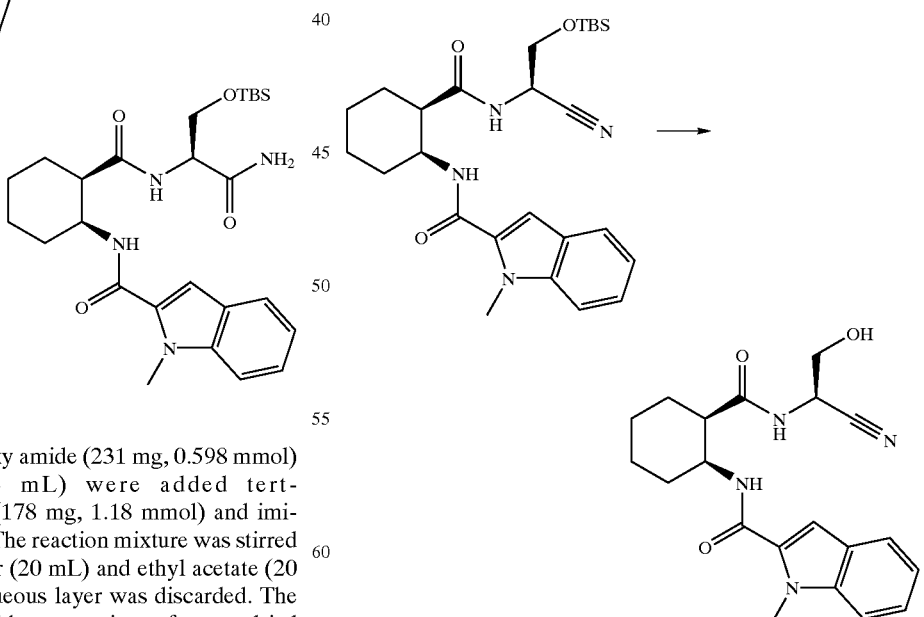

To a 0° C. solution of the TBS-ether (117 mg, 0.242 mmol) in 6 mL of anhydrous THF was added a 1M solution of tert-butylammonium fluoride (0.30 mL, 0.30 mmol) in THF. The reaction mixture was warmed to room temp, concentrated in vacuo and purified by column chromatography (5:95, methanol:dichloromethane) to give 86 mg of the product as a white foam solid. Yield: 96%, MS: 369 (M+H+), mp=78.4–79.0° C.

Example 5

Example of Method C in Tables

N-[2-({[(1S)-1-cyano-2-(4-nitrophenyl)ethyl]amino}carbonyl)cyclohexyl]quinoline-2-carboxamide trifluoroacetate

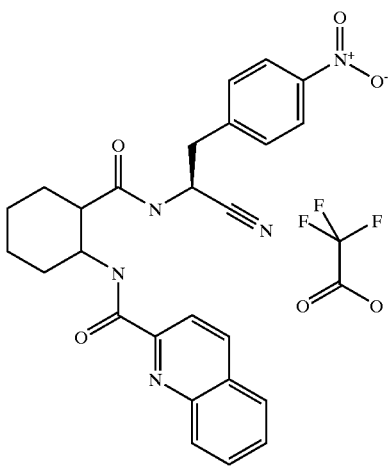

To 5.033 g of 9H-fluoren-9-ylmethoxy-2,4-dimethoxyphenyl(4-hydroxybenzyl)carbamate Rink polystyrene resin in a large glass bubbler was added 20% piperidine/DMF (80 mL). The reaction was bubbled with nitrogen for 30 minutes, filtered, and washed three times with 80 mL of $CH_2Cl_2$, once with MeOH and again with $CH_2Cl_2$. To the resin was added 3 eq DIC (1.4 mL), 0.05 eq. DMAP (1.3 mL of a 0.116 M solution in THF), 3 eq. N-[(9H-fluoren-9-ylmethoxy)carbonyl]-4-nitrophenylalanine (3.9 gr). The resin was then suspended in $CH_2Cl_2$ (80 mL) and bubbled with nitrogen overnight. The reaction was filtered and washed 3 times with 80 mL with $CH_2Cl_2$ then with MeOH and again with $CH_2Cl_2$. To the resin was added 80 mL of 20% piperidine/DMF. The reaction was bubbled with nitrogen for 30 min, filtered and washed three times with 80 mL of $CH_2Cl_2$ then with MeOH and again with $CH_2Cl_2$. To the resin was added 3 eq EDCI (1.7 gr), 1 eq. HOBT (0.41 gr), and 3 eq. (1R,2S)-2-([{2-[(1Z)-prop-1-enyl]-3-vinyl-1H-inden-1-yl]methoxy)carbonyl]amino}cyclohexanecarboxylic acid (3.3 gr). The resin was then suspended in NMP (80 mL) and bubbled overnight. The reaction was then filtered and washed three times with 80 mL of $CH_2Cl_2$, once with MeOH and again with $CH_2Cl_2$ and allowed to dry in a vacuum dessicator.

To 250 mg of this resin in a solid phase extraction vial was added 20% piperidine/DMF (2.5 mL). The reaction was allowed to sit for 30 minutes, filtered and washed three times with 4 mL with $CH_2Cl_2$, once with MeOH and again with $CH_2Cl_2$. To the resin was added 3 eq DIC (56 uL), 0.05 eq. DMAP (52 uL of a 0.116 M soln in THF), 3 eq. quinaldic acid (62.3 mg). The resin was then suspended in $CH_2Cl_2$ (2.5 mL) and rotated overnight. The reaction was then filtered and washed three times with 4 mL of $CH_2Cl_2$, once with MeOH and again with $CH_2Cl_2$. The resin was then treated with 10% TFA/$CH_2Cl_2$ (2.5 ml) for 30 min, filtered and washed twice with 2.5 mL of $CH_2Cl_2$. The filtrate was evaporated on a Speed-Vac and dissolved in $CH_2Cl_2$ (2.5 mL). Burgess reagent (2 eq, 57 mg) was added and the reaction stirred overnight. The reaction was then evaporated on a Speed-Vac and purified by reverse phase high pressure liquid chromatography to yield 1.8 mg of a 95% pure sample.

Example 6

Example of Method D in Tables

N-(cyanomethyl)-2-(quinolin-8-ylamino)cyclohexanecarboxamide

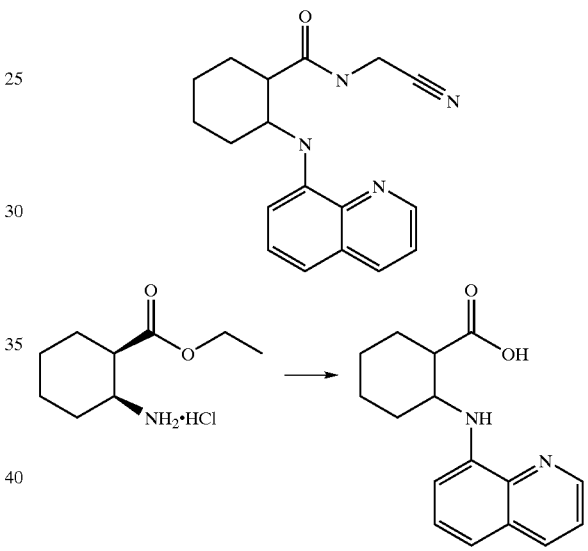

Step 1

To an oven-dried Schlenk flask that was evacuated and backfilled with argon was added 726 mg (3.68 mmol) of ethyl cis-2-amino-1-cyclohexanecarboxylate HCl salt, 56 mg (0.06 mmol, 2 mol % Pd) of $Pd_2(dba)_3$, 77 mg (0.12 mmol, 4 mol %) of rac-BINAP, 881 mg (9.17 mmol) of sodium tert-butoxide, 500 mg (3.06 mmol) of 8-chloroquinoline, and 7.5 mL of toluene. The flask was sealed with a glass stopper and an argon balloon replacing the source. The reaction mixture was then heated to 90° C. and stirred at that temperature for 17 hours. The mixture was allowed to cool to room temperature, taken up in diethyl ether (35 mL), washed three times with saturated brine (30 mL), dried over magnesium sulfate, and concentrated to provide the crude reaction mixture. The crude mixture was re-dissolved in ethyl acetate, partitioned between ethyl acetate and 1N HCl, dried over magnesium sulfate and concentrated to provide 125 mg (15%) of 2-(quinolin-8-ylamino)cyclohexanecarboxylic acid with both cis and trans isomers in 1:1 ratio. Confirmed by $^1H$ NMR.

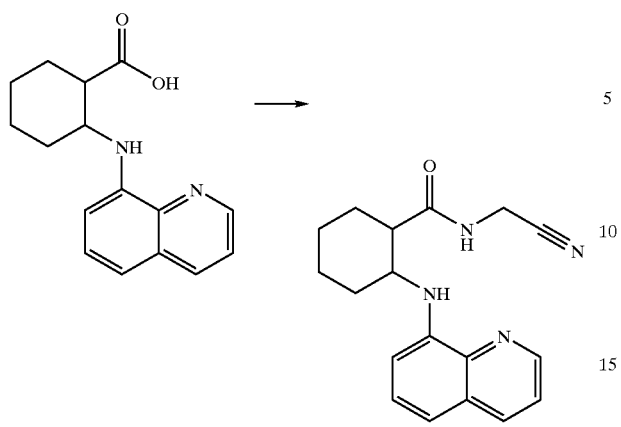

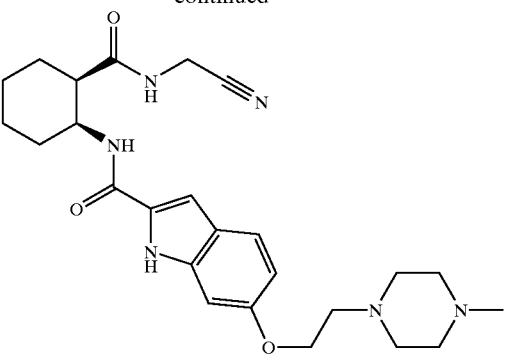

Step 2

To 50 mg (0.19 mmol) of the acid above dissolved in 1.3 mL of DMF was added 18 mg (0.19 mmol) of aminoacetonitrile HCl salt, 37 mg (0.19 mmol) of EDCI, 26 mg (0.19 mmol) of HOBT, and 0.09 mL (0.78 mmol) of N-methylmorpholine. The reaction mixture was stirred at room temperature overnight, partitioned between ethyl acetate and water, dried over magnesium sulfate and concentrated. Column chromatography, eluting with solvent system hexane:ethyl acetate (7:3), and then with solvent system hexane:ethyl acetate (1:1), provided 15 mg (25%) of the corresponding cis/trans product mixture, which is the title compound of N-(cyanomethyl)-2-(quinolin-8-ylamino) cyclohexanecarboxamide, 99% pure by HPLC.

Example 7

N-((1S,2R)-2-{[(cyanomethyl)amino] carbonyl}cylohexyl)-6-[2-(4-methylpiperazin-1-yl) ethoxy]-1H-indole-2-carboxamide

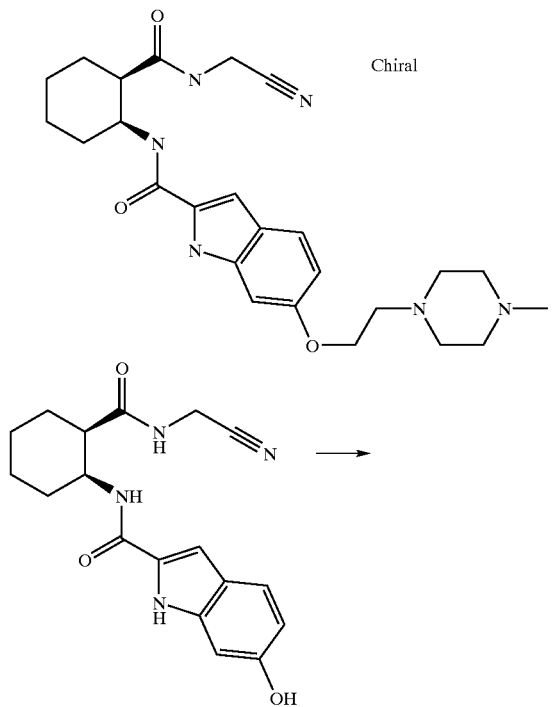

To 85 mg (0.25 mM) 6-Hydroxy-1H-indole-2-carboxylic acid [2-(cyanomethyl-carbamoyl)-cyclohexyl]-amide in 5 ml dichloromethane at 0° C. was added 144 mg (1 mM) 2-(4-Methyl-piperazin-1-yl)ethanol, 262 mg (1 mM) triphenylphosphine and 131 mg (0.75 mM) DEAD. After several hours the mixture was allowed to warm to room temperature and stir overnight. The reaction mixture was purified directly on a preparative TLC plate and eluted with 10% methanol/dichloromethane. The product was then partitioned between 1 M HCl and ethyl acetate, the aqueous layer was neutralized and extracted with ethyl acetate, dried over magnesium sulfate and stripped to give 18.9 mg 6-[2-(4-Methylpiperazin-1-yl)-ethoxy]-1H-indole-2-carboxylic acid [2-(cyanomethyl-carbamoyl)-cyclohexyl]-amide.

Similarly prepared were:

N-((1S,2R)-2-{[(cyanomethyl)amino]carbonyl}cyclohexyl)-1-methyl-6-(2-morpholin-4-ylethoxy)-1H-indole-2-carboxamide using Mitsunobu coupling with 2-Morpholinyl-ethanol.

N-((1S,2R)-2-{[(cyanomethyl)amino]carbonyl}cyclohexyl)-6-(2-morpholin-4-ylethoxy)-1H-indole-2-carboxamide using Mitsunobu coupling with 2-morpholin-4-yl-ethanol.

Example 8

Allyl 2-({[(1S,2R)-2-({[(S)-cyano(cyclopropyl) methyl]amino}carbonyl)cyclohexyl] amino}carbonyl)-1H-indol-6-ylcarbamate

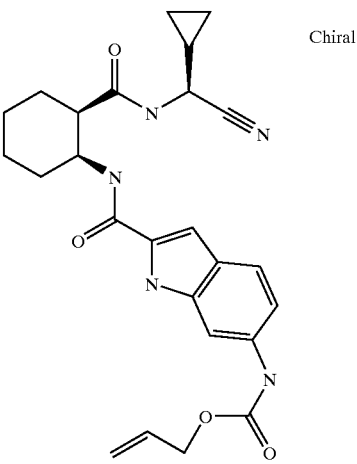

To 2.0 g (8.96 mmol) of 4-aminobenzylalcohol dissolved in 25 mL of dichloromethane and 1.81 mL (2.5 eq., 22.4 mmol) of pyridine at 0° C. was added 950 □L (8.96 mmol) of allyl chloroformate. The mixture was stirred at 0° C. for 1 h, partitioned between dichloromethane and water, dried over magnesium sulfate and concentrated. The product was purified using column chromatography, eluting with 40% ethyl acetate/hexane, to provide 2.154 g allyloxycarbonyl-protected 4-aminobenzyl alcohol, as a colorless oil.

To 2.154 g (10.39 mmol) of the above compound dissolved in 40 mL dichloromethane at 0° C. was added 4.41 g (10.39 mmol) Dess-Martin periodinane. The mixture was stirred at 0° C. for 1 h, partitioned between dichloromethane and water, dried over magnesium sulfate and concentrated. The product was purified using column chromatography, eluting with 40% ethyl acetate/hexane, to provide 1.726 g of allyl 4-formylphenylcarbamate, as a colorless oil.

To a solution of 689 mg (10.13 mmol) sodium ethoxide in 5 mL absolute ethanol at 0° C. was added a solution of 500 mg (2.44 mmol) of allyl 4-formylphenylcarbamate and 1.25 g (9.75 mmol) ethylazidoacetate dissolved in 5 mL absolute ethanol and 1 mL tetrahydrofuran dropwise over 5 minutes. The mixture was stirred at 0° C. for 1.5 h, then partitioned between ethyl acetate and 1 N HCl until neutral. The organic phase was dried over magnesium sulfate, concentrated and purified by column chromatography, eluting with 25% ethyl acetate/hexane to provide 385 mg of ethyl (2E)-3-(4-{[(allyloxy)carbonyl]amino}phenyl)-2-azidoprop-2-enoate as a yellow solid.

385 mg (1.217 mmol) of ethyl (2E)-3-(4-{[(allyloxy)carbonyl]amino}phenyl)-2-azidoprop-2-enoate was dissolved in 25 mL toluene (~0.05M solution). The mixture was heated to 80° C. for 2 h, cooled, and concentrated. Purification by column chromatography, eluting with 25% ethyl acetate/hexane provided 134 mg of ethyl 6-{[(allyloxy)carbonyl]amino}-1H-indole-2-carboxylate as a yellow solid.

To 134 mg (0.465 mmol) of ethyl 6{[(allyloxy)carbonyl]amino}-1H-indole-2-carboxylate dissolved in 5 mL methanol was added 43 mg (1.023 mmol) lithium hydroxide dissolved in 1 mL water. The mixture was stirred at room temperature overnight, partitioned between ethyl acetate and 1 N HCl until neutral, dried over magnesium sulfate and concentrated to provide 118 mg 6-{[(allyloxy)carbonyl]amino}-1H-indole-2-carboxylic acid, as a colorless solid.

Following the procedure of Example 1 but replacing indole-2-carboxylic acid with 6-{[(allyloxy)carbonyl]amino}-1H-indole-2-carboxylic acid gave the title compound as a colorless solid.

Example 9

N-[(1S,2R)-2-({[(S)-cyano(cyclopropyl)methyl]amino}carbonyl)cyclohexyl]-6-[(methylsulfonyl)amino]-1H-indole-2-carboxamide

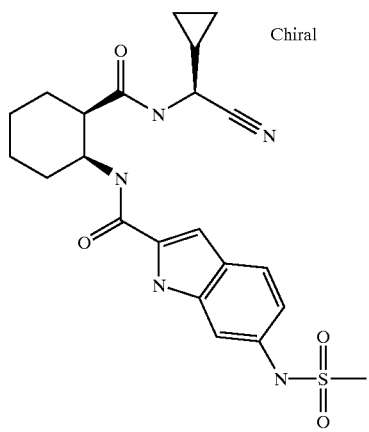

To 4.97 g (40.35 mmol) of 4-aminobenzylalcohol dissolved in 30 mL of was added 9.69 g (44.39 mmol) of di-tert-butyl dicarbonate. The mixture was stirred at room temperature overnight, partitioned between ethyl acetate and water, dried over magnesium sulfate and concentrated to provide 8.4 g t-butyloxycarbonyl-protected 4-aminobenzyl alcohol, as a colorless solid.

To 4.79 g (21.65 mmol) of the above compound dissolved in 50 mL dichloromethane was added 9.19 g (21.65 mmol) Dess-Martin periodinane. The mixture was stirred for 2 h, partitioned between dichloromethane and water, dried over magnesium sulfate and concentrated. The product was purified using column chromatography, eluting with 25% ethyl acetate/hexane, to provide 3.0 g of tert-butyl 4-formylphenylcarbamate as a colorless solid.

To a solution 13.45 mmol of sodium methoxide in 6 mL absolute methanol at 0° C. was added a solution of 717 mg (3.24 mmol) of tert-butyl 4-formylphenylcarbamate and 1.49 g (12.96 mmol) methylazidoacetate dissolved in 6 mL absolute methanol dropwise over 5 minutes. The mixture was stirred at 0° C. for 6 h, then partitioned between ethyl acetate and acetic acid until neutral. The organic phase was dried over magnesium sulfate, concentrated and purified by column chromatography, eluting with 25% ethyl acetate/hexane to provide 551 mg of methyl (2E)-2-azido-3-{4-[(tert-butoxycarbonyl)amino]phenyl}prop-2-enoate as a yellow solid.

851 mg (2.67 mmol) of methyl (2E)-2-azido-3-{4-[(tert-butoxycarbonyl)amino]phenyl}prop-2-enoate was dissolved in 40 mL toluene. The mixture was heated to 80° C. for 2 h, cooled, and concentrated. Purification by column chromatography, eluting with 25% ethyl acetate/hexane provided 551 mg of methyl 6-[(tert-butoxycarbonyl)amino]-1H-indole-2-carboxylate as a yellow solid.

To 551 mg methyl 6-[(tert-butoxycarbonyl)amino]-1H-indole-2-carboxylate dissolved in 15 mL dichloromethane was added 5 mL trifluoroacetic anhydride, and the mixture stirred at room temperature for 1.5 h. P The mixture was partitioned between dichloromethane and 1 N sodium hydroxide until neutral, dried over magnesium sulfate and concentrated. Obtained 360 mg of the crude methyl 6-amino-1H-indole-2-carboxylate. To 200 mg (1.05 mmol) of crude product dissolved in 5 mL dichloromethane and 340 □L pyridine at 0° C. was added 81 □L methanesulfonyl chloride. The mixture was stirred at 0° C. for 1 h, was partitioned between dichloromethane and 1 N hydrochloric acid until neutral, was dried over magnesium sulfate and concentrated to obtain 333 mg of methyl 6-[(methylsulfonyl)amino]-1H-indole-2-carboxylate as crude product.

To 333 mg (1.24 mmol) of methyl 6-[(methylsulfonyl)amino]-1H-indole-2-carboxylate dissolved in 8 mL methanol was added 130 mg (3.10 mmol) lithium hydroxide dissolved in 2 mL water. The mixture was stirred at room temperature overnight, partitioned between ethyl acetate and 1 N hydrochloric acid, was dried over magnesium sulfate and concentrated to obtain 230 mg of 6-[(methylsulfonyl)amino]-1H-indole-2-carboxylic acid.

Following the procedure of Example 1 but replacing indole-2-carboxylic acid with 6-[(methylsulfonyl)amino]-1H-indole-2-carboxylic acid gave the title compound as a colorless solid.

Example 10

N-[(1S,2R)-2-({[(1S)-1-cyano-3-methylbutyl]amino}carbonyl)cyclohexyl]-1,3-benzothiazole-6-carboxamide

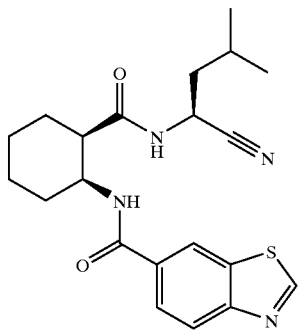

This example illustrates the synthesis of N-[(1S,2R)-2-({[(1S)-1-cyano-3-methylbutyl]amino}carbonyl)cyclohexyl]-1,3-benzothiazole-6-carboxamide starting from ethyl cis-2-amino-1-cyclohexanecarboxylate.

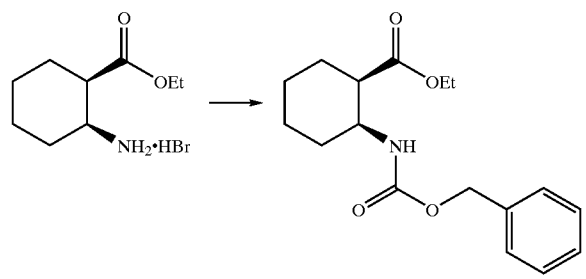

Step 1

To a 0° C. solution of ethyl cis-2-amino-1-cyclohexanecarboxylate HBr salt (22.34 g, 88.6 mmol) in 250 mL of methylene chloride, was added benzylchloroformate (12.6 mL, 88.3 mmol) and 250 mL of an aqueous sodium carbonate solution. The reaction mixture was stirred for 24 h at ambient temperature. The organic layer was separated and washed with 250 mL of water, dried over sodium sulfate, filtered and concentrated to give a crude liquid. The product was purified by column chromatography (10–50:90–50 ethyl acetate/hexanes) to give 26.45 g of a clear liquid. Yield: 98%, MS: 306 (M+H$^+$).

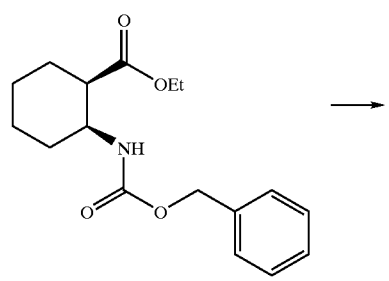

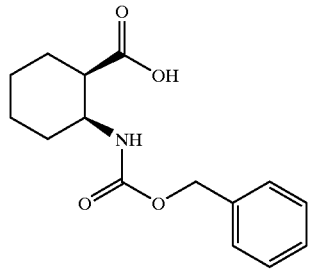

Step 2

The ester (26.45 g, 86.62 mmol) was dissolved in 250 mL of tetrahydrofuran and treated with a solution of lithium hydroxide monohydrate (10.65 g, 256 mmol) in 250 mL of water and stirred at ambient temperature for 24 h. The reaction mixture was cooled to 0° C. and neutralized with 300 mL of a 1N HCl solution. Ethyl acetate (400 mL) was added and the organic layer was separated, dried over sodium sulfate, filtered and concentrated to give a crude solid. The product was purified by recrystallizing from ethyl acetate/hexanes to give 19.60 g of a white solid. Yield: 82%, MS: 278 (M+H$^+$), mp=120.1–123.1° C.

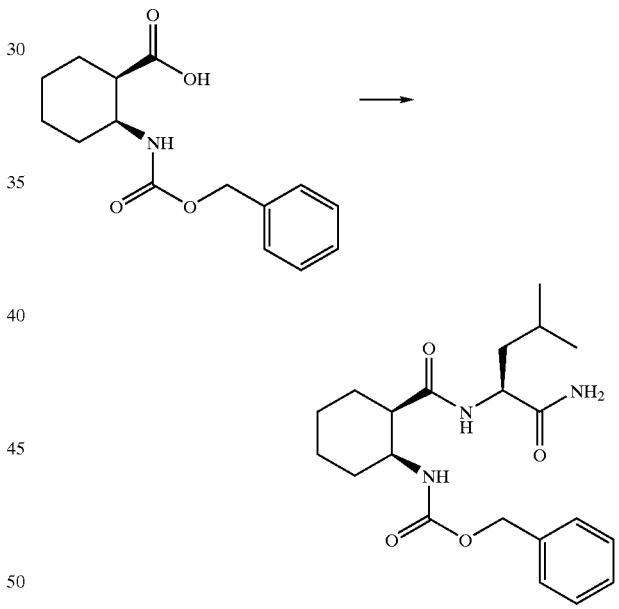

Step 3

To a solution of the carboxylic acid (10.2 g, 36.9 mmol), L-Leucinamide hydrochloride (6.18 g, 40.5 mmol), EDCI hydrochloride (5.48 g, 40.6 mmol), and HOBT (5.48 g, 40.6 mmol) in 100 mL of anhydrous DMF was added N-methylmorpholine (12.0 mL, 109 mmol). The reaction mixture was stirred at ambient temperature for 24 h, then added 300 mL of water and 400 mL of ethyl acetate. The organic layer was separated and washed with two 300 mL portions of a 0.5 M HCl solution, 300 mL of water, then dried over sodium sulfate, filtered and recrystallized from ethyl acetate/hexanes to give 13.2 g of the product as a white solid. Yield: 92%, MS: 412 (M+Na$^+$), mp=188.0–189.5° C.

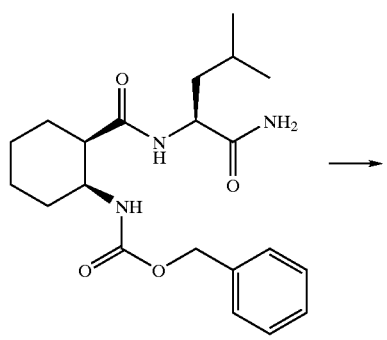

Step 4

To a 0° C. solution of the amide (13.2 g, 33.9 mmol) in 150 mL of anhydrous pyridine was added trifluoroacetic anhydride (5.50 mL, 38.9 mmol) dropwise slowly over a 3 min period. The reaction mixture was stirred for 15 min and then poured into a slurry of ice and 1N HCl solution. The mixture was extracted with 500 mL of ethyl acetate, and washed with three 400 mL portions of 1N HCl, 400 mL of water, dried over sodium sulfate, filtered and concentrated to give a crude solid. Recrystallization from ethyl acetate/hexanes gave 11.3 g of the product as a white solid. Yield: 90%, MS: 394 (M+Na$^+$), mp=103.6–106.5° C.

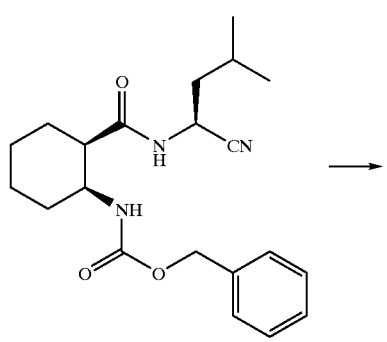

Step 5

A solution of the carbamate (11.3 g, 30.4 mmol) and palladium on activated carbon (1.0 g, 10% by wt.) in 250 mL of ethyl acetate was stirred for 24 h under a hydrogen atmosphere. The reaction mixture was filtered through a pad of celite, concentrated, then treated with a 1N solution of HCl in ether (35 mL). The resulting suspension was filtered and dried to give 5.96 g of the hydrochloride salt of the product as a white hygroscopic powder. Yield: 72%, MS: 238 (M+H$^+$), mp=133.3–135.0° C.

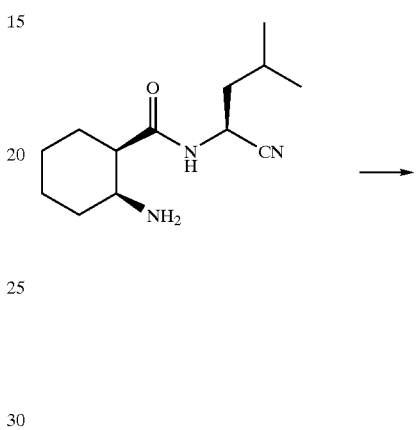

Step 6

To a solution of the amine (220 mg, 0.927 mmol), 1,3-benzothiazole-6-carboxylic acid (184 mg, 1.03 mmol), EDCI hydrochloride (195 mg, 1.02 mmol), HOBT (140 mg, 1.04 mmol) in 6.0 mL of DMF was added N-methylmorpholine (0.3 mL, 2.73 mmol) and stirred at ambient temperature for 24 h. The reaction mixture was partitioned between 30 mL of water and 30 mL of ethyl acetate. The organic layer was washed with two 30 mL portions of 1N HCl solution, 30 mL of water, dried over sodium sulfate, filtered, concentrated and purified by column chromatography (methanol/methylene chloride, 3:97) to give 297 mg of the product as a white solid. Yield: 80%, MS: 399 (M+H$^+$), mp=199.6201.2° C.

Similarly, but replacing 1,3-benzothiazole-6-carboxylic acid with 1H-pyrido[4,3-b]indole-8-carboxylic acid, 2,3,4,5-tetrahydro-2-methyl-monohydrochloride, the above procedure afforded 2-methyl-2,3,4,5-tetrahydro-1H-pyrido[4,3-b]indole-8-carboxylic acid [(1S,2R)-2-((S)-1-cyano-3-methyl-butylcarbamoyl)-cyclohexyl]-amide. Yield: 25.7%, MW: 449.60, MS: 450.3 (M+H)$^+$, 448.3 (M−H)$^−$.

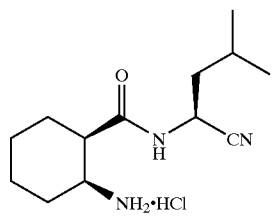

Example 11

N-[(1S,2R)-2-({[(1S)-1-cyano-3-methylbutyl]amino}carbonyl)cyclohexyl]-1-(2-hydroxyethyl)-1H-indole-2-carboxamide

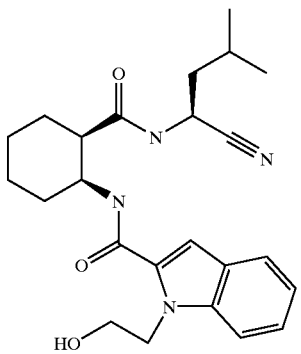

This example illustrates the synthesis of N-[(1S,2R)-2-({[(1S)-1-cyano-3-methylbutyl]amino}carbonyl)cyclohexyl]-1-(2-hydroxyethyl)-1H-indole-2-carboxamide starting from ethyl indole-2-carboxylate.

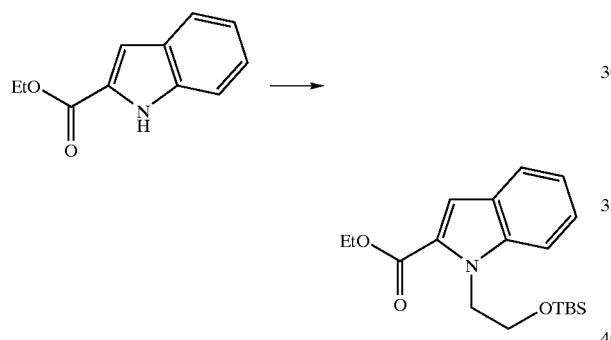

Step 1

To a 0° C. solution of ethyl indole-2-carboxylate (2.82 g, 14.9 mmol) in 25 mL of anhydrous DMF, was added sodium hydride powder (0.45 g, 17.8 mmol) portionwise. The reaction mixture was stirred until gas evolution subsided (10 min), then (2-Bromoethoxy)-tert-butyldimethylsilane (3.50 mL, 16.3 mmol) was added. The reaction mixture was placed into a 30° C. oil bath for 3 h. An additional amount of (2-Bromoethoxy)-tert-butyldimethylsilane (0.50 mL, 2.33 mmol) was added and raised the oil bath temperature to 52° C. for 2 h. The cooled reaction mixture was poured into a slurry of ice water and extracted with 250 mL of ethyl acetate. The organic layer was washed with two 250 mL portions of brine, dried over sodium sulfate, filtered, concentrated, and purified by column chromatography (ethyl acetate/hexanes, 10:90) to give 3.88 g of the product as a clear liquid. Yield: 75%, MS: 348 (M+H$^+$).

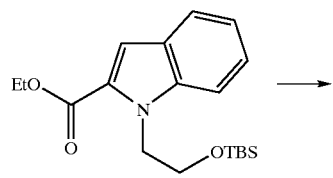

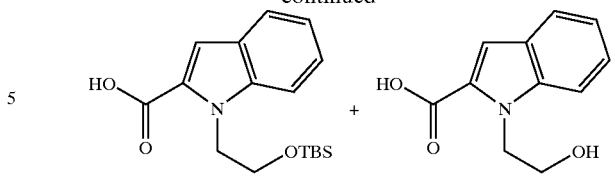

Step 2

To a solution of the above ester (3.82 g, 11.0 mmol) in 40 mL of THF was treated with a solution of lithium hydroxide monohydrate (2.20 g, 52.9 mmol) in 40 mL of water and 20 mL of methanol. The reaction mixture was heated to reflux for 10 min, then cooled and stirred at ambient temperature for 2 h. The reaction mixture was poured onto a slurry of ice and a 1N HCl solution, and extracted with 50 mL of ethyl acetate. The organic layer was washed with 100 mL of water, dried over sodium sulfate, filtered and concentrated to give 2.50 g of a white solid as a 1:1 mixture of two carboxylic acid products (as determined by $^1$H NMR spectroscopy). The mixture was used in the next coupling without further purification.

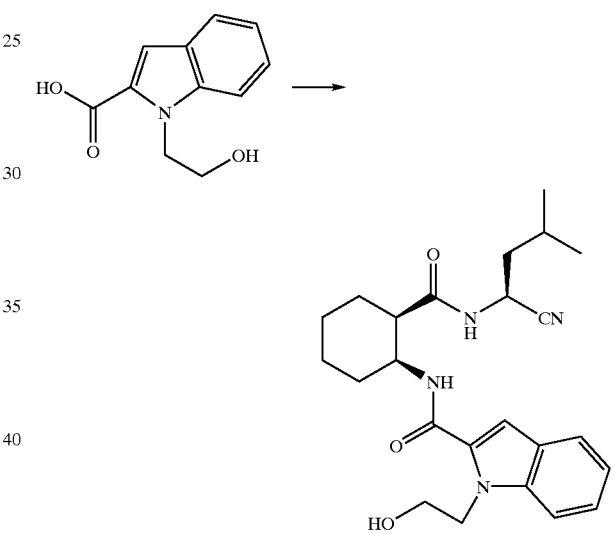

Step 3

The above carboxylic acid (0.67 g, 1.63 mmol, as a 1:1 mixture of alcohol/silylether, see previous scheme), amine (0.45 g, 1.90 mmol), EDCI hydrochloride (0.42 g, 2.20 mmol), HOBT (0.28 g, 2.07 mmol), and N-methylmorpholine (0.50 mL, 4.55 mmol) in 18 mL of anhydrous DMF, were stirred at ambient temperature for 24 h. The reaction mixture was partitioned between 50 mL of water and 50 mL of ethyl acetate. The organic layer was washed with two 50 mL portions of 1N HCl solution, 50 mL of water, then dried over sodium sulfate, filtered, concentrated and purified by column chromatography (40:60 ethyl acetate/hexanes) to give 184 mg of the product as a white foam solid. Yield: 27%, MS: 425.2 (M+H$^+$), mp=59.063.5° C.

Similarly, using 6-chloroindole-2-carboxylic acid and N-alkylating with N-(2-chloroethyl)-morpholine instead of (2-bromoethoxy)-tert-butyldimethylsilane followed by coupling to the appropriate amine, 6-chloro-1-(2-morpholin-4-yl-ethyl)-1H-indole-2-carboxylic acid {(1S,2R)-2-[((S)-cyano-cyclopropyl-methyl)-carbamoyl]-cyclohexyl}-amide was obtained. Yield: 48.3%, MW: 511.25, MS: 512.3 (M+H)$^+$, 510.3 (M-H)$^-$.

Similarly, using 6-chloroindole-2-carboxylic acid and N-alkylating with 2-dimethylaminoethyl chloride instead of (2-bromoethoxy)-tert-butyldimethylsilane followed by coupling to the appropriate amine, 6-chloro-1-(2-dimethylamino-ethyl)-1H-indole-2-carboxylic acid {(1S,2R)-2-[((S)-cyano-cyclopropyl-methyl)-carbamoyl]-cyclohexyl}-amide was obtained. Yield: 12.3%, MW: 469.22, MS: 470.3 (M+H)+, 468.3 (M−H)−.

Similarly, using 6-chloroindole-2-carboxylic acid and N-alkylating with 2-dimethylaminopropyl chloride instead of (2-bromoethoxy)-tert-butyldimethylsilane followed by coupling to the appropriate amine, 6-Chloro-1-(3-dimethylamino-propyl)-1H-indole-2-carboxylic acid {(1S,2R)-2-[((S)-cyano-cyclopropyl-methyl)-carbamoyl]-cyclohexyl}-amide was obtained. Yield: 12.0%, MW: 484.05, MS: 485.02 (M+H)+.

Similarly, using 6-chloroindole-2-carboxylic acid and N-alkylating with 2-morpholinopropyl chloride instead of (2-bromoethoxy)-tert-butyldimethylsilane followed by coupling to the appropriate amine, 1-(3-morpholin-4-yl-propyl)-1H-indole-2-carboxylic acid {(1S,2R)-2-[((S)-cyano-cyclopropyl-methyl)-carbamoyl]-cyclohexyl}-amide was obtained. Yield: 20.0%, MW: 525.2, MS: 526.2 (M+H)+, 524.2 (M−H)−.

Example 12

N-[(1S,2R)-2-({[(1S)-1-cyano-3-methylbutyl]amino}carbonyl)cyclohexyl]-1-methyl-6-(2-pyridin-2-ylethoxy)-1H-indole-2-carboxamide, Compound 4-3

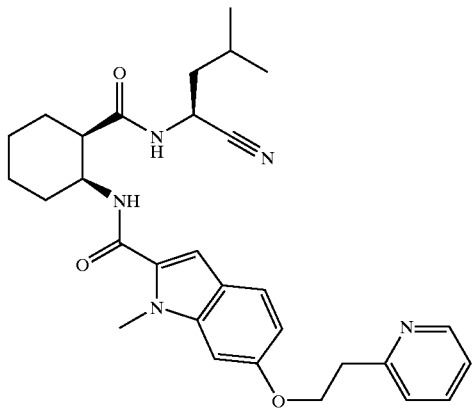

This compound was prepared by a modification of method B-2. An intermediate in Method B-2, N-[(1S,2R)-2-({[(1S)-1-carboxamide-3-methylbutyl]amino}carbonyl)cyclohexyl]-6-hydroxy-1-methyl-1H-indole-2-carboxamide, was subjected to a Mitsonobu coupling.

Mitsunobu Coupling

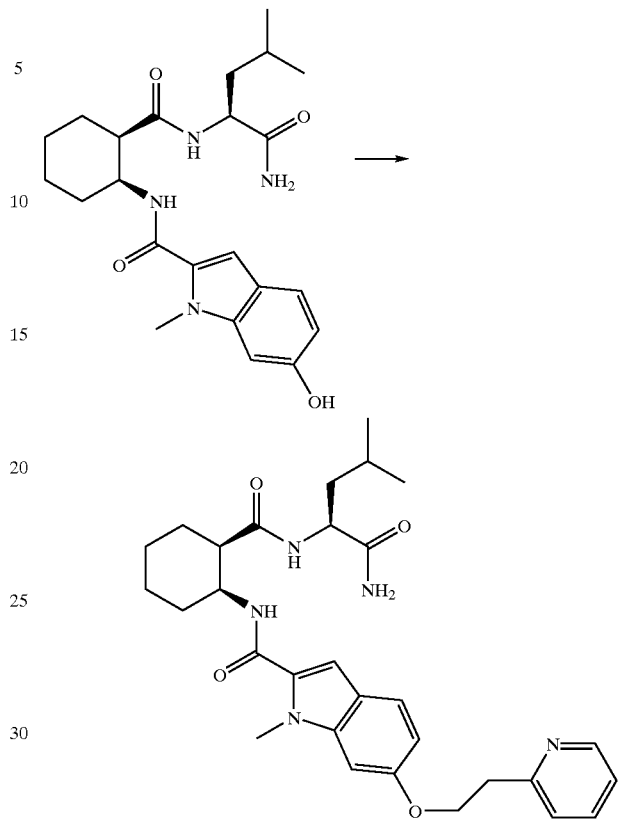

To a flask under nitrogen was added 0.10 gm (0.23 mm) N-[(1S,2R)-2-({[(1S)-1-carboxamide-3-methylbutyl]amino}carbonyl)cyclohexyl]-6-hydroxy-1-methyl-1H-indole-2-carboxamide, 0.122 gm (0.47 mm) triphenylphosphine and 0.057 gm (0.47 mm) 2-pyridin-2-ylethanol along with 3 ml Dimethylformamide. The flask was cooled in an ice-salt bath. 0.074 ml (0.47 mm) Diethyl azodicarboxylate was added in four portions once every twenty minutes. An additional 0.122 gm Triphenyiphosphine, 0.057 gm 2-pyridin-2-ylethanol and 0.074 ml Diethyl azodicarboxylate was added in the same fashion. After stirring overnight at room temperature an additional 0.122 gm triphenyiphosphine and 0.074 ml diethylazodicarboxlyate were added at room temperature. The reaction mixture was concentrated under vacuum to remove solvent and 25 ml ethyl acetate was added. This was extracted three times with 25 ml of 0.1 M hydrochloric acid, the organic layer discarded and the extracts were treated with aqueous sodium carbonate to a pH of 8 and extracted three times with 25 ml ethyl acetate. The extracts were dried over magnesium sulfate, solvent was removed under vacuum and the residue purified on a silica gel preparative TLC plate eluting with 5% methanol 95% dichloromethane to give N-[(1S,2R)-2-({[(1S)-1-carboxamide-3-methylbutyl]amino}carbonyl)cyclohexyl]-1-methyl-6-(2-pyridin-2-ylethoxy)-1H-indole-2-carboxamide.

This product, N-[(1S,2R)-2-({[(1S)-1-carboxamide-3-methylbutyl]amino}carbonyl)cyclohexyl]-1-methyl-6-(2-pyridin-2-ylethoxy)-1H-indole-2-carboxamide is converted by the final step of Method B-2 into the desired N-[(1S,2R)-2-({[(1S)-1-cyano-3-methylbutyl]amino}carbonyl)cyclohexyl]-1-methyl-6-(2-pyridin-2-ylethoxy)-1H-indole-2-carboxamide.

Example 13

6-Hydroxy-1-methyl-1H-indole-2-carboxylic acid and 6-Hydroxy-1H-indole-2-carboxylic acid
6-Hydroxy-1-methyl-1H-indole-2-carboxylic acid This carboxylic acid was used to prepare compounds 2-4, 2-6, 2-14, 2-18, 2-19, 4-2, 4-3 and 4-4 using the procedure of Example 1.

Step 1. N-Methylation

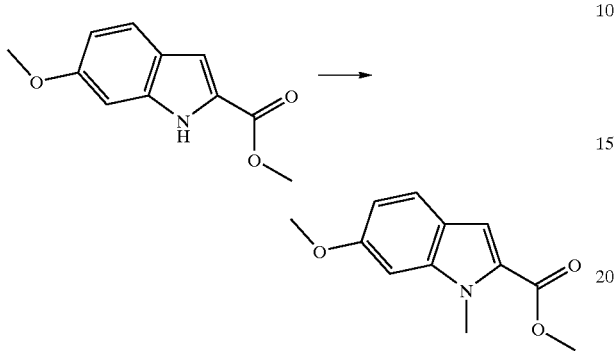

To a flask under nitrogen was added 3.0 grams (60%, 75.2 mM) sodium hydride. The solid was rinsed twice with hexane and 30 ml DMF was added. A solution of 14.03 g (68.4 mM) 6-Methoxy-1H-indole-2-carboxylic acid methyl ester in 15 ml DMF was added in portions. After the gas evolution had stopped the mixture was chilled in an ice bath and 14.07 g (99.13 mM)g iodomethane mixed with 5 ml DMF was added. The mixture was allowed to warm to room temperature and stir overnight. The reaction was quenched with water and a small amount of aqueous HCl. The DMF was removed under vacuum and the residue partitioned between water and ethyl acetate. The ethyl acetate layer was dried over magnesium sulfate, stripped and the solid purified by column chromatography on silica gel. (gradient of 10 to 30% Ethyl acetate/hexane) to give 6-Methoxy-1-methyl-1H-indole-2-carboxylic acid methyl ester, 13.47 g, (M/S 220.2, M+H) as a white solid. This compound was hydrolysed to the carboxylic acid and used to prepare compounds 1-24, 1-33, 1-34, and 2-15 according to the procedure of Example 1.

Step 2. Cleavage of 6-Methoxy Group and Methyl Ester.

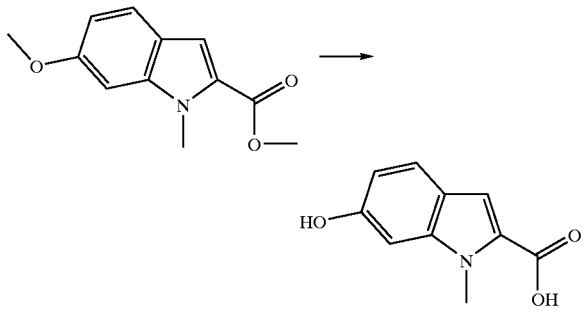

To a flask under nitrogen was added 576 mg (2.63 mM) of 6-Methoxy-1-methyl-1H-indole-2-carboxylic acid methyl ester and 30 ml dichloromethane. The mixture was cooled to −60° C. in dry ice acetone bath and 16 ml 1M boron tribromide in dichloromethane (16 mM) was added. After stirring 45 minutes at −60° C. the mixture was allowed to warm to room temperature and stirred for 5 hours. The mixture was poured into 200 ml saturated sodium bicarbonate solution and stirred for 30 minutes. Hydrochloric acid was added till acidic, ethyl acetate was added and the mixture filtered through a celite plug to remove insoluble solids. The ethyl acetate layer was separated and the aqueous was extracted two more time with ethyl acetate. The combined ethyl acetate layers were dried over magnesium sulfate, filtered and stripped to give 6-Hydroxy-1-methyl-1H-indole-2-carboxylic acid (M/S, ES-, 190.2 M−H).

6-Hydroxy-1H-indole-2-carboxylic acid

6-Methoxy-1H-indole-2-carboxylic acid methyl ester when subjected to Step 2 gave 6-hydroxy-1H-indole-2-carboxylic acid which was used in the preparation of compounds 2-5, 2-13, 2-17, and 2-19 in the manner described in Example 1.

Example 14

6-Imidazol-1-ylmethyl-1H-indole-2-carboxylic acid [(1S,2R)-2-(cyanomethyl-carbamoyl)-cyclohexyl]-amide

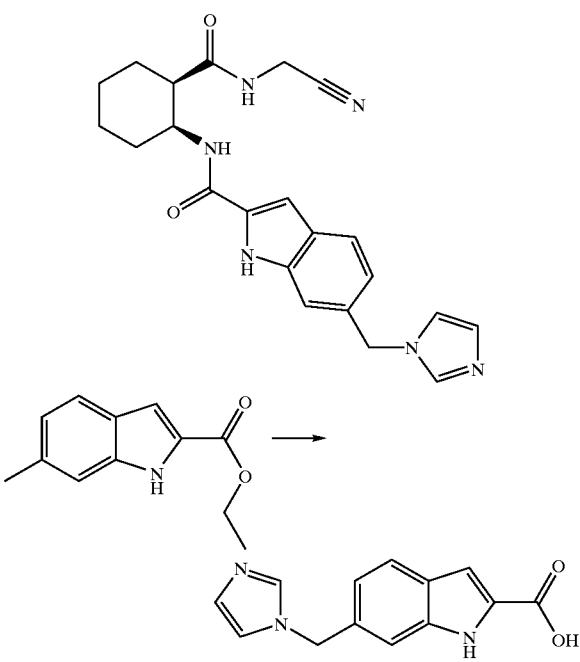

6-Imidazol-1-ylmethyl-1H-indole-2-carboxylic acid was prepared from imidazole and 6-methyl-1H-indole-2-carboxylic acid ethyl ester using the procedures described by Peter E Cross, et. al; Journal of Medicinal Chemistry 1986, 29(9), 1637–43.

6-Imidazol-1-ylmethyl-1H-indole-2-carboxylic acid [(1S, 2R)-2-(cyanomethyl-carbamoyl)-cyclohexyl]-amide was prepared from 6-imidazol-1-ylmethyl-1H-indole-2-carboxylic acid using the coupling procedure of Example 10 and replacing leucinamide with 2-aminoacetamide.

Similarly, using pyrazole and 1-methyl-piperazine respectively in place of imidazole in reaction with 6-methyl-1H-indole-2-carboxylic acid ethyl ester, the compounds 6-pyrazol-1-ylmethyl-1H-indole-2-carboxylic acid and 6-(4-methyl-piperazin)-1-ylmethyl-1H-indole-2-carboxylic acid were prepared. These acids in turn were used to make 6-pyrazol-1-ylmethyl-1H-indole-2-carboxylic acid [(1S, 2R)-2-(cyanomethyl-carbamoyl)-cyclohexyl]-amide and 6-(4-methyl-piperazin-1-ylmethyl)-1H-indole-2-carboxylic acid [(1S,2R)-2-(cyanomethyl-carbamoyl)-cyclohexyl]-amide using the coupling procedure of Example 10.

Using the above procedure, but replacing 6-methyl-1H-indole-2-carboxylic acid ethyl ester with 7-methyl-1H-indole-2-carboxylic acid ethyl ester, 7-imidazol-1-ylmethyl-1H-indole-2-carboxylic acid, 7-pyrazol-1-ylmethyl-1H-indole-2-carboxylic acid and 7-(4-methyl-piperazin)-1-ylmethyl-1H-indole-2-carboxylic acid were prepared. Again using the coupling procedure of Example 10 and replacing leucinamide with 2-aminoacetamide, the compounds 7-imidazol-1-ylmethyl-1H-indole-2-carboxylic acid [(1S,2R)-2-(cyanomethyl-carbamoyl)-cyclohexyl]-amide, 7-pyrazol-1-ylmethyl-1H-indole-2-carboxylic acid [(1S,2R)-2-(cyanomethyl-carbamoyl)-cyclohexyl]-amide and 7-(4-methyl-piperazin-1-ylmethyl)-1H-indole-2-carboxylic acid [(1S,2R)-2-(cyanomethyl-carbamoyl)-cyclohexyl]-amide.

Example 15

3-(3-Dimethylamino-propyl)-1H-indazole-5-carboxylic acid [(1S,2R)-2-((S)-1-cyano-3-methyl-butylcarbamoyl)cyclohexyl]-amide

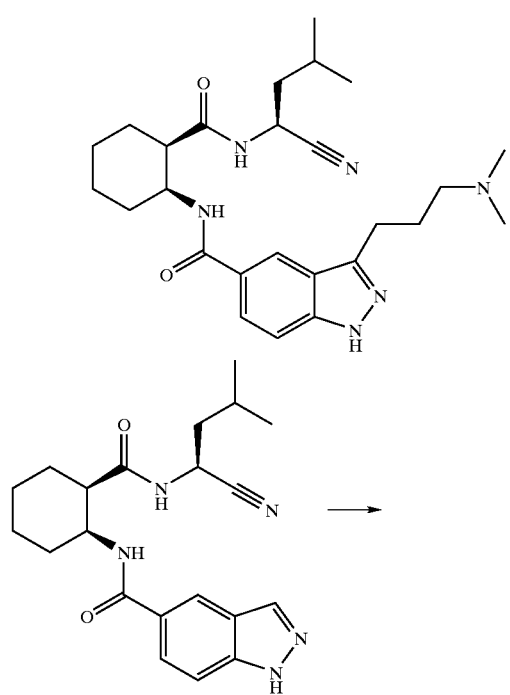

Using the procedures reported by Anca Arnautu et. al., Tetrahedron Letters 2002, 43(15), 2695–2697, N-[(1S,2R)-2-({[(1S)-1-cyano-3-methylbutyl]amino}carbonyl)cyclohexyl]-1H-indazole-5-carboxamide (compound 3-3) was converted to 3-(3-dimethylamino-prop-1-ynyl)-1H-indazole-5-carboxylic acid [(1S,2R)-2-((S)-1-cyano-3-methyl-butylcarbamoyl)-cyclohexyl]-amide.

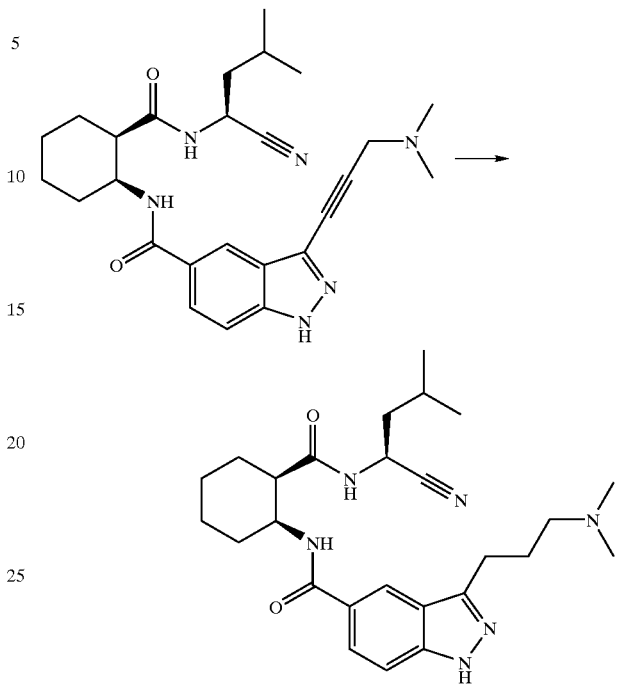

3-(3-dimethylamino-prop-1-ynyl)-1H-indazole-5-carboxylic acid [(1S,2R)-2-((S)-1-cyano-3-methyl-butylcarbamoyl)cyclohexyl]-amide (7 mg) was stirred with 5 mg 10% Pd/CaCO$_3$ in methanol under hydrogen (balloon). After two hours at room temperature the mixture was degassed with nitrogen, filtered through celite to remove the catalyst and the solution concentrated to give 7 mg of 3-(3-dimethylamino-propyl)-1H-indazole-5-carboxylic acid [(1S,2R)-2-((S)-1-cyano-3-methyl-butylcarbamoyl)cyclohexyl]-amide.

Example 16

1-Methyl-1H-indole-2-carboxylic acid {(1S,2R)-2-[(cyano-pyridin-2-yl-methyl)-carbamoyl]-cyclohexyl}-amide

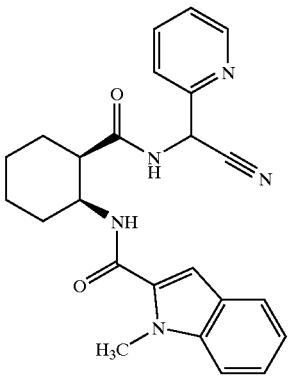

Amino-pyridin-2-yl-acetonitrile hydrobromide was prepared from pyridine-2-carbaldehyde, NaCN, acetic acid, ammonium chloride and ammonia according to the procedure described in WO00/49007.

Amino-pyridin-2-yl-acetonitrile hydrobromide and 2-[(1-Methyl-1H-indole-2-carbonyl)-amino]-cyclohexanecarboxylic acid were coupled as described in Example 1 to provide methyl-1H-indole-2-carboxylic acid {(1S,2R)-2-[(cyano-pyridin-2-yl-methyl)-carbamoyl]-cyclohexyl}-amide.

Similarly, using amino-phenylacetonitrile in place of amino-pyridin-2-yl-acetonitrile, 1-methyl-1H-indole-2-carboxylic acid {(1S,2R)-2-[(cyano-phenyl-methyl)-carbamoyl]cyclohexyl}-amide was prepared.

Example 17

1-Methyl-1H-indole-2-carboxylic acid [(1S,2R)-2-(cyanomethyl-carbamoyl)-cycloheptyl]-amide

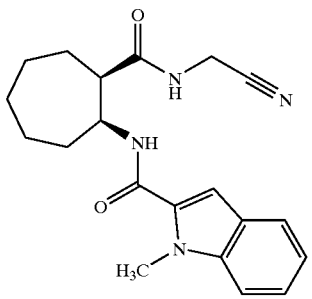

2-[(1-Methyl-1H-indole-2-carbonyl)-amino]-cycloheptanecarboxylic was prepared from 2-Aminocycloheptanecarboxylic acid (Tyger Scientific Inc., Princeton N.J.) using the procedure of Example). 1-Methyl-1H-indole-2-carboxylic acid and aminoacetonitrile hydrochloride were coupled as described in Example 1 to yield 1-Methyl-1H-indole-2-carboxylic acid [(1S,2R)-2-(cyanomethyl-carbamoyl)-cycloheptyl]-amide (compound 98).

Example 18

6-Chloro-1-methyl-1H-indole-2-carboxylic acid [(1S,2R)-2-(cyanomethyl-carbamoyl)-cyclohexyl]-amide

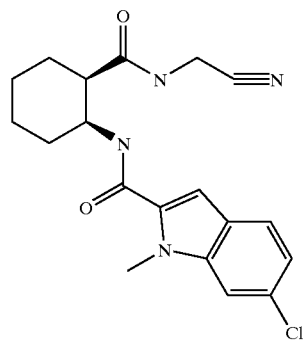

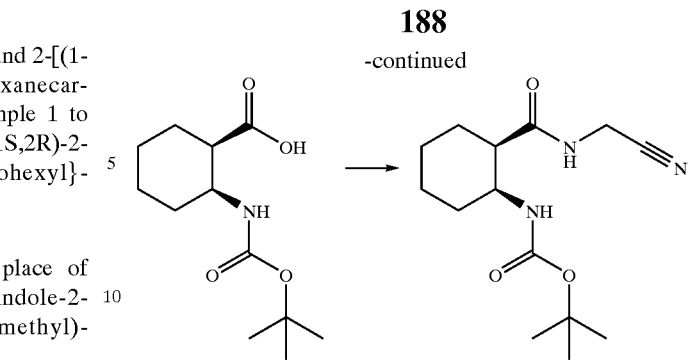

[2-(Cyanomethyl-carbamoyl)-cyclohexyl]-carbamic acid tert-butyl ester

To a solution of (10.33 g, 42.46 mmol) acid in DMF (85 ml) were added aminoacetonitrile HCl salt (4.32 g, 46.70 mmol), EDCI (8.95 g, 46.70 mmol), HOBT (6.31 g (46.70 mmol), and N-methylmorpholine (14.0 ml, 127.38 mmol). The reaction mixture was stirred at room temperature overnight, partitioned between ethyl acetate and water, dried over magnesium sulfate and concentrated. Recrystallization in ethyl acetate: hexane (1:15), provided [2-(cyanomethyl-carbamoyl)-cyclohexyl]-carbamic acid tert-butyl ester (8.05 g, 70%).

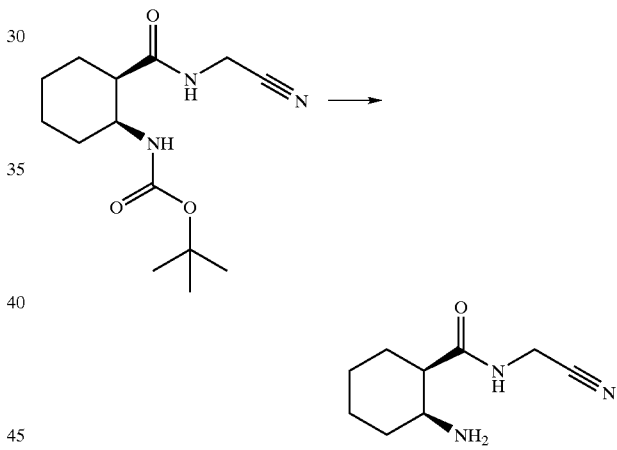

2-Amino-cyclohexanecarboxylic acid cyanomethyl-amide

A solution of [2-(cyanomethyl-carbamoyl)-cyclohexyl]-carbamic acid tert-butyl ester (7.3 g, 25.95 mmol) in formic acid (100 ml) and solution was stirred for four hours. Reaction was concentrated and then dissolved in 10% MeOH/dichloromethane solution (150 ml) Potassium carbonate was added until pH reached 9 and subsequent slurry was stirred vigorously before being filtered through Celite plug. The filtrate was concentrated in vacuo yielding 2-amino-cyclohexanecarboxylic acid cyanomethyl-amide (2.9 g, 62%).

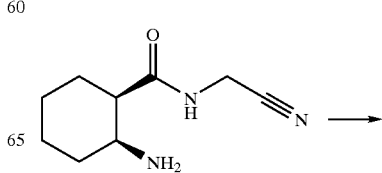

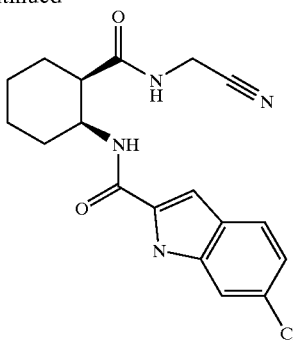

6-Chloro-1H-indole-2-carboxylic acid [2-(cyanomethyl-carbamoyl)-cyclohexyl]-amide To a solution of 2-amino-cyclohexanecarboxylic acid cyanomethyl-amide (6.4 g, 35.31 mmol) in DMF (70 ml), were added HOBT (5.25 g, 38.84 mmol), 6-chloro-2-indolecarboxylic acid (7.60 g, 38.84 mmol), N-methylmorpholine (19.4 ml, 176.45 mmol), and EDCI (7.45 g, 38.84 mmol) respectively at 0° C. The reaction was stirred at room temperature for 16 hours, then 1N HCl (500 ml) was added and the resulting cloudy solution was extracted with ethyl acetate (3×200 ml). The organic layer was filtered through a Celite pad, washed with 1N NaOH (200 ml), brine (200 ml), dried over magnesium sulfate and concentrated in vacuo yielding 6-chloro-1H-indole-2-carboxylic acid [2-(cyanomethyl-carbamoyl)-cyclohexyl]-amide, (6.25 g, 49%).

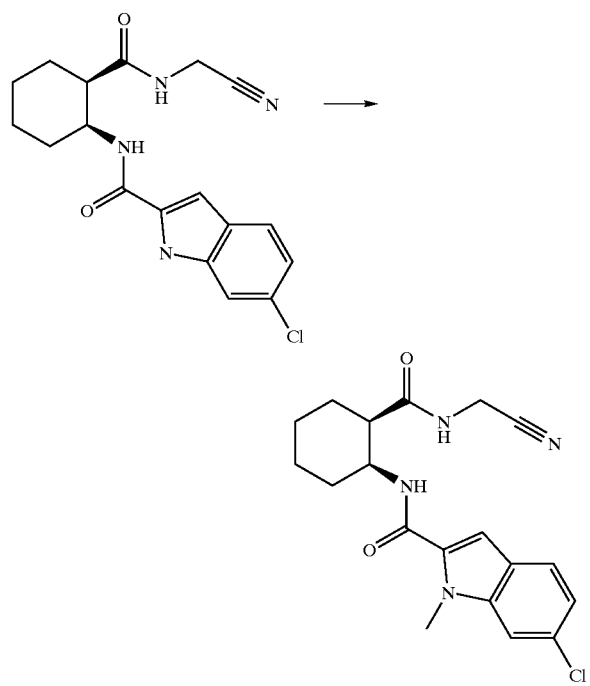

6-Chloro-1-methyl-1H-indole-2-carboxylic acid [2-(cyanomethyl-carbamoyl)-cyclohexyl]-amide To a solution of 6-Chloro-1H-indole-2-carboxylic acid [2-(cyanomethyl-carbamoyl)-cyclohexyl]-amide (6.17 g, 17.19 mmol) in DMF (35 ml) were added NaH as a 60% wt suspension in mineral oil (0.687 g, 17.19 mmol) at 0° C. The slurry was stirred for one hour at room temperature and methyl iodide (1.07 ml, 17.19 mmol) was added. The solution was stirred for four hours and partitioned between ethyl acetate (200 ml) and 1 N HCl (300 ml). The organic layer was washed with water, brine, dried over magnesium sulfate and concentrated. Recrystallizing from ethyl acetate: hexane (1:10) yielded 6-Chloro-1-methyl-1H-indole-2-carboxylic acid [2-(cyanomethyl-carbamoyl)-cyclohexyl]-amide (4.76 g, 74%). [M+H=373].

Example 19

6-Chloro-1-(3-chloro-propyl)-1H-indole-2-carboxylic acid [2-(1-cyano-3-methyl-butylcarbamoyl)cyclohexyl]-amide
(RO4613899-000)

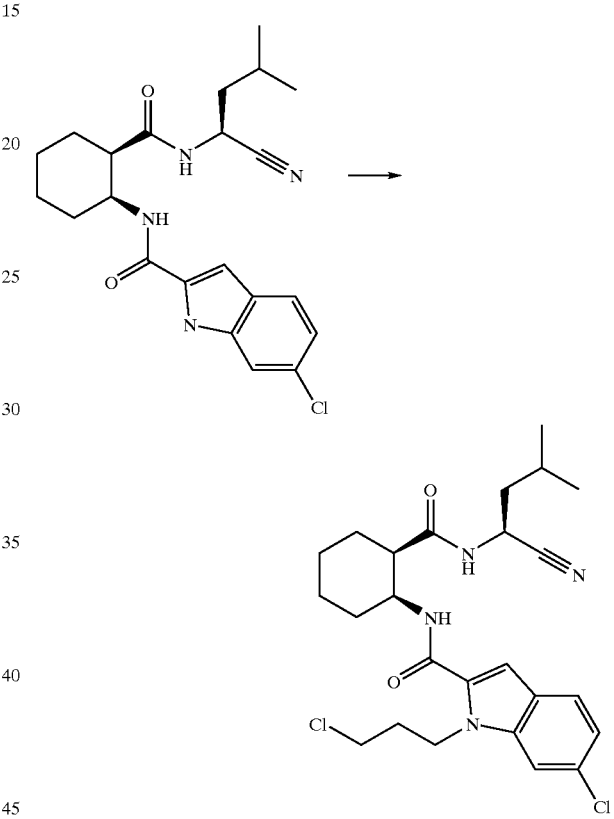

To a stirred solution of 6-chloro-1H-indole-2-carboxylic acid [2-(1-cyano-3-methyl-butylcarbamoyl)-cyclohexyl]-amide from Example 18 (0.428 g, 1.03 mmol) in DMF (3.5 ml) were added NaH (60% dispersion in mineral oil) (0.062 g, 1.54 mmol) at 0° C. The slurry was then stirred at room temperature for one hour followed by the addition of 1-bromo-3-chloropropane (0.13 ml, 1.34 mmol). Reaction was stirred overnight at room temperature and partitioned between 1 N HCl and ethyl acetate. The organic layer was washed with water, brine, dried over magnesium sulfate and concentrated in vacuo. The resulting oil was chromatographed on preparatory silica plates, eluting with 2.5% MeOH/dichloromethane, and yielding 6-chloro-1-(3-chloro-propyl)-1H-indole-2-carboxylic acid [2-(1-cyano-3-methyl-butylcarbamoyl)-cyclohexyl]-amide (0.323 g, 64%). [M+H=492].

Using the above procedure, but alkylating 6-chloro-1H-indole-2-carboxylic acid [2-(1-cyano-3-methyl-butylcarbamoyl)-cyclohexyl]-amide with N',N',-dimethyl-2-chloroethylamine hydrochloride instead of 1-bromo-3- chloropropane, 6-chloro-1-(2-dimethylamino-ethyl)-1H-indole-2-carboxylic acid [2-(1-cyano-3-methyl-butylcarbamoyl)-cyclohexyl]-amide was prepared; [M+H=430].

Similarly, alkylating 6-chloro-1H-indole-2-carboxylic acid [2-(1-cyano-3-methyl-butylcarbamoyl)-cyclohexyl]-amide with N'-(2-chloroethyl)-morpholine hydrochloride in the presence of NaH in DMF yielded 6-chloro-1-(2-morpholin-4-yl-ethyl)-1H-indole-2-carboxylic acid [2-(1-cyano-3-methyl-butylcarbamoyl)-cyclohexyl]-amide; [M+H=529].

Similarly, alkylating 6-chloro-1H-indole-2-carboxylic acid [2-(1-cyano-3-methyl-butylcarbamoyl)-cyclohexyl]-amide with 1-(2-chloroethyl)-4-methylpiperazine dihydrochloride (prepared as described in U.S. Pat. No. 2,800,474) in the presence of NaH in DMF yielded 6-chloro-1-[2-(4-methyl-piperazin-1-yl)-ethyl]-1H-indole-2-carboxylic acid [2-(1-cyano-3-methyl-butylcarbamoyl)-cyclohexyl]-amide [M+H=486].

Similarly, by alkylating 6-chloro-1H-indole-2-carboxylic acid [2-(1-cyano-3-methyl-butylcarbamoyl)-cyclohexyl]-amide with toluene-4-sulfonic acid 2-methanesulfonyl ethyl ester (prepared by the method of Ishidate; Nambara; Yakugaku; Zasshi; *Chem Abstr.*; 1959; 20255) in the presence of NaH in DMF, 6-Chloro-1-(2-methanesulfonyl-ethyl)-1H-indole-2-carboxylic acid [2-(1-cyano-3-methyl-butylcarbamoyl)-cyclohexyl]-amide was prepared; [M+H=522].

In a similar manner, by alkylating 1H-indole-2-carboxylic acid [2-(1-cyano-3-methyl-butylcarbamoyl)-cyclohexyl]-amide with toluene-4-sulfonic acid 2-methanesulfonyl ethyl ester in the presence of NaH in DMF yielded 1-(2-methanesulfonyl-ethyl)-1H-indole-2-carboxylic acid [2-(1-cyano-3-methyl-butylcarbamoyl)-cyclohexyl]-amide; [M+H=487].

Example 20

6-Chloro-1-(3-morpholin-4-yl-propyl)-1H-indole-2-carboxylic acid [2-(1-cyano-3-methyl-butylcarbamoyl)-cyclohexyl]-amide

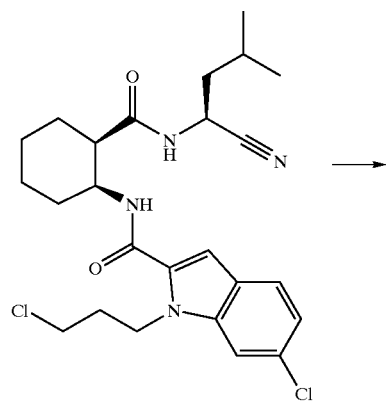

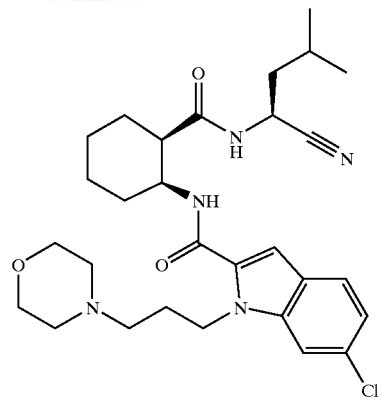

To a stirred slurry of morpholine (0.05 ml, 0.51 mmol) and potassium carbonate (0.09 g, 0.68 mmol) in DMF (1.2 ml) was added 6-Chloro-1-(3-chloro-propyl)-1H-indole-2-carboxylic acid [2-(1-cyano-3-methyl-butylcarbamoyl)-cyclohexyl]-amide from Example 19 (0.17 g, 0.34 mmol) at room temperature. The reaction was stirred for 48 hours before being partitioned between ethyl acetate and 1N NaOH. The organic layer was washed with brine, dried over magnesium sulfate and concentrated in vacuo. The resulting crude oil was chromatographed (5% MeOH/dichloromethane) to yield 6-chloro-1-(3-morpholin-4-yl-propyl)-1H-indole-2-carboxylic acid [2-(1-cyano-3-methyl-butylcarbamoyl)-cyclohexyl]-amide (0.05 g, 27%); [M+H=543].

Using the above procedure and replacing morpholine with N',N'-dimethyl amine (2M in THF), provided 6-chloro-1-(3-dimethylamino-propyl)-1H-indole-2-carboxylic acid [2-(1-cyano-3-methyl-butylcarbamoyl)-cyclohexyl]-amide; [M+H=501].

Example 21

1-[2-(Piperidine-1-sulfonylamino)-ethyl]-1H-indole-2-carboxylic acid [(1S,2R)-2-((S)-1-cyano-3-methyl-butylcarbamoyl)-cyclohexyl]-amide

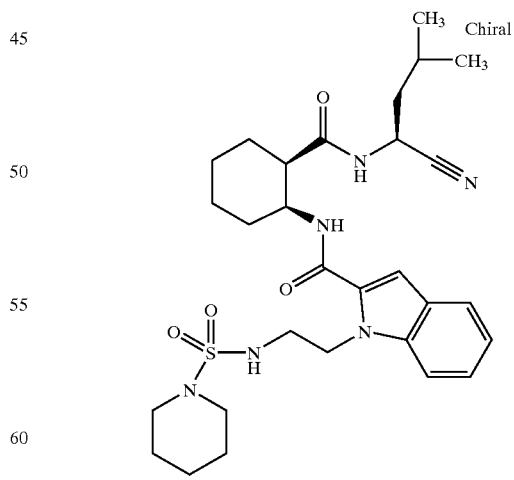

To a 0° C. solution of ethyl 1-(2-hydroxyethyl)-1H-indole-2-carboxylate (203 mg, 0.87 mmol), triphenylphosphine (342 mg, 1.31 mmol), and N-BOC-(piperidine-1-sulfamoyl)amine (322 mg, 1.22 mmol (prepared as described by Z. Regaïnia et al., *Tetrahedron* 2000, 56, 381–387, only replacing bis-2-chloroethylamine with piperidine) in 3 ml of THF was added, dropwise, a solution of diisopropyl azodicarboxylate (0.26 ml, 1.31 mmol) in 1.5 ml of THF. The reaction was stirred at 0° C. for 2.5 h and then concentrated. The residue was dissolved in a small volume of methylene chloride and chromatographed (SiO$_2$, PTLC, 25% EtOAc/hex) to give ethyl 1-{2-[N-BOC-(piperidine-1-sulfamoyl)amino]ethyl}-1H-indole-2-carboxylate (420 mg) as a clear oil. Removal of the BOC group using 30% TFA in methylene chloride, followed by saponification and coupling as described in Example 11 gives 1-[2-(piperidine-1-sulfamoyl-amino)-ethyl]-1H-indole-2-carboxylic acid [2-(1-cyano-3-methyl-butylcarbamoyl)]cyclohexyl amide (120 mg) as a amorphous powder (MS: MH+=571).

Proceeding as described above but substituting dimethylamine hydrochloride for piperidine gave 1-[2-(dimethylsulfamoyl-amino)-ethyl]-1H-indole-2-carboxylic acid [2-(1-cyano-3-methyl-butylcarbamoyl)]cyclohexyl amide (MS: MH+=531).

Example 22

1-[2-(1,1-Dioxo-1λ$^6$-[1,2,5]thiadiazolidin-2-yl) ethyl]-1H-indole-2-carboxylic acid [(1S,2R)-2-((S)-1-cyano-3-methyl-butylcarbamoyl)-cyclohexyl]-amide

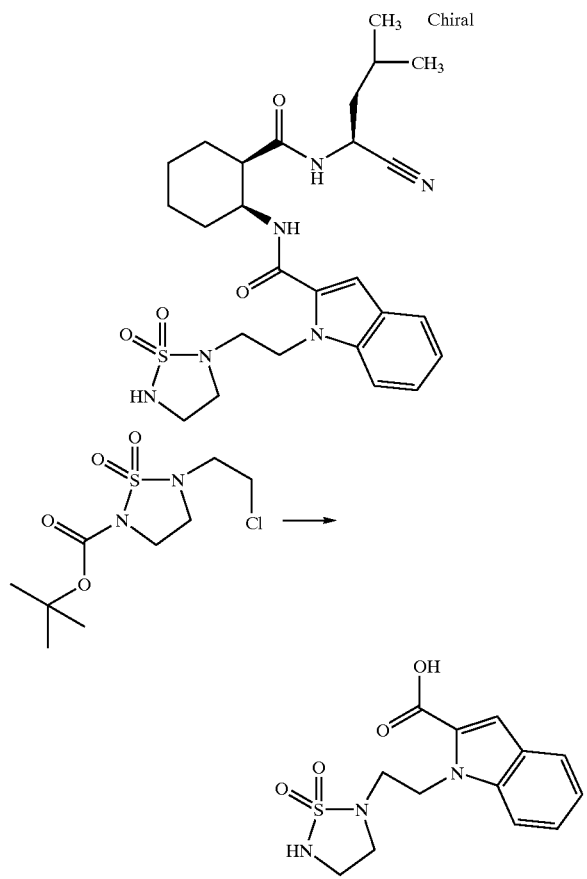

1-[2-(1,1-Dioxo-1λ$^6$-[1,2,5]thiadiazolidin-2-yl)-ethyl]-1H-indole-2-carboxylic acid was prepared from 5-(2-Chloro-ethyl)-1,1-dioxo-1λ$^6$-[1,2,5]thiadiazolidine-2-carboxylic acid tert-butyl ester (Z. Regaïnia et al., *Tetrahedron* 2000, 56, 381–387) using the N-alkylation procedure and saponification described in Example 11, followed by N-Boc deprotection using TFA. This acid was then coupled to the amine as described in Example 10 to give 110 mg of 1-[2-(1,1-Dioxo-1λ$^6$-[1,2,5]thiadiazolidin-2-yl)-ethyl]-1H-indole-2-carboxylic acid [(1S,2R)-2-((S)-1-cyano-3-methyl-butylcarbamoyl)-cyclohexyl]-amide as a white solid. Yield: 47%, MS: 529 (M+1).

Example 23

1-Methyl-1H-indole-2-carboxylic acid [(1S,2R)-2-(cyanomethyl-carbamoyl)-5-methyl-cyclohexyl]-amide

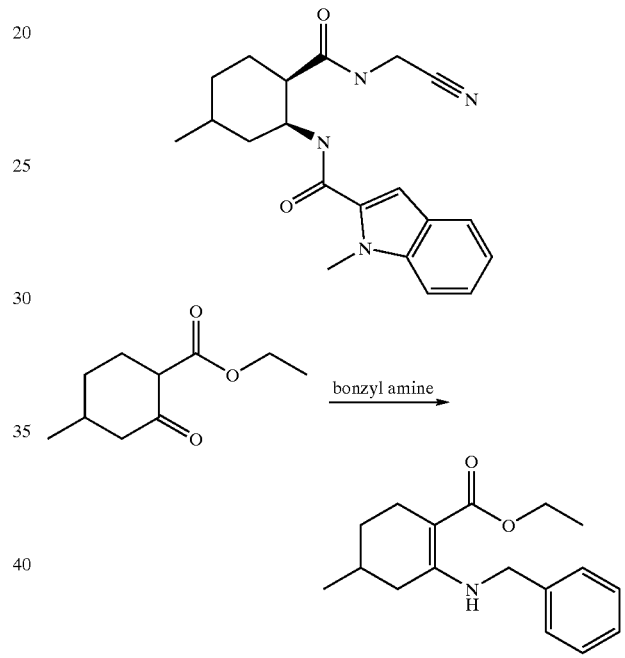

Step 1

In a 500 mL round bottom flask was placed racemic ethyl 4-methyl-2-cyclohexanone-1-carboxylate (6.0 g) and benzylamine (3.8 g). Toluene (190 mL) was added, followed by p-toluene sulfonic acid monohydrate (200 mg). A Dean-Stark apparatus and nitrogen line were attached, and the reaction was heated at reflux using an oil bath. After 3 days, the reaction was cooled to ambient temperature to yield 2-benzylamino-4-methyl-cyclohex-1-enecarboxylic acid ethyl ester (not isolated).

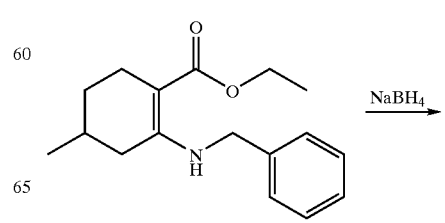

-continued

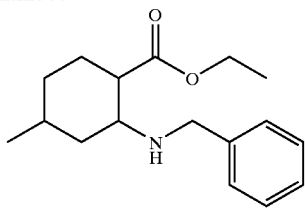

Step 2

In a separate flask, sodium borohydride (3.8 g) was added in portions to isobutyric acid (60 mL) cooled to about 15° C. under nitrogen. After 15 minutes, the reaction was cooled to 0° C. and the above reaction solution containing 2-benzylamino-4-methyl-cyclohex-1-enecarboxylic acid ethyl ester was added dropwise. After stirring for 2 hours, the reaction was carefully quenched with 40 mL of 3 M aqueous hydrochloric acid. The organic layer was separated, and the aqueous layer washed with 50% ethyl acetate/ hexanes. After making the aqueous layer basic with 2M sodium hydroxide, extraction with four portions of ethyl acetate was conducted. The organic layer was concentrated to about 50 mL, cooled to 0° C., and made acidic with 30% HBr in propionic acid. After 1 hour, a solid was collected (1.1 g). The mother liquor was made basic and extracted with ethyl acetate. After concentration, the residue was subjected to flash chromatography using hexanes/ethyl acetate to afford 1.31 g of 2-benzylamino-4-methyl-cyclohexanecarboxylic acid ethyl ester.

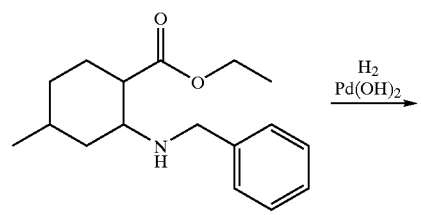

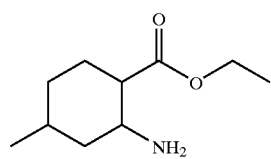

Step 3

2-Benzylamino-4-methylcyclohexanecarboxylic acid ethyl ester (1.0 g) in 40 mL ethanol was treated with 1 mL acetic acid and 100 mg of palladium hydroxide. The mixture was placed under hydrogen atmosphere at 60 psi and allowed to shake for 3 days. After return of the reaction to room pressure, filtration was conducted through a celite pad, washing several times with ethyl acetate. The filtrate was concentrated to afford 1.7 g product.

Using the procedure of Example 1,1-Methyl-1H-indole-2-carboxylic acid [(1S,2R)-2-(cyanomethyl-carbamoyl)-5-methylcyclohexyl]-amide was prepared from the above amino acid. MS; 352.

Similarly using 2-benzylamino-4-methyl-cyclohexanecarboxylic acid ethyl ester with coupling as described in Example 3 with L-alaninamide hydrochloride and L-leucinamide respectively, 1-methyl-1H-indole-2-carboxylic acid {(1S,2R)-2-[(cyano-methyl-methyl)-carbamoyl]-5-methyl-cyclohexyl}-amide and 1-methyl-1H-indole-2-carboxylic acid [(1S,2R)-2-(1-cyano-3-methyl-butylcarbamoyl)-5-methyl-cyclohexyl]-amide were prepared.

Example 24

6-Bromo-1-methyl-1H-indole-2-carboxylic acid [(1S,2R)-2-(cyanomethyl-carbamoyl)-cyclohexyl]-amide

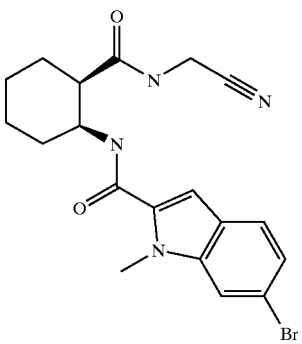

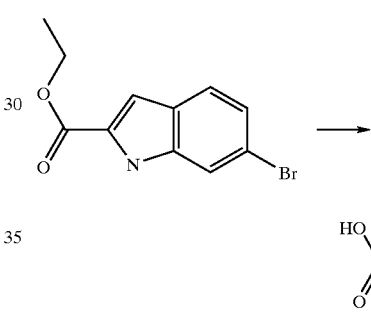

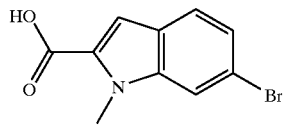

6-Bromo-1-methyl-1H-indole-2-carboxylic acid methyl ester was prepared by N-methylation of 6-bromo-1H-indole-2-carboxylic acid ethyl ester using the procedure described in Example 13 for N-methylation of indole carboxylic acid esters. Ester hydrolysis was performed with LiOH (4 equ.) in methanol-water 4:1, 12 h at room temperature. The reaction mixture was partitioned between ethyl acetate and water. The aqueous phase was acidified to pH~2–3 with 2N HCl and extracted in ethyl acetate. The organic phase was washed with brine, dried (Na$_2$SO$_4$) and evaporated in vacuo to yield 95% of 6-bromo-1-methyl-1H-indole-2-carboxylic acid [(1S,2R)-2-cyanomethyl-carbamoyl)-cyclohexyl]-amide; m/z 253.

Using the procedure of Example 1 with 6-bromo-1-methyl-1H-indole-2-carboxylic acid [(1S,2R)-2-(cyanomethyl-carbamoyl)-cyclohexyl]-amide, (1R,2S)-2-[(6-bromo-1H-indole-2-carbonyl)amino]-cyclohexanecarboxylic acid and aminoacetonitrile HCl salt, 6-bromo-1-methyl-1H-indole-2-carboxylic acid [(1S,2R)-2-(cyanomethyl-carbamoyl)-cyclohexyl]-amide was prepared. Using the same procedure but omitting the N-methylation, 6-bromo-1H-indole-2-carboxylic acid [(1S,2R)-2-(cyanomethyl-carbamoyl)-cyclohexyl]-amide was prepared.

Example 25

6-Pyridin-3-yl-1H-indole-2-carboxylic acid [(1S,2R)-2-((S)-1-cyano-3-methyl-butylcarbamoyl)-cyclohexyl]-amide

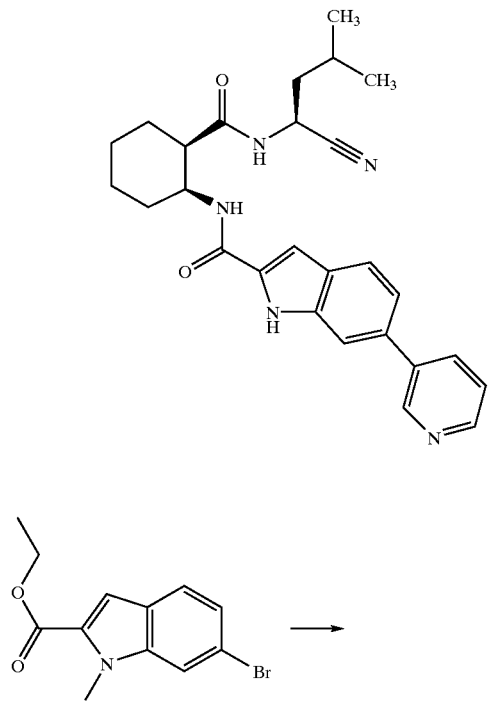

1-Methyl-6-pyridin-3-yl-1H-indole-2-carboxylic acid was prepared from 6-bromo-1-methyl-1H-indole-2-carboxylic acid methyl ester from Example 24 using Suzuki cross coupling reaction conditions as described by Victor J. Hruby et al.; Tetrahedron Letters; 42; 2001; 7717–7719.

From this carboxylic acid 6-pyridin-3-yl-1H-indole-2-carboxylic acid [(1S,2R)-2-((S)-1-cyano-3-methyl-butylcarbamoyl)-cyclohexyl]-amide was prepared using the procedure of Example 10.

Similarly, 1-methyl-6-phenyl-1H-indole-2-carboxylic acid was prepared from 6-bromo-1-methyl-1H-indole-2-carboxylic acid methyl ester and was used to prepare 6-Phenyl-1H-indole-2-carboxylic acid [(1S,2R)-2-((S)-1-cyano-3-methyl-butylcarbamoyl)-cyclohexyl]-amide.

Example 26

6-(2-Methanesulfonyl-ethyl)-1-methyl-1H-indole-2-carboxylic acid [(1S,2R)-2-((S)-1-cyano-3-methyl-butylcarbamoyl)-cyclohexyl]-amide

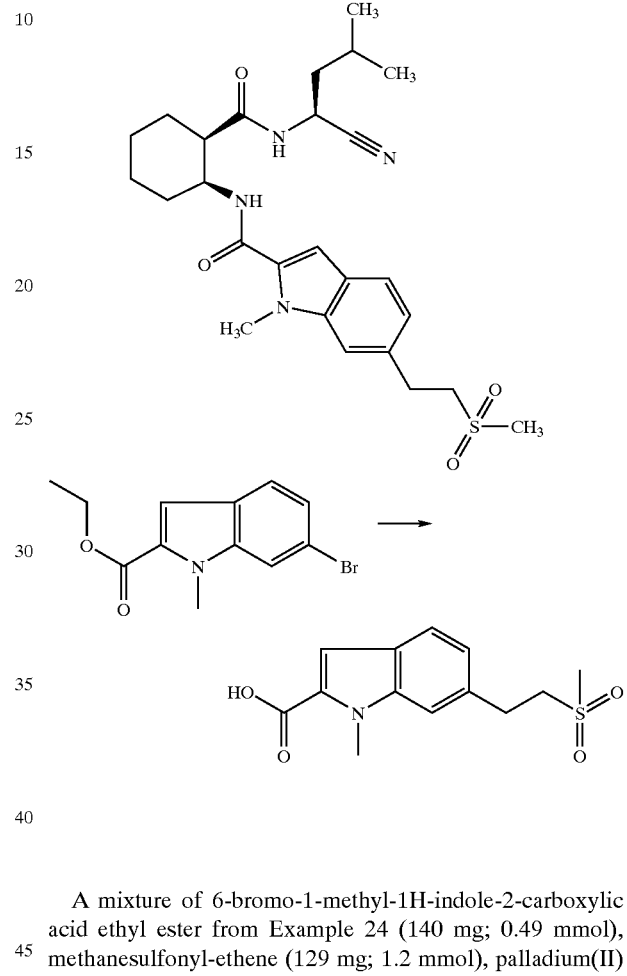

A mixture of 6-bromo-1-methyl-1H-indole-2-carboxylic acid ethyl ester from Example 24 (140 mg; 0.49 mmol), methanesulfonyl-ethene (129 mg; 1.2 mmol), palladium(II) acetate (22 mg; 0.097 mmol), tri-o-tolyl-phosphane (60 mg; 0.10 mmol), and sodium acetate trihydrate (66.6 mg; 0.49 mmol) were placed in 2 ml dimethylformamide and heated at 100° C. with stirring for 15 hours. After cooling, the mixture was partitioned between ethyl acetate and water, washed with brine, dried ($Na_2SO_4$) and evaporated under reduced pressure. Purification by flash chromatography (silica gel, ethyl acetate-hexane 1:1) gave 25 mg (16%) of a colorless oil which was dissolved in 20 ml of methanol and after addition of 5 mg of 10% Pd/C, was subjected to catalytic hydrogenation at room temperature and atmospheric pressure for 2 hours. Filtering the catalyst using celite and evaporation under reduced pressure afforded 20 mg (80%; m/z 310) of a white powder. This compound was dissolved in 3 ml methanol and 1 ml water. To this solution was added (12 mg; 0.28 mmol) of LiOH monohydrate and the mixture was stirred at room temperature for 6 hours. The mixture was partitioned between ethyl acetate and water. The water layer was acidified with 2N HCl to pH~2 and extracted with ethyl acetate. The organic layer was washed with brine and evaporated under reduced pressure affording 18 mg (100%; m/z 280) of 6-(methanesulfonyl-ethyl)-1-methyl-1H-indole-2-carboxylic acid as a white powder.

From the 6-(methanesulfonyl-ethyl)-1-methyl-1H-indole-2-carboxylic acid, 6-(2-methanesulfonylethyl)-1-methyl-1H-indole-2-carboxylic acid [(1S,2R)-2-((S)-1-cyano-3-methyl-butylcarbamoyl)-cyclohexyl]-amide was prepared using the procedure of Example 10.

Example 27

6-(3-Hydroxy-3-methyl-butyl)-1-methyl-1H-indole-2-carboxylic acid [(1S,2R)-2-((S)-1-cyano-3-methyl-butylcarbamoyl)-cyclohexyl]-amide

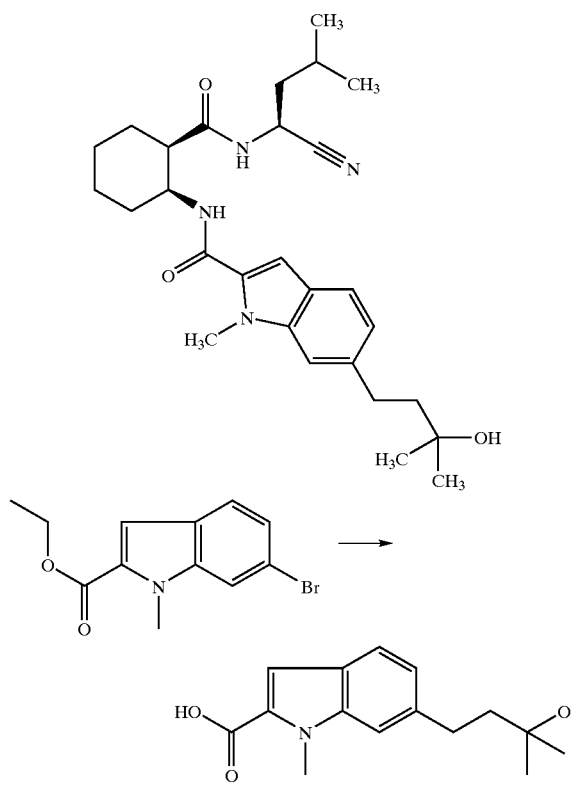

A mixture of 6-bromo-1-methyl-1H-indole-carboxylic acid methyl ester (105 mg; 0.39 mmol), 2-methyl-but-3-en-2-ol (67.5 mg; 0.78 mmol), palladium(II) acetate (8 mg; 0.035 mmol), tri-o-tolyl-phosphane (23.7 mg; 0.078 mmol) and sodium carbonate (41.4 mg; 0.39 mmol) were placed in 4 ml 1,2-dimethoxy-ethane and 200 ul water. The system was heated at 85–90° C. with stirring for 15 hours. After cooling, the mixture was partitioned between ethyl acetate and water, and evaporated under reduced pressure. Purification by flash chromathography (silica gel, ethyl acetate-hexane 1:1) afforded 47 mg (22%) of a colorless oil which was dissolved in 10 ml methanol and subjected to catalytic hydrogenation (10% Pd/C;10 mg) for 3 hours at atmospheric pressure and room temperature. Filtration of catalyst using celite and concentration, followed by purification by flash chromatography (silica gel, 25% ethyl acetate in hexane) afforded 20 mg (42%) white crystals; m/z 276. This compound was dissolved in a mixture of 3 ml tetrahydrofuran, 0.5 ml methanol and 0.5 ml water to which a solution of LiOH monohydrate (18 mg; 0.42 mmol) in 0.5 ml water was added dropwise. The mixture was stirred for 3 h at room temperature and then partitioned between ethyl acetate and water. The aqueous layer was acidified to pH~3 with 2N HCl and extracted with ethyl acetate. The organic layer was washed with brine, dried ($Na_2SO_4$) and evaporated to afford 17 mg of 6-(3-hydroxy-3-methyl-butyl)-1-methyl-1H-indole-carboxylic acid white powder (72%); m/z 260.

Using 6-(methanesulfonyl-ethyl)-1-methyl-1H-indole-2-carboxylic acid, 6-(2-methanesulfonyl-ethyl)-1-methyl-1H-indole-2-carboxylic acid [(1S,2R)-2-((S)-1-cyano-3-methyl-butylcarbamoyl)-cyclohexyl]-amide with the procedure of Example 10, 6-(3-Hydroxy-3-methyl-butyl)-1-methyl-1H-indole-2-carboxylic acid [(1S,2R)-2-((S)-1-cyano-3-methyl-butylcarbamoyl)-cyclohexyl]-amide was prepared.

Example 28

6-(1,1-Dioxo-1$\lambda^6$-[1,2]thiazinan-2-yl)-1-methyl-1H-indole-2-carboxylic acid [(1S,2R)-2-((S)-1-cyano-3-methyl-butylcarbamoyl)-cyclohexyl]-amide

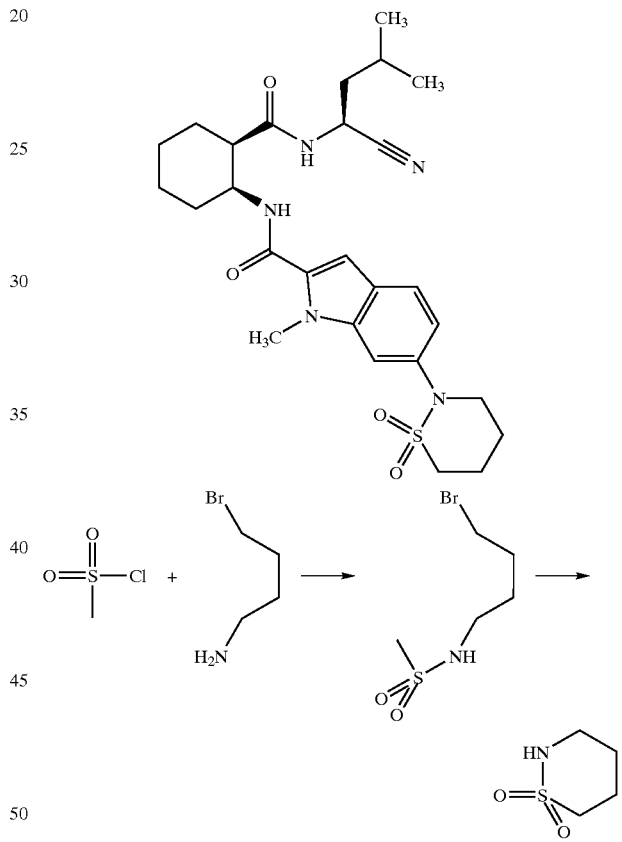

Step 1

3-Bromopropylamine-HBr salt (4.4 g; 0.02 moles) in tetrahydrofuran 43 ml were placed in a three neck round bottom flask under nitrogen. Two dropping funnels were fitted to the flask. One charged with triethylamine (2.02 g; 0.02 moles) and the other charged with methanesulfonyl chloride in 4 ml tetrahydrofuran. The reaction mixture was cooled to 0° C. and the contents of the two dropping funnels were added at the same rate during a 2 h period, while maintaining the internal temperature between 0–10° C. After addition, the resulting white suspension was kept 1 h at room temperature and then filtered. The filtrate and cake rinse were collected in a 100 ml round bottom flask under nitrogen. Diisopropylamine (4.05 g; 0.04 moles) and 1,10-phenantroline (4.1 mg) were added, and the mixture cooled to −30° C. To this reaction mixture was added dropwise n-BuLi 1.6 M (25 ml; 0.04 moles) during a 4 h period while maintaining the internal temperature at −20°–(30°)C. The reaction mixture became deep brown after the addition of the first 1.25 equivalent of n-BuLi and the color remained after the addition was completed. The reaction was warmed to 0° C. and monitored by $^1$H NMR using small aliquots which were partitioned between ethyl acetate and saturated solution of NH$_4$Cl. After 3 h, saturated solution of NH$_4$Cl (12 ml) was added slowly at 0° C. followed by brine (12 ml). The phases were partitioned and the aqueous phase extracted with 20 ml ethyl acetate. The organic phases were combined, washed with 4 ml brine and concentrated in vacuo to about 12 ml. The concentrated solution was cooled to 0° C. for 12 hours and filtered to yield 2 g (74%) of (1,2)thiazinane-1, 1-dioxide as pale yellow needles; m/z 136.

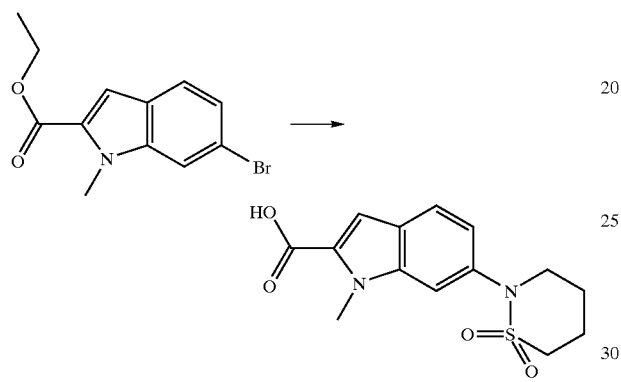

Step 2

A strong glass tube was charged with Pd$_2$(dba)$_3$ (6.4 mg; 0.007 mmol), xantphos (12 mg; 0.02 mmol), 1,2-thiazinane-1,1-dioxide (115 mg; 0.85 mmol), and Cs$_2$CO$_3$ (323 mg; 0.99 mmol). The tube was capped with a rubber septum, evacuated and backfilled with nitrogen. 6-Bromo-1-methyl-1H-indole carboxylic acid ethyl ester (200 mg; 0.71 mmol) in 1 ml of 1,4-dioxane was added through the septum. The septum was replaced with a Teflon screwcap. The tube was sealed, and the mixture was stirred at 100° C. for 64 hours. The reaction mixture was cooled to room temperature, diluted with ethyl acetate (10 ml), filtered, and concentrated in vacuo. The crude material was purified by flash chromatography (silica gel, ethyl acetate-hexane 1:1) to afford 190 mg (66%; m/z 337) of colorless crystals. This compound was dissolved in a mixture of tetrahydrofuran (4 ml), methanol (2 ml) and water (1 ml). To this solution was added dropwise LiOH monohydrate (95 mg; 2.26 mmol) dissolved in 1 ml water and the mixture was stirred at room temperature for 16 h. The reaction mixture was partition between ethyl acetate and water. The aqueous layer was acidified with 2N HCl to pH~3–4 and extracted with ethyl acetate. The organic layer was washed with brine and dried (Na$_2$SO$_4$) and evaporated in vacuo. Yield 131 mg of 6-(1,1-Dioxo-1λ$^6$-[1,2]thiazinan-2-yl)-1-methyl-1H-indole-2-carboxylic acid as a white powder (75%); m/z 307.

From the 6-(methanesulfonyl-ethyl)-1-methyl-1H-indole-2-carboxylic acid prepared as described above, 6-(1,1-Dioxo-1λ$^6$-[1,2]thiazinan-2-yl)-1-methyl-1H-indole-2-carboxylic acid [(1S,2R)-2-((S)-1-cyano-3-methyl-butylcarbamoyl)-cyclohexyl]-amide was prepared using the procedure of Example 10.

Following a similar procedure, isothiazolidine 1,1-dioxide was first prepared using the procedure described by Tatsuo, Tsuri et al., J. Med. Chem. 2000, 43, 2040–2048, and 6-(1,1-Dioxo-1λ$^6$-[1,2]thiazinan-2-yl)-1-methyl-1H-indole-2-carboxylic acid was prepared therefrom using the procedure described above for 6-(1,1-Dioxo-1λ$^6$-[1,2]thiazinan-2-yl)-1-methyl-1H-indole-2-carboxylic acid. This carboxylic acid was in turn used to make (1,1-Dioxo-1λ$^6$-isothiazolidin-2-yl)-1-methyl-1H-indole-2-carboxylic acid [(1S,2R)-2-((S)-1-cyano-3-methyl-butylcarbamoyl)-cyclohexyl]-amide according to the procedure of Example 10.

Example 29

1-Methyl-1H-indole-2-carboxylic acid ((1S,2R)-2-{(S)-1-cyano-3-[4-(2-methoxy-ethyl)-piperazin-1-yl]-propylcarbamoyl}-cyclohexyl)-amide

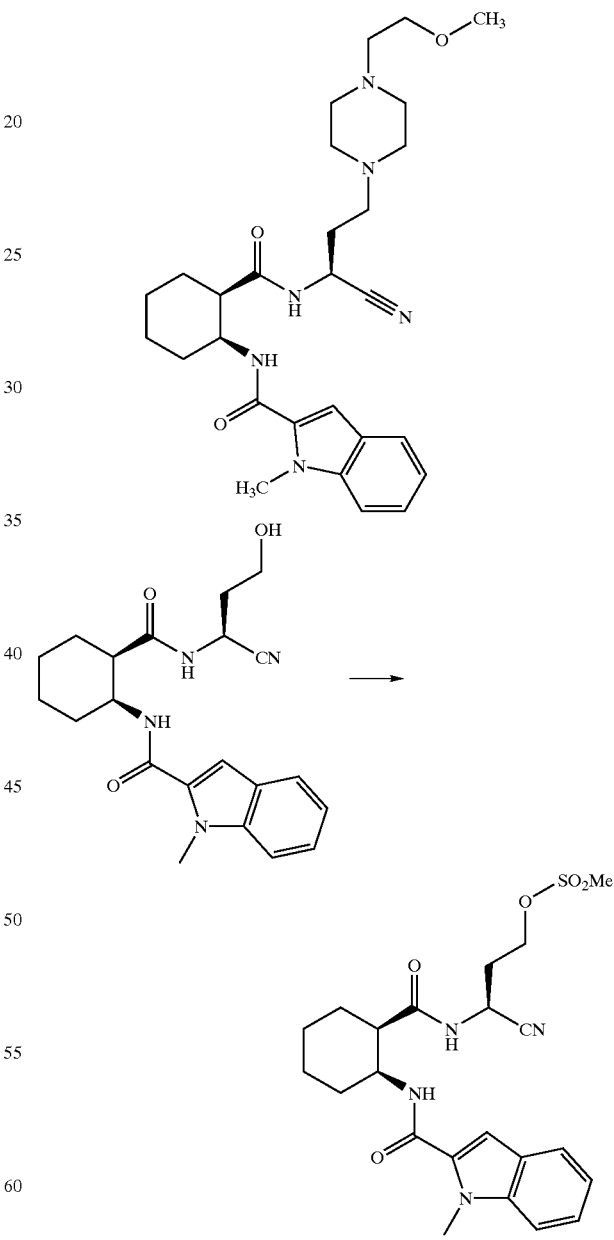

Step 1

To a 0° C. solution of N-[(1S,2R)-2-({[(1R)-1-cyano-2-hydroxyethyl]amino}carbonyl)cyclohexyl]methyl-1H-indole-2-carboxamide from Example 4 (2.07 g, 5.41 mmol)

in anhydrous CH$_2$Cl$_2$ (100 mL) was added methanesulfonic anhydride (1.16 g, 6.66 mmol) and triethylamine (1.0 mL, 7.10 mmol). The reaction mixture was stirred at room temp for 10 min, then added 100 mL of water. The organic layer was separated, dried with sodium sulfate, and concentrated to give 2.53 g (100%) of (S)-3-cyano-3-({(1R,2S)-2-[(1-methyl-1H-indole-2-carbonyl)-amino]-cyclohexanecarbonyl}-amino)-propyl ester as a pale yellow foam. MS: 483 (M+Na$^+$).

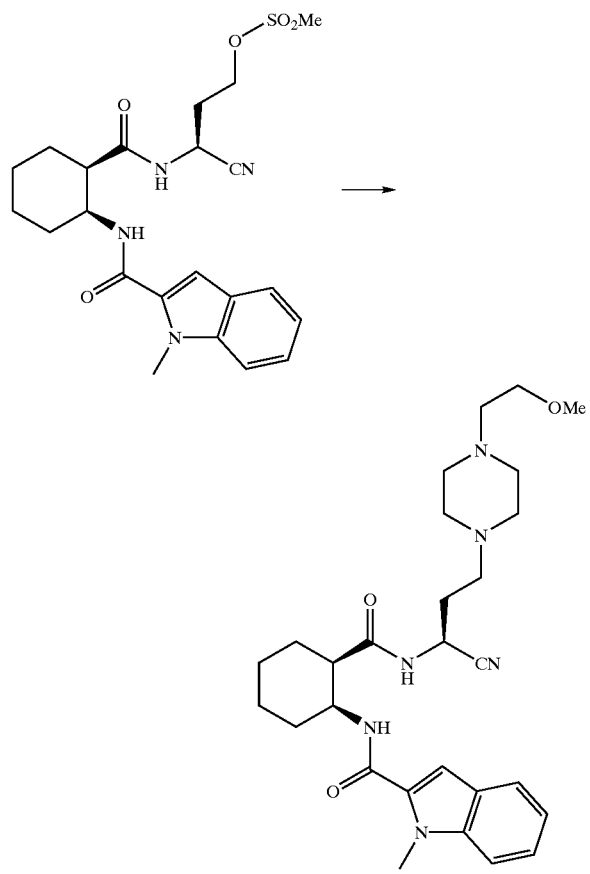

Step 2

To a solution of (S)-3-cyano-3-({(1R,2S)-2-[(1-methyl-1H-indole-2-carbonyl)-amino]-cyclohexanecarbonyl}-amino)-propyl ester (223 mg, 0.484 mmol) in anhydrous DMF (2.0 mL) was added 1-(2-methoxyethyl)-piperizine (214 mg, 1.48 mmol), and the reaction mixture was placed in a 69° C. oil bath for 22 hours. The cooled reaction mixture was partitioned between water (75 mL) and ethyl acetate (75 mL). The organic layer was separated, washed with water (2×75 mL), dried with sodium sulfate, filtered, concentrated, and purified by column chromatography (5:95, MeOH/CH$_2$Cl$_2$) to give 173 mg (70%) of 1-methyl-1H-indole-2-carboxylic acid [(1S,2R)-2-{(S)-1-cyano-3-[4-(2-methoxyethyl)-piperazin-1-yl]-propylcarbamoyl}-cyclohexyl)-amide as an amorphous solid. MS: 509 (M+H$^+$).

Using the above procedure and replacing 1-(2-methoxyethyl)-piperizine with morpholine, 1-methyl-1H-indole-2-carboxylic acid [(1S,2R)-2-((S)-1-cyano-3-morpholin-4-yl-propylcarbamoyl)-cyclohexyl]-amide was similarly prepared.

Example 30

1-Methyl-1H-indole-2-carboxylic acid [(1S,2R)-2-((S)-1-cyano-4-morpholin-4-yl-3-oxo-butylcarbamoyl)-cyclohexyl]-amide

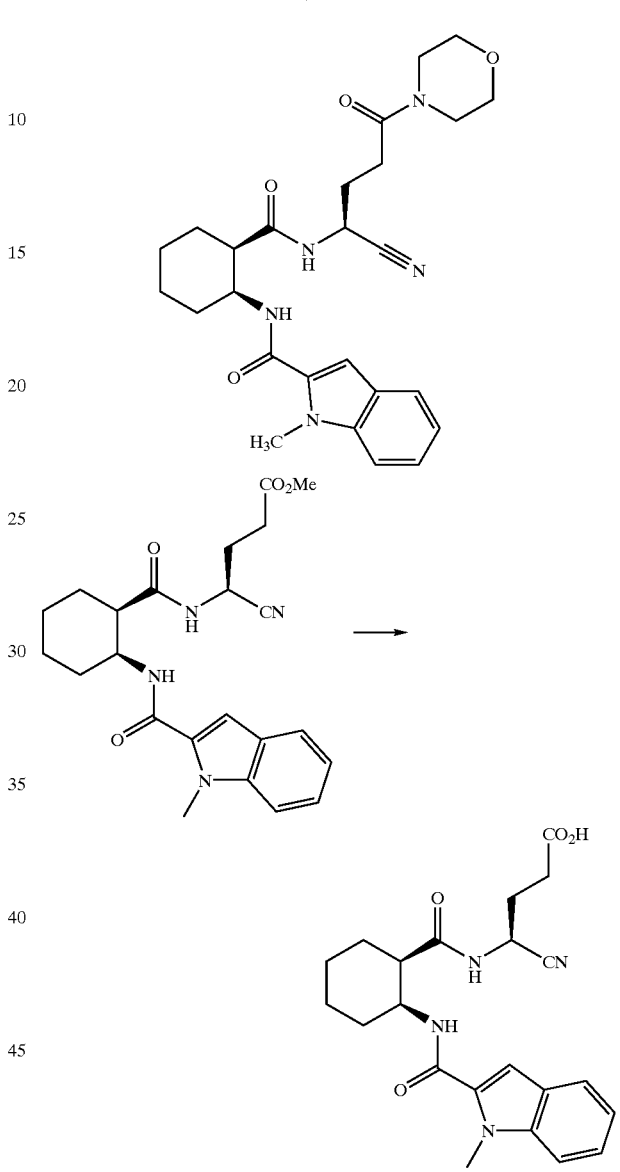

Step 1

To a solution of (S)-4-cyano-4-({(1R,2S)-2-[(1-methyl-1H-indole-2-carbonyl)-amino]-cyclohexanecarbonyl}-amino)-butyric acid methyl ester (prepared as described in Example 3 using glutamic acid amide methyl ester) (572 mg, 1.35 mmol) in 15 mL of THF and 2 mL of MeOH was added a solution of lithium hydroxide hydrate (370 mg, 8.82 mmol) in 15 mL of water. The reaction mixture was stirred at room temp for 30 minutes, then poured into a slurry of ice and 20 mL of a 1N HCl solution. The organic layer was extracted with 50 mL of ethyl acetate, separated, washed with 50 mL of water, dried with sodium sulfate, and concentrated to give 556 mg (100%) of (S)-4-cyano-4-({(1R,2S)-2-[(1-methyl-1H-indole-2-carbonyl)-amino]-cyclohexanecarbonyl}-amino)-butyric acid as a white amorphous solid. MS: 409 (M–H$^+$).

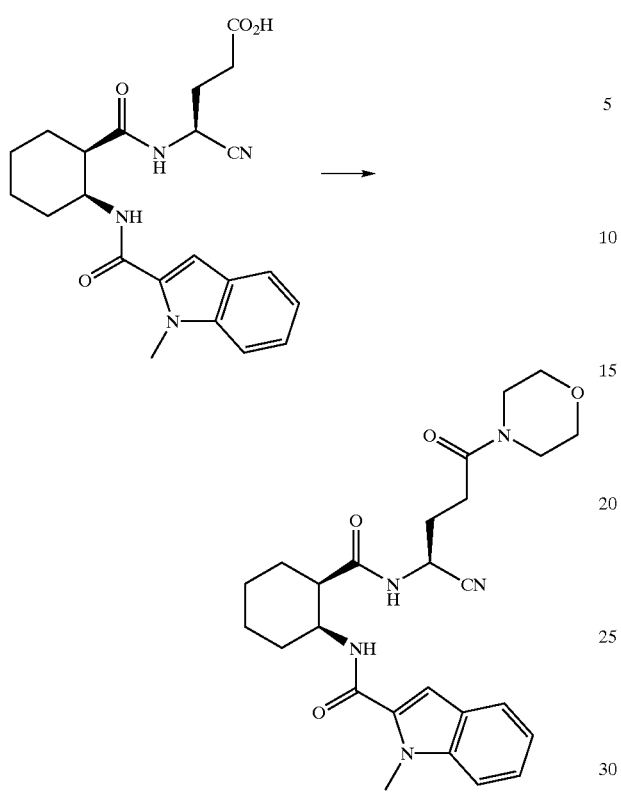

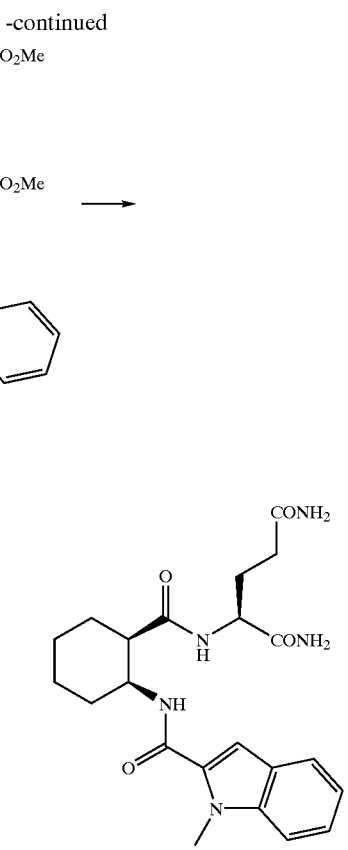

Step 2

The (S)-4-cyano-4-({(1R,2S)-2-[(1-methyl-1H-indole-2-carbonyl)-amino]-cyclohexanecarbonyl}-amino)-butyric acid (140 mg, 0.341 mmol), morpholine (50 μL, 0.57 mmol), EDCI hydrochloride (102 mg, 0.532 mmol), HOBT (50 mg, 0.37 mmol) and N-methyl morpholine (0.10 mL, 0.91 mmol) were dissolved in 5.0 mL of DMF and stirred at room temp for 4 hours. The reaction mixture was partitioned between 50 mL of water and 50 mL of ethyl acetate. The organic layer was washed with water (2×50 mL), dried with sodium sulfate, filtered and concentrated to give 98 mg (60%) of 1-Methyl-1H-indole-2-carboxylic acid [(1S,2R)-2-((S)-1-cyano-4-morpholin-4-yl-4-oxo-butylcarbamoyl)-cyclohexyl]-amide as a white amorphous solid. MS: 480 (M+H⁺).

Example 31

1-Methyl-1H-indole-2-carboxylic acid [(1S,2R)-2-(1,3-dicyano-propylcarbamoyl)-cyclohexyl]-amide

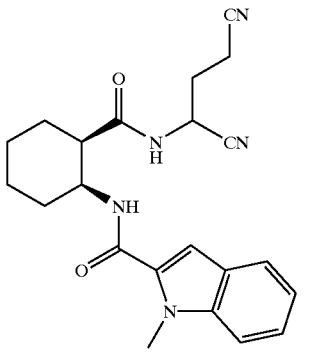

Step 1

(S)-2-({(1R,2S)-2-[(1-Methyl-1H-indole-2-carbonyl)-amino]cyclohexanecarbonyl}-amino)-pentanedioic acid dimethyl ester (prepared using the procedure of Example 3 with glutamic acid dimethyl ester) (0.62 g, 1.4 mmol) was treated with 20 mL of a 7N solution of ammonia (140 mmol) in methanol in a reaction tube, which was sealed and placed in a 70° C. oil bath for 24 hours. The resulting suspension was concentrated to give 0.55 g (93%) of (S)-2-({(1R,2S)-2-[(1-Methyl-1H-indole-2-carbonyl)-amino]-cyclohexanecarbonyl}-amino)-pentanedioic acid diamide as a white solid. MS: 428 (M+H⁺), mp=234.5–235.0° C.

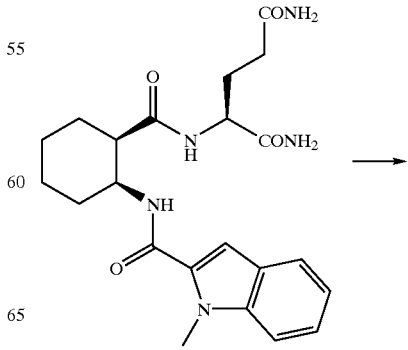

-continued

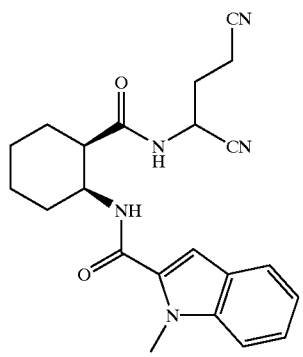

-continued

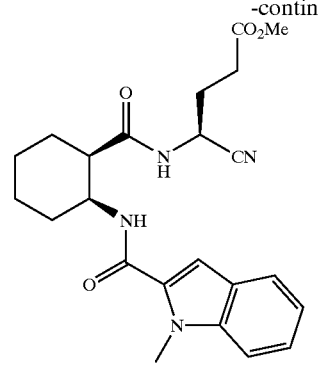

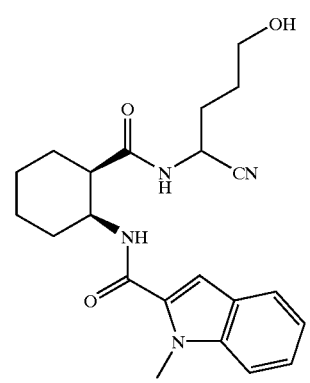

Step 2

To a 0° C. suspension of (S)-2-({(1R,2S)-2-[(1-Methyl-1H-indole-2-carbonyl)-amino]-cyclohexanecarbonyl}-amino)-pentanedioic acid diamide (0.53 g, 1.2 mmol) in 30 mL of anhydrous pyridine and 30 mL of $CH_2Cl_2$ was slowly added trifluoroacetic anhydride dropwise. The resulting yellow reaction mixture was stirred at 0° C. for 15 min, and poured into a slurry of ice and a 1N HCl solution. The mixture was extracted with 250 mL of ethyl acetate, washed with a 1N solution of HCl (3×250 mL), water (250 mL), and dried with sodium sulfate, filtered, concentrated and purified by column chromatography (5:95, $MeOH/CH_2Cl_2$) to give 430 mg (89%) of 1-methyl-1H-indole-2-carboxylic acid [(1S,2R)-2-(1,3-dicyano-propylcarbamoyl)-cyclohexyl]-amide as a light-yellow liquid, which was determined to be a 38:62 ratio of epimers by $^1H$ NMR spectroscopy. MS: 392 (M+H$^+$).

To a solution of (S)-4-cyano-4-({(1R,2S)2-[(1-methyl-1H-indole-2-carbonyl)-amino]-cyclohexanecarbonyl}-amino)-butyric acid methyl ester (obtained from compound 3-8, 209 mg, 0.492 mmol), in 15 mL of MeOH and 15 mL of $CH_2Cl_2$, was added sodium borohydride (100 mg, 2.64 mmol). The reaction mixture was stirred at ambient temperature for 24 hours, concentrated, and purified by column chromatography (3:97, $MeOH/CH_2Cl_2$) to give 83 mg (43%) of 1-methyl-1H-indole-2-carboxylic acid [(1S,2R)-2-(1-cyano-4-hydroxy-butylcarbamoyl)-cyclohexyl]-amide as an amorphous solid. MS: 397 (M+H$^+$).

Example 32

1-Methyl-1H-indole-2-carboxylic acid [(1S,2R)-2-(1-cyano-4-hydroxy-butylcarbamoyl)-cyclohexyl]-amide

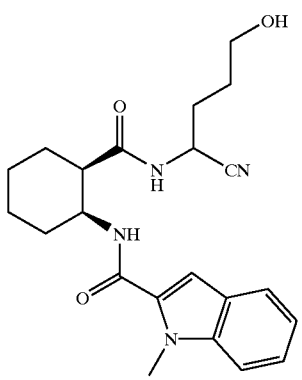

Example 33

1-Methyl-1H-indole-2-carboxylic acid ((1S,2R)-2-{[(S)-cyano-(4-methoxy-benzyl)-methyl]-carbamoyl}-cyclohexyl)-amide

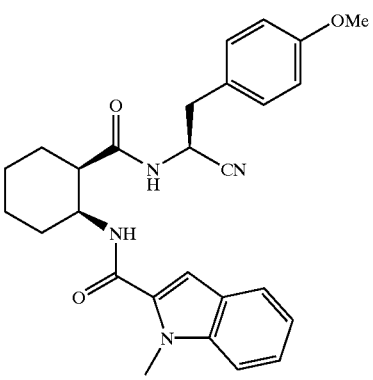

-continued

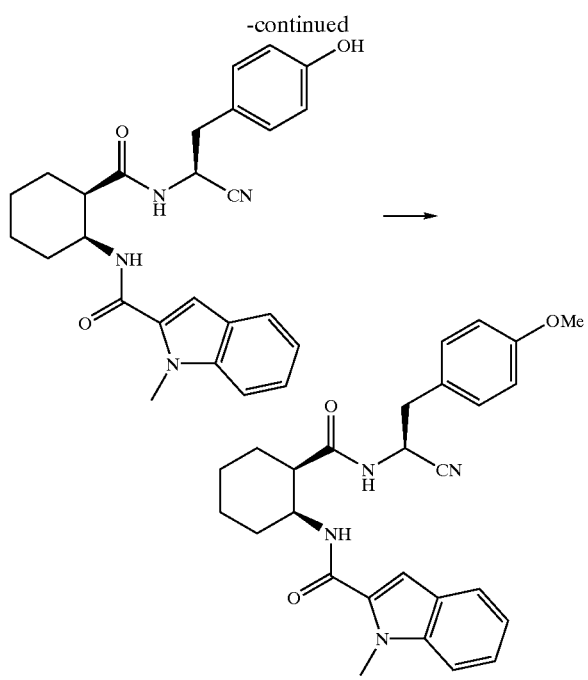

To a solution of 1-Methyl-1H-indole-2-carboxylic acid {(1S,2R)-2-[(S)-1-cyano-2-(4-hydroxy-phenyl)-ethylcarbamoyl]cyclohexyl}-amide (compound 34, 102 mg, 0.229 mmol) in 3 mL of anhydrous DMF, was added sodium hydride powder (15 mg, 0.594 mmol). The reaction mixture was stirred for 5 min. while gas evolution subsided, then methyl iodide (0.2 mL, 3.1 mmol) was added. The reaction mixture was partitioned between 50 mL of water and 50 mL of ethyl acetate, the separated organic layer was washed with water (2×50 mL), dried with sodium sulfate, filtered, concentrated and purified by column chromatography (50:50, ethyl acetate/hexanes) to give 74 mg (70%) of 1-methyl-1H-indole-2-carboxylic acid ((1S,2R)-2-{[(S)-cyano-(4-methoxy-benzyl)-methyl]-carbamoyl}-cyclohexyl)-amide as a white amorphous solid. MS: 459 (M+H$^+$).

Example 34

1-Methyl-1H-indole-2-carboxylic acid ((1S,2R)-2-{[(1-acetyl-piperidin-4-ylmethyl)-cyano-methyl]-carbamoyl}-cyclohexyl)amide

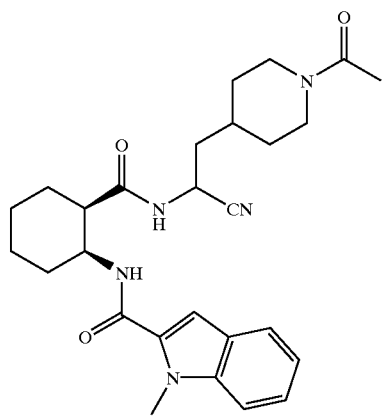

-continued

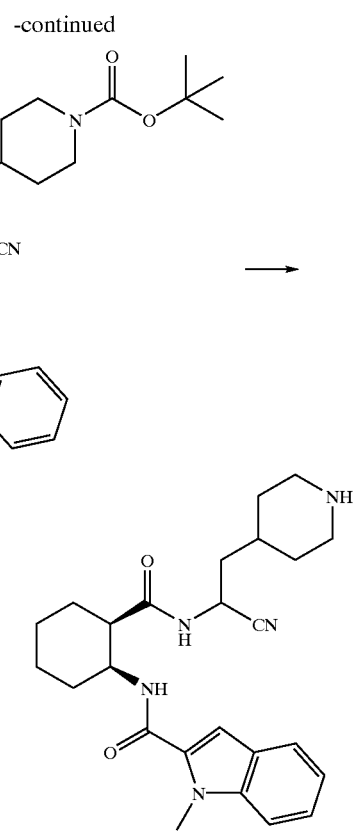

Step 1

To a solution of 4-[2-cyano-2-({(1R,2S)-2-[(1-methyl-1H-indole-2-carbonyl)-amino]-cyclohexanecarbonyl}-amino)-ethyl]-piperidine-1-carboxylic acid tert-butyl ester (1.20 g, 2.24 mmol) in 20 mL of CH$_2$Cl$_2$, was added TFA (4.0 mL, 52 mmol). The reaction mixture was stirred at ambient temperature for 4 hours, concentrated, poured into an aqueous sodium bicarbonate solution, extracted with ethyl acetate, dried with sodium sulfate, and concentrated to give 541 mg (55%) of 1-methyl-1H-indole-2-carboxylic acid {(1S,2R)-2-[(cyano-piperidin-4-ylmethyl-methyl)-carbamoyl]-cyclohexyl}-amide as a pale-yellow amorphous material. MS: 436 (M+H$^+$).

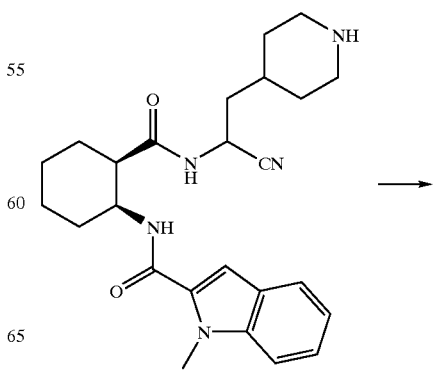

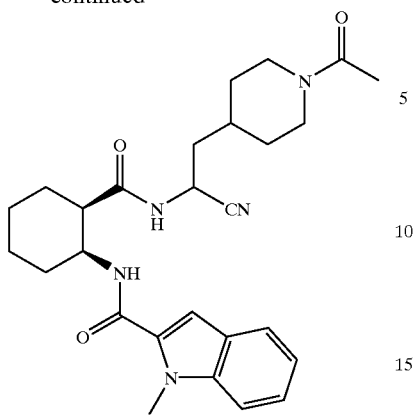

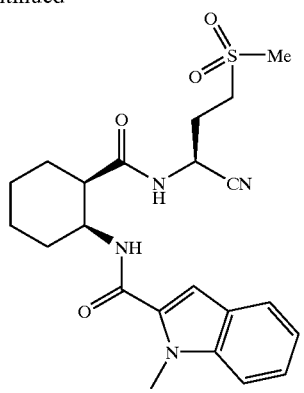

Step 2

To a solution of 1-methyl-1H-indole-2-carboxylic acid {(1S,2R)-2-[(cyano-piperidin-4-ylmethyl-methyl)-carbamoyl]-cyclohexyl}-amide hydrochloride (0.50 g, 1.06 mmol) in 2 mL of DMF, was added 0.5 mL of TEA, acetic anhydride (0.15 mL, 1.59 mmol), and a few crystals of DMAP. The reaction mixture was stirred at ambient temperature for 1 hour, and partitioned between 50 mL of water and 50 mL of ethyl acetate. The separated organic layer was washed with water (2×50 mL), dried with sodium sulfate, filtered, concentrated, and purified by column chromatography (5:95, MeOH/CH$_2$Cl$_2$) to give 165 mg (33%) of 1-methyl-1H-indole-2-carboxylic acid ((1S,2R)-2-{[(1-acetyl-piperidin-4-ylmethyl)-cyano-methyl]-carbamoyl}-cyclohexyl)-amide as a white amorphous solid. MS: 478 (M+H$^+$).

Example 35

1-Methyl-1H-indole-2-carboxylic acid [(1S,2R)-2-((S)-1-cyano-3-methanesulfonyl-propylcarbamoyl)-cyclohexyl]-amide

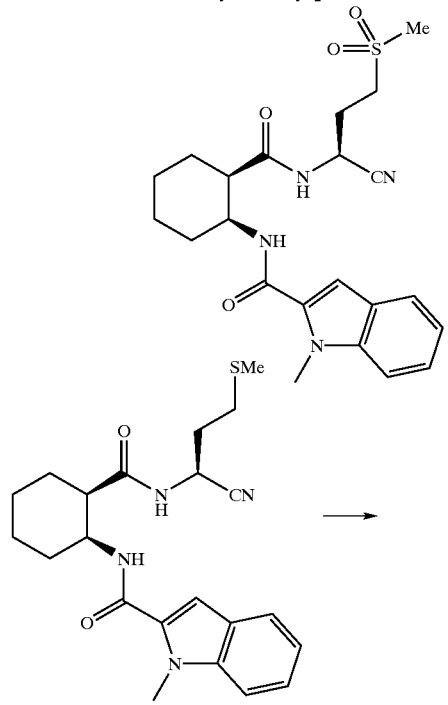

To a solution of 1-methyl-1H-indole-2-carboxylic acid [((1S,2R)-2-((S)-1-cyano-3-methylsulfanyl-propylcarbamoyl)-cyclohexyl]-amide (compound 3-2, 203 mg, 0.492 mmol) in 20 mL of THF, was added Oxone™ (390 mg, 0.634 mmol). The reaction mixture was stirred at ambient temperature for 2 hours, filtered through a pad of celite, dried with sodium sulfate, filtered, concentrated, and purified by column chromatography (5:95, MeOH/CH$_2$Cl$_2$) to give 178 mg (81%) of 1-methyl-1H-indole-2-carboxylic acid [(1S,2R)-2-((S)-1-cyano-3-methanesulfonyl-propylcarbamoyl)-cyclohexyl]-amide as a yellow amorphous solid. MS: 445 (M+H$^+$).

In a variation of the above procedure, 1-methyl-1H-indole-2-carboxylic acid [(1S,2R)-2-((S)-1-cyano-3-methylsulfanyl-propylcarbamoyl)-cyclohexyl]-amide (530 mg, 1.28 mmol) was reacted with MCPBA (710 mg, 3.17 mmol) in 30 mL of CH$_2$Cl$_2$ at 0° C. The resulting yellow reaction mixture was warmed to ambient temperature, concentrated and purified by column chromatography (2–5:98–95, MeOH/CH$_2$Cl$_2$) to give 218 mg (40%) of 1-methyl-1H-indole-2-carboxylic acid [(1S,2R)-2-((S)-1-cyano-3-methanesulfonyl-propylcarbamoyl)-cyclohexyl]-amide (Rf=0.42); and 147 mg (26%) of the sulfone, together with 1-methyl-1H-indole-2-carboxylic acid [(1S,2R)-2-((S)-1-cyano-3-methanesulfinyl-propylcarbamoyl)-cyclohexyl]-amide (Rf=0.48), as yellow amorphous solids.

Example 36

1-Methyl-1H-indole-2-carboxylic acid {(1S,2R)-2-[(cyano-pyridin-4-ylmethyl-methyl)-carbamoyl]-cyclohexyl}-amide

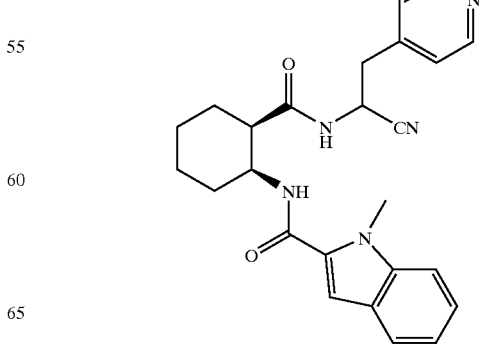

-continued

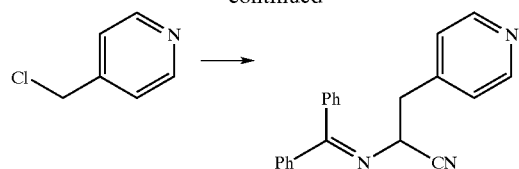

Step 1

To a suspension of sodium hydride (0.54 g, 23 mmol) in anhydrous THF (80 mL) was added portionwise N-(diphenylmethylene)aminoacetonitrile (5.00 g, 23 mmol). The reaction was allowed to stir at room temperature until hydrogen evolution ceased and then cooled to 0° C. for 10 minutes. To the reaction mixture was added a solution of 4-chloromethyl pyridine (3.03 g, 24 mmol) in anhydrous THF (10 mL) and dichloromethane (3 mL). The reaction mixture was stirred at room temperature for 50 minutes and then cooled to 0° C. and was added saturated ammonium chloride (80 mL) and extracted with three 80 mL portions of ethyl acetate. The combined organic layers was dried on sodium sulfate and concentrated to give a viscous oil. Purification by column chromatography (40:60 ethyl acetate:hexane) and trituration with hexanes gave 2-(benzhydrylidene-amino)-3-pyridin-4-yl-propionitrile (4.02 g, 52%).

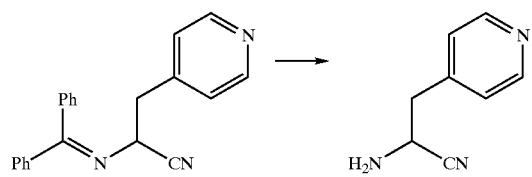

Step 2

To a solution of ethanol (10 mL), water (0.09 mL, 5 mmol), hydrogen chloride (9.6 mL, 1M in diethyl ether) was added a solution of 2-(benzhydrylidene-amino)-3-pyridin-4-yl-propionitrile (1.50 g, 5 mmol) in ethanol (10 mL). The reaction was stirred for 30 minutes, then concentrated to one third volume. The crude residue was triturated with five 30 mL portions of hexane:ether (4:1 vol:vol) and seven 30 mL portions of hexane. The precipitate was dried in vacuo to give 2-amino-3-pyridin-4-yl-propionitrile as an off white powder (1.05 g, 99%).

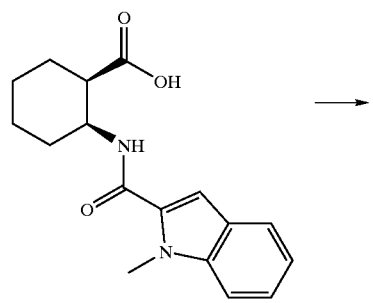

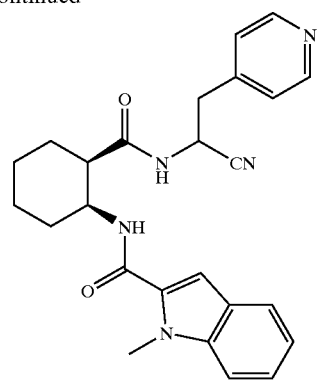

Step 3

To (1R,2S)-2-[(1-methyl-1H-indole-2-carbonyl)-amino]-cyclohexanecarboxylic acid from Example 3 (200 mg, 0.67 mmol) was added EDCI (150 mg, 0.78 mmol), HOBT (110 mg, 0.82 mmol), anhydrous DMF (4 mL), N-methylmorpholine (0.15 mL, 1.3 mmol), and 4-pyridylglycine nitrile hydrochloride salt (4) (160 mg, 1.0 mmol). The reaction mixture was stirred at room temperature for 20 hrs, then 50 mL of water was added and extracted with three 50 mL portions of ethyl acetate. The combined organic layers was washed with three 50 ml portions of water and three 50 mL portions of saturated NaHCO$_3$, dried over sodium sulfate, filtered and concentrated to give a crude foam. Purification by column chromatography (5:95 methanol:dichloromethane) gave 1-methyl-1H-indole-2-carboxylic acid {(1S,2R)-2-[(cyano-pyridin-4-ylmethyl-methyl)-carbamoyl]cyclohexyl}-amide, 165 mg, 58%). MS: 430 (M+H$^+$).

Similarly, 2-amino-3-pyridin-3-yl-propionitrile was prepared, from which 1-methyl-1H-indole-2-carboxylic acid {(1S,2R)-2-[(cyano-pyridin-3-ylmethyl-methyl)-carbamoyl]-cyclohexyl}-amide was obtained (180 mg, 63%). MS: 430 (M+H).

Example 37

1-Methyl-1H-indole-2-carboxylic acid ((1S,2R)-2-{[(2-chloro-pyridin-4-ylmethyl)-cyano-methyl]-carbamoyl}-cyclohexyl)-amide

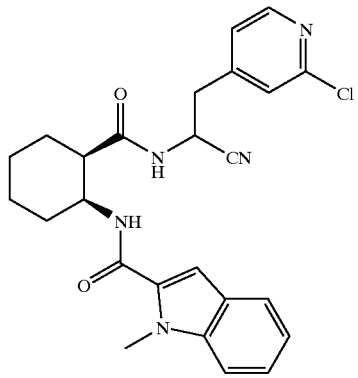

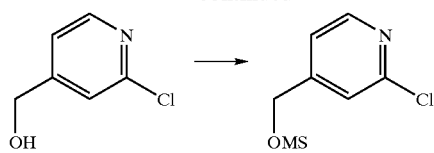

-continued

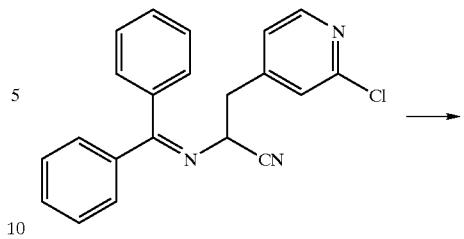

Step 1

To a 0° C. solution of (2-chloro-pyridin-4-yl)-methanol (2.00 g, 13 mmol) (prepared from the corresponding carboxylic acid according to the procedure in U.S. Pat. No. 6,218,537), ethyl acetate (30 mL) and triethylamine (2.9 mL, 21 mmol) was added drop wise methansulfonyl chloride (1.4 mL, 18 mmol). The solution was stirred for 10 minutes and then water (5 mL) was added. The reaction mixture was extracted with three 30 mL portions of ethyl acetate, the organics combined and washed with water (30 mL) and brine (30 mL), dried on sodium sulfate, and concentrated to a crude oil. Pentane was added to the residue and stirred at 0° C. The precipitate was collected and dried in vacuo to give methanesulfonic acid 2-chloro-pyridin-4-ylmethyl ester (3.09 g, 100%).

Step 3

To a solution of ethanol (20 mL), water (0.08 mL, 4 mmol), hydrogen chloride (10.8 mL, 1M in diethylether) was added a solution of 2-(benzhydrylidene-amino)-3-(2-chloro-pyridin-4-yl)-propionitrile (1.50 g, 4 mmol) in ethanol (15 mL) and methanol (5 mL). The reaction was stirred for 20 minutes, then concentrated to one third volume. The crude residue was triturated with hexane (20 mL), ethanol (10 mL), three 30 mL portions of hexane:ether (4:1 vol:vol) and three 30 mL portions of hexane. The precipitate was dried in vacuo to give 2-amino-3-(2-chloro-pyridin-4-yl)-propionitrile as an off white powder (0.90 g, 82%).

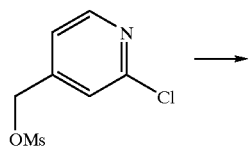

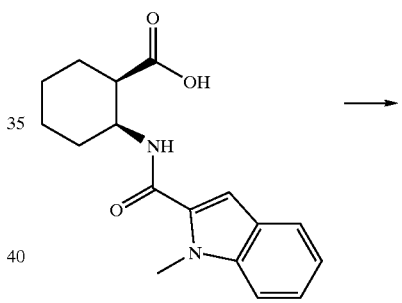

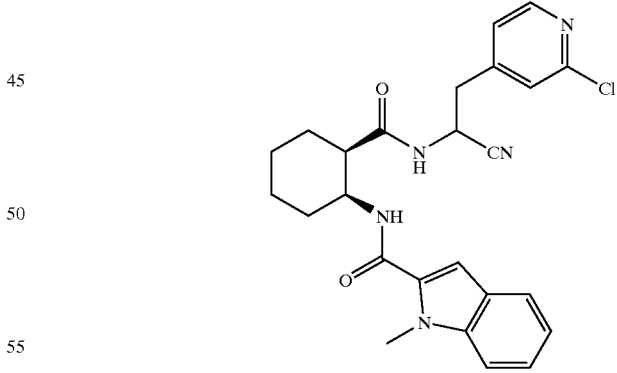

Step 2

To a suspension of sodium hydride (0.34 g, 14 mmol) in anhydrous THF (80 mL) was added portionwise N-(diphenylmethylene)aminoacetonitrile (3.13 g, 14 mmol). The reaction was allowed to stir at room temperature until hydrogen evolution ceased and then cooled to 0° C. for 10 minutes. To the reaction mixture was added a solution of methansulfonic acid 2-chloro-pyridinylmethyl ester (3.00 g, 13 mmol) in anhydrous THF (10 mL). The reaction mixture was stirred at room temperature for 20 minutes and then cooled to 0° C. and was added saturated ammonium chloride (50 mL) and extracted with three 100 mL portions of ethyl acetate. The combined organic layers was dried on sodium sulfate and concentrated to give a viscous oil. Purification by column chromatography (40:60 ethyl acetate:hexane) and trituration with hexanes gave 2-(benzhydrylidene-amino)-3-(2-chloro-pyridin-4-yl)-propionitrile (4.02 g, 52%).

Step 4

To (1R,2S)-2-[(1-methyl-1H-indole-2-carbonyl)amino]-cyclohexanecarboxylic acid from Example 3 (200 mg, 0.67 mmol) was added EDCI (150 mg, 0.78 mmol), HOBT (110 mg, 0.82 mmol), anhydrous DMF (4 mL), N-methylmorpholine (0.15 mL, 1.3 mmol), and 4-(2-chloro) pyridylglycine nitrile hydrochloride (8) (160 mg, 0.88 mmol). The reaction mixture was stirred at room temperature for 42 hrs, then 50 mL of water was added and extracted with four 50 mL portions of ethyl acetate. The combined organic layers was washed with three 50 ml portions of water, dried over magnesium sulfate, filtered and concentrated to give a crude foam. Purification by column chromatography (10:90 methanol:dichloromethane) gave 1-methyl-1H-indole-2-carboxylic acid ((1S,2R)-2-{[(2-chloro-pyridin-4-ylmethyl)-cyano-methyl]-carbamoyl}-cyclohexyl)-amide (231 mg, 75%) MS: 464 (M+H$^+$).

Similarly, using the above procedure but replacing 2-chloro-4-pyridinecarboxylic acid with 2-chloro-6-methylpyridine-4-carboxylic acid gave 1-methyl-1H-indole-2-carboxylic acid ((1S,2R)-2-{[(2-chloro-6-methyl-pyridin-4-ylmethyl)-cyano-methyl]-carbamoyl}-cyclohexyl)-amide (156 mg, 49%). MS: 478 (M+H).

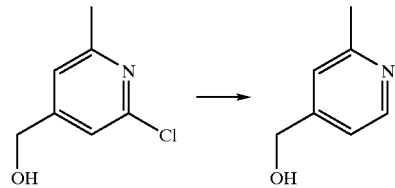

In a variation of the above procedure, a solution of 2-chloro-6-methylpyridine-4-carboxylic, palladium (0.20 g, 10 mol % on carbon), ethyl acetate (45 mL), and triethylamino (2.8 mL, 20 mmol). The reaction mixture was placed under hydrogen at 1 atm for 21 hours. Additional Pearlman's catalyst (0.2 g) was added and the reaction was stirred under hydrogen for an additional 5 hours to effect dechlorination. The mixture was filtered through a pad of celite and concentrated. Purification by column chromatography (5:95 methanol:dichloromethane) gave (2-methyl-pyridin-4-yl)-methanol (1.48 g, 88%). The (2-methyl-pyridin-4-yl)-methanol was used to prepare 2-amino-3-(2-methyl-pyridin-4-yl)-propionitrile, from which 1-methyl-1H-indole-2-carboxylic acid ((1S,2R)-2-{[cyano-(2-methyl-pyridin-4-ylmethyl)-methyl]-carbamoyl}-cyclohexyl)-amide was obtained (186 mg, 62%) in the manner described above. MS: 444 (M+H).

Example 38

1-Methyl-1H-indole-2-carboxylic acid ((1S,2R)-2-{[cyano-(4-hydroxymethyl-benzyl)-methyl]-carbamoyl}-cyclohexyl)-amide

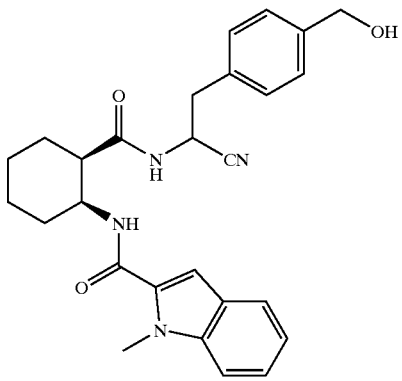

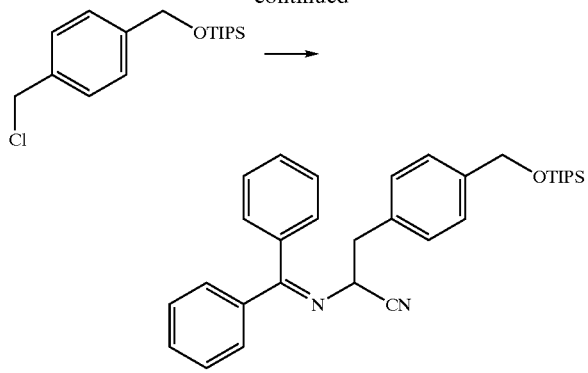

Step 1

To a suspension of sodium hydride (0.08 g, 3.3 mmol) in anhydrous THF (15 mL) was added portionwise N-(diphenylmethylene)aminoacetonitrile (0.74 g, 3.3 mmol). The reaction was allowed to stir at room temperature until hydrogen evolution ceased and then cooled to 0° C. for 10 minutes. To the reaction mixture was added a solution of (4-chloromethyl-benzyloxy)-triisopropyl-silane (1.00 g, 3.2 mmol) (Iqbal, N.; McEwen, C-A.; Knaus, E. *Drug Development Research* 2000, 51, 177; Greene, T. W. *Protective Groups in Organic Chemistry*; John Wiley & Sons, Inc: New York, 1991) in anhydrous THF (5 mL). The reaction mixture was stirred at 0° C. for 1 hour after which saturated ammonium chloride (50 mL) was added and reaction mix extracted with three 50 mL portions of ethyl acetate. The combined organic layers were dried on magnesium sulfate and concentrated the crude material. Purification by column chromatography (10:90 ethyl acetate:hexane) 2-(benzhydrylidene-amino)-3-(4-triisopropylsilanyloxymethyl-phenyl)propionitrile (0.70 g, 44%).

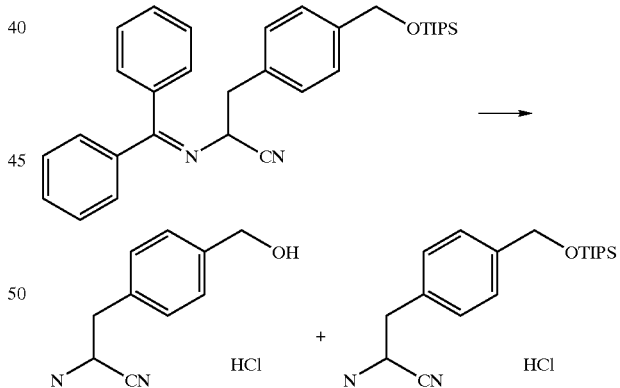

Step 2

To a solution of 2-(benzhydrylidene-amino)-3-(4-triisopropylsilanyloxymethyl-phenyl)propionitrile (0.69 g, 1.4 mmol) and ethanol (5 mL) was added water (0.03 mL, 1.7 mmol), and hydrogen chloride (1.5 mL, 1 M in ether). The reaction mixture was allowed to stir at room temperature for 2 hours and then was concentrated. The residue was triturated with 3:1 hexane:ether (vol:vol) to give a mixture of 2-amino-3-(4-hydroxymethyl-phenyl)-propionitrile and 2-amino-3-(4-triisopropylsilanyloxymethyl-phenyl)-propionitrile. This crude mix was used in the next coupling without further purification.

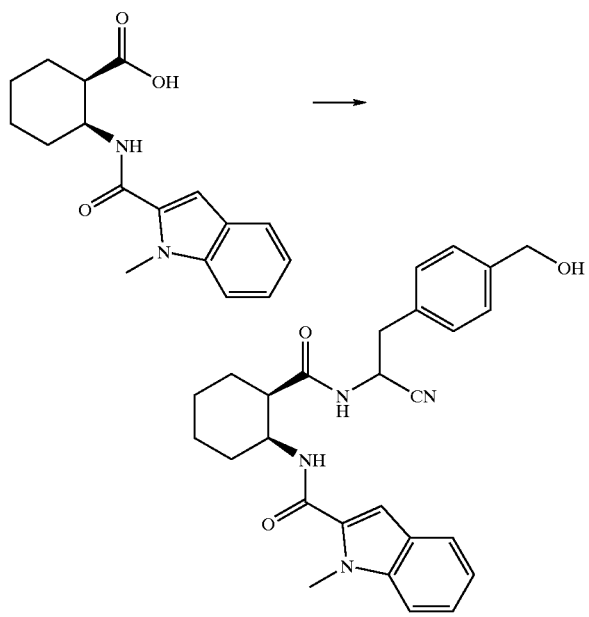

Step 3

To (1R,2S)-2-[(1-methyl-1H-indole-2-carbonyl)-amino]-cyclohexanecarboxylic acid from Example 3 (0.25 g, 0.83 mmol) was added EDCI (0.19 g, 0.99 mmol), HOBT (0.13 g, 0.96 mmol), anhydrous DMF (8 mL), N-methylmorpholine (0.09 mL, 0.82 mmol), and (11) (0.18 g, 0.84 mmol). The reaction mixture was stirred at room temperature for 18 hrs, then 75 mL of water was added and extracted with three 50 mL portions of ethyl acetate. The combined organic layers was washed with three 50 mL portions of water, three 50 mL portions of HCl (1M aq), three 50 mL portions of saturated NaHCO$_3$, dried over magnesium sulfate, filtered and concentrated to give a crude foam. Purification by column chromatography (50:50 ethyl acetate:hexanes) gave 1-methyl-1H-indole-2-carboxylic acid ((1S,2R)-2-{[cyano-(4-hydroxymethyl-benzyl)-methyl]-carbamoyl}-cyclohexyl)-amide (0.20 g, 53%) MS: 459 (M+H$^+$).

Example 39

1-Methyl-1H-indole-2-carboxylic acid {(1S,2R)-2-[((R)-cyano-methoxymethyl-methyl)-carbamoyl]-cyclohexyl}-amide

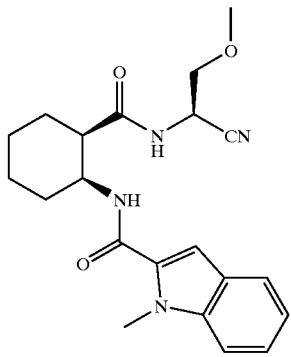

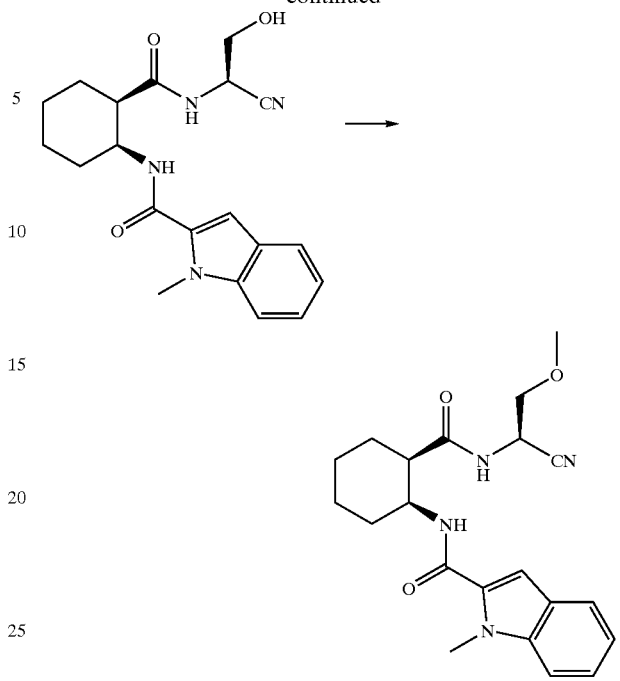

N-[(1S,2R)-2-({[(1R)-1-Cyano-2-hydroxyethyl]amino}carbonyl)cyclohexyl]-1-methyl-1H-indole-2-carboxamide from Example 4 (0.20 g, 0.54 mmol) was dissolved in dichloromethane (8 mL), cooled to 0° C. under nitrogen in the dark, and stirred for 15 minutes. Trimethyloxonium tetrafluoroborate (0.10 g, 0.68 mmol) was added (Sowinski, J. A.; Toogood, P. L. *J. Org. Chem.* 1996, 61, 7671). After 20 minutes, proton sponge (0.14 g, 0.65 mmol) was added, and the reaction was allowed to warm to room temperature and was stirred for 21 hours. The reaction mixture was filtered through a pad of celite and the pad washed with dichloromethane. The filtrate was washed with 1M hydrochloric acid, brine, dried on magnesium sulfate, and concentrated. Purification by column chromatography (5:95 methanol:dichlormethane) gave 1-methyl-1H-indole-2-carboxylic acid {(1S,2R)-2-[((R)-cyano-methoxymethyl-methyl)-carbamoyl]-cyclohexyl}-amide (0.08 g, 38%). MS: 383 (M+H).

Example 40

1-(3-Hydroxy-propyl)-1H-indole-2-carboxylic acid [(1S,2R)-2-(cyanomethyl-carbamoyl)-cyclohexyl]-amide

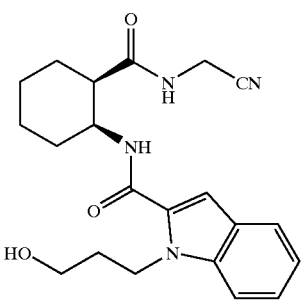

221

-continued

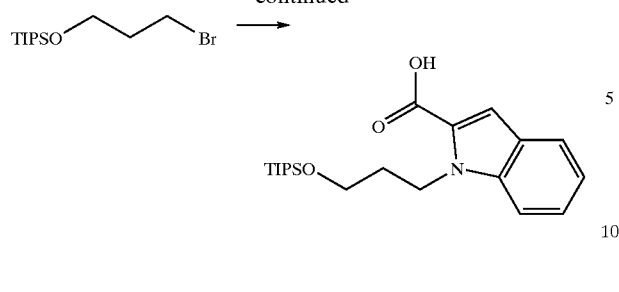

Step 1

(3-Bromo-propoxy)-triisopropyl-silane (prepared from the corresponding alcohol, Greene, T. W. *Protective Groups in Organic Chemistry*; John Wiley & Sons, Inc.: New York, 1991) was reacted with 1H-indole-2-carboxylic acid methyl ester using procedures similar to Example 11 to give 1-(3-triisopropylsilanyloxy-propyl)-1H-indole-2-carboxylic acid as a white solid.

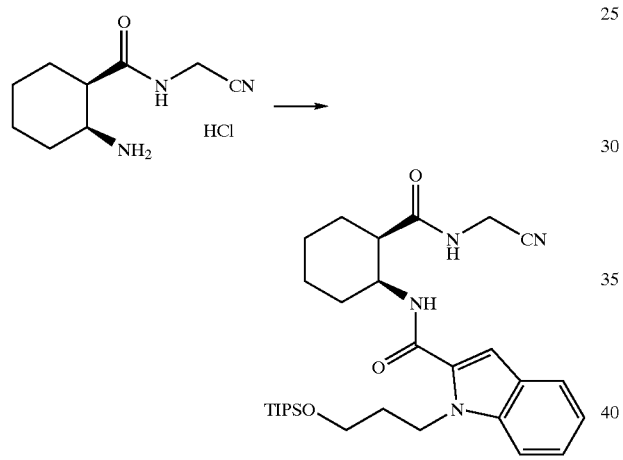

Step 2

(1R,2S)-2-Amino-cyclohexanecarboxylic acid cyanomethyl-amide was coupled with -(3-triisopropyl-silanyloxy-propyl)-1H-indole-2-carboxylic acid using a procedure similar to Example 11 to give 1-(3-triisopropyl-sitanyloxy-propyl)-1H-indole-2-carboxylic acid [(1S,2R)-2-(cyanomethyl-carbamoyl)-cyclohexyl]-amide.

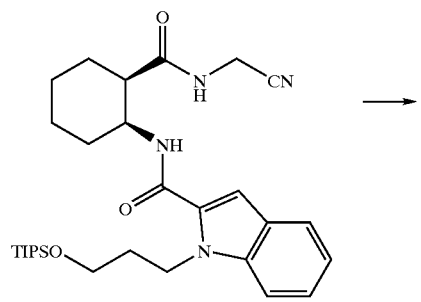

222

-continued

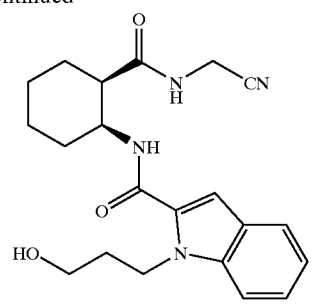

Step 3

1-(3-Triisopropylsilanyloxy-propyl)-1H-indole-2-carboxylic acid [(1S,2R)-2-(cyanomethyl-carbamoyl)-cyclohexyl]-amide was deprotected using the procedure of Example 4 to give 1-(3-hydroxy-propyl)-1H-indole-2-carboxylic acid [(1S,2R)-2-(cyanomethyl-carbamoyl)-cyclohexyl]-amide (101 mg, 88%). MS: 383 (M+H).

Using a similar procedure, 1-(3-Hydroxy-propyl)-1H-indole-2-carboxylic acid [(1S,2R)-2-((S)-1-cyano-3-methyl-butylcarbamoyl)-cyclohexyl]-amide was also prepared (101 mg, 88%, MS: 439 (M+H)).

Example 41

1-[2-(2-Hydroxy-ethoxy)-ethyl]-1H-indole-2-carboxylic acid [(1S,2R)-2-((S)-1-cyano-3-methyl-butylcarbamoyl)-cyclohexyl]-amide

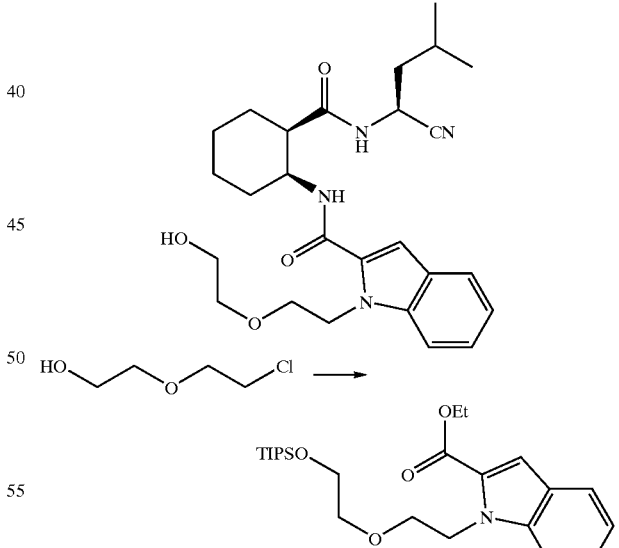

Step 1

Following a similar procedure to Example 11 but replacing (2-bromoethoxy)-tert-butyldimethylsilane with [2-(2-Chloro-ethoxy)-ethoxy]-triisopropyl-silane, gave 1-[2-(2-triisopropylsilanyloxy-ethoxy)-ethyl]-1H-indole-2-carboxylic acid ethyl ester as a colorless oil.

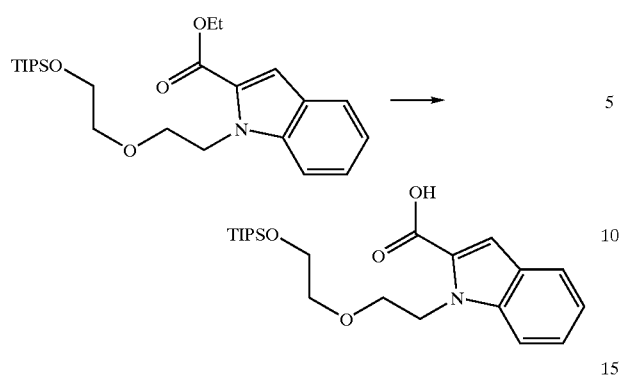

Step 2

1-[2-(2-Triisopropylsilanyloxy-ethoxy)ethyl]-1H-indole-2-carboxylic acid ethyl ester was hydrolyzed to 1-[2-(2-triisopropylsilanyloxy-ethoxy)ethyl]-1H-indole-2-carboxylic acid using the procedure of Example 11.

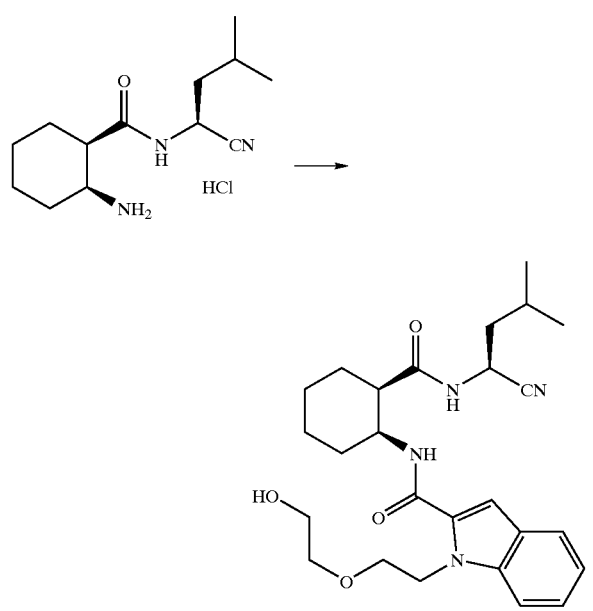

Step 3

(1R,2S)-2-Aminocyclohexanecarboxylic acid ((S)-1-cyano-3-methyl-butyl)-amide was reacted with 1-[2-(2-triisopropylsilanyloxy-ethoxy)-ethyl]-1H-indole-2-carboxylic acid using the procedure of Example 11 to yield 1-[2-(2-triisopropylsilanyloxy-ethoxy)-ethyl]-1H-indole-2-carboxylic acid [(1S,2R)-2-((S)-1-cyano-3-methyl-butylcarbamoyl)cyclohexyl]-amide, which was deprotected using the procedure of example 4 to give 1-[2-(2-hydroxy-ethoxy)-ethyl]-1H-indole-2-carboxylic acid [(1S,2R)-2-((S)-1-cyano-3-methyl-butylcarbamoyl)-cyclohexyl]-amide (0.60 g, 92%). MS: 469 (M+H).

Example 42

1-[2-(2-Methoxy-ethoxy)-ethyl]-1H-indole-2-carboxylic acid [(1S,2R)-2-((S)-1-cyano-3-methyl-butylcarbamoyl)-cyclohexyl]-amide

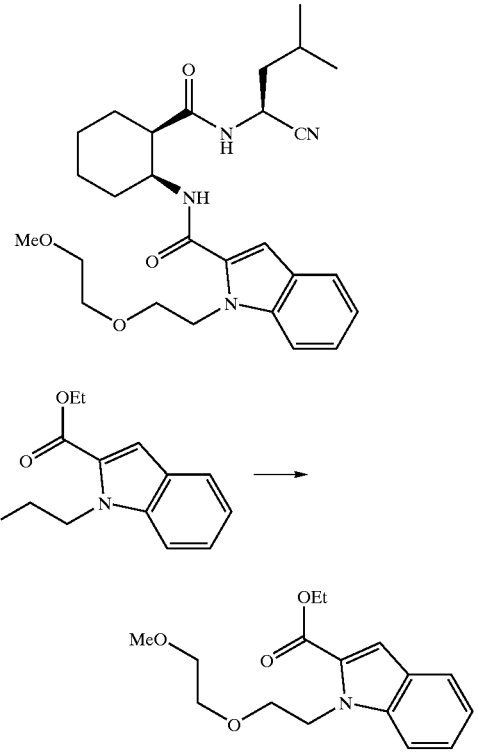

To a suspension of sodium hydride (0.11 g, 4 mmol) and anhydrous DMF (2 mL) was added a solution of 1-[2-(2-Hydroxy-ethoxy)-ethyl]-1H-indole-2-carboxylic acid ethyl ester (0.64 g, 2.3 mmol) in anhydrous DMF (5 mL). The reaction was allowed to stir at room temperature then was added methyl iodide (0.15 mL, 2.4 mmol). The reaction was allowed to stir for an additional 5.5 hours and then was poured onto 50 mL water and extracted with three 50 mL portions of ethyl acetate. The combined organics were washed with three 50 mL portions of water, dried on sodium sulfate, and concentrated. Purification by column chromatography (25:75 ethyl acetate:hexane) gave 1-[2-(2-Methoxy-ethoxy)ethyl]-1H-indole-2-carboxylic acid ethyl ester.

Using the procedure of Example 41, but replacing 1-[2-(2-triisopropylsilanyloxy-ethoxy)-ethyl]-1H-indole-2-carboxylic acid ethyl ester with 1-[2-(2-Methoxy-ethoxy)-ethyl]-1H-indole-2-carboxylic acid ethyl ester, 1-[2-(2-Methoxy-ethoxy)-ethyl]-1H-indole-2-carboxylic acid [(1S,2R)-2-((S)-1-cyano-3-methyl-butylcarbamoyl)-cyclohexyl]-amide was obtained as a white solid (0.27 g, 45%). MS: 483 (M+H).

Example 43

1-(3-Piperidin-1-yl-propyl)-1H-indole-2-carboxylic acid [(1S,2R)-2-((S)-1-cyano-3-methyl-butylcarbamoyl)-cyclohexyl]-amide

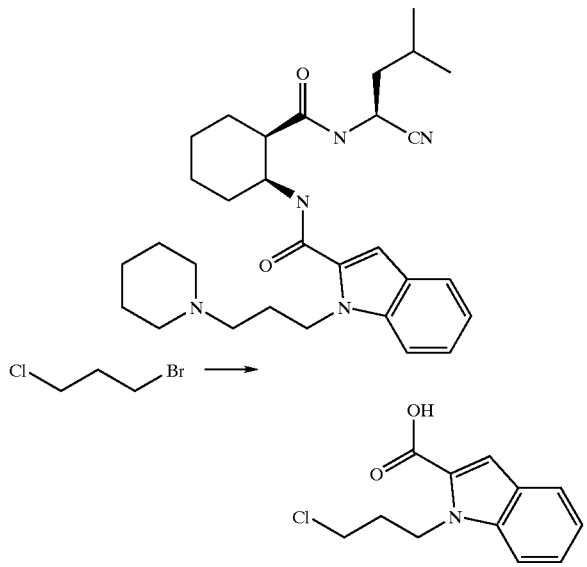

Step 1

1-Bromo-2-chloropropane was reacted with 1H-indole-2-carboxylic acid ethyl ester using the procedure of Example 1 to afford 1-(3-chloro-propyl)-1H-indole-2-carboxylic acid as a white solid.

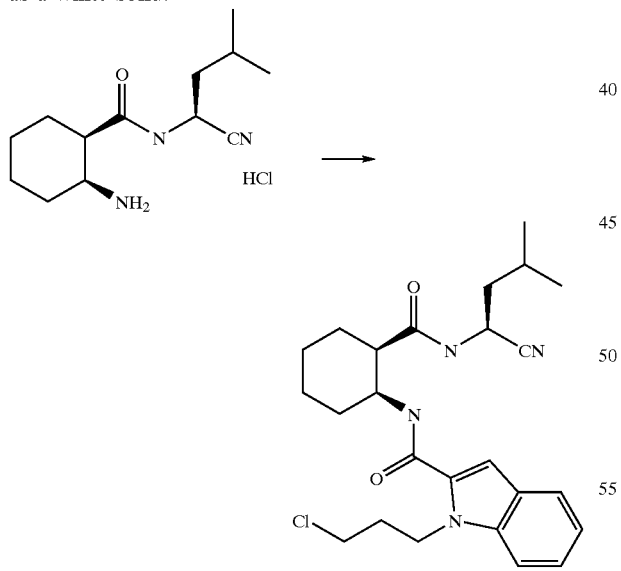

Step 2

(1R,2S)-2-Amino-cyclohexanecarboxylic acid ((S)-1-cyano-3-methyl-butyl)-amide was coupled with afford 1-(3-chloro-propyl)-1H-indole-2-carboxylic acid using the procedure of Example 11 to yield 1-(3-chloro-propyl)-1H-indole-2-carboxylic acid [(1S,2R)-2-((S)-1-cyano-3-methyl-butylcarbamoyl)-cyclohexyl]-amide.

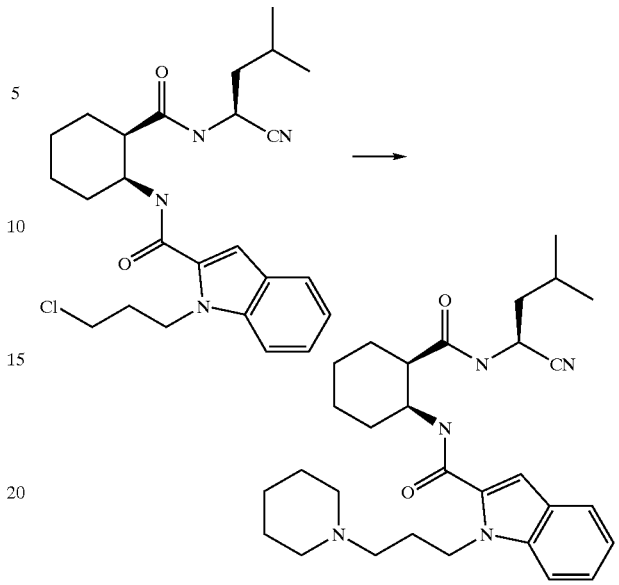

Step 3

To 1-(3-chloro-propyl)-1H-indole-2-carboxylic acid [(1S,2R)-2-((S)-1-cyano-3-methyl-butylcarbamoyl)cyclohexyl]-amide (200 mg, 0.44 mmol) was added sodium iodide (66 mg, 0.44 mmol), acetonitrile (2 mL), and piperidine (0.1 mL, 1.3 mmol). The reaction mixture was heated to 50° C. and stirred for 24 hrs. Water (15 mL) was added to the reaction and extracted with three 20 mL portions of ethyl acetate. The combined organics were washed with saturated NaHCO$_3$ (20 mL), dried on sodium sulfate, and concentrated. Purification by column chromatography (5:95 methanol:chloroform) gave 1-(3-piperidin-1-yl-propyl)-1H-indole-2-carboxylic acid [(1S,2R)-2-((S)-1-cyano-3-methyl-butylcarbamoyl)-cyclohexyl]-amide as a white solid (150 mg, 68%). MS: 506 (M+H).

Similarly, but replacing piperidine with morpholine, 1-(3-morpholin-4-yl-propyl)-1H-indole-2-carboxylic acid [(1S,2R)-2-((S)-1-cyano-3-methyl-butylcarbamoyl)cyclohexyl]-amide was prepared.

Similarly, but replacing piperidine with dimethylamine, 1-(3-dimethylamino-propyl)-1H-indole-2-carboxylic acid [(1S,2R)-2-((S)-1-cyano-3-methyl-butylcarbamoyl)-cyclohexyl]-amide was prepared.

Example 44

6-Chloro-1-(2-hydroxy-ethyl)-1H-indole-2-carboxylic acid [(1S,2R)-2-(cyanomethyl-carbamoyl)-cyclohexyl]-amide

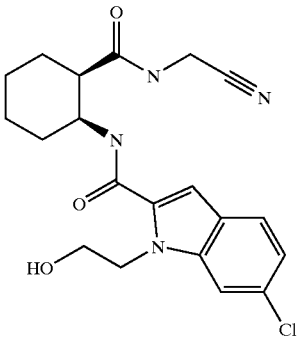

-continued

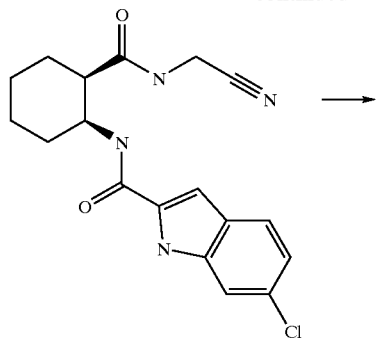

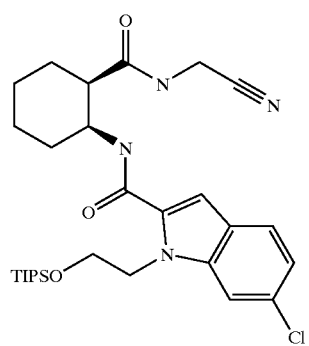

Step 1

6-Chloro-1H-indole-2-carboxylic acid [(1S,2R)-2-(cyanomethylcarbamoyl)-cyclohexyl]-amide from Example 18 was N-alkylated using a procedure similar to that of Example 11, but replacing (2-bromoethoxy)-tert-butyldimethylsilane with (2-bromoethoxy)-triisopropylsilane, to provide 6-chloro-1-{2-[(triisopropylsilanyl)-methoxy]-ethyl}-1H-indole-2-carboxylic acid [(1S,2R)-2-(cyanomethyl-carbamoyl)-cyclohexyl]-amide. Yield: 32%.

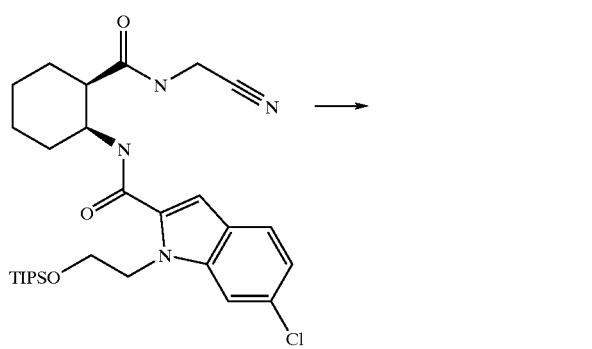

Step 2

To 140 mg (0.25 mmol) of 6-chloro-1-{2-[(triisopropylsilanyl)-methoxy]-ethyl}-1H-indole-2-carboxylic acid [(1S,2R)-2-(cyanomethyl-carbamoyl)-cyclohexyl]-amide dissolved in 20 mL THF was added 66 mg (0.25 mmol) of tetrabutylammonium fluoride (1.0 M in THF). The reaction mixture was stirred at room temperature for several hours, concentrated, and purified by column chromatography eluting with 70% ethyl acetate in hexane to provide 50 mg of 6-chloro-1-(2-hydroxy-ethyl)-1H-indole-2-carboxylic acid [(1S,2R)-2-(cyanomethyl-carbamoyl)-cyclohexyl]-amide. HPLC: 98% pure, yield: 50%, MS: 403 (M+H$^+$).

Similarly, but replacing (2-bromoethoxy)-triisopropylsilane with N-(2-chloroethyl)-morpholine hydrochloride, 6-chloro-1-(2-morpholin-4-yl-ethyl)-1H-indole-2-carboxylic acid [(1S,2R)-2-(cyanomethyl-carbamoyl)-cyclohexyl]-amide was prepared. HPLC: 96% pure, yield: 49%, MS: 472 (M+H$^+$).

Similarly, but replacing (2-bromoethoxy)-triisopropylsilane with N-(gamma-chloropropyl)piperidine hydrochloride, 6-chloro-1-(3-piperidin-1-yl-propyl)-1H-indole-2-carboxylic acid [(1S,2R)-2-(cyanomethyl-carbamoyl)-cyclohexyl]-amide was prepared. HPLC: 95% pure, yield: 40%, MS: 483 (M+H$^+$).

Example 45

6-Chloro-1-(3-hydroxy-propyl)-1H-indole-2-carboxylic acid [(1S,2R)-2-(cyanomethyl-carbamoyl)-cyclohexyl]-amide

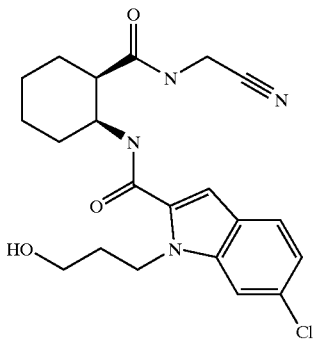

6-Chloro-1-(3-hydroxy-propyl)-1H-indole-2-carboxylic acid [(1S,2R)-2-(cyanomethyl carbamoyl)-cyclohexyl]-amide was prepared by following the procedure of Example 1 using 6-chloro-1-(3-triisopropylsilanyloxy-propyl)-1H-indole-2-carboxylic acid (prepared by the procedure of Example 11), followed by deprotection. HPLC: 85% pure, MS: 417 (M+H$^+$).

Example 46

6-Chloro-1-methyl-1H-indole-2-carboxylic acid [(1S,2R)-2-((S)-1-cyano-3-methylsulfanyl-propylcarbamoyl)-cyclohexyl]-amide

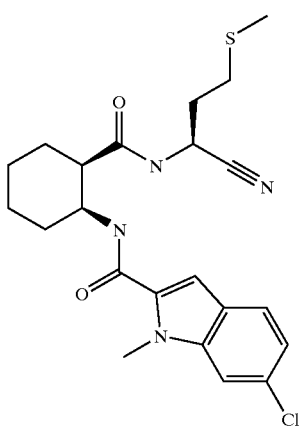

6-Chloro-1-methyl-1H-indole-2-carboxylic acid [(1S,2R)-2-((S)-1-cyano-3-methylsulfanyl-propylcarbamoyl)-cyclohexyl]-amide was prepared by following the procedure of Example 3, and using 6-chloro-1-methylindole-2-carboxylic acid (prepared by the N-methylation procedure of Example 13) together with the commercially available H-Met-NH$_2$ HCl salt as starting materials. HPLC: 99% pure, MS: 447 (M+H$^+$).

Similarly prepared was 6-chloro-1H-indole-2-carboxylic acid [(1S,2R)-2-((S)-1-cyano-3-methylsulfanyl-propylcarbamoyl)-cyclohexyl]-amide using the procedure of Example 3 with commercially available 6-chloroindole-2-carboxylic acid and H-Met-NH$_2$ HCl as starting materials. HPLC: 97% pure, MS: 433 (M+H$^+$).

Example 47

6-Chloro-1-methyl-1H-indole-2-carboxylic acid [(1S,2R)-2-((S)-1-cyano-3-methanesulfonyl-propylcarbamoyl)-cyclohexyl]-amide

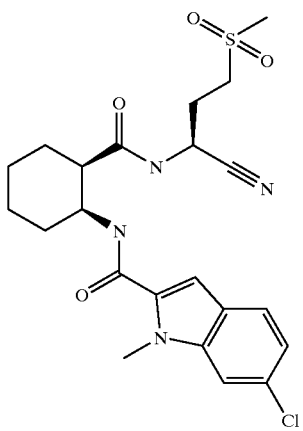

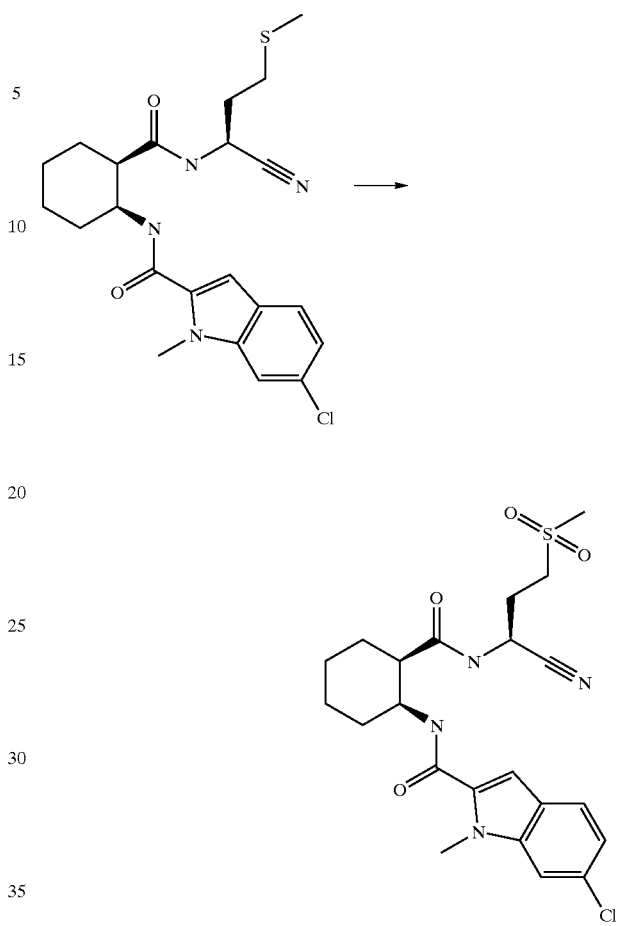

To 230 mg (0.52 mmol) of 6-chloro-1-methyl-1H-indole-2-carboxylic acid [(1S,2R)-2-((S)-1-cyano-3-methylsulfanyl-propylcarbamoyl)cyclohexyl]-amide from Example 46 dissolved in 100 mL dichloromethane was added 1.04 mmol 3-chloroperoxybenzoic acid (m-CPBA) at 0° C. The reaction mixture was stirred at 0° C. for two hours, partitioned between dichloromethane and saturated sodium bicarbonate solution, washed with brine, dried over magnesium sulfate and concentrated. Column chromatography, eluting with 100% ethyl acetate, provided 80 mg of 6-Chloro-1-methyl-1H-indole-2-carboxylic acid [(1S,2R)-2-((S)-1-cyano-3-methanesulfonyl-propylcarbamoyl)cyclohexyl]-amide. HPLC: 91% pure, yield: 32%, MS: 479 (M+H$^+$).

Using the same oxidation procedure on 6-chloro-1H-indole-2-carboxylic acid [(1S,2R)-2-((S)-1-cyano-3-methylsulfanyl-propylcarbamoyl)-cyclohexyl]-amide from Example 46, 6-chloro-1H-indole-2-carboxylic acid [(1S,2R)-2-((S)-1-cyano-3-methanesulfonyl-propylcarbamoyl)cyclohexyl]-amide was prepared. HPLC: 93% pure, yield: 18%, MS: 465 (M+H$^+$).

Example 48

1-Methyl-1H-indole-2-carboxylic acid ((1S,2R)-2-{[(S)-cyano-(4-methanesulfonylamino-benzyl)-methyl]-carbamoyl}-cyclohexyl)-amide

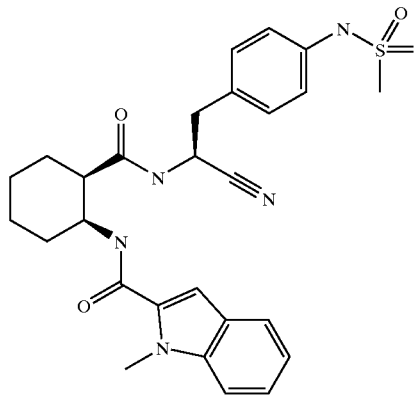

1-Methyl-1H-indole-2-carboxylic acid ((1S,2R)-2-{[(S)-cyano-4-nitro-benzyl)-methyl]-carbamoyl}-cyclohexyl)-amide was prepared by following the general procedure of Example 3, and using p-nitro-phenylalaninamide and the commercially available 1-Methylindole-2-carboxylic acid. The p-nitro-phenylalaninamide was prepared from commercially available H—P-nitro-Phe-OMe HCl salt using the procedure of Example 3. HPLC: 98%, MS: 473 (M+H$^+$).

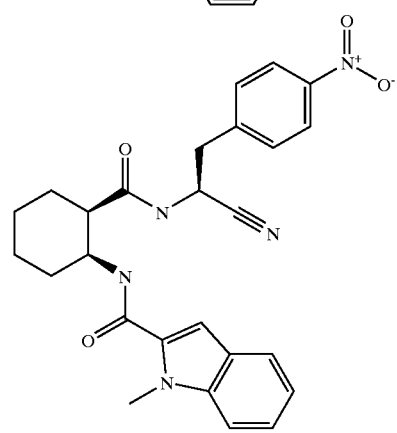

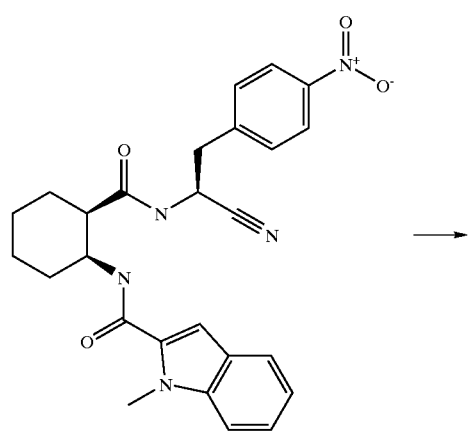

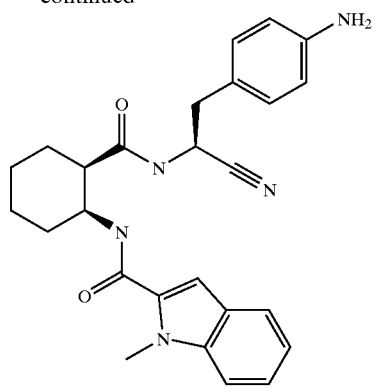

Step 1

To 120 mg (0.25 mmol) of 1-methyl-1H-indole-2-carboxylic acid ((1S,2R)-2-{[(S)-cyano-(4-nitro-benzyl)-methyl]-carbamoyl}-cyclohexyl)-amide dissolved in 5 mL ethyl acetate was added 20 mg activated carbon on charcoal (10% Wt.) and 0.7 mL glacial acetic acid. The reaction mixture was hydrogenated under normal atmosphere (H$_2$ balloon) for two hours, filtered through a cake of celite, washed with water and 10% NaOH aqueous solution, dried over magnesium sulfate, and concentrated to provide 80 mg of 1-methyl-1H-indole-2-carboxylic acid ((1S,2R)-2-{[(S)-(4-amino-benzyl)-cyano-methyl]-carbamoyl}-cyclohexyl)-amide. HPLC: 92% pure, yield: 71%, MS: 444 (M+H$^+$).

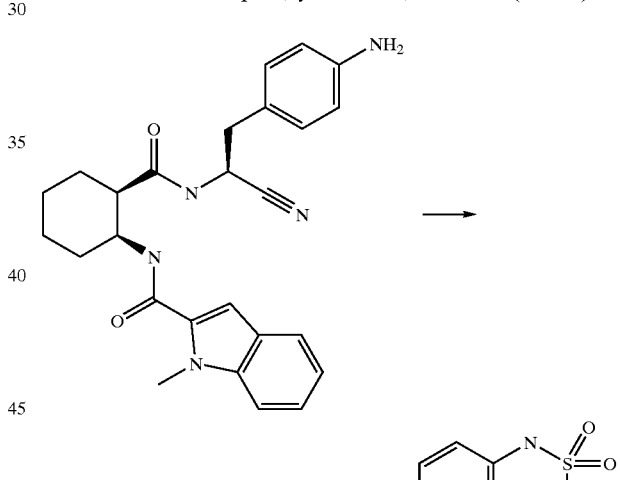

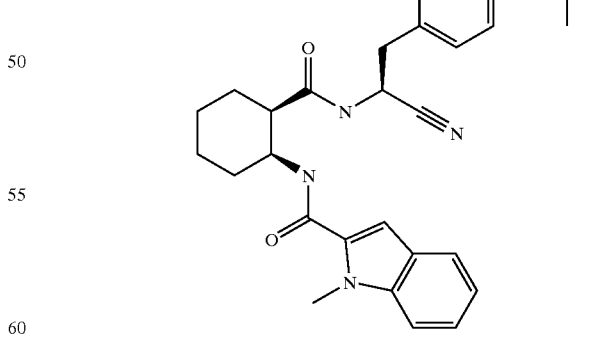

Step 2

To 62 mg (0.14 mmol) of 1-methyl-1H-indole-2-carboxylic acid ((1S,2R)-2-{[(S)-(4-amino-benzyl)cyano-methyl]-carbamoyl}cyclohexyl)-amide dissolved in 1 mL DMF was added 16 mg (0.14 mmol) of methanesulfonyl chloride, 2 mg (0.014 mmol) of 4-dimethylaminopyridine, and 0.031 mL (0.28 mmol) of N-methylmorpholine. The reaction mixture was stirred at room temperature overnight, partitioned between ethyl acetate and water, dried over magnesium sulfate, and concentrated. Reverse phase column chromatography was employed to separate the pure title compound from the unreacted starting material, and provided 10 mg of 1-methyl-1H-indole-2-carboxylic acid ((1S,2R)-2-{[(S)-cyano-(4-methanesulfonylamino-benzyl)-methyl]-carbamoyl}-cyclohexyl)-amide. HPLC: 100% pure, yield: 14%, MS: 522 (M+H$^+$).

Example 49

6-Chloro-1-(3-methanesulfonyl-propyl)-1H-indole-2-carboxylic acid [(1S,2R)-2-(cyanomethyl-carbamoyl)-cyclohexyl]-amide

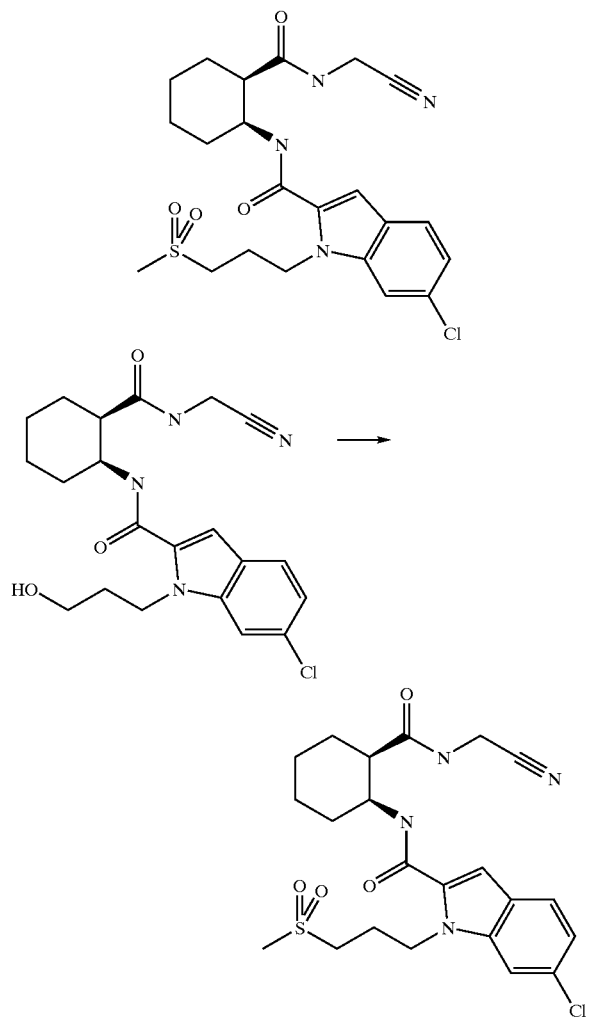

cooled to room temperature, partitioned between ethyl acetate and 5% aqueous sodium thiosulfate solution, washed with water, dried over magnesium sulfate, and concentrated. Column chromatography, eluting with 70% ethyl acetate in hexane, followed by recrystallization from ether provided 50 mg of 6-chloro-1-(3-methanesulfonyl-propyl)-1H-indole-2-carboxylic acid [(1S,2R)-2-(cyanomethyl-carbamoyl)-cyclohexyl]-amide. HPLC: 87% pure, yield: 30%, MS: 479 (M H$^+$).

Example 50

1-Methyl-1H-indole-2-carboxylic acid ((1S,2R)-2-{[(S)-cyano-(4-morpholin-4-yl-benzyl)-methyl]-carbamoyl}-cyclohexyl)-amide

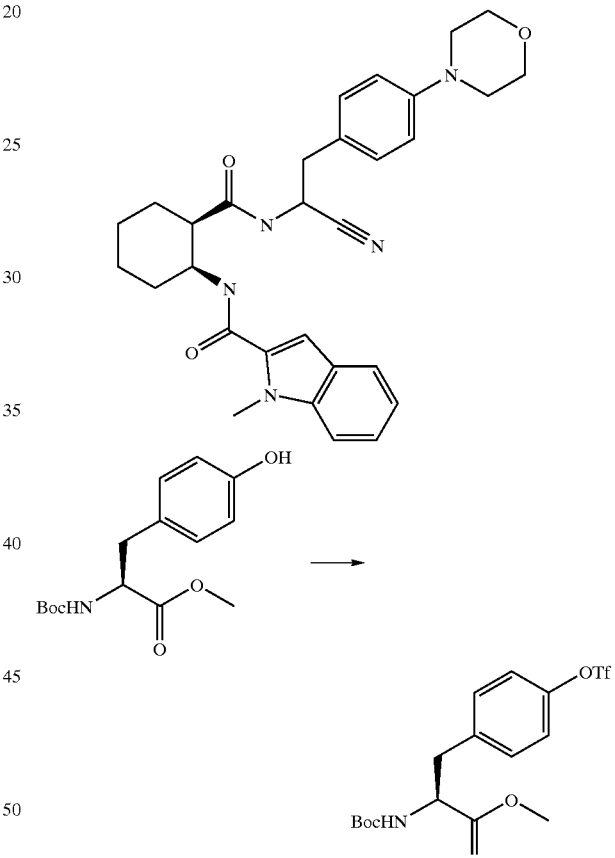

Step 1

To a 0° C. solution of commercially available BOC-tyrosine methyl ester (7.9 g, 26.8 mmol) in pyridine (15 mL) was added trifluoromethanesulfonic anhydride (5 mL, 29.7 mmol) slowly. After stirring at 0° C. for another 5 minutes, the reaction mixture was warmed to room temperature, and stirred at room temperature overnight. The reaction mixture was diluted in water, extracted with ethyl acetate, washed with 1N HCl solution, dried over magnesium sulfate, and concentrated. Column chromatography provided 5.7 g of triflated BOC-tyrosine methyl ester. Yield: 50%.

To 150 mg (0.36 mmol) of 6-Chloro-1-(3-hydroxy-propyl)-1H-indole-2-carboxylic acid [(1S,2R)-2-(cyanomethyl-carbamoyl)-cyclohexyl]-amide (from Example 45) dissolved in 5 mL DMF was added 151 mg (0.58 mmol) triphenylphosphine. At 0° C., N-bromosuccinimide (104 mg, 0.58 mmol) was added in portions. After stirring at room temperature for 30 minutes, sodium methane sulfinate (88 mg, 0.73 mmol) and sodium iodide (6 mg, 0.036 mmol) were added in portions. The reaction mixture was then stirred at 70° C. for 3 hours,

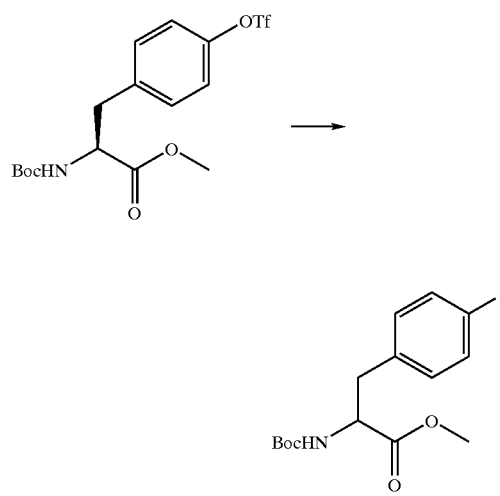

Step 2

To an oven-dried Schlenk flask that was evacuated and backfilled with argon was added 400 mg (0.98 mmol) of the above triflate compound, 13 mg (1.5 mol% Pd) of Pd$_2$(dba)$_3$, 18 mg (3.0 mol%) of rac-BINAP, 428 mg (1.31 mmol) of cesium carbonate, 7 mL of dioxane, and 0.10 mL (1.3 mmol) of morpholine. The reaction mixture was then degassed and backfilled with argon three more times, and was heated to 100° C. and stirred at 100° C. under an argon balloon for 18 hours. The resulting mixture was cooled to room temperature, diluted in ether, filtered through a cake of celite, and concentrated. Column chromatography provided 130 mg of BOC-protected 4-morpholinyl-phenylalanine methyl ester as a racemate. Yield: 38%, MS: 365 (M+H$^+$).

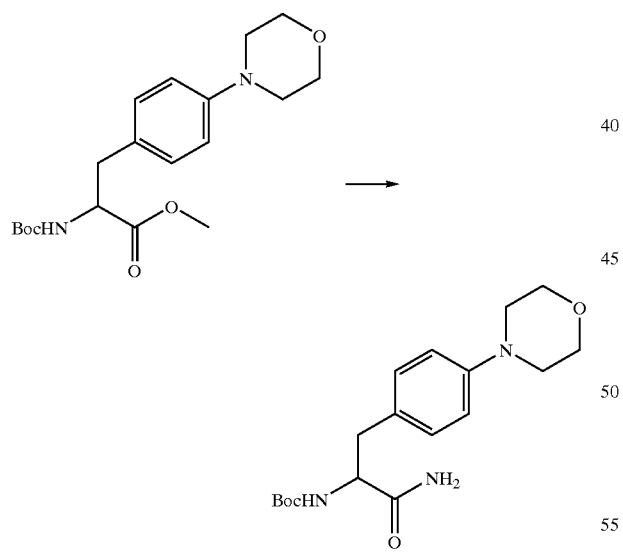

Step 3

To 120 mg (0.33 mmol) of the BOC-protected 4-morpholinyl-phenylalanine methyl ester dissolved in 5 mL of methanol in a bomb was added a 7N solution of ammonia in methanol (5 mL). The bomb was sealed and placed in a 60° C. oil bath overnight. The reaction mixture was cooled to room temperature and concentrated to obtain the BOC-protected 4-morpholinyl-phenylalanine in a crude form, which was used directly for the next reaction below. MS: 350 (M+H$^+$).

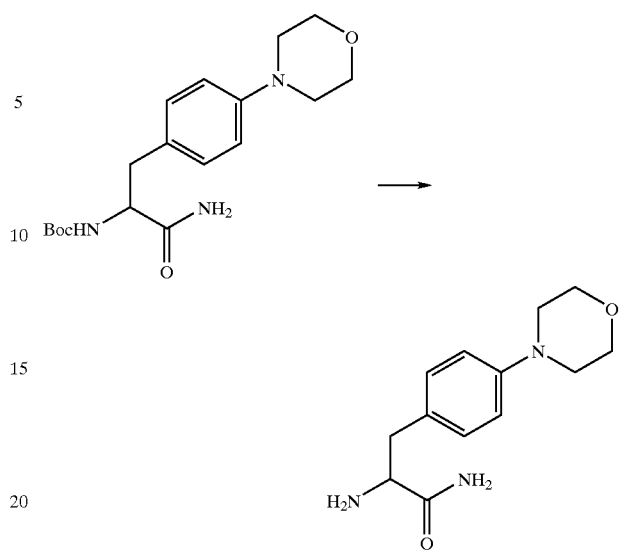

Step 4

To the BOC-protected 4-morpholinyl-phenylalaninamide above dissolved in 3 mL of dichloromethane was added 1 mL of TFA. The reaction mixture was stirred at room temperature overnight, and concentrated to obtain 4-morpholinyl-phenylalaninamide in a crude form, which was used directly for the next reaction. MS: 250 (M+H$^+$).

1-Methyl-1H-indole-2-carboxylic acid ((1S,2R)-2-{[(S)-cyano-(4-morpholinyl-benzyl)-methyl]-carbamoyl}-cyclohexyl)-amide was prepared by following the general procedure of Example 3, using 4-morpholinyl-phenylalaninamide and commercially available 1-Methylindole-2-carboxylic acid. HPLC: 82%, MS: 514 (M+H$^+$).

Example 51

7-[1-(Carbamoyl-hydrazono)ethyl]-1H-indole-2-carboxylic acid [(1S,2R)-2-(cyanomethyl-carbamoyl)-cyclohexyl]-amide

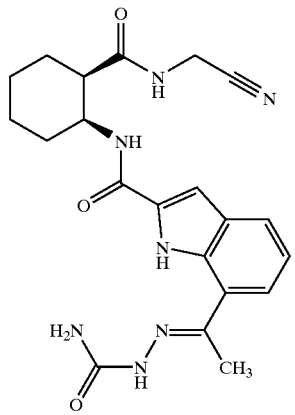

7-Acetyl-1H-indole-2-carboxylic acid [(1S,2R)-2-(cyanomethylcarbamoyl)-cyclohexyl]-amide was reacted with potassium acetate and semicarbazide hydrochloride in methanol and purified by preparative TLC plate to yield 7-[1-(carbamoyl-hydrazono)-ethyl]-1H-indole-2-carboxylic acid [(1S,2R)-2-(cyanomethylcarbamoyl)cyclohexyl]-amide MS: 367 (M+H$^+$).

Example 52

1-(2-Hydroxy-2-methyl-propyl)-1H-indole-2-carboxylic acid [(1S,2R)-2-((S)-1-cyano-3-methyl-butylcarbamoyl)-cyclohexyl]-amide

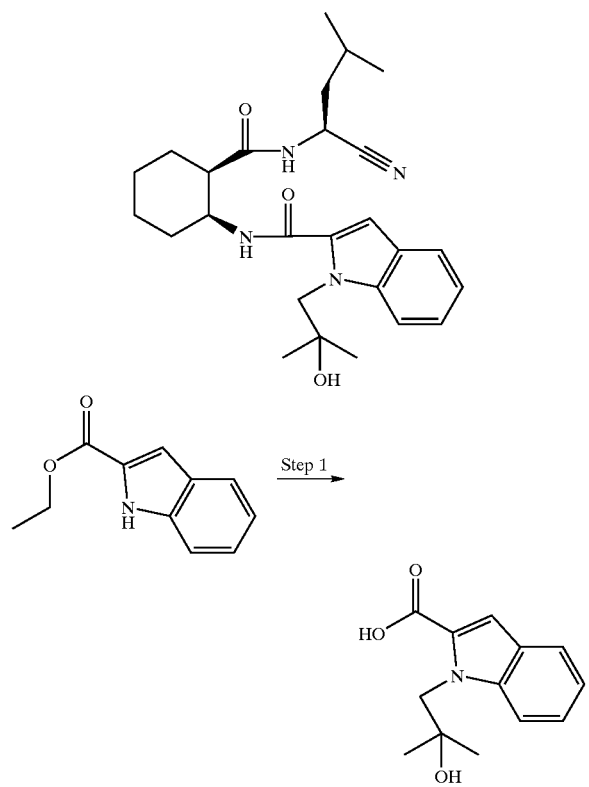

Step 1

To 760 mg of ethyl 2-indole carboxylate (4 mmol) dissolved in 8 ml dimethyl sulfoxide was added 290 mg of crushed potassium hydroxide (4.4 mmol). The mixture was stirred for approximately 30 minutes. 1.8 ml of isobutylene oxide was then added and the mixture was stirred at 50 C for 65 hours. The reaction was worked up by addition of water, 1M HCl to adjust the pH to 4–5, and ethyl acetate. The layers were separated and the ethyl acetate layer was washed with brine and dried over sodium sulfate. Evaporation gave 1-(2-hydroxy-2-methyl-propyl)-1H-indole-2-carboxylic acid (840 mg) as a solid (M–H=233) that was used directly in the next step.

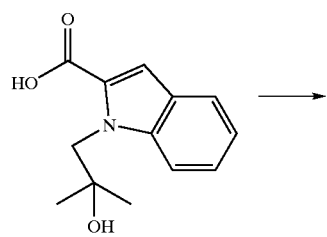

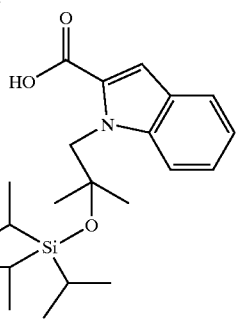

Step 2

100 mg of 1-(2-hydroxy-2-methyl-propyl)-1H-indole-2-carboxylic acid (0.43 mmol) in dichloromethane was cooled in an ice bath. 0.14 ml of 2,6-lutidine (1.2 mmol) was added followed by dropwise addition of triisopropylsilyl triflate (0.9 mmol, J. Chem. Soc., P. T. 1, 1999, 1, 1163). The reaction was then stirred to room temperature over 16 hours. The reaction was quenched by addition of 0.5 M HCl and ethyl acetate. The layers were separated and the organic layer was washed with more 0.5 M HCl, sodium bicarbonate solution and brine. After drying over sodium sulfate and evaporation, the crude product was purified by silica gel chromatography in 10% ethyl acetate/hexanes. 210 mg of a glassy solid was obtained and was then dissolved in 10 ml 40% THF/methanol. 188 mg of potassium carbonate (1.36 mmol) in 2 ml water was added and the mixture stirred for 1 hour. The pH was adjusted to 3 with 1M HCl and solvent was evaporated. The resulting residue was chromatographed (PTLC, 5% MeOH/methylene chloride) to give 1(2-methyl-2-triisopropylsilanyloxy-propyl)-1H-indole-2-carboxylic acid (100 mg) as white solid (MS: M–H=388).

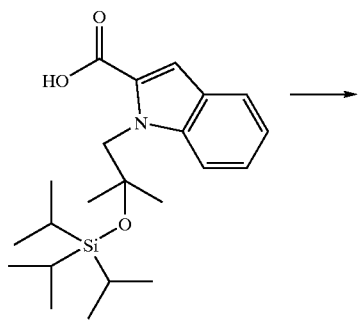

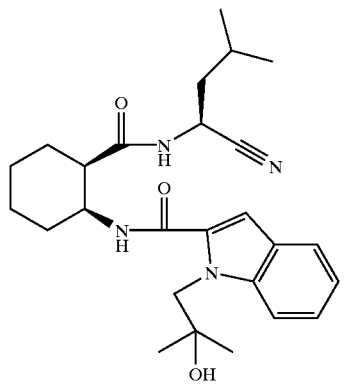

Step 3

Proceeding as described in Example 11, followed by treatment with 1M TBAF in THF at 50° C. for 12 h, 1-(2-Methyl-2-triisopropylsilanyloxy-propyl)-1H-indole-2-carboxylic acid (100 mg, 0.25 mmol) was concerted to 1-(2-hydroxy-2-methyl-propyl)-1H-indole-2-carboxylic acid [2-(1-cyano-3-methyl-butylcarbamoyl)-cyclohexyl]-amide (80 mg; SiO$_2$ PTLC: 50% ethyl acetate/hexanes; mp: 101.5–105.5° C.; MS: M+H=453).

Example 53

1-[2-(2-Hydroxy-ethylamino)ethyl]-1H-indole-2-carboxylic acid [(1S,2R)-2-((S)-1-cyano-3-methyl-butylcarbamoyl)cyclohexyl]-amide

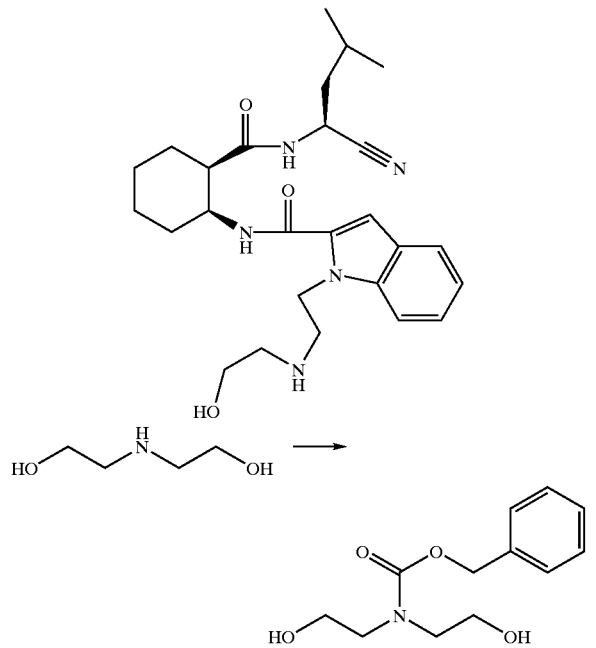

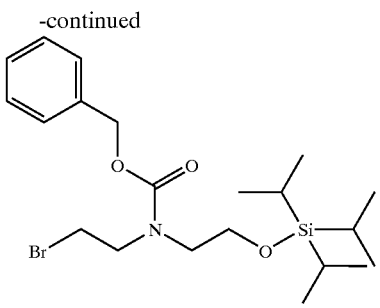

Step 2

Triphenylphosphine (1.15 g, 4.39 mmol) and N-bromosuccinimide (0.79 g, 4.39 mmol) were added to a 0° C. solution of N-Cbz-diethanolamine (1 g, 4.18 mmol) in 40 ml of methylene chloride. The reaction was stirred at room temperature for 4 hours and then cooled to 0° C. 2,6-Lutidine (0.97 ml, 8.36 mmol) was added, followed by the dropwise addition of triisopropylsilyl triflate (1.35 ml, 5 mmol). The reaction was stirred at room temperature for 12 h, diluted with water, and concentrated under vacuum and the residue was extracted with ethyl acetate (2×50 ml). The organic layer was washed with 0.5 M HCl, saturated sodium bicarbonate, brine and dried over sodium sulfate. Evaporation of the solvent followed by chromatography (SiO$_2$ Biotage 40 M, 3%–5% ethyl acetate/hexanes) gave (2-bromo-ethyl)-(2-triisopropylsilanyloxy-ethyl)-carbamic acid benzyl ester (400 mg) as a clear oil.

Step 1

To a 0° C. solution of diethanolamine (1.9 ml, 20 mmol) in 50 ml of THF was added benzyloxycarbonyloxysuccinimide (5.0 g, 20 mmol) followed by the slow addition of a solution of sodium carbonate (3.2 g, 30 mmol) in 50 ml of water. The reaction was stirred at 0° C. for 2 hours, diluted with 50 ml of water, and the majority of the THF was removed under vacuum. The reaction mixture was extracted with ethyl acetate (2×75 ml), washed with brine and dried over sodium sulfate. The solvent was concentrated and the residue was purified by SiO$_2$ chromatography (250 g SiO$_2$, 8% MeOH/methylene chloride) to give N-Cbz-diethanolamine (4.25 g) as a clear oil.

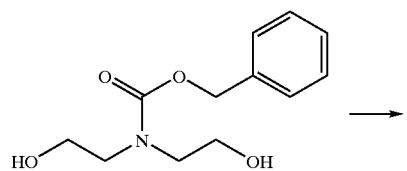

Step 3

Using (2-bromo-ethyl)-(2-triisopropylsilanyloxy-ethyl)-carbamic acid benzyl ester (370 mg, 0.8 mmol) and the procedure described in Example 11, followed by TIPS removal using TBAF/THF and N-Cbz cleavage using 10% Pd/C in ethyl acetate, 1-[2-(2-hydroxy-ethylamino)ethyl]-1H-indole-2-carboxylic acid [2-(1-cyano-3-methyl-butylcarbamoyl)-cyclohexyl]-amide (100 mg) was obtained as a colorless glass (MS: M+H=468).

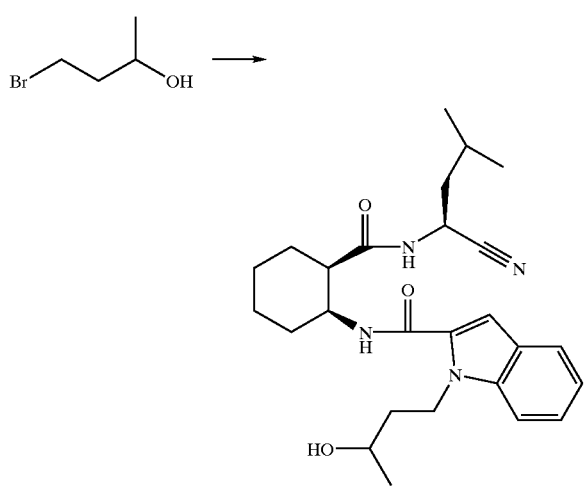

Similarly, using the above procedure, but replacing the (2-bromo-ethyl)-(2-triisopropylsilanyloxy-ethyl)-carbamic acid benzyl ester with 619 mg 3-(bromo-1-methyl-propoxy)-triisopropyl-silane (2 mmol, prepared by O-silylation of 4-Bromo-butan-2-ol (J. Org. Chem., 65, 15, 4524) as described in Example 52), followed by desilylation as in Example 52, yielded 100 mg of 1-(3-hydroxy-butyl)-1H-indole-2-carboxylic acid [2-(1-cyano-3-methyl-butylcarbamoyl)-cyclohexyl]-amide as a mixture of epimers (MS: M+H=453; mp=70–80.5 C).

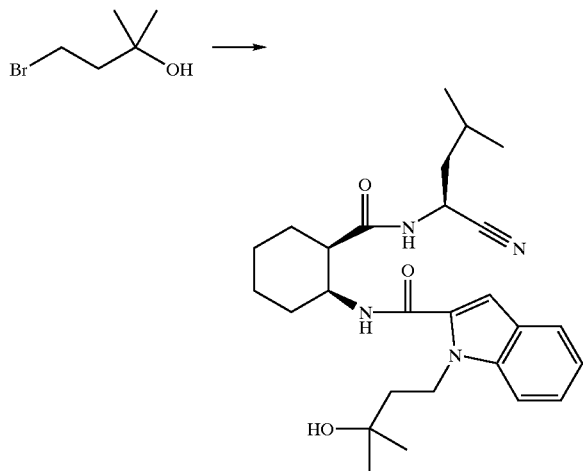

Similarly, by replacing of (2-bromo-ethyl)-(2-triisopropylsilanyloxy-ethyl)-carbamic acid benzyl ester with 808 mg of 3-(Bromo-1,1-dimethyl-propoxy)-triisopropyl-silane (2.5 mmol, prepared by O-silylation of 4-Bromo-2-methyl-butan-2-ol (Biorg. Med. Chem., 9, 525)), followed by desilylation in the manner of Example 52, gave 130 mg of 1-(3-Hydroxy-3-methyl-butyl)-1H-indole-2-carboxylic acid [2-(1-cyano-3-methyl-butylcarbamoyl)-cyclohexyl]-amide (MS: M+H=467; mp=77.8–84.1 C).

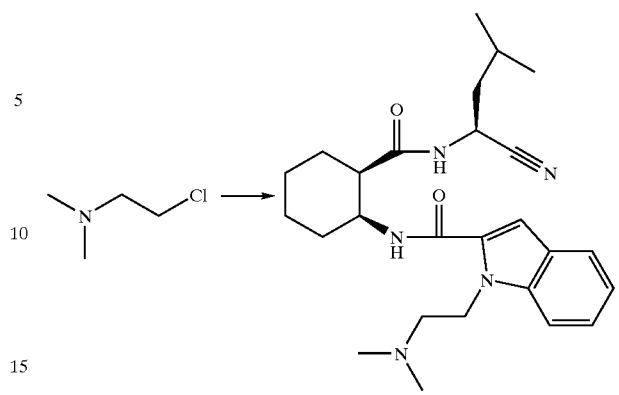

Again following the above procedure, except using 168 mg (2-chloro-ethyl)-dimethyl-amine, hydrochloride salt instead of (2-bromoethyl)-(2-triisopropylsilanyloxy-ethyl)-carbamic acid benzyl ester and followed by treatment with 1 equivalent of HCl in ether, gave 100 mg 12-Dimethyl-amino-ethyl)-1H-indole-2-carboxylic acid [2-(1-cyano-3-methyl-butylcarbamoyl)-cyclohexyl]-amide, hydrochloride salt (MS: M+H=452; mp=67–78.9 C).

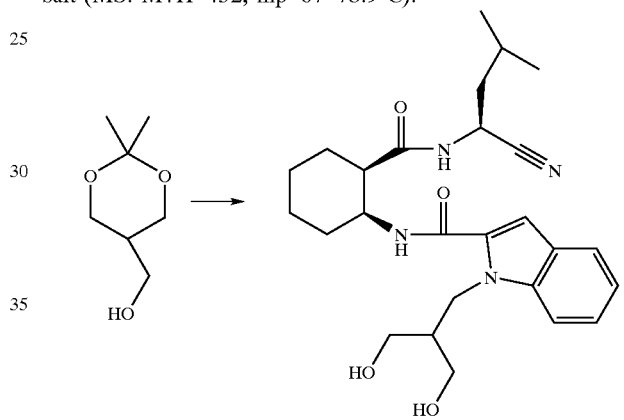

Following the above procedure except using 530 mg 5-Bromomethyl-2,2-dimethyl-[1,3]dioxane (2.53 mmol, prepared by bromation of 2,2-Dimethyl-[1,3]dioxan-5-yl)-methanol as in J. Am. Chem. Soc., 95,26,8756) in place of (2-bromo-ethyl)-(2-triisopropylsilanyloxy-ethyl)carbamic acid benzyl ester followed by deprotection of the diol using Dowex 50WX-400 (Carb. Res. 65, 229) gave 130 mg 1-(3-Hydroxy-2-hydroxymethyl-propyl)-1H-indole-2-carboxylic acid [2-(1-cyano-3-methyl-butylcarbamoyl)-cyclohexyl]-amide (MS: M+H=469; mp=77.6–91.2 C).

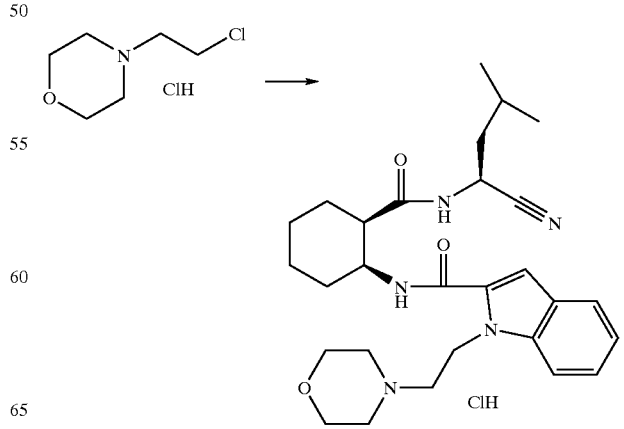

Proceeding as described above except using 0.164 g 4-(2-chloro-ethyl)-morpholine, hydrochloride salt instead of (2-bromo-ethyl)-(2-triisopropylsilanyloxy-ethyl)-carbamic acid benzyl followed by treatment with 1 equivalent of HCl in ether gave 190 mg 1-(2-morpholin-4-yl-ethyl)-1H-indole-2-carboxylic acid [2-(1-cyano-3-methyl-butylcarbamoyl)-cyclohexyl]-amide, hydrochloride salt (MS: M+H=494; mp=206.5–210 C).

Example 54

1-Piperidin-4-ylmethyl-1H-indole-2-carboxylic acid [2-(1-cyano-3-methyl-butylcarbamoyl)-cyclohexyl]-amide

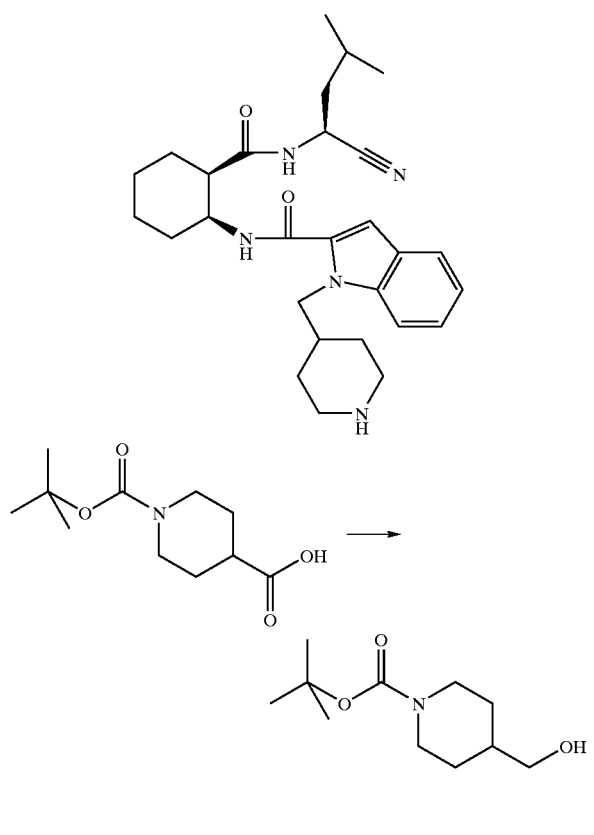

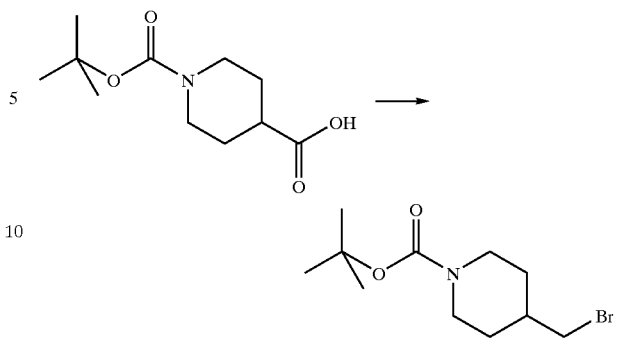

Step 1

To 5 g of N-BOC-isonipecotic acid (21.8 mmol, Bachem) dissolved in 100 ml THF, cooled in a dry ice/acetone bath, was slowly added 43.6 ml 1 M borane-THF complex in THF (43.6 mmol). The reaction was stirred to −40 C and then replaced with an ice/water bath. After 3 hours the reaction was neutralized by careful addition of water and then worked up by addition of ethyl acetate and 1 M HCl. The layers were separated and the aqueous layer was extracted one more time with ethyl acetate. The combined ethyl acetate layers were washed with brine, dried over sodium sulfate and evaporated to give 4.9 g 4-hydroxymethyl-piperidine-1-carboxylic acid tert-butyl ester (MS: M+H=238).

Step 2

To 3.4 g of 4-hydroxymethyl-piperidine-1-carboxylic acid tert-butyl ester (15.79 mmol) in 80 ml of THF, cooled in an ice/water bath, was added 4.76 g triphenylphosphine (18.16 mmol) and then 6.05 g total of carbon tetrabromide (18.16 mmol) in two portions. The reaction was stirred to room temperature over 16 hours. 1.2 g carbon tetrabromide (3.6 mmol) was added twice more over 24 hours before the reaction mixture was filtered. Approximately 240 ml of diethyl ether was added and the resulting mixture was filtered and evaporated. The residue was purified by chromatography on silica gel in 5–10% ethyl acetate/hexanes to give 3.3 g 4-bromomethyl-piperidine-1-carboxylic acid tert-butyl ester (MS: M+H=263/265).

Step 3

Using 306 mg of 4-bromomethyl-piperidine-1-carboxylic acid tert-butyl ester (1.1 mmol) and proceeding as described in Example 11, except for the use of potassium hydroxide and dimethyl sulfoxide as in Example 52 instead of sodium hydride and DMF, followed by BOC deprotection using 40% formic acid in dichloromethane and treatment with 1 equivalent of HCl in ether gave 80 mg 1-piperidin-4-ylmethyl-1H-indole-2-carboxylic acid [2-(1-cyano-3-methyl-butylcarbamoyl)-cyclohexyl]-amide, hydrochloride salt (MS: M+H=478; mp=128–142.2 C).

Example 55

1-(1-Methyl-piperidin-4-ylmethyl-1H-indole-2-carboxylic acid [2-(1-cyano-3-methyl-butylcarbamoyl)-cyclohexyl]-amide

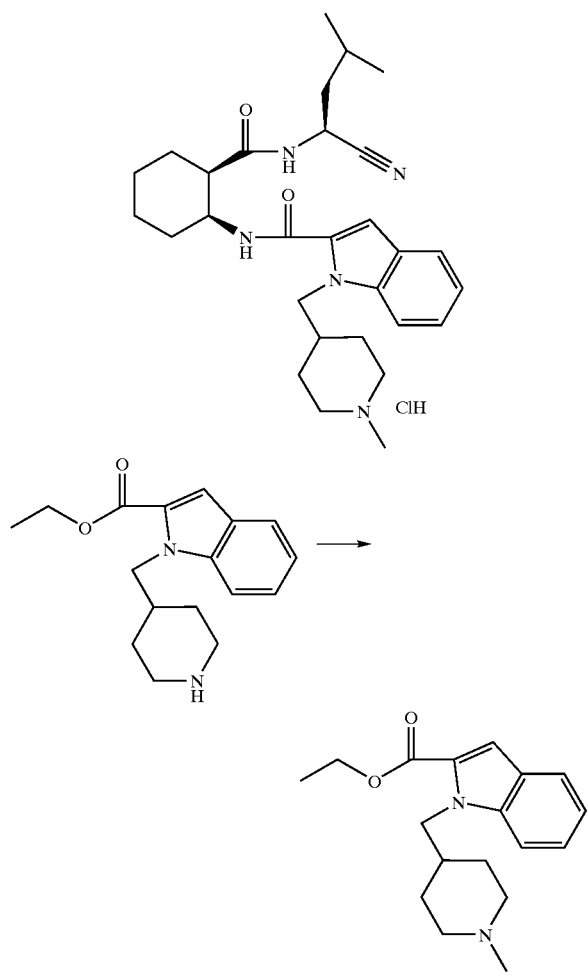

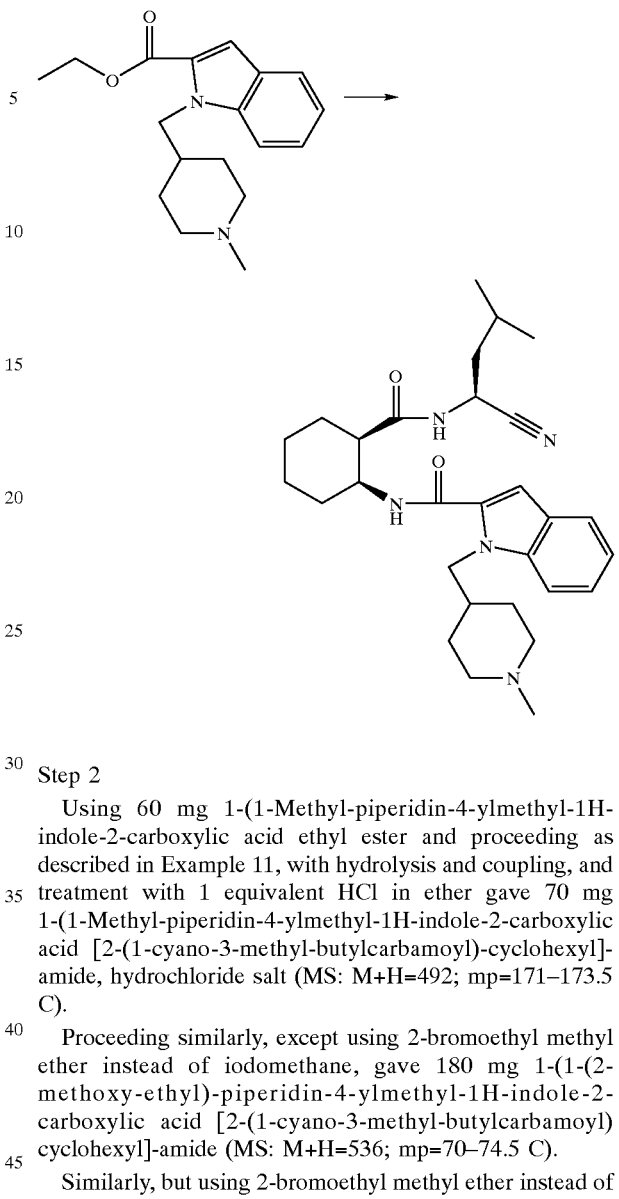

Step 1

4-Bromomethyl-piperidine-1-carboxylic acid tert-butyl ester was prepared as described in steps 1 and 2 of Example 54, and was used to alkylate 1H-indole-2-carboxylic acid ethyl ester under the conditions described in step 3 of Example 54, to provide 1-(1-tert-Butoxycarbonyl-piperidin-4-ylmethyl)-1H-indole-2-carboxylic acid ethyl ester (MS: M+H=387). 0.325 g of 1-(1-tert-Butoxycarbonyl-piperidin-4-ylmethyl)-1H-indole-2-carboxylic acid ethyl ester (0.84 mmol) was BOC deprotected using 20% TFA in dichloromethane, neutralized by washing with sodium bicarbonate solution, and then redissolved in 8 ml DMF. A total of 0.062 ml iodomethane (1 mmol) was added followed by 0.35 g potassium carbonate (2.5 mmol). The reaction mixture was stirred for 20 hours and then taken up in ethyl acetate and water. The layers were separated, the aqueous layer was extracted with ethyl acetate, the combined ethyl acetate layers were washed with water twice, dried over sodium sulfate and evaporated. The residue was purified by silica gel chromatography in 7% methanol/dichloromethane giving 60 mg 1-(1-Methyl-piperidin-4-ylmethyl-1H-indole-2-carboxylic acid ethyl ester (MS: M+H=301).

Step 2

Using 60 mg 1-(1-Methyl-piperidin-4-ylmethyl-1H-indole-2-carboxylic acid ethyl ester and proceeding as described in Example 11, with hydrolysis and coupling, and treatment with 1 equivalent HCl in ether gave 70 mg 1-(1-Methyl-piperidin-4-ylmethyl-1H-indole-2-carboxylic acid [2-(1-cyano-3-methyl-butylcarbamoyl)-cyclohexyl]-amide, hydrochloride salt (MS: M+H=492; mp=171–173.5 C).

Proceeding similarly, except using 2-bromoethyl methyl ether instead of iodomethane, gave 180 mg 1-(1-(2-methoxy-ethyl)-piperidin-4-ylmethyl-1H-indole-2-carboxylic acid [2-(1-cyano-3-methyl-butylcarbamoyl) cyclohexyl]-amide (MS: M+H=536; mp=70–74.5 C).

Similarly, but using 2-bromoethyl methyl ether instead of iodomethane and coupling the indole carboxylic acid with the appropriate amine gave 1-[1-(2-Methoxy-ethyl)-piperidin-4-ylmethyl]-1H-indole-2-carboxylic acid [2-cyanomethyl-carbamoyl)-cyclohexyl]-amide (MS: M+H=480, mp=121.9–138.2 C).

Similarly, but using 4-(3-Bromo-propyl)-piperidine-1-carboxylic acid tert-butyl ester instead of 4-bromomethyl-piperidine-1-carboxylic acid tert-butyl ester and 2.6 equivalents of iodomethane instead of 1.2 equivalents, gave 43 mg 4-(3-{2-[2-(1-Cyano-3-methyl-butylcarbamoyl)cyclohexyl-carbamoyl]-indol-1-yl}-propyl)-1,1-dimethyl-piperidinium chloride (MS: M+H=534; mp=133–137.5 C).

Similarly, except using 4-(3-Bromo-propyl)-piperidine-1-carboxylic acid tert-butyl ester instead of 4-Bromomethyl-piperidine-1-carboxylic acid tert-butyl ester and using 2-bromoethyl methyl ether instead of iodomethane gave 1-{3-[1-(2-Methoxy-ethyl)-piperidin-4-yl]-propyl}-1H-indole-2-carboxylic acid [2-(1-cyano-3-methyl-butylcarbamoyl)-cyclohexyl]-amide (MS: M+H=564; mp=56.8–58 C).

Example 56

1-[2-(1-Methyl-piperidin-4-yl)-ethyl]-1H-indole-2-carboxylic acid [2-(1-cyano-3-methyl-butylcarbamoyl)-cyclohexyl]-amide

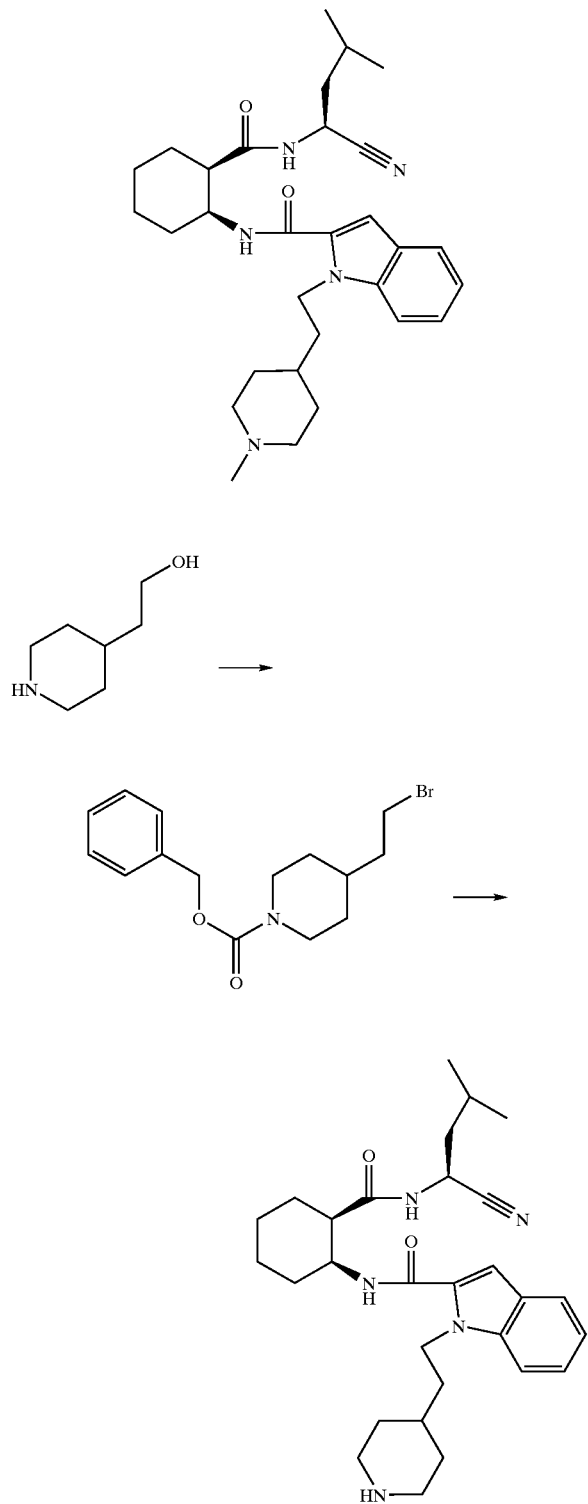

2-piperidin-4-yl-ethanol was protected by reaction with Cbz-Cl, and brominated as in Example 53, Step 2, to provide 4-(2-bromo-ethyl)-piperidine-1-carboxylic acid benzyl ester. The 4-(2-bromo-ethyl)-piperidine-1-carboxylic acid benzyl ester was then reacted with 1H-Indole-2-carboxylic acid [(1S,2R)-2-((S)-1-cyano-3-methyl-butylcarbamoyl)-cyclohexyl]-amide as in Example 53 Step 3. After Cbz deprotection using triethylsilane, palladium acetate and triethylamine (Tet. Lett. 29, 24, 2983) and treatment with 1 equivalent HCl in ether, 1-(2-piperidin-4-yl-ethyl)-1H-indole-2-carboxylic acid [2-(1 cyano-3-methyl-butylcarbamoyl)-cyclohexyl]-amide, hydrochloride salt was obtained (MS: M+H=492; mp=171–173.5 C).

Step 2

70 mg 1-(2-piperidin-4-yl-ethyl)-1H-indole-2-carboxylic acid [2-(1-cyano-3-methyl-butylcarbamoyl)-cyclohexyl]-amide (0.142 mmol) from step 1 was alkylated by the method of Example 55 using iodomethane and potassium carbonate. After treatment with 1 equivalent of HCl in ether, 30 mg of 1-[2-(1-Methyl-piperidin-4-yl)-ethyl]-1H-indole-2-carboxylic acid [2-(1-cyano-3-methyl-butylcarbamoyl)-cyclohexyl]-amide, hydrochloride salt was obtained (MS: M+H=506; mp=140–148 C).

Similarly, except using 2-bromoethyl methyl ether instead of iodomethane gave 30 mg of 1-{2-[1-(2-Methoxy-ethyl)-piperidin-4-yl]-ethyl}-1H-indole-2-carboxylic acid [2-(1-cyano-3-methyl-butylcarbamoyl)-cyclohexyl]-amide, hydrochloride salt (MS: M+H=550; mp=112–119 C).

Example 57

1-(3-Piperidin-4-yl-propyl)-1H-indole-2-carboxylic acid [2-(1-cyano-3-methyl-butylcarbamoyl)-cyclohexyl]-amide

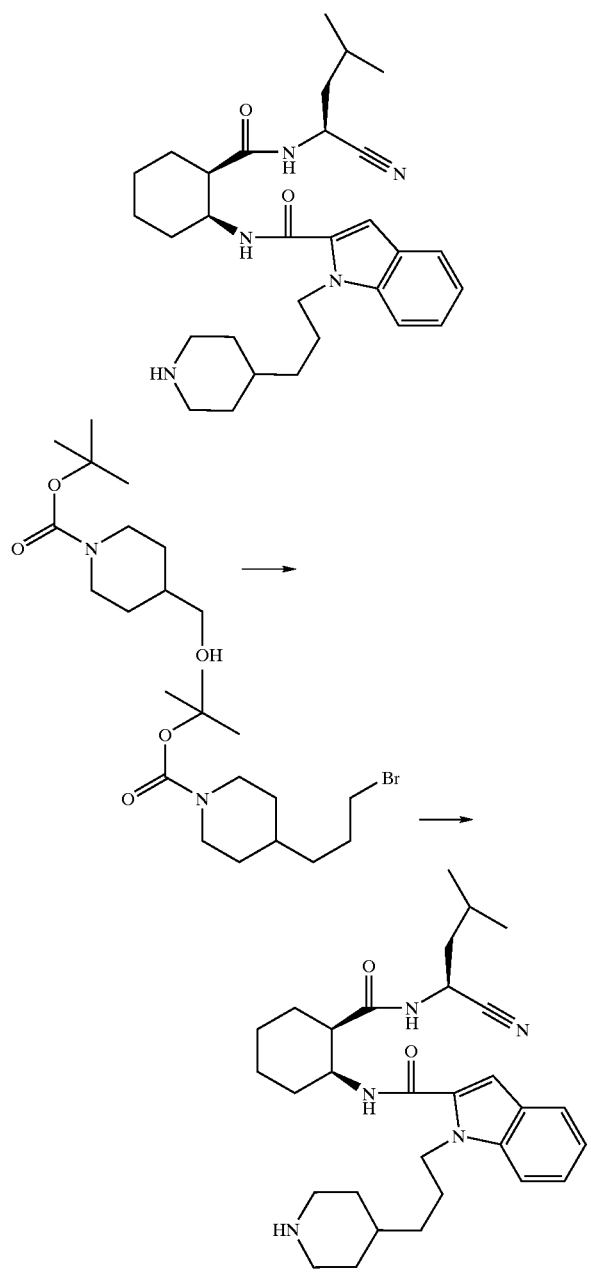

3.4 g 4-Hydroxymethyl-piperidine-1-carboxylic acid tert-butyl ester (15.79 mmol) from Example 54, step 1 was used in the reaction scheme described in EP 0 478 363 B1 to yield 2.7 g 4-(3-bromo-propyl)-piperidine-1-carboxylic acid tert-butyl ester.

Proceeding as described in Example 54, Step 3, 673 mg of 4-(3-bromo-propyl)-piperidine-1-carboxylic acid tert-butyl ester (2.2 mmol) was conyerted to approximately 180 mg 1-(3-Piperidin-4-yl-propyl)-1H-indole-2-carboxylic acid [2-(1-cyano-3-methyl-butylcarbamoyl)-cyclohexyl]-amide, hydrochloride salt (MS: M+H=506; mp=146.4–146.9 C).

Example 58

Inhibitory Activity of the Compounds of the Invention Against Cathepsin K, S, L and B The inhibitory activity of the compounds against cathepsin K, S, L and B was tested at room temperature in 96-wells opaque white polystyrene plates (Costar). The cathepsin K inhibitory activity was tested as follows:

5 µl of an inhibitor diluted in 5 mM sodium phosphate, NaCl 15 mM pH 7.4 containing 1% DMSO (final concentrations: 10–0.0001 µM) were preincubated for 10 min with 35 µl of human recombinant cathepsin K (final concentration: 1 nM) diluted in assay buffer (100 mM sodium acetate pH 5.5 containing 5 mM EDTA and 20 mM cysteine). After addition of 10 µl of the fluorogenic substrate Z-Leu-Arg-MCA diluted in assay buffer (final concentration: 5 µM), increase of fluorescence (excitation at 390 nm and emission at 460 nm) was measured for 7.5 min every 45 sec. The initial velocity (RFU/min) was derived from the linear fit of the 11 reading points.

The cathepsin B inhibitory activity was assayed under the same conditions as the cathepsin K inhibitory activity using human liver cathepsin B (Calbiochem) at a final concentration of 1 nM.

The cathepsin L inhibitory activity was assayed under the same conditions as the cathepsin K inhibitory activity using human liver cathepsin L (Calbiochem) at a final concentration of 3 nM.

Cathepsin S inhibitory activity was assayed analogeously to the cathepsin K inhibitory activity, except that the buffer was 100 mM potassium phosphate, 5 mM EDTA, 5 mM DTT (freshly added), 0.01% Triton X-100, pH 6.5 and the fluorogenic substrate was Z-Val-Val-Arg-MCA (Bachem) (final concentration: 20 µM). Human recombinant cathepsin S (Wiederanders et al., Eur. J. Biochem. 1997, 250, 745–750) was used at a final concentration of 0.5 nM.

Using the above assays, the compounds of the invention were found to selectively inhibit Cathepsin K.

Example 59

Formulations

Pharmaceutical preparations for delivery by various routes are formulated as shown in the following Tables. "Active ingredient" or"Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration

| Ingredient | % wt./wt. |
|---|---|
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration

| Ingredient | Amount |
|---|---|
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation

| Ingredient | % wt./wt. |
|---|---|
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | grams |
|---|---|
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025–0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50–100 microliters of formulation per actuation. A typical dosing schedule is 2–4 sprays every 4–12 hours.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of the formula (I):

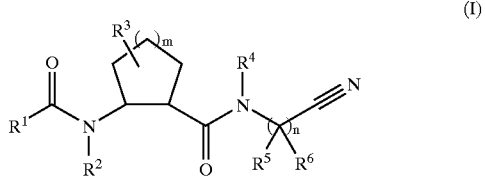

(I)

wherein:
    m is from 1 to 3;
    n is 1 or 2;
    p is from 0 to 2;
    $R^1$ is: optionally substituted indolyl; optionally substituted indazolyl; optionally substituted benzothiazole; optionally substituted indolizinyl; optionally substituted tetrahydropyridoindolyl; optionally substituted pyridinylthiophene-2-yl; or optionally substituted benzopyrrolothiazolyl;
    $R^2$, $R^3$, $R^4$ and $R^5$ each independently is hydrogen or alkyl; and R⁶ is; hydrogen; alkyl; cycloalkyl; or —(CRᵃRᵇ)_q—A:
  wherein Rᵃ and Rᵇ each independently is hydrogen or alkyl, q is from 0 to 4, and wherein A is:
    hydroxy; alkoxy; cyano; optionally substituted phenyl; optionally substituted pyridyl; optionally substituted imidazolyl; optionally substituted thienyl; —S(O)_r—Rᶜ wherein r is from 0 to 2 and Rᶜ is hydrogen or alkyl; —CORᵈ wherein Rᵈ is: hydroxy; alkoxy; morpholinyl; or cycloalkylamino; or —NRᵉRᶠ wherein Rᵉ and Rᶠ each independently is hydrogen or alkyl, or Rᵉ and Rᶠ together with the nitrogen to which they are attached may form a five or six membered ring that optionally includes an additional heteroatom selected from O, N and S;
and pharmaceutically acceptable salts, or solvates thereof.

2. The compound of claim 1, wherein R¹ is indolyl optionally substituted with one or more of: halo; alkyl; hydroxyalkyl; morpholinylalkyl; dialkylaminoalkyl; piperidinylalkyl; hydroxyalkoxyalkyl; alkoxyalkoxyalkyl; alkylsulfonylalkyl; hydroxyalkylaminoalkyl; alkylsulfonylalkyl; hydroxyalkylaminoalkyl; 1,1-dioxothiadiaolinyl; piperidinsulfonylalkyl; dialkylaminosulfonylalkyl; pipeazinylalkyl; pyrazolylalkyl; imidazolylalkyl; 1,1-dioxothiazinanyl; pyridinyl; piperidinylsulfonylaminoalkyl; dialkylaminosulfonylaminoalkyl; or 1,1-dioxoisothiazolidinyl.

3. The compound of claim 2, wherein m is 2.

4. The compound of claim 3, wherein n is 1.

5. The compound of claim 4, wherein R¹ is: optionally substituted indol-2-yl; optionally substituted indol-6-yl; optionally substituted indol-7-yl; or optionally substituted indazol-5-yl.

6. The compound of claim 5, wherein R¹ optionally substituted indol-2-yl.

7. The compound of claim 6, wherein R¹ is indol-2-yl substituted at the 6-position or 7-position with: fluoro; chloro; bromo; piperidin-3-yl; 2-methanesulfonyl-ethyl; pyrazol-1-yl-methyl; 3-hydroxy-3-methyl-butyl; 1,1-dioxo-1λ⁶-isothiazolidin-2-yl; 1,1-dioxo-1λ⁶-[1,2]thiazinan-2-yl; 4-methyl-piperazin-1-ylmethyl; pyrazol-1-ylmethyl; imidazol-1-ylmethyl; 3-hydroxy-3-methyl-butyl; phenyl; 4-chlorophenyl; 1-(acetyl-hydrazono)-ethyl.

8. The compound of claim 6, wherein R¹ is indol-2-yl substituted at the 1-position with: alkyl; hydroxyalkyl; morpholinylalkyl; dialkylaminoalkyl; piperidinylalkyl; hydroxyalkoxyalkyl; alkoxyalkoxyalkyl; alkylsulfonylalkyl; hydroxyalkylaminoalkyl; 1,1-dioxothiadiaolinyl; piperidin-sulfonylalkyl; dialkylaminosulfonylalkyl; piperazinylalkyl; pyrazinlylalkyl; imidazolylalkyl; piperidinylsulfonylaminoalkyl; or dialkylaminosulfonylaminoalkyl.

9. The compound of claim 7, wherein R¹ is indol-2-yl substituted at the 1-position with: alkyl; hydroxyalkyl; morpholinylalkyl; dialkylaminoalkyl; piperidinylalkyl; hydroxyalkoxyalkyl; alkoxyalkoxyalkyl; alkylsulfonylalkyl; hydroxyalkylaminoalkyl; 1,1-dioxothiadiaolinyl; piperidin-sulfonylalkyl; dialkylaminosulfonylalkyl; piperazinylalkyl; pyrazolylalkyl; imidazolylalkyl; piperidinylsulfonylaminoalkyl; or dialkylaminosulfonylaminoalkyl.

10. The compound of claim 6, wherein R¹ is indol-2-yl substituted at the 1-position with: methyl; 2-hydroxy-ethyl; 3-hydroxy-propyl; 3-hydroxy-butyl; 3-hydroxy-2-hydroxymethyl-propyl; 2-hydroxy-2-methyl-propyl; 3-hydroxy-3-methyl-butyl; 2-(2-hydroxy-ethoxy)-ethyl; 2-(2-methoxy-ethoxy)-ethyl; 2-dimethylamino-ethyl; 3-dimethylamino-propyl; 2-methanesulfonyl-ethyl; 2-(2-hydroxy-ethyl-amino)-ethyl; 2-morpholin-4-yl-ethyl; 3-morpholin-4-yl-propyl; piperidin-4-yl-methyl; 2-piperidin-4-yl-ethyl; 3-piperidin-1-yl-propyl; 1-methyl-piperidin-4-yl-methyl; 2-(1-methyl-piperidin-4-yl)-ethyl; 3-(1,1-dimethyl-piperidinium)-ethyl; 1-(2-methoxy-ethyl)-piperidin-4-yl-methyl; 2-[1-(2-methoxy-ethyl)-pipeidin-4-yl]-ethyl; 3-[1-(2-methoxy-ethyl)-piperidin-4-yl]-propyl; 2-(piperidin-1-sulfonylamino)-ethyl; 2-(1,1-dioxo-1λ⁶-[1,2,5]thiadiazolidin-2-yl)-ethyl; 2-(dimethylamino-1-sulfonylamino)-ethyl; 4-methyl-piperazin-1-ylmethyl; 3-methanesulfonyl-propyl; 2-methanesulfonyl-ethyl; 4-methyl-piperazin-1-yl)-ethyl; 3-chloro-propyl; methanesulfonyl; or 2-methoxy-ethyl.

11. The compound of claim 7, wherein R¹ is indol-2-yl substituted at the 1-position with: methyl; 2-hydroxy-ethyl; 3-hydroxy-propyl; 3-hydroxy-butyl; 3-hydroxy-2-hydroxymethyl-propyl; 2-hydroxy-2-methyl-propyl; 3-hydroxy-3-methyl-butyl; 2-(2-hydroxy-ethoxy)-ethyl; 2-(2-methoxy-ethoxy)-ethyl; 2-dimethylamino-ethyl; 3-dimethylamino-propyl; 2-methanesulfonyl-ethyl; 2-(2-hydroxy-ethyl-amino)-ethyl; 2-morpholin-4-yl-ethyl; 3-morpholin-4-yl-propyl; piperidin-4-yl-methyl; 2-piperidin-4-yl-ethyl; 3-piperidin-1-yl-propyl; 1-methyl-piperidin-4-yl-methyl; 2-(1-methyl-piperidin-4-yl)-ethyl; 3-(1,1-dimethyl-piperidinium)-ethyl; 1-(2-methoxy-ethyl)-piperidin-4-yl-methyl; 2-[1-(2-methoxy-ethyl)-piperidin-4-yl]-ethyl; 3-[1-(2-methoxy-ethyl)-piperidin-4-yl]-propyl; 2-(piperidine-1-sulfonylamino)-ethyl; 2-(1,1-dioxo-1λ⁶-[1,2,5]thiadiazolidin-2-yl)-ethyl; 2-(dimethylamino-1-sulfonylamino)-ethyl; 4-methyl-piperazin-1-ylmethyl; 3-methanesulfonyl-propyl; 2-methanesulfonyl-ethyl; 2-(4-methyl-piperazin-1-yl)-ethyl; 3-chloro-propyl; methanesulfanyl; or 2-methoxy-ethyl-(1,1-dioxo-1λ⁶-[1,2,5]thiadiazolidin-2-yl)-ethyl; or 2-(dimethylamino-1-sulfonylamino)-ethyl.

12. The compound of claim 6, wherein R⁶ is: hydrogen; alkyl; or cycloalkyl.

13. The compound of claim 12, wherein R¹ is indol-2-yl substituted at the 1-position with alkyl.

14. The compound of claim 12, wherein R¹ is indol-2-yl substituted at the 1-position with a hydroxyalkyl selected from: 2-hydroxy-ethyl; 3-hydroxy-propyl; 3-hydroxy-butyl, 3-hydroxy-2-hydroxymethyl-propyl; 2-hydroxy-2-methyl-propyl; and 3-hydroxy-3-methyl-butyl; and 2-(2-hydroxy-ethoxy)-ethyl.

15. The compound of claim 12, wherein R¹ is indol-2-yl substituted at the 1-position with an aminoalkyl selected from: 2-dimethylamino-ethyl; and 3-dimethylamino-propyl.

16. The compound of claim 12, wherein R¹ is indol-2-yl substituted at the 1-position with a piperidinylalkyl selected from: piperidin-4-yl-methyl; 2-piperidin-4-yl-ethyl; 3-piperidin-1-yl-propyl; 1-methyl-piperidin-4-yl-methyl; 2-(1-methyl-piperidin-4-yl)-ethyl; 3-(1,1-dimethyl-piperidinium)-ethyl; 1-(2-methoxy-ethyl)-piperidin-4-yl-methyl; 2-[1-(2-methoxy-ethyl)-piperidin-4-yl]-ethyl; 3-[1-(2-methoxy-ethyl)-piperidin-4-yl]-propyl; and 2-(piperidine-1-sulfonylamino)-ethyl.

17. The compound of claim 12, wherein R¹ is indol-2-yl substituted at the 1-position with a morpholinylalkyl selected from: 2-morpholin-4-yl-ethyl; and 3-morpholin-4-yl-propyl.

18. The compound of claim 12, wherein R¹ is indol-2-yl substituted at the 1-position with; 2-(2-hydroxy-ethoxy)-ethyl; 2-(2-methoxy-ethoxy)-ethyl; or 2-(2-methoxy-ethoxy)-ethyl.

19. The compound of claim 6, wherein R⁶ is: hydrogen; isobutyl; cyclopropyl; 2-methanesulfanyl-ethyl; 2-methanesulfonyl-ethyl; pyridin-2-yl; 2-(methane sulfuric acid)-ethyl; phenyl; 4-nitrobenzyl; 4-aminobenzyl; 4-methoxybenzyl; 4-methanesulfonylaminobenzyl; 2-dimethylamino-ethyl; 4-(4-morpholinyl)-benzyl; pyridin-4-yl-methyl; pyridin-3-yl-methyl; 2-chloro-5-methyl-pyridin-4-yl-methyl; 2-methyl-pyridin-4-yl-methyl; 2-chloro-pyridin-4-yl-methyl; 3-hydroxy-propyl; 2-(4-methyl-piperazin-1-yl)-ethyl; 2-[4-(2-methoxy-ethyl)-piperazin-1-yl]-ethyl; 2-cyano-ethyl; 1-methyl-imidazol-4-yl-methyl; 1-morpholin-4-yl-propan-1-one-3-yl; N-cyclopropyl-propionamid-3-yl; or methyl propionate-3-yl.

20. The compound of claim 19, wherein $R^1$ is indol-2-yl substituted at the 1-position with: methyl; 2-hydroxy-ethyl; 3-hydroxy-propyl; 3-hydroxy-butyl; 3-hydroxy-2-hydroxymethyl-propyl; 2-hydroxy-2-methyl-propyl; 3-hydroxy-3-methyl-butyl; 2-(2-hydroxy-ethoxy)-ethyl; 2-(2-methoxy-ethoxy)-ethyl; 2-dimethylamino-ethyl; 3-dimethylamino-propyl; 2-methanesulfonyl-ethyl; 2-(2-hydroxy-ethyl-amino)-ethyl; 2-morpholin-4-yl-ethyl; 3-morpholin-4-yl-propyl; piperidin-4-yl-methyl; 2-piperidin-4-yl-ethyl; 3-piperidin-1-yl-propyl; 1-methyl-piperidin-4-yl-methyl; 2-(1-methyl-piperidin-4-yl)-ethyl; 3-(1,1-dimethyl-piperidinium)-ethyl; 1-(2-methoxy-ethyl)-piperidin-4-yl-methyl; 2-[1-(2-methoxy-ethyl)-piperidin-4-yl]-ethyl; 3-[1-(2-methoxy-ethyl)-piperidin-4-yl]-propyl; 2-(piperidine-1-sufonylamino)-ethyl; 2-(1,1-dioxo-1$\lambda^6$-[1,2,5]thiadiazolidin-2-yl)-ethyl; 2-(dimethylamino-1-sulfonylamino)-ethyl; 4-methyl-piperazin-1-ylmethyl; 3-methanesulfonyl-propyl; 2-methanesulfonyl-ethyl; 2-(4-methyl-piperazin-1-yl)-ethyl; 3-chloro-propyl; methane-sulfonyl; or 2-methoxy-ethyl-(1,1-dioxo-1$\lambda^6$-[1,2,5]thiadiazolidin-2-yl)-ethyl; or 2-(dimethylamino-1-sulfonylamino)-ethyl.

21. The compound of claim 19, wherein $R^1$ is indol-2-yl substituted at the 6-position with: fluoro; chloro; bromo; piperidin-3-yl; 2-methanesulfanyl-ethyl; pyrazol-1-yl-methyl; 3-hydroxy-3-methyl-butyl; 1,1-dioxo-1$\lambda^6$-isothiazolidin-2-yl; or 1,1-dioxo-1$\lambda^6$-[1,2]thiazinan-2-yl.

22. The compound of claim 19, wherein $R^1$ is indol-2-yl substituted at the 1-position with alkyl.

23. The compound of claim 19, wherein $R^1$ is indol-2-yl substituted al the 1-position with a hydroxyalkyl selected from: 2-hydroxy-ethyl; 3-hydroxy-propyl; 3-hydroxy-butyl; 3-hydroxy-2-hydroxymethyl-propyl; 2-hydroxy-2-methyl-propyl; and 3-hydroxy-3-methyl-butyl.

24. The compound of claim 19, wherein $R^1$ is indol-2-yl substituted at the 1-position with an aminoalkyl selected from: 2-dimethylamino-ethyl; and 3-dimethylamino-propyl.

25. The compound of claim 19, wherein $R^1$ is indol-2-yl substituted at the 1-position with a piperidinylalkyl selected from: piperidin-4-yl-methyl; 2-piperidin-4-yl-ethyl; 3-piperidin-1-yl-propyl; 1-methyl-piperidin-4-yl-methyl; 2-(1-methyl-piperidin-4-yl)-ethyl; 3-(1,1-dimethyl-piperidinium)-ethyl; 1-(2-methoxy-ethyl)-piperidin-4-yl-methyl; 2-[1-(2-methoxy-ethyl)-piperidin-4-yl]-ethyl; 3-[4-(2-methoxy-ethyl)-piperidin-4-yl]-propyl; and 2-(piperidine-1-sulfonylamino)-ethyl.

26. The compound of claim 19, wherein $R^1$ is indol-2-yl substituted at the 1-position with a morpholinylalkyl selected from: 2-morpholin-4-yl-ethyl; and 3-morpholin-4-yl-propyl.

27. The compound of claim 19, wherein $R^1$ is indol-2-yl substituted at the 1-position with: 2-(2-hydroxy-ethoxy)-ethyl; 2-(2-methoxy-ethoxy)-ethyl; or 2-(2-methoxy-ethoxy)-ethyl.

28. The compound of claim 4, wherein $R^1$ is: 1-methyl-1H-indol-2-yl; 5-fluoro-1-methyl-1H-indol-2-yl; 6-chloro-1H-indol-2-yl; 6-chloro-1-methyl-1H-indol-2-yl; 6-bromo-1H-indol-2-yl; 6-bromo-1-methyl-1H-indol-2-yl; 1-(2-hydroxy-ethyl)-1H-indol-2-yl; 1-(3-hydroxy-propyl)-1H-indol-2-yl; 1-(3-hydroxy-butyl)-1H-indol-2-yl; 1-(3-hydroxy-2-hydroxymethyl-propyl)-1H-indol-2-yl; 1-(2-hydroxy-2-methyl-propyl)-1H-indol-2-yl; 1-(3-hydroxy-3-methyl-butyl)-1H-indol-2-yl; 1-[2-(2-hydroxy-ethoxy)-ethyl]-1H-indol-2-yl; 1-[2-(2-methoxy-ethoxy)-ethyl]-1H-indol-2-yl; 1-[2-(2-methoxy-ethoxy)-ethyl]-1H-indol-2-yl; 1-(2-dimethylamino-ethyl)-1H-indol-2-yl; 1-(-dimethylamino-propyl)-1H-indol-2-yl; 1-(2-morpholin-4-yl-ethyl)-1H-indol-2-yl; 1-(3-morpholin-4-yl-propyl)-1H-indol-2-yl; 1-(piperidin-4-yl-methyl)-1H-indol-2-yl; 1-(2-piperidin-4-yl-ethyl)-1H-indol-2-yl; 1-(3-piperidin-1-yl-propyl)1H-indol-2-yl; 1-(1-methyl-piperidin-4-yl-methyl)-1H-indol-2-yl; 1-[2-(1-methyl-piperidin-4-yl)-ethyl]-1H-indol-2-yl; 1-[3-(1,1-dimethyl-piperidinium)-ethyl]-1H-indol-2-yl; 1-[1-(2-methoxy-ethyl)-piperidin-4-yl-methyl]-1H-indol-2-yl; 1-{2-[1-(2-methoxy-ethyl)-piperidin-4-yl]-ethyl}-1H-indol-2-yl; 1-{3-[1-(2-methoxy-ethyl)-piperidin-4-yl]-propyl}-1H-indol-2-yl; 1-(2-(piperidine-1-sulfonylamino)-ethyl)-1H-indol-2-yl; 1-(2-methanesulfonyl-ethyl)-1H-indol-2-yl; 1-[2-(2-hydroxy-ethyl-amino)-ethyl]-1H-indol-2-yl; 1-[2-(1,1-dioxo-1$\lambda^6$-[1,2,5]thiadiazolidin-2-yl)-ethyl]-1H-indol-2-yl; or 1-[2-(dimethylamino-1-sulfonylamino)-ethyl]-1H-indol-2-yl.

29. The compound of claim 28, wherein $R^6$ is: hydrogen; isobutyl; cyclopropyl; 2-methanesulfanyl-ethyl; 2-methanesulfonyl-ethyl; pyridin-2-yl; 2-(methane sulfonic acid)-ethyl; phenyl; 4-nitrobenzyl; 4-aminobenzyl; 4-methoxybenzyl; 4-methanesulfonylaminobenzyl; 2-dimethylamino-ethyl; 4-(4-morpholinyl)-benzyl; pyridin-4-yl-methyl; pyridin-3-yl-methyl; 2-chloro-5-methyl-pyridin-4-yl-methyl; 2-methyl-pyridin-4-yl-methyl; 2-chloro-pyridin-4-yl-methyl; 3-hydroxy-propyl; 2-(4-methyl-piperazin-1-yl)-ethyl; 2-[4-(2-methoxy-ethyl)-piperazin-1-yl]-ethyl; 2-cyano-ethyl; 1-methyl-imidazol-4-yl-methyl; 1-morpholin-4-yl-propan-1-one-3-yl; N-cyclopropyl-propionamid-3-yl; or methyl propionate-3-yl.

30. The compound of claim 4, wherein $R^1$ is indol-5-yl.

31. The compound of claim 4, wherein $R^1$ is indol-5-yl substituted at the 1-position with: alkyl; hydroxyalkyl; morpholinylalkyl; dialkylaminoalkyl; piperidinylalkyl; hydroxyalkoxyalkyl; alkoxyalkoxyalkyl; alkylsulfonylalkyl; hydroxyalkylaminoalkyl; 1,1-dioxothiadianlinyl; piperidin-sulfonylalkyl; dialkylaminosulfonylalkyl; piperazinylalkyl; pyrazolylalkyl; imidazolylalkyl; piperidinylsulfonylaminoalkyl; or dialkylaminosulfonylaminoalkyl.

32. The compound of claim 4, wherein $R^1$ is indol-5-yl substituted at the 1-position with: methyl; 2-hydroxy-ethyl; 3-hydroxy-propyl; 3-hydroxy-butyl; 3-hydroxy-2-hydroxylmethyl-propyl; 2-hydroxy-2-methyl-propyl; 3-hydroxy-3-methyl-butyl; 2-(2-hydroxy-ethoxy)-ethyl; 2-(2-methoxy-ethoxy)-ethyl; 2-dimethylamino-ethyl; 3-dimethylamino-propyl; 2-methanesulfonyl-ethyl; 2-(2-hydroxy-ethyl-amino)-ethyl; 2-morpholin-4-yl-ethyl; 3-morpholin-4-yl-propyl; piperidin-4-yl-methyl; 2-piperidin-4-yl-ethyl; 3-piperidin-1-yl-propyl; 1-methyl-piperidin-4-yl-methyl; 2-(1-methyl-piperidin-4-yl)-ethyl; 3-(1,1-dimethyl-piperidinium)-ethyl; 1-(2-methoxy-ethyl)-piperidin-4-yl-methyl; 2-[1-(2-methoxy-ethyl)-piperidin-4-yl]-ethyl; 3-[1-(2-methoxy-ethyl)-piperidin-4-yl]-propyl; 2-(piperidine-1-sulfonylamino)-ethyl; 2-(1,1-dioxo-1$\lambda^6$-[1,2,5]thiadiazolidin-2-yl)-ethyl; or 2-(dimethylamino-1-sulfonylamino)-ethyl.

33. The compound of claim 28, wherein $R^6$ is: hydrogen; isobutyl; cyclopropyl; 2-methanesulfanyl-ethyl;

2-methanesulfonyl-ethyl; pyridin-2-yl; 2-(methane sulfonic acid)-ethyl; phenyl; 4-nitrobenzyl; 4-aminobenzyl; 4-methoxybenzyl; 4-methanesulfonylaminobenzyl; 2-dimethylamino-ethyl; 4-(4-morpholinyl)-benzyl; pyridin-4-yl-methyl; pyridin-3-yl-methyl; 2-chloro-5-methyl-pyridin-4-yl-methyl; 2-methyl-pyridin-4-yl-methyl; 2-chloro-pyridin-4-yl-methyl; 3-hydroxy-propyl; 2-(4-methyl-piperazin-1-yl)-ethyl; 2-[4-(2-methoxy-ethyl)-piperazin-1-yl]-ethyl; 2-cyano-ethyl; 1-methyl-imidazol-4-yl-methyl; 1-morpholin-4-yl-propan-1-one-3-yl; N-cyclopropyl-propionamid-3-yl; or methyl propionate-3-yl.

34. The compound of claim 30, wherein $R^6$ is: hydrogen; isobutyl; cyclopropyl; 2-methanesulfanyl-ethyl; 2-methanesulfonyl-ethyl; pyridin-2-yl; 2-(methane sulfonic acid)-ethyl; phenyl; 4-nitrobenzyl; 4-aminobenzyl; 4-methoxybenzyl; 4-methanesulfonylaminobenzyl; 2-dimethylamino-ethyl; 4-(4-morpholinyl)-benzyl; pyridin-4-yl-methyl; pyridin-3-yl-methyl; 2-chloro-5-methyl-pyridin-4-yl-methyl; 2-methyl-pyridin-4-yl-methyl; 2-chloro-pyridin-4-yl-methyl; 3-hydroxy-propyl; 2-(4-methyl-piperazin-1-yl)-ethyl; 2-[4-(2-methoxy-ethyl)-piperazin-1-yl]-ethyl; 2-cyano-ethyl; 1-methyl-imidazol-4-yl-methyl; 1-morpholin-4-yl-propan-1-one-3-yl; N-cyclopropyl-propionamid-3-yl; or methyl propionate-3-yl.

35. The compound of claim 4, wherein $R^1$ is: 1-(3-morpholin-4-yl-propyl)-1H-indol-5-yl; 1-(2-dimethyl-amino-ethyl)-1H-indol-5-yl; 1-(3-dimethylamino-propyl)-1H-indol-5-yl; or 2-methyl-2,3,4,5-tetrahydro-1H-pyrido[4,3-b]indol-5-yl.

36. The compound of claim 35, wherein $R^6$ is: hydrogen; isobutyl; cyclopropyl; 2-methanesulfanyl-ethyl; 2-methanesulfonyl-ethyl; pyridin-2-yl; 2-(methane sulfonic acid)-ethyl; phenyl; 4-nitrobenzyl; 4-aminobenzyl; 4-methoxybenzyl; 4-methanesulfonylaminobenzyl; 2-dimethylamino-ethyl; 4-(4-morpholinyl)-benzyl; pyridin-4-yl-methyl; pyridin-3-yl-methyl; 2-chloro-5-methyl-pyridin-4-yl-methyl; 2-methyl-pyridin-4-yl-methyl; 2-chloro-pyridin-4-yl-methyl; 3-hydroxy-propyl; 2-(4-methyl-piperazin-1-yl)-ethyl; 2-[4-(2-methoxy-ethyl)-piperazin-1-yl]-ethyl; 2-cyano-ethyl; 1-methyl-imidazol-4-yl-methyl; 1-morpholin-4-yl-propan-1-one-3-yl; N-cyclopropyl-propionamid-3-yl; or methyl propionate-3-yl.

37. The compound of claim 41, wherein $R^1$ is 5-(6-methyl-pyridin-2-yl)-thiophene-2-yl.

38. The compound of claim 41, wherein $R^1$ is benzo[d]pyrrolo[2,1-b]thiazol-yl.

39. The compound of claim 1, wherein said compound is selected from; 6-Chloro-1H-indole-2-carboxylic acid [(1S,2R)-2-(cyanomethyl-carbamoyl)-cyclohexyl]-amide; 6-Chloro-1-methyl-1H-indole-2-carboxylic acid [(1S,2R)-2-(cyanomethyl-carbamoyl)-cyclohexyl]-amide; 1-(2-Hydroxy-ethyl)-1H-indole-2-carboxylic acid [(1S,2R)-2-((S)-1-cyano-3-methyl-butylcarbamoyl)-cyclohexyl]-amide; 1-Methyl-1H-indole-2-carboxylic acid [(1S,2R)-2-(1-cyano-3-methyl-butylcarbamoyl)-5-methyl-cyclohexyl]-amide; 6-Fluoro-1-methyl-1H-indole-2-carboxylic acid [(1S,2R)-2-[((S)-cyano-cyclopropyl-methyl)-carbamoyl]-cyclohexyl)-amide; 6-fluoro-1-methyl-1H-indole; 5-Fluoro-1-methyl-1H-indole-2-carboxylic acid [(1S,2R)-2-((S)-1-cyano-3-methylsulfanyl-propylcarbamoyl)-cyclohexyl]-amide; 1-(3-Hydroxy-propyl)-1H-indole-2-carboxylic acid [(1S,2R)-2-(cyanomethyl-carbamoyl)-cyclohexyl]-amide; 1-(3-Hydroxy-propyl)-1H-indole-2-carboxylic acid [(1S,2R)-2-((S)-1-cyano-3-methyl-butylcarbamoyl)-cyclohexyl]-amide; 1-(3-Morpholin-4-yl-propyl)-1H-indole-2-carboxylic acid [(1S,2R)-2-((S)-1-cyano-3-methyl-butylcarbamoyl)-cyclohexyl]-amide; 1-Methyl-1H-indole-2-carboxylic acid {(1S,2R)-2-[(cyano-pyridin-2-yl-methyl)-carbamoyl]-cyclohexyl}-amide; 1-(2-Hydroxy-ethyl)-1H-indole-2-carboxylic acid {(1S,2R)-2-[((S)-cyano-cyclopropyl-methyl)-carbamoyl]-cyclohexyl}-amide; Methanesulfonic acid (S)-3-cyano-3-({(1R,2S)-2-[(1-methyl-1H-indole-2-carbonyl)-amino]-cyclohexanecarbonyl}-amino)-propyl ester; 1-Methyl-1H-indole-2-carboxylic acid {(1S,2R)-2-[(cyano-phenyl-methyl)-carbamoyl]-cyclohexyl}-amide; 1-(2-Dimethylamino-ethyl)-1H-indole-2-carboxylic acid [(1S,2R)-2-((S)-1-cyano-3-methyl-butylcarbamoyl)-cyclohexyl]-amide; 1-(2-Morpholin-4-yl-ethyl)-1H-indole-2-carboxylic acid [(1S,2R)-2-((S)-1-cyano-3-methyl)-butylcarbamoyl)-cyclohexyl]-amide; 1-(3-Hydroxy-butyl)-1H-indole-2-carboxylic acid [(1S,2R)-2-((S)-1-cyano-3-methyl-butylcarbamoyl)-cyclohexyl]-amide; 6-Chloro-1-(2-hydroxy-ethyl)-1H-indole-2-carboxylic acid [(1S,2R)-2-(cyanomethyl-carbamoyl)-cyclohexyl]-amide; 1-(3-Piperidin-1-yl-propyl)-1H-indole-2-carboxylic acid [(1S,2R)-2-((S)-1-cyano-3-methyl-butylcarbamoyl)-cyclohexyl]-amide; 6-Bromo-1H-indole-2-carboxylic acid [(1S,2R)-2-((S)-1-cyano-3-methyl-butylcarbamoyl)-cyclohexyl]-amide; 6-Bromo-1-methyl-1H-indole-2-carboxylic acid [(1S,2R)-2-((S)-1-cyano-3-methyl-butylcarbamoyl)-cyclohexyl]-amide; 1-(3-Hydroxy-2-hydroxymethyl-propyl)-1H-indole-2-carboxylic acid [(1S,2R)-2-((S)-1-cyano-3-methyl-butylcarbamoyl)-cyclohexyl]-amide; 1-(3-Hydroxy-3-methyl-butyl)-1H-indole-2-carboxylic acid [(1S,2R)-2-((S)-1-cyano-3-methyl-butylcarbamoyl)-cyclohexyl]-amide; 1-(3-Hydroxy-propyl)-1H-indole-2-carboxylic acid [(1S,2R)-2-(cyanomethyl-carbamoyl)-cyclohexyl]-amide; 1-(3-Dimethylamino-propyl)-1H-indole-2-carboxylic acid [(1S,2R)-2-((S)-1-cyano-3-methyl-butylcarbamoyl)-cyclohexyl]-amide; 1-[2-(2-Hydroxy-ethoxy)-ethyl]-1H-indole-2-carboxylic acid [(1S,2R)-2-((S)-1-cyano-3-methyl-butylcarbamoyl)-cyclohexyl]-amide; 1-[2-(2-Methoxy-ethoxy)-ethyl]-1H-indole-2-carboxylic acid [(1S,2R)-2-((S)-1-cyano-3-methyl-butylcarbamoyl)-cyclohexyl]-amide; 6-Bromo-1-methyl-1H-indole-2-carboxylic acid [(1S,2R)-2-(cyanomethyl-carbamoyl)-cyclohexyl]-amide; 6-Bromo-1H-indole-2-carboxylic acid [(1S,2R)-2-(cyanomethyl-carbamoyl)-cyclohexyl]-amide; 1-(2-Methanesulfonyl-ethyl)-1H-indole-2-carboxylic acid [(1S,2R)-2-((S)-1-cyano-3-methyl-butylcarbamoyl)-cyclohexyl]-amide; 6-Chloro-1-(2-morpholin-4-yl-ethyl)-1H-indole-2-carboxylic acid [(1S,2R)-2-(cyanomethyl-carbamoyl)-cyclohexyl]-amide; 6-Chloro-1-(3-piperidin-1-yl-propyl)-1H-indole-2-carboxylic acid [(1S,2R)-2-(cyanomethyl-carbamoyl)-cyclohexyl]-amide; 6-Chloro-1-methyl-1H-indole-2-carboxylic acid [(1S,2R)-2-((S)-1-cyano-3-methylsulfanyl-propylcarbamoyl)-cyclohexyl]-amide; 6-Chloro-1H-indole-2-carboxylic acid [(1S,2R)-2-((S)-1-cyano-3-methylsulfanyl-propylcarbamoyl)-cyclohexyl]-amide; 1-Methyl-1H-indole-2-carboxylic acid {(1S,2R)-2-[(cyano-pyridin-4-ylmethyl-methyl)-carbamoyl]-cyclohexyl}-amide; 1-Methyl-1H-indole-2-carboxylic acid {(1S,2R)-2-[(cyano-pyridin-3-ylmethyl-methyl)-carbamoyl]-cyclohexyl}-amide; 6-Chloro-1-(3-hydroxy-propyl)-1H-indole-2-carboxylic acid [(1S,2R)-2-((S)-1-cyano-3-methyl-butylcarbamoyl)-cyclohexyl]-amide; 6-Chloro-1-methyl-1H-indole-2-carboxylic acid [(1S,2R)-2-((S)-1-cyano-3-methanesulfonyl-propylcarbamoyl)-cyclohexyl]-amide; 1-(1-Methylpiperidin-4-ylmethyl)-1H-indole-2-carboxylic acid [(1S,2R)-2-((S)-1-cyano-3-methyl-butylcarbamoyl)-cyclohexyl]-amide; 1-[1-(2-Methoxy-ethyl)-piperidin-4-ylmethyl]-1H-indole-2-carboxylic acid [(1S,2R)-2-((S)-1-cyano-3-methyl-butylcarbamoyl)-cyclohexyl]-amide; 1-Methyl-1H-indole-2-carboxylic acid {(1S,2R)-2-[(S)-1-cyano-3-(4-methyl-piperazin-1-yl)-propylcarbamoyl]-cyclohexyl}-amide; 5-Fluoro-1-methyl-1H-indole-2-carboxylic acid [(1S,2R)-2-((S)-1-cyano-3-methanesulfonyl-propylcarbamoyl)-cyclohexyl]-amide; morpholin-4-yl-ethyl)-1H-indole-2-carboxylic acid [(1S,2R)-2-((S)-1-cyano-3-methyl-butylcarbamoyl)-cyclohexyl]-amide; 1-[3-[1-(2-Methoxy-ethyl)-piperidin-4-yl]-propyl}-1H-indole-2-carboxylic acid [(1S,2R)-2-((S)-1-cyano-3-methyl-butylcarbamoyl)-cyclohexyl]-amide; 6-Pyridin-3-yl-1H-indole-2-carboxylic acid [(1S,2R)-2-((S)-1-cyano-3-methyl-butylcarbamoyl)-cyclohexyl]-amide; 1-[2-(2-Hydroxy-ethylamino)-ethyl]-1H-indole-2-carboxylic acid [(1S,2R)-2-((S)-1-cyano-3-methyl-butylcarbamoyl)-cyclohexyl]-amide; 1-{2-[1-(2-Methoxy-ethyl)-piperidin-4-yl]-ethyl}-1H-indole-2-carboxylic acid [(1S,2R)-2-((S)-1-cyano-3-methyl-butylcarbamoyl)-cyclohexyl]-amide; 1-[2-(1-Methyl-piperidin-4-yl)-ethyl]-1H-indole-2-carboxylic acid [(1S,2R)-2-((S)-1-cyano-3-methyl-butylcarbamoyl)-cyclohexyl]-amide; 1-(2-Hydroxy-2-methyl-propyl)-1H-indole-2-carboxylic acid [(1S,2R)-2-((S)-1-cyano-3-methyl-butylcarbamoyl)-cyclohexyl]-amide; 6-Chloro-1-(2-morpholin-4-yl-ethyl)-1H-indole-2-carboxylic acid {(1S,2R)-2-[((S)-cyano-cyclopropyl-methyl)-carbamoyl]-cyclohexyl}-amide; 6-Chloro-1-(2-dimethylamino-ethyl)-1H-indole-2-carboxylic acid {(1S,2R)-2-[((S)-cyano-cyclopropyl-methyl)-carbamoyl]-cyclohexyl}-amide; 1-Methyl-1H-indole-2-carboxylic acid ((1S,2R)-2-{[(2-chloro-6-methyl-pyridin-4-ylmethyl)-cyano-methyl]-carbamoyl}-cyclohexyl)-amide; 1-Methyl-1H-indole-2-carboxylic acid ((1S,2R)-2-{[cyano-(2-methyl-pyridin-4-ylmethyl)-methyl]-carbamoyl}-cyclohexyl)-amide; 1-[2-(1,1-Dioxo-1λ⁶-[1,2,5]thiadiazolidin-2-yl)-ethyl]-1H-indole-2-carboxylic acid [(1S,2R)-2-((S)-1-cyano-3-methyl-butylcarbamoyl)-cyclohexyl]-amide; 6-Chloro-1-(3-dimethylamino-propyl)-1H-indole-2-carboxylic acid {(1S,2R)-2-[((S)-cyano-cyclopropyl-methyl)-carbamoyl]-cyclohexyl}-amide; 1-[2-(Piperidine-1-sulfonylamino)-ethyl]-1H-indole-2-carboxylic acid [(1S,2R)-2-((S)-1-cyano-3-methyl-butylcarbamoyl)-cyclohexyl]-amide; 1-[2-(Dimethylamino-1-sulfonylamino)-ethyl]-1H-indole-2-carboxylic acid [(1S,2R)-2-((S)-1-cyano-3-methyl-butylcarbamoyl)-cyclohexyl]-amide; 1-Methyl-1H-indole-2-carboxylic acid ((1S,2R)-2-{[(S)-cyano-(4-nitro-benzyl)-methyl]-carbamoyl}-cyclohexyl)-amide; 1-Methyl-1H-indole-2-carboxylic acid ((1S,2R)-2-{[(S)-cyano-(4-morpholin-4-yl-benzyl)-methyl]-carbamoyl}-cyclohexyl)-amide; 1-Methyl-1H-indole-2-carboxylic acid ((1S,2R)-2-{[(S)-(4-amino-benzyl)-cyano-methyl]-carbamoyl}-cyclohexyl)-amide; 6-(2-Methanesulfonyl-ethyl)-1-methyl-1I 1-indole-2-carboxylic acid [(1S,2R)-2-((S)-1-cyano-3-methyl-butylcarbamoyl)-cyclohexyl]-amide; 1-Methyl-1H-indole-2-carboxylic acid ((1S,2R)-2-{[(2-chloro-pyridin-4-ylmethyl)-cyano-methyl-carbamoyl}-cyclohexyl)-amide; 1-Methyl-1H-indole-2-carboxylic acid [(1S,2R)-2-(1,3-dicyano-propylcarbamoyl)-cyclohexyl]-amide; 1-(3-Morpholin-4-yl-propyl)-1H-indole-2-carbamylic acid {(1S,2R)-2-[((S)-cyano-cyclopropyl-methyl)-carbamoyl]-cyclohexyl}-amide; 1-Methyl-1H-indole-2-carboxylic acid [(1S,2R)-2-(1-cyano-4-hydroxy-butylcarbamoyl)-cyclohexyl]-amide; 1-(3-Piperidin-4-yl-propyl)-1H-indole-2-carboxylic acid [(1S,2R)-2-(1-cyano-3-methyl-butylcarbamoyl)-cyclohexyl]-amide; 6-(4-Methyl-piperazin-1-ylmethyl)-1H-indole-2-carboxylic acid [(1S,2R)-2-(cyanomethyl-carbamoyl)-cyclohexyl]-amide; 6-Pyrazol-1-ylmethyl-1H-indole-2-carboxylic acid [(1S,2R)-2-(cyanomethyl)-carbamoyl)-cyclohexyl]-amide; 6-Imidazol-1-ylmethyl-1H-indole-2-carboxylic acid [(1S,2R)-2-(cyanomethyl-carbamoyl)-cyclohexyl]-amide; 1-Methyl-1H-indole-2-carboxylic acid [(1S,2R)-2-((S)-1-cyano-4-morpholin-4-yl-4-oxo-butylcarbamoyl)-cyclohexyl]-amide; 1-Methyl-1H-indole-2-carboxylic acid {(1S,2R)-2-[(S)-1-cyano-2-(1-methyl-1H-imidazol-4-yl)-ethylcarbamoyl]-cyclohexyl}-amide; 6-Chloro-1-(3-dimethylamino-propyl)-1H-indole-2-carboxylic acid [(1S,2R)-2-((S)-1-cyano-3-methyl-butylcarbamoyl)-cyclohexyl]-amide; 6-Chloro-1-(2-dimethylamino-ethyl)-1H-indole-2-carboxylic acid [(1S,2R)-2-((S)-1-cyano-3-methyl-butylcarbamoyl)-cyclohexyl]-amide; 6-Chloro-1-(3-morpholin-4-yl-propyl)-1H-indole-2-carboxylic acid [(1S,2R)-2-((S)-1-cyano-3-methyl-butylcarbamoyl)-cyclohexyl]-amide; 1-Methyl-1H-indole-2-carboxylic acid ((1S,2R)-2-{[(S)-cyano-(4-methoxy-benzyl)-methyl]-carbamoyl}-cyclohexyl)-amide; 1-Methyl-1H-indole-2-carboxylic acid [(1S,2R)-2-((S)-1-cyano)-3-cyclopropylcarbamoyl-propylcarbamoyl)-cyclohexyl]-amide; 1-Methyl-1H-indole-2-carboxylic acid [(1S,2R)-2-((S)-1-cyano-3-dimethylamino-propylcarbamoyl)-cyclohexyl]-amide; 1-Methyl-1H-indole-2-carboxylic acid ((1S,2R)-2-{(S)-1-cyano-3-[4-(2-methoxy-ethyl)-piperazin-1-yl]-propylcarbamoyl}-cyclohexyl)-amide; 1-Piperidin-4-ylmethyl-1H-indole-2-carboxylic acid [(1S,2R)-2-(1-cyano-3-methyl-butylcarbamoyl)-cyclohexyl ]-amide; 1-Methyl-1H-indole-2-carboxylic acid ((1S,2R)-2-{[(S)-cyano-(4-methanesulfonylamino-benzyl)-methyl]-carbamoyl}-cyclohexyl)-amide; 1-[1-(2-Methoxy-ethyl)-piperidin-4-ylmethyl]-1H-indole-2-carboxylic acid [(1S,2R)-2-(cyanomethyl-carbamoyl)-cyclohexyl]-amide; 6-(1,1-Dioxo-1λ⁶-[1,2]thiazinan-2-yl)-1-methyl-1H-indole-2-carboxylic acid [(1S,2R)-2-((S)-1-cyano-3-methyl-butylcarbamoyl)-cyclohexyl]-amide; 6-(1,1-Dioxo-1λ⁶-isothiazolidin-2-yl)-1-methyl-1H-indole-2-carboxylic acid [(1S,2R)-2-((S)-1-cyano-3-methyl-butylcarbamoyl)-cyclohexyl]-amide; 1-(3-Morpholin-4-yl-propyl)-1H-indole-5-carboxylic acid [(1S,2R)-2-((S)-1-cyano-3-methyl-butylcarbamoyl)-cyclohexyl]-amide; 1-(2-Dimethylamino-ethyl)-1H-indole-5-carboxylic acid [(1S,2R)-2-((S)-1-cyano-3-methyl-butylcarbamoyl)-cyclohexyl]-amide; 1-(3-Dimethylamino-propyl)-1H-indole-5-carboxylic acid [(1S,2R)-2-((S)-1-cyano-3-methyl-butylcarbamoyl)-cyclohexyl]-amide; 2-Methyl-2,3,4,5-tetrahydro-1H-pyridin[4,3-b]indole-8-carboxylic acid [(1S,2R)-2-((S)-1-cyano-3-methyl-butylcarbamoyl)-cyclohexyl]-amide; 6-Methyl)-1H-indole-2-carboxylic acid [(1S,2R)-2-(cyanomethyl-carbamoyl)-cyclohexyl]-amide; 6-(3-Hydroxy-3-methyl-butyl)-1-methyl-1H-indole-2-carboxylic acid [(1S,2R)-2-((S)-1-cyano-3-methyl-butylcarbamoyl)-cyclohexyl]-amide; 1-(2-Piperidin-4-yl-ethyl)-1H-indole-2-carboxylic acid [(1S,2R)-2-((S)-1-cyano-3-methyl-butylcarbamoyl)-cyclohexyl]-amide; 4-(3-{2-[(1S,2R)-2-((S)-1-Cyano-3-methyl-butylcarbamoyl)-cyclohexylcarbamoyl]-indol-1-yl}-propyl)-1,1-dimethyl-piperidinium; chloride; 1H-Indole-5-carboxylic acid [(1S,2R)-2-(cyanomethyl-carbamoyl)-cyclohexyl]-amide; 5-(6-Methyl-pyridin-2-yl)-thiophene-2-carboxylic acid [(1S,2R)-2-(cyanomethyl-carbamoyl)-cyclohexyl]-amide Benzo[d]pyrrolo[2,1-b]thiazole-2-carboxylic acid [(1S,2R)-2-((S)-1-cyano-3-methyl-butylcarbamoyl)-cyclohexyl]-amide; 1H-Indole-5- carboxylic acid [(1S,2R)-2-((S)-1-cyano-3-methyl-butylcarbamoyl)-cyclohexyl]-amide; 1H-Indole-6-carboxylic add [(1S,2R)-2-((S)-1-cyano-3-methyl-butylcarbamoyl)-cyclohexyl]-amide; 1-Methyl-1H-indole-2-carboxylic acid {(1S,2R)-2-[((R)-cyano-methoxymethyl-methyl)-carbamoyl]-cyclohexyl}-amide; (S)-4-Cyano-4-({(1R,2S)-2-[(1- methyl-1H-indole-2-carbonyl)-amino]-cyclohexanecarbonyl}-amino)-butyric acid methyl ester; 1-Methyl-1H-indole-2-carboxylic acid [(1S,2R)-2-(cyanomethyl-carbamoyl)-cycloheptyl)-amide.

40. The compound of claim 1, wherein said compound is of the formula (II):

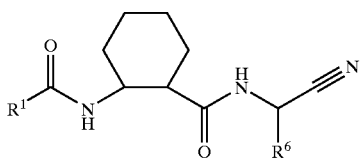

(II)

and wherein $R^1$ and $R^6$ are as defined in claim 1.

41. The compound of claim 40, wherein $R^1$ is: 1-methyl-1H-indol-2-yl; 5-fluoro-1-methyl-1H-indol-2-yl; 6-chloro-1H-indol-2-yl; 6-chloro-1-methyl-1H-indol-2-yl; 6-bromo-1H-indol-2-yl; 6-bromo-1-methyl-1H-indol-2-yl; 1-(2-hydroxy-ethyl)-1H-indol-2-yl; 1-(3-hydroxy-propyl)-1H-indol-2-yl; 1-(3-hydroxy-butyl)-1H-indol-2-yl; 1-(3-hydroxy-2-hydroxymethyl-propyl)-1H-indol-2-yl; 1-(2-hydroxy-2-methyl-propyl)-1H-indol-2-yl; 1-(3-hydroxy-3-methyl-butyl)-1H-indol-2-yl; 1-[2-(2-hydroxy-ethoxy)-ethyl]-1H-indol-2-yl; 1-[2-(2-methoxy-ethoxy)-ethyl]-1H-indol-2-yl; 1-[2-(2-methoxy-ethoxy)-ethyl]-1H-indol-2-yl; 1-(2-dimethylamino-ethyl)-1H-indol-2-yl; 1-(-dimethylamino-propyl)-1H-indol-2-yl; 1-(2-morpholin-4-yl-ethyl)-1H-indo]-2-yl; 1-(3-morpholin-4-yl-propyl)-1H-indo]-2-yl; 1-(piperidin-4-yl-methyl)-1H-indo]-2-yl; 1-(2-piperidin-4-yl-ethyl)-1H-indo]-2-yl; 1-(3-piperidin-1-yl-propyl)-1H-indol-2-yl; 1-(1-methyl-piperidin-4-yl-methyl)-1H-indol-2-yl; 1-(2-(1-methyl-piperidin-4-yl)-ethyl]-1H-indol-2-yl; 1-[3-(1,1-dimethyl-piperidinium)-ethyl]-1H-indol-2-yl; 1-[1-(2-methoxy-ethyl)-piperidin-4-yl-methyl]-1H-indol-2-yl; 1-{2-[1-(2-methoxy-ethyl)-piperidin-4-yl}-ethyl)-1H-indo]-2-yl; 1-{3-[1-(2-methoxy-ethyl)-piperidin-4-yl]-propyl}-1H-indol-2-yl; 1-[2-(piperidine-1-sulfonylamino)-ethyl]-1H-indol-2-yl; 1-(2-methanesulfonyl-ethyl)-1H-indol-2-yl; 1-[2-(2-hydroxy-ethyl-amino)-ethyl]-1H-indol-2-yl; 1-[2-(1,1-dioxo-1$\lambda^6$-[1,2,5]thiadiazolidin-2-yl)-ethyl]-1H-indol-2-yl; or 1-[2-(dimethylamino-1-sulfonylamino)-ethyl]-1H-indol-2-yl.

42. The compound of claim 40, wherein $R^6$ is: hydrogen; isobutyl; cyclopropyl; 2-methanesulfanyl-ethyl; 2-methanesulfonyl-ethyl; pyridin-2-yl; 2-(methane sulfonic acid)-ethyl; phenyl; 4-nitrobenzyl; 4-aminobenzyl; 4-methoxybenzyl; 4-methanesulfonylaminobenzyl; 2-dimethylamino-ethyl; 4-(4-morpholinyl)-benzyl; pyridin-4-yl-methyl; pyridin-3-yl-methyl; 2-chloro-5-methyl-pyridin-4-yl-methyl; 2-methyl-pyridin-4-yl-methyl; 2-chloro-pyridin-4-yl-methyl; 3-hydroxy-propyl; 2-(4-methyl-piperazin-1-yl)-ethyl; 2-[4-(2-methoxy-ethyl)-piperazin-1-yl]-ethyl; 2-cyano-ethyl; 1-methyl-imidazol-4-yl-methyl; 1-morpholin-4-yl-propan-1-one-3-yl; N-cyclopropyl-propionamid-3-yl; or methyl propionate-3-yl.

43. The compound of claim 40, wherein $R^1$ is: 1-(3-morpholin-4-yl-propyl)-1H-indol-5-yl; 1-(2-dimethylamino-ethyl)-1H-indol-5-yl; 1-(3-dimethylamino-propyl)-1H-indol-5-yl; or 2-methyl-2,3,4,5-tetrahydro-1H-pyrido[4,3-b]indol-5-yl of the formula (III).

44. The compound of claim 40, wherein said compound is of the formula III:

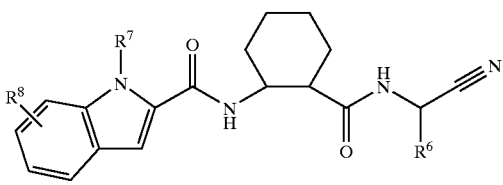

(III)

wherein:

$R^6$ is as defined in claim 40;

$R^7$ is: hydrogen; alkyl; hydroxyalkyl; morpholinylalkyl; dialkylaminoalkyl; piperidinylalkyl; hydroxyalkoxyalkyl; alkoxyalkoxyalkyl; alkylsulfonylalkyl; hydroxyalkylaminoalkyl; 1,1-dioxothiadiaolinyl; piperidinsulfonylalkyl; dialkylaminosulfonylalkyl; piperazinylalkyl; pyrazolylalkyl; imidazolylalkyl; piperidinylsulfonylaminoalkyl; or dialkylaminosulfonylaminoalkyl; and $R^8$ is: hydrogen; halo; piperidinyl; alkylsulfonylalkyl; pyrazolylalkyl; hydroxy-3-methyl-butyl; 1,1-dioxoisothiazolidinyl; or 1,1-dioxo-thiazinanyl.

45. The compound of claim 44, wherein $R^7$ is: hydrogen; methyl; 2-hydroxy-ethyl; 3-hydroxy-propyl; 3-hydroxybutyl; 3-hydroxy-2-hydroxymethyl-propyl; 2-hydroxy-2-methyl-propyl; 3-hydroxy-3-methyl-butyl; 2-(2-hydroxyethoxy)-ethyl; 2-(2-methoxy-ethoxy)-ethyl; 2-dimethylamino-ethyl; 3-dimethylamino-propyl; 2-methanesulfonyl-ethyl; 2-(2-hydroxy-ethyl-amino)-ethyl; 2-morpholin-4-yl-ethyl; 3-morpholin-4-yl-propyl; piperidin-4-yl-methyl; 2-piperidin-4-yl-ethyl; 3-piperidin-1-yl-propyl; 1-methyl-piperidin-4-yl-methyl; 2-(1-methyl-piperidin-4-yl)-ethyl; 3-(1,1-dimethyl-piperidinium)-ethyl; 1-(2-methoxy-ethyl)-piperidin-4-yl-methyl; 2-[1-(2-methoxy-ethyl)-piperidin-4-yl]-ethyl; 3-[1-(2-methoxy-ethyl)-piperidin-4-yl]-propyl; 2-(piperidine-1-sulfonylamino)-ethyl; 2-(1-dioxo-1$\lambda^6$-[1,2,5]thiadiazolidin-2-yl)-ethyl; or 2-(dimethylamino-1-sulfonylamino)-ethyl.

46. The compound of claim 44, wherein $R^8$ is: fluoro; chloro; bromo; piperidin-3-yl; 2-methanesulfanyl-ethyl; pyrazol-1-yl-methyl; 3-hydroxy-3-methyl-butyl; 1,1-dioxo-1$\lambda^6$-isothiazolidin-2-yl; or 1,1-dioxo-1$\lambda^6$-[1,2]thiazinan-2-yl.

47. The compound of claim 1, wherein $R^1$ is optionally substituted indazol-5-yl.

48. The compound of claim 47, wherein $R^1$ is 3-(3-dimethylamino-propyl)-indazol-5-yl; 2-(3-dimethylamino-propyl)-indazol-5-yl; 1-(3-dimethylamino-propyl)-indazol-5-yl; 2-(2-dimethylamino-ethyl)-indazol-5-yl; or; 1-(2-dimethylamino-ethyl)-indazol-5-yl.

49. The compound of claim 1, wherein $R^1$ is optionally substituted tetrahydropyridoindolyl.

50. The compound of claim 49, wherein $R^1$ is 2-methyl-2,3,4,5-tetrahydro-1H-pyrido[4,3-b]indol-8-yl.

51. The compound of claim 1, wherein $R^1$ is optionally substituted pyridinylthiophene-2-yl.

52. The compound of claim 1, wherein $R^1$ is 5-(6-methyl-pyridin-2-yl)-thiaphene-2-yl.

53. The compound of claim 1, wherein $R^1$ is optionally substituted benzopyrrolothiazolyl.

54. The compound of claim 53, wherein $R^1$ is optionally substituted beno[d]pyrrolo[2,1-b]thiazole-2-yl.

55. A pharmaceutical composition comprising a compound of claim 1 and a pharmaceutically acceptable carrier and/or adjuvant.

56. A method for the treatment of osteoporosis, breast tumor, breast tumor-derived bone metastusis, instable angina pectoris and/or plaque rupture in a human being or animal, which method comprises administering a therapeutically effective amount a compound according to claim 1 to the human being or animal.

57. A method of preparing a compound of claim 1, comprising:

a) reacting a compound of formula (IV):

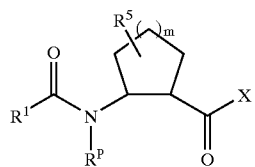

(V)

wherein X is a leaving group and $R^1$, $R^2$, $R^3$ and m are defined in claim 1;

with a compound of formula (VI):

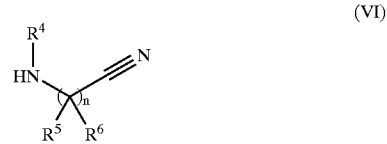

(VI)

wherein $R^4$, $R^5$, $R^6$ and n are as defined in claim 1; or b) reacting a compound of formula (VII):

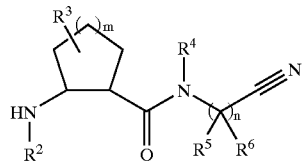

wherein $R^2$, $R^3$, $R^4$, $R^5$ and $R^6$ are us defined in claim 1, with a compound of formula (VIII)

(VIII)

wherein X is a leaving group and $R^1$ is as defined in claim 1;

to provide a compound of formula (I).

* * * * *